(12) United States Patent
Mrsny et al.

(10) Patent No.: US 11,246,915 B2
(45) Date of Patent: *Feb. 15, 2022

(54) CHOLIX TOXIN-DERIVED FUSION MOLECULES FOR ORAL DELIVERY OF BIOLOGICALLY ACTIVE CARGO

(71) Applicant: Applied Molecular Transport Inc., South San Francisco, CA (US)

(72) Inventors: Randall J. Mrsny, Los Altos Hills, CA (US); Tahir Mahmood, Burlingame, CA (US)

(73) Assignee: Applied Molecular Transport Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/004,686

(22) Filed: Aug. 27, 2020

(65) Prior Publication Data
US 2021/0220446 A1 Jul. 22, 2021

Related U.S. Application Data

(63) Continuation of application No. 16/151,533, filed on Oct. 4, 2018, now Pat. No. 10,799,565, which is a continuation of application No. 15/616,140, filed on Jun. 7, 2017, now Pat. No. 10,130,688, which is a continuation-in-part of application No. 15/309,177, filed on Nov. 4, 2016, now Pat. No. 10,624,955, which is a continuation-in-part of application No. 14/733,940, filed as application No.
(Continued)

(51) Int. Cl.
| | |
|---|---|
| *A61K 38/20* | (2006.01) |
| *A61K 38/45* | (2006.01) |
| *A61K 39/395* | (2006.01) |
| *C07K 16/24* | (2006.01) |
| *C07K 14/54* | (2006.01) |
| *A61K 38/16* | (2006.01) |
| *A61K 38/26* | (2006.01) |
| *A61K 38/48* | (2006.01) |
| *A61K 38/49* | (2006.01) |
| *A61K 38/50* | (2006.01) |
| *A61K 38/51* | (2006.01) |
| *A61K 38/27* | (2006.01) |
| *A61K 38/17* | (2006.01) |

(52) U.S. Cl.
CPC ............ *A61K 38/45* (2013.01); *A61K 38/164* (2013.01); *A61K 38/166* (2013.01); *A61K 38/1793* (2013.01); *A61K 38/20* (2013.01); *A61K 38/2066* (2013.01); *A61K 38/26* (2013.01); *A61K 38/27* (2013.01); *A61K 38/482* (2013.01); *A61K 38/49* (2013.01); *A61K 38/50* (2013.01); *A61K 38/51* (2013.01); *C07K 14/5428* (2013.01); *C07K 16/241* (2013.01); *C12Y 204/02036* (2013.01); *C12Y 304/21068* (2013.01); *C12Y 304/21073* (2013.01); *C12Y 305/04004* (2013.01); *C12Y 402/02001* (2013.01); *C07K 2317/76* (2013.01); *C07K 2319/00* (2013.01); *C07K 2319/21* (2013.01); *C07K 2319/30* (2013.01); *C07K 2319/32* (2013.01); *C07K 2319/50* (2013.01); *C07K 2319/55* (2013.01); *C07K 2319/60* (2013.01); *C07K 2319/90* (2013.01)

(58) Field of Classification Search
None
See application file for complete search history.

(56) References Cited

U.S. PATENT DOCUMENTS

| | | | |
|---|---|---|---|
| 2,643,653 | A | 6/1953 | Heidrich |
| 4,414,148 | A | 11/1983 | Jansen et al. |

(Continued)

FOREIGN PATENT DOCUMENTS

| | | | |
|---|---|---|---|
| CN | 101522214 | A | 9/2009 |
| CN | 102227447 | A | 10/2011 |

(Continued)

OTHER PUBLICATIONS

Altschul et al. Basic local alignment search tool. J Mol Biol 215(3):403-410 (1990).

(Continued)

*Primary Examiner* — Padmavathi Baskar
(74) *Attorney, Agent, or Firm* — Wilson Sonsini Goodrich & Rosati

(57) ABSTRACT

The present disclosure relates to pharmaceutical compositions comprising a non-naturally occurring fusion molecule and one or more pharmaceutically acceptable carriers, formulated for oral delivery to a subject, and designed to provide for improved, effective therapies for treatment of, e.g., inflammatory diseases, autoimmune diseases, cancer, metabolic disorders, and growth deficiency disorders. The present disclosure relates to a non-toxic mutant form of the *Vibrio cholera* Cholix gene (ntCholix), a variant of Cholix truncated at amino acid $A^{386}$ (Cholix$^{386}$) and the use of other various Cholix-derived polypeptide sequences to enhance intestinal delivery of biologically-active therapeutics. The systems and methods described herein provide for: the ability to deliver macromolecule doses without injections; the ability to deliver cargo such as siRNA or antisense molecules into intracellular compartments where their activity is required; and the delivery of nanoparticles and dendrimer-based carriers across biological membranes.

Figure 1:
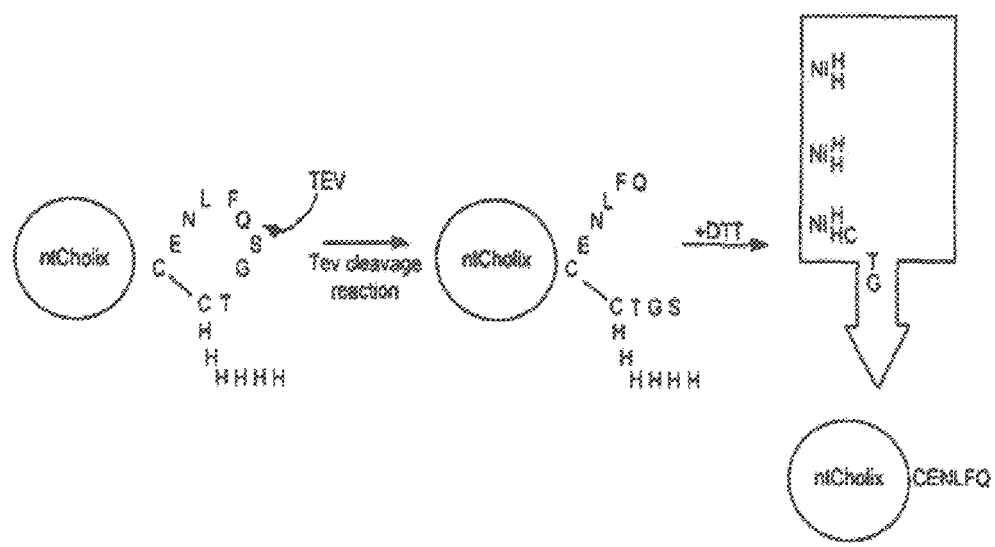

2 Claims, 9 Drawing Sheets
Specification includes a Sequence Listing.

Related U.S. Application Data

PCT/US2015/029795 on May 7, 2015, now abandoned, which is a continuation of application No. 13/822,435, filed as application No. PCT/US2011/001602 on Sep. 15, 2011, now Pat. No. 9,090,691.

(60) Provisional application No. 61/990,054, filed on May 7, 2014, provisional application No. 61/403,394, filed on Sep. 15, 2010.

(56) References Cited

U.S. PATENT DOCUMENTS

| | | |
|---|---|---|
| 4,458,066 A | 7/1984 | Caruthers et al. |
| 4,569,789 A | 2/1986 | Blattler et al. |
| 4,659,839 A | 4/1987 | Nicolotti et al. |
| 4,671,958 A | 6/1987 | Rodwell et al. |
| 4,680,338 A | 7/1987 | Sundoro |
| 4,683,195 A | 7/1987 | Mullis et al. |
| 4,699,784 A | 10/1987 | Shih et al. |
| 5,272,065 A | 12/1993 | Inouye et al. |
| 5,328,984 A | 7/1994 | Pastan et al. |
| 5,512,658 A | 4/1996 | Pastan et al. |
| 5,589,384 A | 12/1996 | Lipscombe et al. |
| 5,602,095 A | 2/1997 | Pastan et al. |
| 5,668,255 A | 9/1997 | Murphy |
| 5,696,237 A | 12/1997 | Fitzgerald et al. |
| 5,807,832 A | 9/1998 | Russell-Jones et al. |
| 5,817,633 A | 10/1998 | Heerze et al. |
| 5,863,745 A | 1/1999 | Fitzgerald et al. |
| 5,917,021 A | 6/1999 | Lee |
| 5,922,680 A | 7/1999 | Fjellestad-Paulsen et al. |
| 5,965,406 A | 10/1999 | Murphy |
| 5,997,856 A | 12/1999 | Hora et al. |
| 6,007,791 A | 12/1999 | Coombes et al. |
| 6,022,950 A | 2/2000 | Murphy |
| 6,051,405 A | 4/2000 | Fitzgerald et al. |
| 6,086,900 A | 7/2000 | Draper |
| 6,086,918 A | 7/2000 | Stern et al. |
| 6,133,229 A | 10/2000 | Gibson et al. |
| 6,174,529 B1 | 1/2001 | Michael et al. |
| 6,251,392 B1 | 6/2001 | Hein et al. |
| 6,255,284 B1 | 7/2001 | McGregor et al. |
| 6,391,296 B1 | 5/2002 | Okano et al. |
| 6,440,419 B1 | 8/2002 | Hein et al. |
| 6,488,926 B1 | 12/2002 | Khan et al. |
| 6,525,102 B1 | 2/2003 | Chen et al. |
| 6,573,237 B2 | 6/2003 | Rinella et al. |
| 6,592,847 B1 | 7/2003 | Weissleder et al. |
| 6,613,332 B1 | 9/2003 | Michael et al. |
| 6,673,574 B2 | 1/2004 | Stern et al. |
| 6,759,207 B2 | 7/2004 | Weber et al. |
| 6,838,553 B1 | 1/2005 | Hwang et al. |
| 7,053,200 B1 | 5/2006 | Zoghbi et al. |
| 7,193,055 B2 | 3/2007 | Daugherty et al. |
| 7,314,625 B2 | 1/2008 | Fitzgerald |
| 7,314,632 B1 | 1/2008 | Fitzgerald |
| 7,335,361 B2 | 2/2008 | Liao et al. |
| 7,378,100 B2 | 5/2008 | Chang et al. |
| 7,465,455 B2 | 12/2008 | Chang et al. |
| 7,544,361 B2 | 6/2009 | Arakawa et al. |
| 7,595,054 B2 | 9/2009 | Liao et al. |
| 7,611,714 B2 | 11/2009 | Mrsny |
| 7,618,635 B2 | 11/2009 | Chang et al. |
| 7,666,991 B2 | 2/2010 | Mrsny |
| 7,713,737 B2 | 5/2010 | Mrsny |
| 7,727,538 B2 | 6/2010 | Quinn et al. |
| 7,824,695 B1 | 11/2010 | Fitzgerald et al. |
| 7,964,200 B2 | 6/2011 | Mrsny et al. |
| 8,092,806 B2 | 1/2012 | Wallach et al. |
| 8,092,809 B2 | 1/2012 | Fitzgerald |
| 8,206,950 B2 | 6/2012 | Liao et al. |
| 8,309,102 B2 | 11/2012 | Mrsny et al. |
| 8,372,407 B2 | 2/2013 | Liao et al. |
| 8,637,646 B2 | 1/2014 | Wells et al. |
| 8,790,897 B2 | 7/2014 | Quinn et al. |
| 8,993,295 B2 | 3/2015 | Seed et al. |
| 9,090,691 B2 | 7/2015 | Mrsny et al. |
| 9,481,714 B2 | 11/2016 | Wu et al. |
| 9,657,063 B2 | 5/2017 | Kuo et al. |
| 10,010,602 B2 | 7/2018 | Chien et al. |
| 10,130,688 B2 | 11/2018 | Mrsny et al. |
| 10,143,726 B2 | 12/2018 | Oft |
| 10,400,013 B2 | 9/2019 | Liao et al. |
| 10,617,741 B2 | 4/2020 | Mrsny et al. |
| 10,617,767 B2 | 4/2020 | Mrsny et al. |
| 10,624,955 B2 | 4/2020 | Mrsny et al. |
| 10,624,956 B2 | 4/2020 | Mrsny et al. |
| 10,624,957 B2 | 4/2020 | Mrsny et al. |
| 10,786,555 B2 | 9/2020 | Mrsny et al. |
| 10,786,556 B2 | 9/2020 | Mrsny et al. |
| 10,799,565 B2 * | 10/2020 | Mrsny ............... A61P 31/04 |
| 11,027,020 B2 | 6/2021 | Mrsny et al. |
| 2003/0186386 A1 | 10/2003 | Hansen et al. |
| 2007/0148131 A1 | 6/2007 | Mrsny |
| 2008/0317761 A1 | 12/2008 | Cines et al. |
| 2009/0081235 A1 | 3/2009 | Fitzgerald et al. |
| 2009/0092660 A1 | 4/2009 | Mrsny |
| 2009/0142341 A1 | 6/2009 | Pastan et al. |
| 2009/0148401 A1 | 6/2009 | Mrsny |
| 2009/0155297 A1 | 6/2009 | Mrsny |
| 2009/0305978 A1 | 12/2009 | Zane |
| 2010/0151005 A1 | 6/2010 | Muro-Galindo et al. |
| 2010/0196277 A1 | 8/2010 | Desimone et al. |
| 2011/0130331 A1 | 6/2011 | Guyon et al. |
| 2011/0250199 A1 | 10/2011 | Fitzgerald et al. |
| 2012/0258104 A1 | 10/2012 | Echeverri et al. |
| 2012/0276190 A1 | 11/2012 | Fitzgerald |
| 2014/0065172 A1 | 3/2014 | Echeverri et al. |
| 2015/0265718 A1 | 9/2015 | Mrsny et al. |
| 2015/0265719 A1 | 9/2015 | Mrsny et al. |
| 2016/0068583 A1 | 3/2016 | Van et al. |
| 2016/0222362 A1 | 8/2016 | Zhang et al. |
| 2016/0263020 A1 | 9/2016 | Yan et al. |
| 2016/0287670 A1 | 10/2016 | Van et al. |
| 2017/0015747 A1 | 1/2017 | Thompson et al. |
| 2018/0028614 A1 | 2/2018 | Huang et al. |
| 2018/0353610 A1 | 12/2018 | Mrsny et al. |
| 2019/0015441 A1 | 1/2019 | Shachar et al. |
| 2019/0255107 A1 | 8/2019 | Kuchroo et al. |
| 2019/0290688 A1 | 9/2019 | Bar-Sagi et al. |
| 2020/0140511 A1 | 5/2020 | Porat et al. |
| 2021/0154304 A1 | 5/2021 | Maclean et al. |

FOREIGN PATENT DOCUMENTS

| | | |
|---|---|---|
| CN | 103249401 A | 8/2013 |
| EP | 0188256 A2 | 7/1986 |
| EP | 0532090 A2 | 3/1993 |
| EP | 1522585 A1 | 4/2005 |
| EP | 1000163 B1 | 10/2005 |
| EP | 1000162 B1 | 9/2006 |
| EP | 1749833 A1 | 2/2007 |
| EP | 1450855 B1 | 8/2009 |
| EP | 1379273 B1 | 9/2009 |
| EP | 1757615 B1 | 8/2011 |
| EP | 1882478 B1 | 3/2012 |
| EP | 3402810 A1 | 11/2018 |
| EP | 3474884 A2 | 5/2019 |
| EP | 3554346 A1 | 10/2019 |
| EP | 3554541 A1 | 10/2019 |
| JP | 2008515808 A | 5/2008 |
| KR | 20140014068 A | 2/2014 |
| WO | WO-2006044205 A2 | 4/2006 |
| WO | WO-2008021234 A2 | 2/2008 |
| WO | WO-2009014650 A2 | 1/2009 |
| WO | WO-2009026328 A2 | 2/2009 |
| WO | WO-2009115531 A2 | 9/2009 |
| WO | WO-2009149281 A1 | 12/2009 |
| WO | WO-2010040105 A2 | 4/2010 |
| WO | WO-2010046783 A2 | 4/2010 |
| WO | WO-2012036746 A1 | 3/2012 |
| WO | WO-2012101235 A1 | 8/2012 |
| WO | WO-2012110596 A1 | 8/2012 |
| WO | WO-2013003824 A1 | 1/2013 |

(56) References Cited

FOREIGN PATENT DOCUMENTS

| WO | WO-2013130913 A1 | 9/2013 |
|---|---|---|
| WO | WO-2015113005 A1 | 7/2015 |
| WO | WO-2015171965 A2 | 11/2015 |
| WO | WO-2015171965 A3 | 3/2016 |
| WO | WO-2016146833 A1 | 9/2016 |
| WO | WO-2018183931 A1 | 10/2018 |
| WO | WO-2019133647 A1 | 7/2019 |
| WO | WO-2019173787 A1 | 9/2019 |
| WO | WO-2020096695 A1 | 5/2020 |

OTHER PUBLICATIONS

Aman et al. A mutant cholera toxin B subunit that binds GM1-ganglioside but lacks immunomodulatory or toxic activity. PNAS 98(15):8536-8541 (Jul. 17, 2001).
Apostolaki et al. Nasal Delivery of Antigen with the B Subunit of *Escherichia coli* Heat-Labile Enterotoxin Augments Antigen-Specific T-Cell Clonal Expansion and Differentiation. Infection and Immunity 72(7):4072-4080 (Jul. 2004). DOI: 10.1128/IAI.72.7.4072-4080.2004.
Arango Duque et al. Macrophage cytokines: involvement in immunity and infectious diseases. Frontiers in Immunology, vol. 5, Article 491, 12 pages (Oct. 7, 2014).
Asadullah et al. Interleukin-10 Therapy—Review of a New Approach. Pharmacological Reviews 55(2):241-269 (2003). DOI: https://doi.org/10.1124/pr.55.2.4.
AU2011302645 Office Action dated Oct. 30, 2014.
AU2015255834 Office Action dated Jan. 15, 2020.
Awasthi et al. Development of a PCR-restriction fragment length polymorphism assay for detection and subtyping of cholix toxin variant genes of Vibrio cholerae. Journal of Medical Microbiology 63(5):667-673 (May 1, 2014). DOI: 10.1099/jmm.0.070797-0.
Awasthi et al. Novel Cholix Toxin Variants, ADP-Ribosylating Toxins in Vibriocholerae Non-O1/Non-O139 Strains, and Their Pathogenicity. Infection and Immunity 81(2):531-541 (Feb. 2013). Published ahead of print Dec. 10, 2012.
Backert et al. STAT3 Activation in Th17 and Th22 Cells Controls IL-22-Mediated Epithelial Host Defense during Infectious Colitis. J Immunol 193(7):3779-3791 (Oct. 1, 2014). Prepublished online Sep. 3, 2014. doi: 10.4049/jimmunol.1303076.
Baseman, et al. Diphtheria Pathogenesis in Guinea Pig Tracheal Organ Culture. Infection And Immunity 10.5 (1974): 1146-1151.
Basset et al. Cholera-Like Enterotoxins and Regulatory T cells. Toxins 2:1774-1795 (Jul. 6, 2010). doi: 10.3390/toxins2071774.
Beddoe, et al. Structure, biological functions and applications of the AB5 toxins. Trends in Biochemical Sciences. 35.7 (2010): 411-418.
Bishop-Lilly et al. Genome Sequencing of 15 Clinical Vibrio Isolates, Including 13 Non-O1/Non-O139 Serogroup Strains. Genome Announc2(5):e00893-14 (Sep. 11, 2014). doi:10.1128/genomeA.00893-14.
Boirivant et al. Oral Administration of Recombinant Cholera Toxin Subunit B Inhibits IL-12-Mediated Murine Experimental (Trinitrobenzene Sulfonic Acid) Colitis. J Immunol 166:3522-3532 (2001). doi: 10.4049/jimmunol.166.5.3522.
Bone et al. Modulation of B lymphocyte signalling by the B subunit of *Escherichia coli* heat-labile enterotoxin. International Immunology 14(6):647-658 (2002).
Bork, Article Metrics and Usage Statistics Center. Genome Research 10 (2000): 398-400.
Bowie et al. Deciphering the message in protein sequences: tolerance to amino acid substitutions. Science 247:1306-1310 (1990).
Bublin et al. Use of a genetic cholera toxin B subunit/allergen fusion molecule as mucosal delivery system with immunosuppressive activity against Th2 immune responses. Vaccine 25(50):8395-8404 (Dec. 5, 2007). DOI: https://doi.org/10.1016/j.vaccine.2007.10.003. Available online Oct. 22, 2007.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Chernoff et al. A randomized, controlled trial of IL-10 in humans. Inhibition of inflammatory cytokine production and immune responses. J Immunol 154:5492-5499 (1995).
CN201580036678.8 Office Action dated Jan. 22, 2020 (w/ English translation).
CN201580036678.8 Office Action dated Jan. 3, 2019 (w/ English translation).
Colombel et al. Interleukin 10 (Tenovil) in the prevention of postoperative recurrence of Crohn's disease. Gut 49:42-46 (2001).
Co-pending U.S. Appl. No. 16/779,350, inventors Liu; Keyi et al., filed Jan. 31, 2020.
Co-pending U.S. Appl. No. 16/884,456, inventors Mrsny; Randall J. et al., filed May 27, 2020.
Dalmas et al. A role for interleukin-22 in the alleviation of metabolic syndrome. Nature Medicine 20(12):1379-1381 (Dec. 2014). Published online Nov. 2, 2014. doi: 10.1038/nm.3748.
Deng, et al. Molecular mechanisms of the cytotoxicity of ADP-ribosylating toxins. Annual Review of Microbiology 62 (2008): 271-288.
Donaldson et al. Mucosal administration of the B subunit of *E. coli* heat-labile enterotoxin promotes the development of Foxp3-expressing regulatory T cells. Mucosal Immunology 4(2):227-238 (Mar. 2011). Published online Oct. 13, 2010. doi: 10.1038/mi.2010.65.
Donaldson et al. The *Escherichia coli* heat-labile enterotoxin B subunit protects from allergic airway disease development by inducing CD4+ regulatory T cells. Mucosal Immunology 6(3):535-546 (May 2013). Published online Oct. 3, 2012. doi: 10.1038/mi.2012.93.
Dudakov et al. Interleukin-22: immunobiology and pathology. Annu Rev Immunol 33:747-785 (Mar. 21, 2015). doi:10.1146/annurev-immunol-032414-112123.
Dumoutier et al. Cloning and Characterization of IL-10-Related T Cell-Derived Inducible Factor (IL-TIF), a Novel Cytokine Structurally Related to IL-10 and Inducible by IL-9. J Immunol 164:1814-1819 (2000). doi: 10.4049/jimmunol.164.4.1814.
Dumoutier et al. IL-TIF/IL-22: genomic organization and mapping of the human and mouse genes. Genes and Immunity 1:488-494 (2000).
EP11825567.8 Office Action dated Feb. 23, 2017.
EP15788688.8 Office Action dated Apr. 22, 2020.
EP15788688.8 Office Action dated Jun. 17, 2019.
EP15788688.8 Partial Supplementary European Search Report dated Nov. 27, 2017.
EP15788688.8 Extended European Search Report dated Mar. 8, 2018.
European search report and search opinion dated Nov. 24, 2014 for EP Patent Application No. 11825567.8.
Fedorak et al. Recombinant Human Interleukin 10 in the Treatment of Patients With Mild to Moderately Active Crohn's Disease. Gastroenterology 119:1473-1482 (2000).
Fiorentino et al. IL-10 acts on the antigen-presenting cell to inhibit cytokine production by Th1 cells. J Immunol 146(10):3444-3451 (May 15, 1991).
Fitzgerald, et al. Pseudomonas exotoxin-mediated selection yields cells with altered expression of low-density lipoprotein receptor-related protein. Journ of Cell Biology, 129.6 (1995): 1533-1541.
Frankel et al. Characterization of diphtheria fusion proteins targeted to the human interleukin-3 receptor. Protein Engineering 13(8):575-581 (2000).
Fraser et al. Mutant *Escherichia coli* Heat-Labile Toxin B Subunit That Separates Toxoid-Mediated Signaling and Immunomodulatory Action from Trafficking and Delivery Functions. Infection and Immunity 71 (3):1527-1537 (Mar. 2003). DOI: 10.1128/IAI.71.3.000-000.2003.
Gallagher et al. Cloning, expression and initial characterisation of interleukin-19 (IL-19), a novel homologue of human interleukin-10 (IL-10). Genes & Immunity 1:442-450 (2000).
Garlanda et al. The Interleukin-1 Family: Back to the Future. Immunity 39:1003-1018 (Dec. 12, 2013).

(56) References Cited

OTHER PUBLICATIONS

Gasche et al. IL-10 Secretion and Sensitivity in Normal Human Intestine and Inflammatory Bowel Disease. Journal of Clinical Immunology 20(5):362-370 (2000).
GenBank Accession No. AAW80252. Version No. AAW80252.1 hypothetical exotoxin A [Vibrio cholerae]. Record created Feb. 9, 2005. 2 pages. Retrieved Nov. 11, 2019 at URL: https://www.ncbi.nlm.nih.gov/protein/58615288?report=ipg.
GenBank Accession No. AKB06426. Version No. AKB06426.1. exotoxin A catalytic family protein [Vibrio cholerae]. Record created Apr. 6, 2015. 2 pages. Retrieved Aug. 30, 2019 at URL: https://www.ncbi.nlm.nih.gov/protein/AKB06426.
GenBank Accession No. ALH24940. Version No. ALH24940.1. cholix toxin [Vibrio cholerae], Record created Oct. 11, 2015. 2 pages. Retrieved Sep. 6, 2019 at URL: https://www.ncbi.nlm.nih.gov/protein/ALH24940.1.
GenBank Accession No. ALI16365. Version No. ALI16365.1. truncated cholix toxin [Vibrio cholerae]. Record created Oct. 12, 2015. 2 pages. Retrieved Sep. 9, 2019 at URL: https://www.ncbi.nlm.nih.gov/protein/ALI16365.1.
GenBank Accession No. ALI16366. Version No. ALI16366.1. truncated cholix toxin [Vibrio cholerae]. Record created Oct. 12, 2015. 2 pages. Retrieved Sep. 9, 2019 at URL: https://www.ncbi.nlm.nih.gov/protein/ALI16366.1.
GenBank Accession No. ALI87044. Version No. ALI87044.1. cholix toxin [Vibrio cholerae], Record created Oct. 14, 2015. 2 pages. Retrieved Aug. 30, 2019 at URL: https://www.ncbi.nlm.nih.gov/protein/ALI87044.1.
GenBank Accession No. ALJ02941. Version No. ALJ02941.1. cholix toxin [Vibrio cholerae], Record created Oct. 18, 2015. 2 pages. Retrieved Sep. 6, 2019 at URL: https://www.ncbi.nlm.nih.gov/protein/ALJ02941.1.
GenBank Accession No. BAM72568. Version No. BAM72568.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72568.1.
GenBank Accession No. BAM72569. Version No. BAM72569.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72569.1.
GenBank Accession No. BAM72570. Version No. BAM72570.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72570.1.
GenBank Accession No. BAM72571. Version No. BAM72571.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72571.1.
GenBank Accession No. BAM72573. Version No. BAM72573.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72573.1.
GenBank Accession No. BAM72574. Version No. BAM72574.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72574.1.
GenBank Accession No. BAM72575. Version No. BAM72575.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72575.1.
GenBank Accession No. BAM72576. Version No. BAM72576.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72576.1.
GenBank Accession No. BAM72582. Version No. BAM72582.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72582.1.
GenBank Accession No. BAM72585. Version No. BAM72585.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72585.1.
GenBank Accession No. BAM72587. Version No. BAM72587.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72587.1.
GenBank Accession No. BAM72590. Version No. BAM72590.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72590.1.
GenBank Accession No. BAM72593. Version No. BAM72593.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72593.1.
GenBank Accession No. BAM72594. Version No. BAM72594.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72594.1.
GenBank Accession No. BAM72595. Version No. BAM72595.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72595.1.
GenBank Accession No. BAM72596. Version No. BAM72596.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72596.1.
GenBank Accession No. BAM72610. Version No. BAM72610.1. cholix toxin, partial [Vibrio cholerae]. Record created Dec. 14, 2012. 2 pages. Retrieved Sep. 9, 2019 at URL: https://www.ncbi.nlm.nih.gov/protein/BAM72610.1.
GenBank Accession No. BAM72611. Version No. BAM72611.1. cholix toxin, partial [Vibrio cholerae]. Record created Dec. 14, 2012. 2 pages. Retrieved Sep. 6, 2019 at URL: https://www.ncbi.nlm.nih.gov/protein/BAM72611.1.
GenBank Accession No. EFH75651. Version No. EFH75651.1. conserved hypothetical protein [Vibrio cholerae RC385], Record created Jun. 4, 2010. 2 pages. Retrieved Sep. 6, 2019 at URL: https://www.ncbi.nlm.nih.gov/protein/EFH75651.1.
GenBank Accession No. KFD89501. Version No. KFD89501.1. exotoxin A binding family protein [Vibrio cholerae]. Record created Jul. 31, 2014. pages. Retrieved Sep. 6, 2019 at URL: https://www.ncbi.nlm.nih.gov/protein/KFD89501.1.
GenBank Accession No. KFD96741. Version No. KFD96741.1. exotoxin A binding family protein [Vibrio cholerae]. Record created Jul. 31, 2014. 2 pages. Retrieved Sep. 9, 2019 at URL: https://www.ncbi.nlm.nih.goV/protein/KFD96741.1.
GenBank Accession No. KFE28160. Version No. KFE28160.1. exotoxin A binding family protein [Vibrio cholerae]. Record created Jul. 31, 2014. 2 pages. Retrieved Sep. 6, 2019 at URL: https://www.ncbi.nlm.nih.gov/protein/KFE28160.1.
GenBank Accession No. KNH55243. Version No. KNH55243.1. hypothetical protein A59_2898 [Vibrio cholerae 623-39], Record created Aug. 5, 2015. 2 pages. Retrieved Sep. 6, 2019 at URL: https://www.ncbi.nlm.nih.gov/protein/KNH55243.1.
GenBank Accession No. P01241. Somatotropin. Record created Jul. 21, 1986. 12 pages. Retrieved Aug. 29, 2019 at URL: https://www.ncbi.nlm.nih.gov/protein/P01241.
GenBank Accession No. Q5EK40. Version No. Q5EK40.1. Cholix toxin. Record created Feb. 9, 2005. 9 pages. Retrieved Aug. 30, 2019 at URL: https://www.ncbi.nlm.nih.gov/protein/Q5EK40.1.
GenBank Accession No. WP_000941100. Version No. WP_000941100.1. Multispecies: cholix toxin [Vibrio], Record created Feb. 5, 2013. 1 page. Retrieved Sep. 9, 2019 at URL: https://www.ncbi.nlm.nih.gov/protein/WP_000941100.1.
GenBank Accession No. WP_002044040. Version No. WP_002044040.1. cholix toxin [Vibrio cholerae]. Record created May 4, 2013. 1 page. Retrieved Sep. 9, 2019 at URL: https://www.ncbi.nlm.nih.gov/protein/WP_002044040.1.
GenBank Accession No. WP_032467916. Version No. WP_032467916.1. cholixtoxin [Vibrio cholerae]. Record created Oct. 4, 2014. 1 page. Retrieved Sep. 9, 2019 at URL: https://www.ncbi.nlm.nih.gov/protein/WP_032467916.1.

(56) References Cited

OTHER PUBLICATIONS

GenBank Accession No. WP_032482668. Version No. WP_032482668.1. cholixtoxin [Vibrio cholerae]. Record created Oct. 4, 2014. 1 page. Retrieved Sep. 9, 2019 at URL: https://www.ncbi.nlm.nih.gov/protein/WP_032482668.1.

GenBank Accession No. WP_033932701. Version No. WP_033932701.1. cholixtoxin [Vibrio cholerae]. Record created Dec. 5, 2014. 1 page. Retrieved Sep. 9, 2019 at URL: https://www.ncbi.nlm.nih.gov/protein/WP_033932701.1.

GenBank Accession No. WP_042988437. Version No. WP_042988437.1. cholixtoxin [Vibrio cholerae]. Record created Feb. 17, 2015. 1 page. Retrieved Sep. 9, 2019 at URL: https://www.ncbi.nlm.nih.gov/protein/WP_042988437.1.

GenBank Accession No. WP_057552180. Version No. WP_057552180.1. cholixtoxin [Vibrio cholerae]. Record created Nov. 10, 2015. 1 page. Retrieved Sep. 9, 2019 at URL: https://www.ncbi.nlm.nih.gov/protein/WP_057552180.1.

GenBank Accession No. WP_057557199. Version No. WP_057557199.1. cholixtoxin [Vibrio cholerae]. Record created Nov. 10, 2015. 1 page. Retrieved Sep. 9, 2019 at URL: https://www.ncbi.nlm.nih.gov/protein/WP_057557199.1.

GenBank Accession No. WP_069648100. Version No. WP_069648100.1. cholix toxin [Vibrio cholerae]. Record created Sep. 20, 2016. 1 page. Retrieved Sep. 9, 2019 at URL: https://www.ncbi.nlm.nih.gov/protein/WP_069648100.1.

GenBank Accession No. WP_071178365. Version No. WP_071178365.1. cholix toxin [Vibrio cholerae]. Record created Nov. 2, 2016. 1 page. Retrieved Sep. 9, 2019 at URL: https://www.ncbi.nlm.nih.gov/protein/WP_071178365.1.

GenBank Accession No. WP_071186455. Version No. WP_071186455.1. cholix toxin [Vibrio cholerae]. Record created Nov. 2, 2016. 1 page. Retrieved Sep. 9, 2019 at URL: https://www.ncbi.nlm.nih.gov/protein/WP_071186455.1.

GenBank Accession No. WP_076008260. Version No. WP_076008260.1. cholix toxin [Vibrio cholerae]. Record created Jan. 19, 2017. 1 page. Retrieved Sep. 9, 2019 at URL: https://www.ncbi.nlm.nih.gov/protein/WP_076008260.1.

GenBank Accession No. WP_076025263. Version No. WP_076025263.1. cholix toxin [Vibrio cholerae]. Record created Jan. 19, 2017. 1 page. Retrieved Sep. 9, 2019 at URL: https://www.ncbi.nlm.nih.gov/protein/WP_076025263.1.

GenBank Accession No. WP_084980904. Version No. WP_084980904.1. cholix toxin [Vibrio cholerae]. Record created Apr. 21, 2017. 1 page. Retrieved Sep. 9, 2019 at URL: https://www.ncbi.nlm.nih.gov/protein/WP_084980904.1.

Gupta, et al. Permeation of insulin, calcitonin and exenatide across Caco-2 monolayers: measurement using a rapid, 3-day system. PloS one 8.2 (2013): e57136.

Hajishengallis et al. Type II Heat-labile Enterotoxins: Structure, Function, and Immunomodulatory Properties. Vet Immunol Immunopathol 152(1-2):68-77 (Mar. 15, 2013). doi:10.1016/j.vetimm.2012.09.034.

Hakomori et al. Ganglioside receptors: a brief overview and introductory remarks. Adv Exp Med Biol174:333-9 (1984).

Hasnain et al. Glycemic control in diabetes is restored by therapeutic manipulation of cytokines that regulate beta cell stress. Nature Medicine 20(12):1417-1426 (Dec. 2014). Published online Nov. 2, 2014. doi: 10.1038/nm.3705.

Herfarth et al. IL-10 therapy in Crohn's disease: at the crossroads. Gut 50:146-147 (2002).

Huhn et al. Pharmacodynamics of subcutaneous recombinant human interleukin-10 in healthy volunteers. Clin Pharmacol Ther 62:171-180 (1997).

IL248768 Office Action dated Jan. 14, 2020 (w/ English translation).

Image Integrity, Nature.com, 5 pages (Apr. 28, 2017), also available at http://www.nature.com/authors/policies/image.html.

Jeong, et al. siRNA Conjugate Delivery Systems. Bioconjugate Chemistry, 20.1 2009 (published online Nov. 2008): 5-14.

Johnson et al. Complete Genome Assemblies for Two Single-Chromosome Vibrio cholerae Isolates, Strains 1154-74 (Serogroup O49) and 10432-62 (Serogroup O27). Genome Announc 3(3):e00462-15 (May 14, 2015). 2 pages. doi:10.1128/genomeA.00462-15.

Josephson et al. Crystal Structure of the IL-10/IL-10R1 Complex Reveals a Shared Receptor Binding Site. Immunity 15(1):35-46 (Jul. 2001). DOI: https://doi.org/10.1016/S1074-7613(01)00169-8.

JP2013-529128 Office Action dated Sep. 1, 2015 (w/ English translation).

JP2017-511547 Office Action dated Nov. 27, 2019 (w/ English machine translation).

JP2017-511547 Office Action dated Feb. 27, 2019 (w/ English translation).

Jørgensen, et al. Cholix toxin, a novel ADP-ribosylating factor from Vibrio cholerae. Journal of Biological Chemistry 283.16 (Apr. 18, 2008): 10671-10678.

Jung et al. Biodegradable nanoparticles for oral delivery of peptides: is there a role for polymers to affect mucosal uptake? Eur J Pharm Biopharm. Jul. 2000;50(1):147-60.

Killeen, et al. Conformational integrity of a recombinant toxoid of Pseudomonas aeruginosa exotoxin A containing a deletion of glutamic acid-553. Biochimica et Biophysica Acta (BBA)—Molecular Basis of Disease 1138.2 (1992): 162-166.

Knappe et al. Induction of a Novel Cellular Homolog of Interleukin-10, AK155, by Transformation of T Lymphocytes with Herpesvirus Saimiri. J Virol 74(8): 3881-3887 (Apr. 2000).

Kondo et al. Activity of immunotoxins constructed with modified Pseudomonas exotoxin A lacking the cell recognition domain. J Biol Chem 263(19):9470-9475 (Jul. 5, 1988).

Kounnas, et al. The alpha 2-macroglobulin receptor/low density lipoprotein receptor-related protein binds and internalizes Pseudomonas exotoxin A. Journal of Biological Chemistry 267.18 (1992): 12420-12423.

Kumar et al. Genome Sequence of Non-O1 Vibrio cholerae PS15. Genome Announcements 1(1):e00227-12 (Jan./Feb. 2013). 2 pages.

Lans et al. Role of tumor necrosis factor on toxicity and cytokine production after isolated hepatic perfusion. Clin Cancer Res 7(4):784-790 (Apr. 2001).

Larkin et al. Calnuc Function in Endosomal Sorting of Lysosomal Receptors. Traffic 17:416-432 (2016). Uncorrected manuscript published online Jan. 12, 2016. Published online Feb. 12, 2016. DOI: 10.1111/tra.12374.

Lazar, et al., Transforming growth factor alpha: mutation of aspartic acid 47 and leucine 48 results in different biological activities, Mar. 1988, Molecular and Cellular Biology, 8(3):1247-1252.

Lejeune et al. Interleukin-22 (IL-22) Activates the JAK/STAT, ERK, JNK, and p38 MAP Kinase Pathways in a Rat Hepatoma Cell Line. Pathways that are Shared with and Distinct from IL-10. J Biol Chem 277(37):33676-33682 (Sep. 13, 2002). Published, JBC Papers in Press, Jun. 26, 2002, DOI 10.1074/jbc.M204204200.

Li et al. Role of interleukin-22 in inflammatory bowel disease. World J Gastroenterol 20(48):18177-18188 (Dec. 28, 2014). DOI: 10.3748/wjg.v20.i48.18177.

Lin et al. Different Types of Cell Death Induced by Enterotoxins. Toxins 2:2158-2176 (Aug. 11, 2010). doi:10.3390/toxins2082158.

Luross et al. *Escherichia coli* Heat-Labile Enterotoxin B Subunit Prevents Autoimmune Arthritis Through Induction of Regulatory CD4+ T Cells. Arthritis & Rheumatism 46(6):1671-1682 (Jun. 6, 2002). DOI 10.1002/art.10328.

Mahato et al. Emerging trends in oral delivery of peptide and protein drugs. Crit Rev Ther Drug Carrier Syst. 2003;20(2-3):153-214.

Mattoo et al. Interactions of bacterial effector proteins with host proteins. Curr Opin Immunol. Aug. 2007;19(4):392-401.

Mekalanos et al. Cholera toxin genes: nucleotide sequence, deletion analysis and vaccine development. Nature 306:551-557 (1983).

Merritt et al. Crystal structure of cholera toxin B-pentamer bound to receptor GM1 pentasaccharide. Protein Science 3:166-175 (1994).

Mühl et al. IL-22 in tissue-protective therapy. British Journal of Pharmacology 169:761-771 (2013).

Milling et al. Regulation of intestinal immunity: Effects of the oral adjuvant *Escherichia coli* heat-labile enterotoxin on heat-labile enterotoxin on migrating dendritic cells. Eur. J. Immunol. 37:87-99 (2007). DOI 10.1002/eji.200636199.

(56) References Cited

OTHER PUBLICATIONS

Mitamura, et al., "Diphtheria Toxin Binds to the Epidermal Growth Factor (EGF)-like Domain of Human Heparin-binding EGF-like Growth Factor/Diphtheria Toxin Receptor and Inhibits Specifically Its Mitogenic Activity," J Biol Chem 270(3):1015-1019 (1995).

Mitoma et al. Mechanisms for cytotoxic effects of anti-tumor necrosis factor agents on transmembrane tumor necrosis factor α-expressing cells: Comparison among infliximab, etanercept, and adalimumab. Arthritis Rheum 58(5):1248-1257 (May 2008). doi: 10.1002/art.23447.

Mizoguchi. Healing of intestinal inflammation by IL-22. Inflamm Bowel Dis 18(9):1777-1784 (Sep. 2012). doi: 10.1002/ibd.22929.

Montfrans et al. Prevention of colitis by interleukin-10—transduced T lymphocytesin the SCID mice transfer model. Gastroenterology 123:1865-1876 (2002).

Moore et al. Interleukin-10 and the interleukin-10 receptor. Annu Rev Immunol 19:683-765 (2001). DOI: 10.1146/annurev.immunol. 19.1.683.

Mowat et al. Regional specialization within the intestinal immune system. Nature Reviews Immunology 14:667-685 (Oct. 2014).

Mrsny, et al. Bacterial toxins as tools for mucosal vaccination. Drug Discovery Today. 2002; 4:247-258.

Mrsny et al. Mucosal administration of a chimera composed of Pseudomonas exotoxin and the gp120 V3 loop sequence of HIV-1 induces both salivary and serum antibody responses. Vaccine 17(11-12):1425-1433 (Mar. 17, 1999).

Mrsny, Lessons from nature: "Pathogen-Mimetic" systems for Mucosal Nano-medicines, Advanced Drug Delivery Reviews, vol. 61 :172-192 (online Dec. 24, 2008).

Mudrak et al. Heat-Labile Enterotoxin: Beyond GM1 Binding. Toxins 2:1445-1470 (Jun. 14, 2010). doi:10.3390/toxins2061445.

Nagalakshmi et al. Interleukin-22 activates STAT3 and induces IL-10 by colon epithelial cells. International Immunopharmacology 4:679-691 (2004).

Nashar et al. Cross-linking of cell surface ganglioside GM1 induces the selective apoptosis of mature CD8+ T lymphocytes. International Immunology 8(5):731-736 (1996).

Nashar et al. Modulation of B-cell activation by the B subunit of *Escherichia coli* enterotoxin: receptor interaction up-regulates MHC class II, B7, CD40, CD25 and ICAM-1. Immunology 91:572-578 (1997).

Nashar et al. Potent immunogenicity of the B subunits of *Escherichia coli* heat-labile enterotoxin: Receptor binding is essential and induces differential modulation of lymphocyte subsets. Proc Natl Acad Sci USA 93:226-230 (Jan. 1996).

Neurath. Cytokines in inflammatory bowel disease. Nature Reviews Immunology 14:329-342 (May 2014).

Notice of Allowance dated May 11, 2015 for U.S. Appl. No. 13/822,435.

O'Farrell et al. IL-10 inhibits macrophage activation and proliferation by distinct signaling mechanisms: evidence for Stat3-dependent and -independent pathways. The EMBO Journal 17(4):1006-1018(1998).

Office action dated Apr. 8, 2016 for U.S. Appl. No. 14/733,940.
Office action dated May 4, 2017 for U.S. Appl. No. 14/733,946.
Office action dated Jun. 12, 2014 for U.S. Appl. No. 13/822,435.
Office action dated Jun. 13, 2017 for U.S. Appl. No. 14/733,940.
Office action dated Jul. 8, 2015 for U.S. Appl. No. 14/733,940.
Office action dated Sep. 9, 2016 for U.S. Appl. No. 14/733,946.
Office action dated Oct. 19, 2017 for U.S. Appl. No. 15/309,177.
Office action dated Dec. 2, 2013 for U.S. Appl. No. 13/822,435.
Office action dated Dec. 30, 2015 for U.S. Appl. No. 14/733,946.

Ola et al. Protection of non-obese diabetic mice from autoimmune diabetes by *Escherichia coli* heat-labile enterotoxin B subunit. Immunology 117:262-270 (2005). doi:10.1111/j.1365-2567.2005. 02294.x.

Pai et al. Anti-tumor activities of immunotoxins made of monoclonal antibody B3 and various forms of Pseudomonas exotoxin. Proc Natl Acad Sci U S A 88:3358-3362 (Apr. 1991).

Pakula et al. Genetic Analysis of Protein Stability and Function. Annu. Rev. Genet. 23:289-310 (1989).

PCT International Search Report and Written Opinion dated Feb. 6, 2012 for PCT/US2011/001602.

PCT International Search Report and Written Opinion dated Nov. 13, 2015 for PCT/US2015/29795.

Peng et al. [High level expression, purification and cytotoxicity of IL-10(18-57)-PE40], Sheng Wu Gong Cheng Xue Bao 22(1):87-93 (Jan. 2006).

Petsko, et al. Protein structure and function. New Science Press Ltd., (2004): 129-165.

Pitman et al. Receptor mediated apoptosis of CD8+T cells by the B subunits of cholera-like enterotoxins. Biochemical Society Transactions 26:S338 (1998). One page.

Plant et al. Modulation of the Immune Response by the Cholera-like Enterotoxins. Current Topics in Medicinal Chemistry 4:509-519 (2004).

Plant et al. The B subunit of *Escherichia coli* heat labile enterotoxin abrogates oral tolerance, promoting predominantly Th2-type immune responses. Eur J Immunol 33:3186-3195 (2003).

Purdy et al. A Glimpse into the Expanded Genome Content of Vibrio cholerae through Identification of Genes Present in Environmental Strains. Journal of Bacteriology 187(9):2992-3001 (May 2005). DOI: 10.1128/JB.187.9.2992-3001.2005.

Purdy et al. Diversity and distribution of cholix toxin, a novel ADP-ribosylating factor from Vibrio cholerae. Environmental Microbiology Reports 2(1):1 98-207 (Feb. 2010). First published Feb. 8, 2010. DOI: https://doi.org/10.1111/j.1758-2229.2010.00139.x.

Raveney et al. The B Subunit of *Escherichia coli* Heat-Labile Enterotoxin Inhibits Th1 but Not Th17 Cell Responses in Established Experimental Autoimmune Uveoretinitis. Investigative Ophthalmology & Visual Science 49(9):4008-4017 (Sep. 2008).

Richards et al. Protective Mucosal Immunity to Ocular Herpes Simplex Virus Type 1 Infection in Mice by Using *Escherichia coli* Heat-Labile Enterotoxin B Subunit as an Adjuvant. Journal of Virology 75(4):1664-1671 (Feb. 2001). DOI: 10.1128/JVI.75.4. 1664-1671.2001.

Rodighiero, et al. Structural Basis for the Differential Toxicity of Cholera Toxin and *Escherichia coli* Heat-labile Enterotoxin. The Journal of Biological Chemistry 274.77 (1999): 3962-3969.

Romagnani. Th1/Th2 cells. Inflamm Bowel Dis 5(4):285-294 (Nov. 1999).

Rosenblum et al. Preclinical Safety Evaluation of Recombinant Human Interleukin-10. Regulatory Toxicology and Pharmacology 35:56-71 (2002). doi:10.1006/rtph.2001.1504.

"Roszak et al. Survival strategies of bacteria in the natural environment. Microbiol Rev. Sep. 1987; 51(3): 365-379.".

Rother. Diabetes Treatment—Bridging the Divide. N Engl J Med. 356(15):1499-1501 (Apr. 12, 2007). doi:10.1056/NEJMp078030.

RU2016147734 Office Action dated Dec. 24, 2019 (w/ English translation).

RU2016147734 Office Action dated May 28, 2019 (w/ English translation).

Rubas et al. Flux Measurements across Caco-2 Monolayers May Predict Transport in Human Large Intestinal Tissue. J Pharm Sci 85(2):165-169 (Feb. 1996).

Rubas et al. An integrated method to determine epithelial transport and bioactivity of oral drug candidates in vitro. Pharm Res 13(1):23-26 (Jan. 1996).

Rubas et al. Comparison of the permeability characteristics of a human colonic epithelial (Caco-2) cell line to colon of rabbit, monkey, and dog intestine and human drug absorption. Pharm Res.10(1):113-118 (1993).

Ruddock et al. Assembly of the B Subunit Pentamer of *Escherichia coli* Heat-labile Enterotoxin. J Biol Chem 271 (32):19118-19123 (Aug. 9, 1996).

Ruddock et al. Kinetics of Acid-mediated Disassembly of the B Subunit Pentamer of *Escherichia coli* Heat-labile Enterotoxin. J Biol Chem 270(50):29953-29958 (Dec. 15, 1995).

Sabat et al. Therapeutic opportunities of the IL-22—IL-22R1 system. Nature Reviews Drug Discovery 13:21-38 (Jan. 2014).

(56) References Cited

OTHER PUBLICATIONS

Saidi et al. Prevalence of Vibrio cholerae O1 El Tor variant in a cholera-endemic zone of Kenya. Journal of Medical Microbiology 63:415-420 (2014). First published online Mar. 1, 2014. doi:10.1099/jmm.0.068999-0.

Salmond et al. The B Subunit of *Escherichia coli* Heat-Labile Enterotoxin Induces Both Caspase-Dependent and -Independent Cell Death Pathways in CD8+ T Cells. Infection and Immunity 72(10):5850-5857 (Oct. 2004).

Sarnovsky, et al. Initial characterization of an immunotoxin constructed from domains II and III of cholera exotoxin. Cancer Immunol. Immunother., 59.5 2010 (published online Nov. 2009):737-746.

Schreiber et al. G4424: Safety and tolerance of rHuIL-10 treatment in patients with mild/moderate active ulcerative colitis. Gastroenterology vol. 114, Supplement 1, pp. A1080-A1081 (Apr. 15, 1998). DOI: https://doi.org/10.1016/S0016-5085(98)84395-3.

Schreiber et al. Immunoregulatory Role of Interleukin 10 in Patients With Inflammatory Bowel Disease. Gastroenterology 108:1434-1444 (1995).

Schreiber et al. Safety and Efficacy of Recombinant Human Interleukin 10 in Chronic Active Crohn's Disease. Gastroenterology 119:1461-1472 (2000).

Schwager et al. Preclinical characterization of DEKAVIL (F8-IL10), a novel clinical-stage immunocytokine which inhibits the progression of collagen-induced arthritis. Arthritis Research & Therapy 11:R142 (Sep. 25, 2009). 15 pages, doi: 10.1186/ar2814.

Shealy et al. Anti-TNF antibodies: lessons from the past, roadmap for the future. Handb Exp Pharmacol181:101-129 (2008).

Siegall et al. Functional Analysis of Domains II, Ib, and III of Pseudomonas Exotoxin. J Biol Chem 264(24):14256-14261 (Aug. 25, 1989).

Simmons et al. Immunomodulation Using Bacterial Enterotoxins. Scand J Immunol 53:518-226 (2001).

Simon, et al. Novel bacterial ADP-ribosylating toxins: structure and function. Nature Reviews Microbiology 12.9 (2014): 599-611.

Sims et al. The IL-1 family: regulators of immunity. Nature Reviews Immunology 10:89-102 (Feb. 2010). Published online Jan. 18, 2010.

Sonnenberg et al. Border patrol: regulation of immunity, inflammation and tissue homeostasis at barrier surfaces by IL-22. Nature Immunology 12(5):383-390 (May 2011). Published online Apr. 19, 2011. doi:10.1038/ni.2025.

Soriani et al. *Escherichia coli* Enterotoxin B Subunit Triggers Apoptosis of CD8+ T Cells by Activating Transcription Factor c-Myc. Infection and Immunity 69(8):4923-4930 (Aug. 2001).

Spooner et al. Retrograde transport pathways utilised by viruses and protein toxins. Virology Journal, 3:26 (2006).

Stochholm et al. Incidence of GH deficiency—a nationwide study. Eur J Endocrinol 155(1):61-71 (2006).

Sugimoto et al. IL-22 ameliorates intestinal inflammation in a mouse model of ulcerative colitis. J Clin Invest 118(2):534-544 (Feb. 2008). doi: 10.1172/JCI33194.

Sun et al. Cholera toxin B subunit: An efficient transmucosal carrier-delivery system for induction of peripheral immunological tolerance. Proc Natl Acad Sci USA 91:10795-10799 (Nov. 1994).

Tachiiri et al. Genomic structure and inducible expression of the IL-22 receptor α chain in mice. Genes and Immunity 4:153-159 (2003). doi:10.1038/sj.gene.6363934.

Takeuchi et al. Mucoadhesive nanoparticulate systems for peptide drug delivery. Adv Drug Deliv Rev 47(1):39-54 (Mar. 23, 2001).

Taverner, et al. Enhanced paracellular transport of insulin can be achieved via transient induction of myosin light chain phosphorylation. Journal of Controlled Release 210 (2015): 189-197.

Tokuriki et al. Stability effects of mutations and protein evolvability. Curr. Opin. Struc. Biol. 19:596-604 (2009).

Turcanu et al. Modulation of human monocytes by *Escherichia coli* heat-labile enterotoxin B-subunit; altered cytokine production and its functional consequences. Immunology 106:316-325 (2002).

Turgeon et al. Yeast as a tool for characterizing mono-ADP-ribosyltransferase toxins. FEMS Microbiology Letters 300(1):97-106 (Nov. 2009). Published online Sep. 28, 2009. DOI: https://doi.org/10.1111/j.1574-6968.2009.01777.x.

U.S. Appl. No. 15/616,140 Notice of Allowance dated Aug. 28, 2018.
U.S. Appl. No. 16/207,655 Office Action dated Feb. 19, 2019.
U.S. Appl. No. 15/309,177 Notice of Allowance dated Dec. 13, 2019.
U.S. Appl. No. 15/309,177 Notice of Allowance dated Mar. 8, 2019.
U.S. Appl. No. 15/309,177 Notice of Allowance dated Nov. 2, 2018.
U.S. Appl. No. 15/309,177 Office Action dated Aug. 24, 2018.
U.S. Appl. No. 15/309,177 Office Action dated Jun. 25, 2019.
U.S. Appl. No. 15/309,177 Office Action dated Mar. 16, 2018.
U.S. Appl. No. 16/207,611 Notice of Allowance dated Dec. 13, 2019.
U.S. Appl. No. 16/207,611 Office Action dated Mar. 14, 2019.
U.S. Appl. No. 16/207,637 Notice of Allowance dated Dec. 13, 2019.
U.S. Appl. No. 16/207,637 Office Action dated Mar. 14, 2019.
U.S. Appl. No. 16/207,655 Office Action dated Aug. 30, 2019.
U.S. Appl. No. 16/207,655 Office Action dated Dec. 6, 2019.
U.S. Appl. No. 16/220,923 Office Action dated Dec. 9, 2019.
U.S. Appl. No. 16/220,923 Office Action dated Mar. 12, 2019.
U.S. Appl. No. 16/414,671 Notice of Allowance dated Dec. 10, 2019.
U.S. Appl. No. 16/414,686 Notice of Allowance dated Dec. 5, 2019.
U.S. Appl. No. 16/207,655 Office Action dated Feb. 28, 2019.

Van Deventer et al. Multiple Doses of Intravenous Interleukin 10 in Steroid-Refractory Crohn's Disease. Gastroenterology 113(2):383-389 (1997).

Veas et al. Chapter 4: IL-22 Induces an Acute-Phase Response Associated to a Cohort of Acute Phase Proteins and Antimicrobial Peptides as Players of Homeostasis, pp. 85-104. Acute Phase Proteins—Regulation and Functions of Acute Phase Proteins. Published online Oct. 3, 2011. ISBN: 978-953-307-252-4, InTech.

Vreugdenhil et al. Lipopolysaccharide Binding Protein Serum and Amyloid A Secretion by Human Intestinal Epithelial Cells During the Acute Phase Response. J Immunol 163:2792-2798 (1999).

Wang et al. Interleukin-22 alleviates metabolic disorders and restores mucosal immunity in diabetes. Nature 514:237-241 (Oct. 9, 2014). Published online Aug. 6, 2014. doi: 10.1038/nature13564.

Wang et al. Methods to determine intestinal permeability and bacterial translocation during liver disease. J Immunol Methods 421:44-53 (Jun. 2015). Epub Jan. 13, 2015. doi:10.1016/j.jim.2014.12.015.

Wedekind et al. Refined crystallographic structure of Pseudomonas aeruginosa exotoxin A and its implications for the molecular mechanism of toxicity. J Mol Biol. Dec. 7, 2001;314(4):823-37.

Weise et al. Tyrosine Residues in the Cytoplasmic Domains Affect Sorting and Fusion Activity of the Nipah Virus Glycoproteins in Polarized Epithelial Cells. Journal of Virology 84(15):7634-7641 (Aug. 2010). Published ahead of print May 19, 2010. DOI: 10.1128/JVI.02576-09.

Weiss et al. Cloning of murine IL-22 receptor alpha 2 and comparison with its human counterpart. Genes and Immunity 5:330-336 (2004). Published online Jun. 17, 2004. doi:10.1038/sj.gene.6364104.

Weldon, et al. A guide to taming a toxin-recombinant immunotoxins constructed from Pseudomonas exotoxin A for the treatment of cancer. FEBS Journal 278.23 (2011): 4683-4700.

Wileman, et al. Receptor-mediated endocytosis. Biochemical Journal 232.1 (1985): 1-14.

Williams et al. Prevention of autoimmune disease due to lymphocyte modulation by the B-subunit of *Escherichia coli* heat-labile enterotoxin. Proc Natl Acad Sci USA 94:5290-5295 (May 1997).

Wolk et al. Deficiency of IL-22 Contributes to a Chronic Inflammatory Disease: Pathogenetic Mechanisms in Acne Inversa. J Immunol 186:1228-1239 (2011). Prepublished online Dec. 8, 2010. doi: 10.4049/jimmunol.0903907.

Wolk et al. Is there an interaction between interleukin-10 and interleukin-22? Genes and Immunity 6:8-18 (2005).

(56) References Cited

OTHER PUBLICATIONS

Wolk et al. Cutting edge: immune cells as sources and targets of the IL-10 family members? J Immunol 168(11):5397-5402 (2002).
Woodley, J.F. Enzymatic barriers for GI peptide and protein delivery. Crit Rev Ther Drug Carrier Syst. 1994;11(2-3):61-95.
Wu. Identification of Endoplasmic Reticulum Export Motifs forG Protein-Coupled Receptors. Methods in Enzymol 521:189-202 (2013). DOI: https://doi.org/10.1016/B978-0-12-391862-8.00010-7.
Wu. Regulation of α2B-Adrenergic Receptor Export Trafficking by Specific Motifs. Prog Mol Biol Transl Sci 132:227-244 (2015). DOI: https://doi.org/10.1016/bs.pmbts.2015.03.004.
Xia et al. Tyrphostin-8 Enhances Transferrin Receptor-Mediated Transcytosis in Caco-2 Cells and Increases Hypoglycemic Effect of Orally Administered Insulin-Transferrin Conjugate in Diabetic Rats. Pharmaceutical Res 18(2):191-195 (Feb. 2001).
Xia et al. Hypoglycemic Effect of Insulin-Transferrin Conjugate in Streptozotocin-Induced Diabetic Rats. J Pharmacol Experiment Therap 295(2):594-600 (2000).
Xu et al. IL-22 secreting CD4+ T cells in the patients with neuromyelitis optica and multiple sclerosis. J Neuroimmunol 261 (1-2):87-91 (Aug. 15, 2013). Epub May 28, 2013. doi: 10.1016/j.jneuroim.2013.04.021.
Yates, et al. Stealth and Mimicry by Deadly Bacterial Toxins. Trends Biochemical Science 31 (2006): 123-133.
Zdanov. Structural analysis of cytokines comprising the IL-10 family. Cytokine & Growth Factor Reviews 21(5):325-330 (Oct. 2010). Available online Sep. 16, 2010. DOI: https://doi.org/10.1016/j.cytogfr.2010.08.003.
Zenewicz et al. IL-22 but not IL-17 provides protection to hepatocytes during acute liver inflammation. Immunity 27(4): 647-659 (Oct. 2007).
Zenewicz et al. Innate and adaptive interleukin-22 protects mice from inflammatory bowel disease. Immunity 29(6):947-957 (Dec. 19, 2008). doi:10.1016/j.immuni.2008.11.003.
Co-pending U.S. Appl. No. 16/997,781, inventors Mrsny; Randall J. et al., filed Aug. 19, 2020.
Co-pending U.S. Appl. No. 17/015,011, inventors Liu; Keyi et al., filed Sep. 8, 2020.
Co-pending U.S. Appl. No. 17/129,376, inventors Hunter; Thomas Carl et al., filed Dec. 21, 2020.
IN3153/DELNP/2013 Hearing Notice dispatched Jul. 30, 2020.
Mrsny. Breaking Through the Biological Barriers that Limit Protein Drug Delivery. Bangor University, United Kingdom (Presentation.) (Aug. 6, 2015.) 26 pages.
Mrsny. Breaking Through the Biological Barriers that Limit Protein Drug Delivery. (Presentation.) Controlled Release Society, Florence, Italy (Nov. 8, 2014.) 43 pages.
Mrsny. Breaking Through the Biological Barriers that Limit Protein Drug Delivery. (Presentation.) Tours, France (Jul. 2, 2015.) 25 pages.
Mrsny. Molecular mechanisms of transcytosis pathways: Drug delivery thru epithelial and endothelial barriers. (Presentation.) (Dec. 3, 2010). 42 pages.
Mrsny. Molecular mechanisms of transcytosis pathways: Drug delivery thru epithelial and endothelial barriers. (Presentation.) Emory University, Atlanta, GA, United States. (Sep. 24, 2010). 51 pages.
Mrsny. Molecular mechanisms of transcytosis pathways: Drug delivery thru epithelial and endothelial barriers. (Presentation.) Nanomedicine and Drug Delivery Symposium (NanoDDS), University of Nebraska Omaha, Omaha, NE, United States. (Oct. 3, 2010.) 42 pages.
Mrsny. Overcoming Biological Barriers that Limit Peptide and Protein Drug Delivery. Berlin, Germany (Presentation.) (May 23, 2016.) 26 pages.
Mrsny. Overcoming Biological Barriers that Limit Peptide and Protein Drug Delivery. Denver, CO, United States (Presentation.) (Nov. 17, 2016.) 15 pages.
Mrsny. Overcoming Biological Barriers that Limit Peptide and Protein Drug Delivery. (Presentation.) (Jun. 14, 2016.) 36 pages.
Mrsny. Overcoming Biological Barriers that Limit Peptide and Protein Drug Delivery. University of California San Francisco, CA, United States (Presentation.) (Mar. 24, 2016.) 36 pages.
Mrsny. Paracellular and Transcellular Strategies to Enhance Oral Protein Delivery. (Presentation.) San Francisco, CA, United States (Mar. 15, 2013.) 41 pages.
Mrsny. Paracellular and Transcellular Strategies to Enhance Oral Protein Delivery. (Presentation.) Seoul, South Korea (Mar. 15, 2012.) 54 pages.
Mrsny. Paracellular and Transcellular Strategies to Enhance Oral Protein Delivery. (Presentation.) University of California, Santa Barbara, CA, United States. (Feb. 26, 2013.) 54 pages.
Mrsny. Permeation of barriers for GI and pulmonary drug delivery. (Presentation.) Gordon Research Conference, New Hampshire, United States. (Aug. 13, 2012.) 46 pages.
Mrsny. Strategies to Enhance the Oral Delivery of Therapeutic Proteins and Peptides. (Presentation.) Berlin, Germany. (Sep. 28, 2011.) 42 pages.
Mrsny. Strategies to Enhance the Oral Delivery of Therapeutic Proteins and Peptides. (Presentation.) Dunedin, New Zealand (Feb. 15, 2012). 42 pages.
Mrsny. Strategies to Enhance the Oral Delivery of Therapeutic Proteins and Peptides. (Presentation.) Nottingham, United Kingdom. (Sep. 2, 2011.) 42 pages.
Mrsny. Strategies to Enhance the Oral Delivery of Therapeutic Proteins and Peptides. (Presentation.) San Francisco, CA, United States. (Jun. 20, 2011.) 42 pages.
Mrsny. Strategies to Enhance the Oral Delivery of Therapeutic Proteins and Peptides. (Presentation.) The University of Sheffield, Sheffield, United Kingdom. (Jan. 16, 2012.) 42 pages.
Mrsny. TJ Regulation using Cell-Penetrating Peptides. (Presentation.) University of Copenhagen, Denmark (May 12, 2015.) 62 pages.
Mrsny. Understanding & Developing the Science Behind Oral Protein and Peptide Delivery. (Presentation.) Nottingham, United Kingdom (Jan. 22, 2014.) 48 pages.
Mrsny. Understanding & Developing the Science Behind Oral Protein Delivery: An Academic Case Study. (Presentation.) Berlin, Germany (Feb. 20, 2013.) 39 pages.
Mrsny. Understanding & Developing the Science Behind Oral Protein Delivery. (Presentation.) University of North Carolina at Chapel Hill, Chapel Hill, North Carolina, United States. (May 28, 2014.) 37 pages.
Mrsny. Understanding & Developing the Science Behind Oral Protein Delivery. (Presentation.) University of Westminster, London, United Kingdom. (Mar. 15, 2013). 40 pages.
Mrsny. Understanding & Developing the Science Behind Oral Protein Delivery. (Presentation.) Academy of Pharmaceutical Sciences, Edinburgh, United Kingdom.(Sep. 3, 2013). 40 pages.
Mrsny. Understanding & Developing the Science Behind Oral Protein Delivery. (Presentation.) University College Dublin, Dublin, Ireland (May 22, 2013). 44 pages.
Mrsny. Understanding & Developing the Science Behind Oral Protein Delivery. (Presentation.) University of East Anglia, Norwich, United Kingdom (Jun. 27, 2013). 43 pages.
Mrsny. Understanding Exotoxin Transcytosis for the Application of Oral Protein Delivery. Dresden, Germany (Presentation.) (Nov. 12, 2015.) 26 pages.
BR11-2013-006088-3 Office Action dated Apr. 13, 2021 (w/ English translation).
Capra et al. Predicting functionally important residues from sequence conservation. Bioinformatics 23(15):1875-1882 (2007). Advance Access publication May 22, 2007.
EP19717013.7 Office Action dated May 20, 2021.
Gray et al. Cloning, nucleotide sequence, and expression in *Escherichia coli* of the exotoxin A structural gene of Pseudomonas aeruginosa. Proc Natl Acad Sci, vol. 81, pp. 2645-2649 (May 1984).
PCT/US2019/050708 International Preliminary Report on Patentability dated May 11, 2021.
PH1-2016-502447 Office Action dated Mar. 12, 2021.
BR112016025866-5 Office Action dated Sep. 14, 2021 (w/ English translation).
CA2,948,346 Office Action dated Jun. 2, 2021.

(56) References Cited

OTHER PUBLICATIONS

Challa et al. Bacterial Toxin Fusion Proteins Elicit Mucosal Immunity against a Foot-and-Mouth Disease Virus Antigen When Administered Intranasally to Guinea Pigs. Adv Virol, vol. 2011, Article ID 713769 (2011). 11 pages.
Challa et al. Non-toxic Pseudomonas aeruginosa exotoxin A expressing the FMDV VP1 G-H loop for mucosal vaccination of swine against foot and mouth disease virus. Vaccine 25 (2007) 3328-3337. Available online Jan. 12, 2007.
CN201580036678.8 Office Action dated Jul. 28, 2021 (w/ English translation).
EP19881649.8 Extended European Search Report dated Oct. 18, 2021.
GenBank Accession No. AY876053. Version No. AY876053.1. Vibrio cholerae strain TP hypothetical protein gene, partial cds; hypothetical exotoxin A (toxA) gene, complete cds; and hypothetical protein gene, partial cds. Record created Feb. 9, 2005. 2 pages. Retrieved Sep. 28, 2021 at URL: https://www.ncbi.nlm.nih.gov/nuccore/AY876053.
JP2020-147344 Office Action with Search Report dated Sep. 7, 2021 (w/ English translation).
KR10-2016-7034104 Office Action dated Sep. 30, 2021 (w/ English translation).
PCT/US2021/032097 International Search Report and Written Opinion dated Jul. 30, 2021.
U.S. Appl. No. 16/884,456 Office Action dated Oct. 20, 2021.
U.S. Appl. No. 17/129,376 Office Action dated Jun. 29, 2021.

\* cited by examiner

Cholix<sup>415</sup>-TEV-IL-10 Fusion Molecule

```
MVEEALNIFD ECRSPCSLTP EPGKPIQSKL SIPGDVVLDE GVLYYSMTIN DEQNDIKDED KGESIITIGE
FATVRATRHY VSQDAPFGVI NLDITTENGT KTYSFNRKES EFAINWLVPI GEDSPASIKI SIDELDQQRN
IIEVPKLYSI DLDNQTLEQW KTQGNVSFSV TRPEHNIAIS WPSVSYKAAQ KEGSRHKRWA HWHTGLALCW
LVPIDAIYNY ITQQNCTLGD NWFGGSYETV AGTPKAITVK QGIEQKPVEQ RIHFSKKNAM EALAAHRVCG
VPLETLARSR KPRDLPDDLS CAYNAQQIVS LFLATRILFT HIDSIFTLNL DGQEPEVAER LDDLRRINEN
NPGMVIQVLT VARQIYNDYV THHPGLTPEQ TSAGAQAADI LSLFCPDADK SCVASNSDQA NINIES**GGGG
SGGGENLYFQ S**PGQGTQSEN SCTHFPGNLP NMLRDLRDAF SRVKTFFQMK DQLDNLLLKE SLLEDFKGYL
GCQALSEMIQ FYLEEVMPQA ENQDPDIKAH VNSLGENLKT LRLRLRRCHR FLPCENKSKA VEQVKNAFNK
LQEKGIYKAM SEFDIFINYI EAYMTMKIRN (SEQ ID NO: 122)
```

Cholix<sup>415</sup>-(G<sub>4</sub>S)<sub>3</sub>-IL-10 Fusion Molecule

```
MVEEALNIFD ECRSPCSLTP EPGKPIQSKL SIPGDVVLDE GVLYYSMTIN DEQNDIKDED KGESIITIGE
FATVRATRHY VSQDAPFGVI NLDITTENGT KTYSFNRKES EFAINWLVPI GEDSPASIKI SIDELDQQRN
IIEVPKLYSI DLDNQTLEQW KTQGNVSFSV TRPEHNIAIS WPSVSYKAAQ KEGSRHKRWA HWHTGLALCW
LVPIDAIYNY ITQQNCTLGD NWFGGSYETV AGTPKAITVK QGIEQKPVEQ RIHFSKKNAM EALAAHRVCG
VPLETLARSR KPRDLPDDLS CAYNAQQIVS LFLATRILFT HIDSIFTLNL DGQEPEVAER LDDLRRINEN
NPGMVIQVLT VARQIYNDYV THHPGLTPEQ TSAGAQAADI LSLFCPDADK SCVASNSDQA NINIES**GGGG
SGGGGSGGGG S**PGQGTQSEN SCTHFPGNLP NMLRDLRDAF SRVKTFFQMK DQLDNLLLKE SLLEDFKGYL
GCQALSEMIQ FYLEEVMPQA ENQDPDIKAH VNSLGENLKT LRLRLRRCHR FLPCENKSKA VEQVKNAFNK
LQEKGIYKAM SEFDIFINYI EAYMTMKIRN (SEQ ID NO: 123)
```

FIG. 3

CHOLIX TOXIN-DERIVED FUSION MOLECULES FOR ORAL DELIVERY OF BIOLOGICALLY ACTIVE CARGO

RELATED PATENT APPLICATIONS

This application is a continuation of U.S. patent application Ser. No. 16/151,533, filed Oct. 4, 2018, which is a continuation of U.S. patent application Ser. No. 15/616,140, filed Jun. 7, 2017, now U.S. Pat. No. 10,130,688, which is a continuation-in-part of U.S. patent application Ser. No. 14/733,940, filed Jun. 8, 2015, which is a continuation of U.S. patent application Ser. No. 13/822,435, filed Mar. 12, 2013 now U.S. Pat. No. 9,090,691, which is a U.S. National Stage Application pursuant to 35 U.S.C. § 371 of PCT/US2011/001602, filed Sep. 15, 2011, which claims benefit of U.S. Provisional Application No. 61/403,394, filed Sep. 15, 2010; U.S. patent application Ser. No. 15/616,140 is a continuation-in-part of U.S. patent application Ser. No. 15/309,177, filed Nov. 4, 2016, now U.S. Pat. No. 10,624,955, which is a U.S. National Stage Application pursuant to 35 U.S.C. § 371 of PCT/US2015/029795, filed May 7, 2015, which claims benefit of U.S. Provisional Application No. 61/990,054, filed on May 7, 2014, each incorporated in its entirety by reference herein.

SEQUENCE LISTING

The instant application contains a Sequence Listing which has been submitted electronically in ASCII format and is hereby incorporated by reference in its entirety. Said ASCII copy, created on Jul. 21, 2020, is named 40566_701_307_SL.txt and is 314,354 bytes in size.

TECHNICAL FIELD

The field of the present invention relates, in part, to a strategy for novel pharmaceutical applications. More specifically, the present invention relates to a non-toxic mutant form of the *Vibrio cholera* Cholix gene (ntCholix), a variant of Cholix truncated at amino acid $A^{386}$ (Cholix$^{386}$) and the use of other various Cholix-derived polypeptide sequences to enhance intestinal delivery of biologically-active therapeutics. Importantly, the systems and methods described herein provide for the following: the ability to deliver macromolecule doses without injections; the ability to deliver cargo, such as (but not limited to) siRNA or antisense molecules into intracellular compartments where their activity is required; and the delivery of nanoparticles and dendrimer-based carriers across biological membranes, which otherwise would have been impeded due to the barrier properties of most such membranes.

Oral delivery of biologically active polypeptides (referring to a polymer composed of amino acid residues; typically also defined as proteins or peptides) has been a long-standing goal of the pharmaceutical industry. Unfortunately, the numerous physical, physiological, and biological barriers of the gastrointestinal (GI) tract are designed to inhibit uptake of proteins and peptides until they can be sufficiently degraded for absorption through amino acid and di- or tri-peptide transporters; and/or to traffic the proteins and peptides intracellularly to destructive lysosome compartments after endosomal uptake at the luminal surface. As such, the feasibility of polypeptide uptake from the intestine in a manner similar to that achievable with, e.g., small molecules, has been limited and low oral bioavailability continues to be a problem for most polypeptides and proteins.

While there have been some promising results from clinical studies evaluating various biologically active polypeptides for the treatment of diseases such as cancer, inflammatory diseases, immune diseases, growth deficiency disorders, etc., and several DNA-based therapeutics have been FDA approved for such uses, these therapeutics often fail to really reach their optimum potential, as there is often marginal or inadequate overall efficacy due to inherent limitations such as short biological half-life which prevents the delivery of optimal therapeutically effective dosages, and/or detrimental side effects and toxicities observed at the therapeutically effective doses. Moreover, many such therapeutics require multiple dosing regimens, necessitating continuous administration intravenously or by frequent subcutaneous injections, which are burdensome on the patients and caregivers.

Future clinical studies directed toward evaluating the promising biologically active polypeptides could benefit greatly from new methods and/or pharmaceutical compositions that could be used to orally administer such polypeptides to a human subject.

BACKGROUND ART

The majority of currently-approved small molecule drugs are absorbed across the mucosa of the small intestine to provide delivery to the systemic circulation. In fact, small molecule drugs are selected based upon their stability and efficient absorption across intestinal mucosae. A similar oral delivery of biologically-active polypeptides (referring to a polymer composed of amino acid residues; typically defined as a protein or peptide) has been a long-standing goal of the pharmaceutical industry. As the gastrointestinal (GI) tract is designed to digest dietary proteins and peptides, there are numerous physical, physiological, and biological barriers that limit the feasibility of therapeutic proteins and peptides uptake from the intestine in a manner similar to that achievable with small molecules; Mahato, R. I., et al., *Crit Rev Ther Drug Carrier Syst*, 20(2-3):p. 153-214 (2003).

A number of technologies have been identified that can be used to protect therapeutic proteins and peptides through the stomach, allowing them to reach the absorptive surface of epithelial cells in the small intestine and separating them from the gastric and intestinal environments that function to destroy dietary proteins and peptides. Unfortunately, however, the efficient transport across this simple, single layer of cells remains a substantial barrier due to the intracellular trafficking to destructive lysosome compartments after endosomal uptake of polypeptides at the luminal surface; Woodley, J. F., *Crit Rev Ther Drug Carrier Syst*, 11(2-3):p. 61-95 (1994). Indeed, this barrier is designed to inhibit uptake of proteins and peptides until these macromolecules can be sufficiently degraded for absorption through amino acid and di- or tri-peptide transporters. In this regard, a number of efforts have been examined to overcome the physical, physiological, and biological barriers of the intestinal mucosae.

There are two basic routes across the simple epithelium that constitutes the cellular barrier of the intestinal mucosae. Specifically, once across the covering mucus layer, a molecule could move between adjacent epithelial cells (paracellular route) or move through cells (transcellular route) via a series of vesicles that traffic within, but do not mingle, contents with the cytoplasm; T. Jung et al., *Eur J Pharm*

*Biopharm*, 50:147-160 (2000). In other words, in both routes, a transport protein or peptide therapeutic does not enter into the cell but rather stays in an environment external to the cell's cytoplasm.

The primary barrier to casual movement of therapeutic protein and peptide movement through the paracellular route is a complex of proteins at the apical neck of these cells known as the tight junction (TJ). While transient opening and closing of TJ structures can facilitate transport of peptides across intestinal epithelia, this approach has key limitations: e.g., it does not work well for molecules above ~5 kDa; it has the potential for non-selective entry of materials into the body from the intestinal lumen; and it represents a route that involves only a small fraction of the surface area of the intestinal epithelium.

The primary barrier to casual migration of protein or peptide therapeutics across cells via the transcellular route is a default vesicle trafficking that delivers the contents of these vesicles to a destructive (lysosomal) pathway. As compared to the paracellular route, movement through the vesicular transcellular route can accommodate materials as large as 100 nm in diameter, involves essentially the entire epithelial cell surface, and can be highly selective in uptake of materials through the use of receptor-ligand interactions for vesicle entry. Thus, the transcellular route is very appealing for the epithelial transport of protein or peptide therapeutics if the destructive pathway can be avoided.

Some pathogens have solved the trafficking barrier problem, as demonstrated by the efficient transcytosis of secreted polypeptide virulence factors which function to facilitate and/or stabilize infection of a host. Exotoxins represent a class of proteins released by a variety of microorganisms which function as potent virulence factors. Exotoxins function on multi-cellular organisms with the capacity to acts as potent toxins in man; Roszak, D. B., and Colwell, R. R., *Microbiol Rev* 51:365-379 (1987). These proteins commonly kill or inactivate host cells through mechanisms that involve selective disruption of protein synthesis. Accordingly, only a few molecules are required to kill, consistent with the observation that bacterial exotoxins are some of the most toxic agents known. A subset of these proteins comprised of the family of proteins that consists of diphtheria toxin (DT) from *Corynebacterium diphtheria*, exotoxin A from *Pseudomonas aeruginosa* (PE), and a recently identified protein termed Cholix from *Vibrio cholera* function to intoxicate host cells via the ADP-ribosylation of elongation factor 2 (EF2); Yates, S. P., et al., *Trends Biochem Sci*, 31:123-133 (2006). These exotoxins are synthesized as a single chain of amino acids that fold into distinct domains that have been identified as having specific functions in targeting, entry, and intoxication of host cells.

The biology of exotoxin A from *Pseudomonas aeruginosa* (PE) has recently been described; Mrsny, R. J., et al., *Drug Discov Today*, 7(4): p. 247-58 (2002). PE is composed of a single chain of 613 amino acids having a theoretical molecular weight (MW) of 66828.11 Da, an isoelectric point (pI) of 5.28, and that functionally folds into three discrete domains, denoted domain I (Ala$^1$-Glu$^{252}$), domain II (Gly$^{253}$-Asn$^{364}$), domain III (Gly$^{405}$-Lys$^{613}$, and which contains a ADP-ribosyltransferase activity site), and a short disulfide-linked loop linking domains II and III which is known as the Ib loop (Ala365-Gly404). The organization of these domains at pH 8.0 have determined from crystal diffraction at a resolution of ~1.5 Å; Wedekind, J. E. et al., *J Mol Biol*, 314:823-837 (2001). Domain I (Ia+Ib) has a core formed from a 13-stranded β-roll, domain II is composed of six α-helices, and domain III has a complex α/β-folded structure. Studies have supported the idea that the modular nature of PE allows for distinct domain functions: domain I binds to host cell receptors, domain II is involved in membrane translocation, and domain III functions as an ADP-ribosyltransferase. It appears that PE is secreted by *P. aeruginosa* in close proximity to the epithelial cell apical surface, possibly in response to environmental cues and/or cellular signals; Deng, Q. and J. T. Barbieri, *Annu Rev Microbiol*, 62:p. 271-88 (2008). Once secreted, internalization into cells occurs after domain I of PE binds to the membrane protein α2-macroglobulin, a protein which is also known as the low-density lipoprotein receptor-related protein 1 (LRP1) or CD91; see, e.g., FitzGerald, D. J., et al., *J Cell Biol*, 129(6):p. 1533-41 (1995); Kounnas, M. Z., et al., *J Biol Chem*, 267(18): p. 12420-3 (1992). Following internalization, PE avoids trafficking to the lysosome and is instead efficiently delivered to the basolateral surface of the cell where it is released in a biologically-active form; Mrsny, R. J., et al., *Drug Discov Today*, 7(4): p. 247-58 (2002). Once across the epithelium, PE functions as a virulence factor by entering into CD91-positive cells within the submucosal space (macrophage and dendritic cells) where it then intersects with an unfolding pathway that leads to the cytoplasmic delivery of domain III; see, e.g., Mattoo, S., Y. M. Lee, and J. E. Dixon, *Curr Opin Immunol*, 19(4): p. 392-401 (2007); Spooner, R. A., et al., *Virol J*, 3: p. 26 (2006).

*Vibrio cholerae* bacterium is best known for its eponymous virulence agent, cholera toxin (CT), which can cause acute, life-threatening massive watery diarrhea. CT is a protein complex composed of a single A subunit organized with a pentamer of B subunits that binds to cell surface Gm' ganglioside structures at the apical surface of epithelia. CT is secreted by *V. cholera* following horizontal gene transfer with virulent strains of *V. cholerae* carrying a variant of lysogenic bacteriophage called CTXf or CTXφ. Recent cholera outbreaks, however, have suggested that strains of some serogroups (non-01, non-O139) do not express CT but rather use other virulence factors. Detailed analyses of non-O1, non-O139 environmental and clinical data suggested the presence of a novel putative secreted exotoxin with some similarity to PE.

Jorgensen, R. et al., *J Biol Chem*, 283(16):10671-10678 (2008) reported that some strains of *V. cholerae* did, in fact, contain a protein toxin having similarity to PE and which they termed Cholix toxin (Cholix). Compared to PE, Cholix has a slightly larger theoretical MW (70703.89 Da) and a slightly more acidic theoretical pI (5.12). The crystal structure of the 634 amino acid Cholix protein has been resolved to ~2 Å. The domain structure and organization was found to be somewhat similar to PE: domain I (Val$^1$-Lys$^{265}$), domain II (Glu$^{266}$-Ala$^{386}$), domain III (Arg$^{426}$-Lys$^{634}$), and a Ib loop (Ala$^{387}$-Asn$^{425}$). Additional structural similarity to PE includes: a furin protease site for cellular activation; a C-terminal KDEL sequence that can route the toxin to the endoplasmic reticulum of the host cell; and an ADP-ribosyltransferase activity site within domain III.

Remarkably, PE and Cholix share no significant genetic and limited similarity by amino acid alignment. Searching the genome of *V. cholera* for PE-like nucleotide sequences fails to result in a match of any kind. It is only at the protein sequence level is there the hint that an PE-like protein could be produced by this bacterium. Even here, there is only a 32% homology between the amino acid sequences of PE and Cholix with similarities (42% homology) being focused in the ADP ribosylation elements of domain III, and with low levels of amino acid homology (~15-25%) for most segments of domains I and II for the two proteins. Moreover, this overall arrangement of Cholix relative to PE is even more striking since these two proteins with similar elements were derived from two distinct directions: P. aeruginosa is a GC-rich bacterium while V. cholera is AT-rich. That these two toxins evolved from two different genetic directions to arrive at nearly the same structure but with only 32% amino acid homology suggests that structural and functional similarities of Cholix and PE are likely based upon similar survival pressures rather than through similar genetic backgrounds. The very low amino acid homology of domains I and II for these two proteins stress the functional importance of the folded structures of these two proteins and not their amino acid sequences.

The C-terminal portion of Cholix and PE appear to function in the intoxication of cells through ADP-ribosylation of EF2 in comparable ways. Recent studies where the latter half of Cholix (domain I deleted) targeted to cancer cells through conjugation to an antibody directed to the transferrin receptor suggests that the C-terminal portions of PE and Cholix involved in ADP-ribosylation of EF2 are indeed functionally similar; Sarnovsky, R., et al., *Cancer Immunol Immunother* 59:737-746 (2010). While this distal portion of Cholix is 36% identical and 50% similar to PE, polyclonal antisera raised in animals as well as sera from patients having neutralizing immune responses to this same distal portion of PE failed to cross-react with this latter portion of Cholix. Similarly, antisera raised to this Cholix failed to cross-react with PE. This data suggests that while both PE and Cholix share a capacity to intoxicate cells through a similar mechanism and that these two proteins share a common core structure, there are striking differences in their elements that are expressed at the surface of these proteins.

As previous studies using PE have demonstrated that this toxin readily transports across polarized monolayers of epithelial cells in vitro and in vivo without intoxication; Mrsny, R. J., et al., *Drug Discov Today*, 7(4): p. 247-58 (2002), the present inventors have commenced research to further evaluate the properties and biology of Cholix, with a particular focus on the functional aspects of the proximal portions of Cholix; specifically, the use of domains I and II to facilitate transport across intestinal epithelial monolayers. As domains I and IIa appeared to be the only essential elements of PE required for epithelial transcytosis, it was particularly important to examine these same domains in Cholix. As stated previously, there is only ~15%-25% amino acids homology over most of the regions that would be considered to be part of domains I and IIa. The present inventors examined the domains though a series of studies: monitoring the biological distribution of Cholix following application to epithelial surfaces in vivo, assessment of Cholix transcellular transport characteristics across polarized epithelial cell monolayers in vitro, and delivery of a biologically-active cargo genetically integrated into the Cholix protein at its C-terminus. Preliminary data generated by genetically fusing the first two domains of Cholix (amino acids 1-386) to green fluorescent protein (GFP) or chemically coupling these expressed domains to 100 nm diameter latex beads demonstrated that Cholix attached to 100 nm latex beads were observed to transport across intestinal epithelial monolayers in vitro and in vivo. That the GFP cargo retained its fluorescent character during and after the transcytosis process also support the contention that Cholix utilizes a non-destructive (or privileged) trafficking pathway through polarized epithelial cells. This outcome bodes well for its (repeated) application as a tool to deliver biologically active cargos across epithelial barriers of the body, such as those in the respiratory and gastrointestinal tracts.

Also of important note from the preliminary studies is the observation which suggests an apparent cell receptor interaction difference between PE and Cholix. As stated previously, PE enters into epithelial cells after domain I of PE binds to the membrane protein α2-macroglobulin, a protein which is also known as the low-density lipoprotein receptor-related protein 1 (LRP1) or CD91. While the exact identity of the surface receptor for Cholix has not been established, preliminary studies suggest that Cholix does not intoxicate some cell lines that express CD91 but intoxicates some cell lines that do express CD91. It is currently unclear what other receptors, beyond CD91, might be involved epithelial transcytosis of PE. Nevertheless, Cholix and PE appear to have distinct cell receptor interactions, demonstrating clear differences that are sufficient to suggest very different and unanticipated applications for both oral biologics and the intracellular delivery of bioactive agents.

DISCLOSURE OF THE INVENTION

The present invention is based on the membrane-trafficking properties of Cholix and the demonstration that Cholix transports efficiently across polarized epithelial cells of the airway and intestine, suggesting that Cholix-derived polypeptide sequences (including the proximal elements of the protein) can be used for the efficient transcytosis of protein and nanoparticles, representing a strategy for novel pharmaceutical applications.

As such, one aspect of the present invention is to provide isolated delivery constructs (e.g., genetic fusions or chemical constructs) comprising a transporter domain (e.g., a Cholix-derived polypeptide sequence) and a cargo. Both the transport domain and cargo may be expressed/linked in varying stoichiometric ratios and spatial organization. Different cargos may also be expressed/linked on the same construct. In preferred embodiments such cargo may include one, or any of: proteins, peptides, small molecules, siRNA, PNA, miRNA, DNA, plasmid, and antisense.

Another aspect of the present invention is to provide for the ability to deliver cargo, such as macromolecules, without injections.

Another aspect of the present invention is to provide for the ability to deliver cargo, such as (but not limited to) macromolecules, small molecules, siRNA, PNA, miRNA, DNA, plasmid and antisense molecules, into intracellular compartments where their activity is required.

Another aspect of the present invention is to provide for the transport of cargo via delivery of nanoparticles and/or dendrimer-based carriers across biological membranes.

Methods of administration/delivery contemplated for use in the present invention include, e.g., oral administration, pulmonary administration, intranasal administration, buccal administration, sublingual administration, ocular administration (including, but not limited to, delivery to the vitreous, cornea, conjunctiva, sclera, and posterior and anterior compartments of the eye), topical application, injection (needle or needle-free), intravenous infusion, microneedle application, administration via a drug depot formulation, administration via intrathecal application, administration via intraperitoneal application, administration via intra-articular application, delivery intracellularly, delivery across blood brain barrier, delivery across blood retina barrier, administered for local delivery and action, and/or delivered for systemic delivery.

In yet another aspect, the invention provides a pharmaceutical composition comprising the delivery constructs and a pharmaceutically acceptable carrier.

The present disclosure relates to pharmaceutical compositions comprising novel, non-naturally occurring fusion molecules and one or more pharmaceutically acceptable carriers, formulated for oral delivery, and designed to provide for improved, effective therapies for treatment of, e.g., inflammatory diseases and/or autoimmune diseases and/or cancers.

The present disclosure is based in part on the inventors' unique insight that oral delivery of a pharmaceutical composition comprising a fusion molecule which comprises a modified Cholix toxin coupled to a biologically active cargo may, among other things, provide the following advantages: a) in embodiments wherein the modified Cholix toxin is coupled to the biologically active cargo without a linker, or with a non-cleavable linker, the anchoring effect of the modified Cholix toxin by its receptor(s) at the surface of, e.g., immune cells that also express the receptor for the biologically active cargo, can allow for greater exposure of the biologically active cargo at the surface of the targeted cells and provide a synergistic effect by binding to both the Cholix receptor and the biologically active cargo receptor; b) in embodiments wherein the modified Cholix toxin is coupled to the biologically active cargo with a linker that is cleavable by an enzyme present at a basolateral membrane of an epithelial cell, or an enzyme present in the plasma of the subject, such cleavage will allow the biologically active cargo to be released from the remainder of the fusion molecule soon after transcytosis across the epithelial membrane c) the direct delivery of the biologically active cargo to the submucosal-GI space and hepatic-portal system may reduce the systemic toxicity observed when the cargo are administered by parenteral routes, as well as enabling access to the submucosal target biology that was difficult to target via non-oral or GI routes; d) once transported across the GI epithelium, the fusion molecules of the disclosure will exhibit extended half-life in serum, that is, the biologically active cargo of the fusion molecules will exhibit an extended serum half-life compared to the biologically active cargo in its non-fused state; e) oral administration of the fusion molecule can deliver a higher effective concentration of the delivered biologically active cargo to the liver of the subject than is observed in the subject's plasma; and f) the ability to deliver the biologically active cargo to a subject without using a needle to puncture the skin of the subject, thus improving such subjects' quality of life by avoiding pain or potential complications associated therewith, in addition to improved patient/care-giver convenience and compliance.

Thus, in one aspect, the present disclosure relates to pharmaceutical compositions comprising a non-naturally occurring fusion molecule and one or more pharmaceutically acceptable carriers, formulated for oral delivery, wherein the fusion molecule comprises a modified Cholix toxin coupled to a biologically active cargo to be delivered to a subject, wherein the Cholix toxin is non-toxic.

In one aspect, the present disclosure relates to pharmaceutical compositions comprising a non-naturally occurring fusion molecule and one or more pharmaceutically acceptable carriers, formulated for oral delivery, wherein the fusion molecule comprises a modified Cholix toxin coupled to a biologically active cargo to be delivered to a subject, wherein the Cholix toxin is non-toxic, and wherein the fusion molecule has the ability to activate the receptor for the biologically active cargo, or to enable the catalytic process of a catalytically-active material.

In various embodiments, the fusion molecules of the pharmaceutical compositions comprise a modified Cholix toxin truncated at an amino acid residue within Cholix toxin domain II. In various embodiments, the fusion molecules comprise a truncated Cholix toxin having the amino acid sequence set forth in, e.g., SEQ ID NO: 3, SEQ ID NO: 4, SEQ ID NO: 5, SEQ ID NO: 6, SEQ ID NO: 7, SEQ ID NO: 8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 or SEQ ID NO: 41.

In various embodiments, the fusion molecules of the pharmaceutical compositions comprise a modified Cholix toxin truncated at an amino acid residue within Cholix toxin domain Ib. In various embodiments, the fusion molecules comprise a truncated Cholix toxin having the amino acid sequence set forth in, e.g., SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In various embodiments, the fusion molecules of the pharmaceutical compositions comprise a modified Cholix toxin wherein domain III has been truncated or mutated. In various embodiments, the fusion molecules comprise a mutated Cholix toxin having the amino acid sequence set forth in SEQ ID NO: 81 wherein the amino acid residue E581 of SEQ ID NO: 1 has been deleted (designated herein as "Cholix AF581").

In various embodiments, the fusion molecules of the pharmaceutical compositions comprise a modified Cholix toxin wherein domain Ia has been mutated.

In various embodiments, the biologically active cargo is selected from e.g., a macromolecule, small molecule, peptide, polypeptide, nucleic acid, mRNA, miRNA, shRNA, siRNA, antisense molecule, antibody, DNA, plasmid, vaccine, polymer nanoparticle, or catalytically-active material.

In various embodiments, the biologically active cargo is an enzyme selected from hyaluronidase, streptokinase, tissue plasminogen activator, urokinase, or PGE-adenosine deaminase.

In various embodiments, the biologically active cargo is a polypeptide that is a modulator of inflammation in the GI tract selected from, e.g., interleukin-10, interleukin-19, interleukin-20, interleukin-22, interleukin-24, or interleukin-26. In various embodiments, the biologically active polypeptide is interleukin-10 having the amino acid sequence set forth is SEQ ID NO: 82. In various embodiments, the biologically active polypeptide is interleukin-19 having the amino acid sequence set forth is SEQ ID NO: 83. In various embodiments, the biologically active polypeptide is interleukin-20 having the amino acid sequence set forth is SEQ ID NO: 84. In various embodiments, the biologically active polypeptide is interleukin-22 having the amino acid sequence set forth is SEQ ID NO: 85. In various embodiments, the biologically active polypeptide is interleukin-24 having the amino acid sequence set forth is SEQ ID NO: 86. In various embodiments, the biologically active polypeptide is interleukin-26 having the amino acid sequence set forth is SEQ ID NO: 87. In various embodiments, the biologically active cargo is a modulator of inflammation in the GI tract that is a small molecule. In various embodiments, the biologically active cargo is a modulator of inflammation in the GI tract that is an antisense or siRNA molecule.

In various embodiments, the biologically active cargo is a TNFSF inhibitor that is an antibody, or a fragment thereof, or an artificial construct comprising an antibody or fragment thereof, or an artificial construct designed to mimic the binding of an antibody or fragment thereof to its antigen. In various embodiments, the biologically active cargo is a TNFSF inhibitor that is a soluble TNFSF receptor fusion protein. In various embodiments, the biologically active cargo is a TNFSF inhibitor that is a small molecule. In various embodiments, the biologically active cargo is a TNFSF inhibitor that is an antisense or siRNA molecule.

In various embodiments, the biologically active cargo is an antibody comprising the heavy chain variable region amino acid sequence set forth in SEQ ID NO: 88 and light chain variable region amino acid sequence set forth in SEQ ID NO: 89. In various embodiments, the biologically active cargo is an antibody comprising the heavy chain variable region amino acid sequence set forth in SEQ ID NO: 90 and light chain variable region amino acid sequences set forth in SEQ ID NO: 91. In various embodiments, the biologically active cargo is a soluble TNFSF receptor fusion protein dimer comprising the amino acid sequence set forth in SEQ ID NO: 92.

In one aspect, the present disclosure relates to pharmaceutical compositions comprising novel, non-naturally occurring fusion molecules and one or more pharmaceutically acceptable carriers, formulated for oral delivery, and designed to provide for improved, effective therapies for treatment of metabolic disorders, e.g., Type 1 Diabetes and Type 2 Diabetes. Oral delivery of biologically active polypeptides (referring to a polymer composed of amino acid residues; typically also defined as proteins or peptides) has been a long-standing goal of the pharmaceutical industry. Unfortunately, the numerous physical, physiological, and biological barriers of the gastrointestinal (GI) tract are designed to inhibit uptake of proteins and peptides until they can be sufficiently degraded for absorption through amino acid and di- or tri-peptide transporters; and/or to traffic the proteins and peptides intracellularly to destructive lysosome compartments after endosomal uptake at the luminal surface. As such, the feasibility of polypeptide uptake from the intestine in a manner similar to that achievable with, e.g., small molecules, has been limited and low oral bioavailability continues to be a problem for most polypeptides and proteins.

In various embodiments, the present disclosure relates to pharmaceutical compositions comprising a non-naturally occurring fusion molecule and one or more pharmaceutically acceptable carriers, formulated for oral delivery, wherein the fusion molecule comprises a modified Cholix toxin coupled to a glucose-lowering agent to be delivered to a subject.

In various embodiments, the present disclosure is based in part on that oral delivery of a pharmaceutical composition comprising a fusion molecule which comprises a modified Cholix toxin coupled to a glucose-lowering agent may, among other things, provide the following advantages: a) in embodiments wherein the modified Cholix toxin is coupled to the glucose-lowering agent without a linker, the anchoring effect of the modified Cholix toxin by its receptor(s) at the surface of cells that also express the receptor for the glucose-lowering agent, can allow for greater exposure of the glucose-lowering agent at the surface of the targeted cells; b) in embodiments wherein the modified Cholix toxin is coupled to the glucose-lowering agent with a linker that is cleavable by an enzyme present at a basal-lateral membrane of an epithelial cell, or an enzyme present in the plasma of the subject, such cleavage will allow the glucose-lowering agent to be released from the remainder of the fusion molecule soon after transcytosis across the epithelial membrane; c) the direct delivery of the glucose-lowering agent to the submucosal-GI space and hepatic-portal system may reduce the systemic toxicity observed when the glucose-lowering agents are administered by parenteral routes, as well as enabling access to the submucosal target biology that was difficult to target via non-oral or GI routes; d) the direct delivery of the glucose-lowering agent to the submucosal-GI space and hepatic-portal system may provide for improved dosing regimens, including less frequent insulin injections; and e) the ability to deliver the glucose-lowering agent to a subject without using a needle to puncture the skin of the subject, thus improving such subjects' quality of life by avoiding pain or potential complications associated therewith.

In various embodiments, the glucose-lowering agent is selected from e.g., a macromolecule, small molecule, peptide, polypeptide, nucleic acid, mRNA, miRNA, shRNA, siRNA, antisense molecule, antibody, DNA, plasmid, vaccine, polymer nanoparticle, or catalytically-active material. In various embodiments, the glucose-lowering agent is an incretin or incretin mimetic. In various embodiments, the glucose-lowering agent is a GLP-1. In various embodiments, the glucose-lowering agent is a GLP-1 agonist. In various embodiments, the glucose-lowering agent is an exendin. In various embodiments, the glucose-lowering agent is a glucose inhibitory protein receptor (GIPR) agonist.

In various embodiments, the glucose-lowering agent is a GLP-1 agonist that is a peptide. In various embodiments, the glucose-lowering agent is a GLP-1 agonist that is a small molecule. In various embodiments, the glucose-lowering agent is a GLP-1 agonist that is an antisense or siRNA molecule. In various embodiments, the glucose-lowering agent is a GLP-1 agonist that is an antibody, or a fragment thereof, or an artificial construct comprising an antibody or fragment thereof, or an artificial construct designed to mimic the binding of an antibody or fragment thereof to its antigen.

In various embodiments, the biologically active cargo is a glucose-lowering agent that is a GLP-1 agonist peptide comprising the amino acid sequence set forth in SEQ ID NO: 93. In various embodiments, the biologically active cargo is a glucose-lowering agent that is a GLP-1 agonist peptide comprising the amino acid sequence set forth in SEQ ID NO: 94.

In one aspect, the present disclosure relates to pharmaceutical compositions comprising novel, non-naturally occurring fusion molecules and one or more pharmaceutically acceptable carriers, formulated for oral delivery, and designed to provide for improved, effective therapies for treatment of growth hormone deficiency, and like disorders.

In various embodiments, the present disclosure relates to pharmaceutical compositions comprising a non-naturally occurring fusion molecule and one or more pharmaceutically acceptable carriers, formulated for oral delivery, wherein the fusion molecule comprises a modified Cholix toxin coupled to a growth hormone (GH) to be delivered to a subject.

In various embodiments, the present disclosure is based in part on the inventors' unique insight that oral delivery of a pharmaceutical composition comprising a fusion molecule which comprises a modified Cholix toxin coupled to a growth hormone may, among other things, provide the following advantages: a) in embodiments wherein the modified Cholix toxin is coupled to the growth hormone with a linker that is cleavable by an enzyme present at a basolateral membrane surface of an epithelial cell, or an enzyme present in the plasma of the subject, such cleavage will allow the growth hormone to be released from the remainder of the fusion molecule soon after transcytosis across the epithelial membrane; b) the direct delivery of the growth hormone to the submucosal-GI space and hepatic-portal system may reduce systemic toxicities observed when the growth hormones are administered by parenteral routes, as well as enabling access to the submucosal target biology that was difficult to target via non-oral or GI routes (e.g., provide a more efficient induction of IGF-1 relative to systemic delivery via subcutaneous (sc) injection); c) the direct delivery of the growth hormone to the submucosal-GI space and hepatic-portal system may provide for improved dosing regimens; d) oral delivery will achieve a brief pulse of growth hormone to the liver that is more consistent with serum level observed in growing children, and this pulse profile is not achievable by sc injection; and e) the ability to deliver the growth hormone to a subject without using a needle to puncture the skin of the subject, thus improving such subjects' quality of life by avoiding pain or potential complications associated therewith, in addition to improved patient/care-giver convenience and compliance.

In various embodiments, the growth hormone is selected from e.g., a macromolecule, small molecule, peptide, polypeptide, nucleic acid, mRNA, miRNA, shRNA, siRNA, antisense molecule, antibody, DNA, plasmid, vaccine, polymer nanoparticle, or catalytically-active material. In various embodiments, the growth hormone is human growth hormone (or a variant thereof), growth hormone 2, or growth hormone-releasing hormone. In various embodiments, the growth hormone is human growth hormone (somatotropin) comprising the amino acid sequence set forth in SEQ ID NO: 95.

In various embodiments, the fusion molecules comprise a modified Cholix toxin directly coupled to a biologically active cargo. In various embodiments, the biologically active cargo is directly coupled to the C-terminus of the Cholix toxin.

In various embodiments, the fusion molecules comprise a modified Cholix toxin chemically coupled to a biologically active cargo.

In various embodiments, the fusion molecules comprise a Cholix toxin coupled to a biologically active cargo by a non-cleavable linker. In various embodiments, the non-cleavable linker comprises the amino acid sequence of, e.g., SEQ ID NO: 96, SEQ ID NO: 97, SEQ ID NO: 98 or SEQ ID NO: 99.

In various embodiments, the fusion molecules comprise a Cholix toxin coupled to a biologically active cargo by a cleavable linker. In various embodiments, the linker is cleavable by an enzyme that is present at a basolateral membrane of a polarized epithelial cell of the subject. In various embodiments, the linker is cleavable by an enzyme that is present in the plasma of said subject. In various embodiments, the cleavable linker comprises the amino acid sequence of, e.g., SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120.

In various embodiments, the fusion molecules comprise a Cholix toxin coupled to a biologically active cargo by a cleavable linker, wherein the cleavable linker comprises an amino acid sequence that is known to be a substrate for tobacco etch virus (TEV) protease. In various embodiments, the cleavable linker comprises the amino acid sequence of, e.g., SEQ ID NO: 121.

In various embodiments, the fusion molecule comprises the amino acid sequence set forth in SEQ ID NO: 122. (this is Cholix$^{415}$-TEV-IL-10)

In various embodiments, the fusion molecule comprises the amino acid sequence set forth in SEQ ID NO: 123. (this is Cholix$^{415}$-(G$_4$S)$_3$—IL-10)

In another aspect, the present disclosure provides a method of treating an inflammatory disease in a subject, comprising orally administering a pharmaceutical composition of the present disclosure to the subject. In various embodiments, the inflammatory disease is selected from an inflammatory bowel disease, psoriasis or bacterial sepsis. In various embodiments, the inflammatory bowel disease is Crohn's disease, ulcerative colitis, collagenous colitis, lymphocytic colitis, ischaemic colitis, diversion colitis, Behcet's syndrome or indeterminate colitis.

In another aspect, the present disclosure provides a method of treating an autoimmune disease in a subject, comprising orally administering a pharmaceutical composition of the present disclosure to the subject. In various embodiments, the autoimmune disease is systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, or scleroderma.

In another aspect, the present disclosure provides a method of treating a cancer in a subject, comprising orally administering a pharmaceutical composition of the present disclosure to the subject. In various embodiments, the cancer to be treated includes, but is not limited to, non-Hodgkin's lymphomas, Hodgkin's lymphoma, chronic lymphocytic leukemia, hairy cell leukemia, acute lymphoblastic leukemia, multiple myeloma, carcinomas of the bladder, kidney ovary, cervix, breast, lung, nasopharynx, malignant melanoma and rituximab resistant NHL and leukemia.

In another aspect, the present disclosure provides a method of treating a subject having a metabolic disorder, said method comprising orally administering a fusion molecule of the present disclosure in an amount sufficient to treat said disorder, wherein said metabolic disorder is diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, or hyperlipidemia.

In another aspect, the present disclosure provides a method of treating a subject having a fatty liver disease (e.g., nonalcoholic fatty liver disease (NAFLD); nonalcoholic steatohepatitis (NASH)), a gastrointestinal disease, or a neurodegenerative disease, said method comprising orally administering a fusion molecule of the present disclosure in an amount sufficient to treat said disease.

In another aspect, the present disclosure provides a method of treating a subject having a GH deficient growth disorder, said method comprising orally administering a fusion molecule of the present disclosure in an amount sufficient to treat said disorder, wherein said disorder is growth hormone deficiency (GHD), Turner syndrome (TS), Noonan syndrome, Prader-Willi syndrome, short stature homeobox-containing gene (SHOX) deficiency, chronic renal insufficiency, and idiopathic short stature short bowel syndrome, GH deficiency due to rare pituitary tumors or their treatment, and muscle-wasting disease associated with HIV/AIDS.

In another aspect, the present disclosure relates to the use of a non-naturally occurring fusion molecule of the present invention for the preparation of a medicament for treatment, prophylaxis and/or prevention of an inflammatory disease in a subject in need thereof.

In another aspect, the present disclosure relates to the use of a non-naturally occurring fusion molecule of the present invention for the preparation of a medicament for treatment, prophylaxis and/or prevention of an autoimmune disease in a subject in need thereof.

In another aspect, the present disclosure relates to the use of a non-naturally occurring fusion molecule of the present invention for the preparation of a medicament for treatment, prophylaxis and/or prevention of a cancer in a subject in need thereof.

In another aspect, the present disclosure relates to the use of a non-naturally occurring fusion molecule of the present invention for the preparation of a medicament for treatment, prophylaxis and/or prevention of a metabolic disorder in a subject in need thereof.

In another aspect, the present disclosure relates to the use of a non-naturally occurring fusion molecule of the present invention for the preparation of a medicament for treatment, prophylaxis and/or prevention of a fatty liver disease in a subject in need thereof.

In another aspect, the present disclosure relates to the use of a non-naturally occurring fusion molecule of the present invention for the preparation of a medicament for treatment, prophylaxis and/or prevention of GH deficient growth disorder in a subject in need thereof.

In other aspects, the present disclosure provides polynucleotides that encode the non-naturally occurring modified Cholix toxin-biologically active cargo fusion molecules of the present disclosure; vectors comprising polynucleotides encoding non-naturally occurring modified Cholix toxin-biologically active cargo fusion molecules of the disclosure; optionally, operably-linked to control sequences recognized by a host cell transformed with the vector; host cells comprising vectors comprising polynucleotides encoding non-naturally occurring modified Cholix toxin-biologically active cargo fusion molecules of the disclosure; a process for producing a non-naturally occurring modified Cholix toxin-biologically active cargo fusion molecule of the disclosure comprising culturing host cells comprising vectors comprising polynucleotides encoding non-naturally occurring modified Cholix toxin-biologically active cargo fusion molecules of the disclosure such that the polynucleotide is expressed; and, optionally, recovering the non-naturally occurring modified Cholix toxin-biologically active cargo fusion molecule from the host cell culture medium.

BRIEF DESCRIPTION OF THE DRAWINGS

FIG. 1 depicts an overview of the strategy used for the C-terminal modification of ntCholix to facilitate fusion with a cargo, in this instance, the cargo being Alexa488 fluorescent dye.

FIG. 2 depicts the transport of ntCholix-Alexa488® across polarized intestinal epithelial cells in vitro. Caco-2 cell monolayers were exposed to test materials for 4 hr. The percentage of material transported was determined by standard curve analysis of fluorescence present in the samples and presented as an average (N=4). BSA-Alexa488 was used as a control.

FIG. 3 depicts the genetic constructions of two exemplary Cholix toxin-IL-10 fusion molecules evaluated herein. The N-terminus of a human IL-10 monomer sequence was genetically attached to the C-terminus of a modified Cholix toxin ($Cholix^{415}$) using a stable non-cleavable linker sequence ($(G_4S)_3$) or a linker sequence that is a known substrate for the tobacco etch virus (TEV) protease. Each construct also contains an N-terminal Methionine (M).

FIG. 4 is a ribbon diagram representation of an exemplary "dimer Cholix toxin-IL-10" fusion molecule after refolding that would be driven by IL-10 dimerization. The first 415 amino acids of Cholix toxin (SEQ ID NO: 1) are connected through a 16 amino acid linker (not shown) to connect with the human IL-10 sequence. IL-10 dimerization is envisaged to result in purple $Cholix^{415}$/blue hIL-10 and orange $Cholix^{415}$/green organization shown.

FIG. 5 is a coomassie stained SDS PAGE of $Cholix^{415}$-TEV-IL-10 (depicted as "C") and $Cholix^{415}$-$(G_4S)_3$-IL-10 (depicted as "N") following induction and expression from inclusion bodies. The expressed fusion molecules demonstrate the anticipated molecular size of ~66 kDa that was comparable to the calculated mass of 66380.78 and 65958.25 Daltons, respectively. SeeBlue® Plus2 Prestained MW standards are shown.

FIG. 6 is bar graph depicting the results of a flow cytometry assay using a mouse macrophage-derived J774.2 cell line treated with an exemplary Cholix toxin-IL-10 fusion molecules of the present disclosure at two concentrations. % proliferation was measured at 48 hours post treatment. Values represent n=4±standard deviation. The data shows that "dimer $Cholix^{415}$-$(G_4S)_3$-IL-10" fusion molecule demonstrates biologically active IL-10.

FIG. 7 is a line graph depicting the results of an assay wherein the dimer $Cholix^{415}$-$(G_4S)_3$-IL-10 fusion molecule was tested for effects on the barrier properties of Caco-2 cell monolayers in vitro. Fluorescein-labeled 70 kDa dextran and varying concentrations of dimer $Cholix^{415}$-$(G_4S)_3$-IL-10 fusion molecule was added to the apical surface of these monolayers and the cumulative amount of florescence detected in the basal compartment monitored over time by collecting 150 μL volumes with replacement. Cumulative Basal Dextran levels (pmol) are plotted vs time. Each line represents the average (n=4) of basal fluorescence values measured at 0, 15, 30, 45, 60, 90, 120, 180, and 240 min.

FIG. 8 is a line graph depicting the results of an assay wherein the dimer $Cholix^{415}$-$(G_4S)_3$-IL-10 fusion molecule was tested for effects on the barrier properties of Caco-2 cell monolayers in vitro. Fluorescein-labeled 70 kDa dextran and varying concentrations of dimer $Cholix^{415}$-$(G_4S)_3$-IL-10 fusion molecule was added to the apical surface of these monolayers and the cumulative amount of florescence detected in the basal compartment monitored over time.

FIGS. 9A and 9B are line graphs depicting the results an ELISA assay evaluating the ability of the dimer $Cholix^{415}$-$(G_4S)_3$-IL-10 fusion molecule to move across Caco-2 cell monolayers. The cumulative amount of dimer $Cholix^{415}$-$(G_4S)_3$-IL-10 fusion molecule reaching the basal compartment over time following an apical addition at various concentrations denoted in the legend. Each line represents the average (n=4) of basal IL-10 levels measured at 0, 15, 30, 45, 60, 90, 120, 180, and 240 min. Cumulative IL-10 transported over time graphed over a range of 6A=8000 fmol IL-10 expanded and 6B=1000 fmol IL-10.

MODE(S) FOR CARRYING OUT THE INVENTION

As those in the art will appreciate, the foregoing description describes certain preferred embodiments of the invention in detail, and is thus only representative and does not depict the actual scope of the invention. It is also to be understood that the terminology used herein is for the purpose of describing particular embodiments only, and is not intended to limit the scope of the invention defined by the appended claims.

Unless defined otherwise, all technical and scientific terms used herein have the meaning commonly understood by a person skilled in the art to which this invention belongs. As used herein, the following terms have the meanings ascribed to them unless specified otherwise.

The studies underlying the present invention relate to the use of Cholix-derived polypeptide sequences as the transporter domain to be used to prepare isolated delivery constructs to enhance intestinal delivery of biologically-active therapeutics. Importantly, the systems and methods described herein provide for the following: the ability to deliver macromolecule doses without injections; the ability to deliver "cargo" into intracellular compartments where their activity is required; and the delivery of nanoparticles and/or dendrimer-based carriers across biological membranes, which otherwise would have been impeded due to the barrier properties of most such membranes.

Mature Cholix toxin ("Cholix") is an extremely active monomeric protein (molecular weight 70 kD) secreted by *Vibrio cholerae*, and which is composed of three prominent globular domains (Ia, II, and III) and one small subdomain (Ib) that connects domains II and III. The amino acid sequence of mature Cholix is provided in Jorgensen, R. et al., *J Biol Chem*, 283(16):10671-10678 (2008) and references cited therein. The Cholix-derived polypeptide sequences used in the preparation of the isolated delivery constructs of the present invention will be derived from the reported 634 amino acid protein sequence of mature Cholix.

Accordingly, the delivery constructs of the present invention comprise a transporter domain. A "transporter domain" as used herein refers to structural domains which are capable of performing certain functions, e.g., cell recognition (i.e., comprise a receptor binding domain) and transcytosis (i.e., comprise a transcytosis domain). Generally, the transporter domains to be used in the preparation of the delivery constructs of the present invention are Cholix-derived polypeptide sequences that have structural domains corresponding to the functional domains, e.g., Ia and II, of Cholix.

In addition to the portions of the molecule that correspond to Cholix functional domains, the delivery constructs of this invention can further comprise a macromolecule for delivery to a biological compartment of a subject. In certain embodiments, the macromolecule is selected from the group of a nucleic acid, a peptide, a polypeptide, a protein, a polysaccharide, and a lipid. In further embodiments, the polypeptide is selected from the group consisting of polypeptide hormones, cytokines, chemokines, growth factors, and clotting factors that are commonly administered to subjects by injection. The sequences of all of these macromolecules are well known to those in the art, and attachment of these macromolecules to the delivery constructs is well within the skill of those in the art using standard techniques.

The macromolecule can be introduced into any portion of the delivery construct that does not disrupt a cell-binding or transcytosis activity. The macromolecule is connected to the remainder of the delivery construct through a cleavable linker. "Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc. when there is such a change in environment following transcytosis of the delivery construct across a polarized epithelial membrane.

In certain embodiments, the delivery constructs further comprise a second macromolecule that is selected from the group consisting of a nucleic acid, a peptide, a polypeptide, a protein, a lipid, and a small organic molecule and a second cleavable linker, wherein cleavage at said second cleavable linker separates said second macromolecule from the remainder of said construct. In certain embodiments, the first macromolecule is a first polypeptide and said second macromolecule is a second polypeptide. In certain embodiments, the first polypeptide and the second polypeptide associate to form a multimer. In certain embodiments, the multimer is a dimer, tetramer, or octamer. In further embodiments, the dimer is an antibody.

In certain embodiments, the macromolecule can be selected to not be cleavable by an enzyme present at the basal-lateral membrane of an epithelial cell. For example, the assays described in the examples can be used to routinely test whether such a cleaving enzyme can cleave the macromolecule to be delivered. If so, the macromolecule can be routinely altered to eliminate the offending amino acid sequence recognized by the cleaving enzyme. The altered macromolecule can then be tested to ensure that it retains activity using methods routine in the art.

In certain embodiments, the first and/or the second cleavable linker is cleavable by an enzyme that exhibits higher activity on the basal-lateral side of a polarized epithelial cell than it does on the apical side of the polarized epithelial cell. In certain embodiments, the first and/or the second cleavable linker is cleavable by an enzyme that exhibits higher activity in the plasma than it does on the apical side of a polarized epithelial cell.

In certain embodiments, the cleavable linker can be selected based on the sequence, in the case of peptide, polypeptide, or protein macromolecules for delivery, to avoid the use of cleavable linkers that comprise sequences present in the macromolecule to be delivered. For example, if the macromolecule comprises AAL, the cleavable linker can be selected to be cleaved by an enzyme that does not recognize this sequence.

In addition to the portions of the molecule that correspond to Cholix functional domains, the delivery constructs of this invention can further comprise a "cargo" for delivery into intracellular compartments where their activity is required. A "cargo" as used herein includes, but is not limited to: macromolecules, small molecules, siRNA, PNA, miRNA, DNA, plasmid and antisense molecules. Other examples of cargo that can be delivered according to the present invention include, but are not limited to, antineoplastic compounds, such as nitrosoureas, e.g., carmustine, lomustine, semustine, strepzotocin; methylhydrazines, e.g., procarbazine, dacarbazine; steroid hormones, e.g., glucocorticoids, estrogens, progestins, androgens, tetrahydrodesoxycaricosterone; immunoactive compounds such as immunosuppressives, e.g., pyrimethamine, trimethopterin, penicillamine, cyclosporine, azathioprine; and immunostimulants, e.g., levamisole, diethyl dithiocarbamate, enkephalins, endorphins; antimicrobial compounds such as antibiotics, e.g., .beta.-lactam, penicillin, cephalosporins, carbapenims and monobactams, .beta.-lactamase inhibitors, aminoglycosides, macrolides, tetracyclins, spectinomycin; antimalarials, amebicides; antiprotazoals; antifungals, e.g., amphotericin .beta., antivirals, e.g., acyclovir, idoxuridine, ribavirin, trifluridine, vidarbine, gancyclovir; parasiticides; anthelmintic; radiopharmaceutics; gastrointestinal drugs; hematologic compounds; immunoglobulins; blood clotting proteins, e.g., antihemophilic factor, factor IX complex; anticoagulants, e.g., dicumarol, heparin Na; fibrinosylin inhibitors, e.g., tranexamic acid; cardiovascular drugs; peripheral anti-adrenergic drugs; centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, e.g., phentolamine; anti-anginal drugs; cardiac glycosides; inodilators, e.g., amrinone, milrinone, enoximone, fenoximone, imazodan, sulmazole; antidysrhythmics; calcium entry blockers; drugs affecting blood lipids, e.g., ranitidine, bosentan, rezulin; respiratory drugs; sypathomimetic drugs, e.g., albuterol, bitolterol mesylate, dobutamine HCl, dopamine HCl, ephedrine So, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propranolol HCl; antimuscarinic drugs, e.g., anisotropine methylbromide, atropine SO.sub.4, clinidium Br, glycopyrrolate, ipratropium Br, scopolamine HBr; neuromuscular blocking drugs; depolarizing drugs, e.g., atracurium besylate, hexafluorenium Br, metocurine iodide, succinylcholine Cl, tubocurarine Cl, vecuronium Br; centrally acting muscle relaxants, e.g., baclofen; neurotransmitters and neurotransmitter agents, e.g., acetylcholine, adenosine, adenosine triphosphate; amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K.sup.+channel toxins; antiparkinson drugs, e.g., amaltidine HCl, benztropine mesylate, carbidopa; diuretic drugs, e.g., dichlorphenamide, methazolamide, bendroflumethiazide, polythiazide; antimigraine drugs, e.g., carboprost tromethamine mesylate, methysergide maleate.

The transporter domains of the delivery constructs of the present invention generally comprise a receptor binding domain. The receptor binding domain can be any receptor binding domain known to one of skill in the art without limitation to bind to a cell surface receptor that is present on the apical membrane of an epithelial cell. Preferably, the receptor binding domain binds specifically to the cell surface receptor. The receptor binding domain should bind to the cell surface receptor with sufficient affinity to allow endocytosis of the delivery construct.

In certain embodiments, the receptor binding domain can comprise a peptide, a polypeptide, a protein, a lipid, a carbohydrate, or a small organic molecule, or a combination thereof. Examples of each of these molecules that bind to cell surface receptors present on the apical membrane of epithelial cells are well known to those of skill in the art. Suitable peptides or polypeptides include, but are not limited to, bacterial toxin receptor binding domains, such as the receptor binding domains from PE, cholera toxin, Cholix toxin, botulinum toxin, diptheria toxin, shiga toxin, shiga-like toxin, etc.; antibodies, including monoclonal, polyclonal, and single-chain antibodies, or derivatives thereof, growth factors, such as EGF, IGF-I, IGF-II, IGF-III etc.; cytokines, such as IL-1, IL-2, IL-3, IL-6, etc; chemokines, such as MIP-1a, MIP-1b, MCAF, IL-8, etc.; and other ligands, such as CD4, cell adhesion molecules from the immunoglobulin superfamily, integrins, ligands specific for the IgA receptor, etc. The skilled artisan can select the appropriate receptor binding domain based upon the expression pattern of the receptor to which the receptor binding domain binds.

The receptor binding domain can be attached to the remainder of the delivery construct by any method or means known by one of skill in the art to be useful for attaching such molecules, without limitation. In certain embodiments, the receptor binding domain is expressed together with the remainder of the delivery construct as a fusion protein. Such embodiments are particularly useful when the receptor binding domain and the remainder of the construct are formed from peptides or polypeptides.

The transporter domains of the delivery constructs of the present invention furthe comprise a transcytosis domain. The transcytosis domain can be any transcytosis domain known by one of skill in the art to effect transcytosis of chimeric proteins that have bound to a cell surface receptor present on the apical membrane of an epithelial cell. In preferred embodiments, the transcytosis domain is domain II of Cholix.

Without intending to be limited to any particular theory or mechanism of action, the transcytosis domain is believed to permit the trafficking of the delivery construct through a polarized epithelial cell after the construct binds to a receptor present on the apical surface of the polarized epithelial cell. Such trafficking through a polarized epithelial cell is referred to herein as "transcytosis." This trafficking permits the release of the delivery construct from the basal-lateral membrane of the polarized epithelial cell.

For the delivery of cargo intended for intracellular activity, the delivery construct comprises an endocytosis domain to traffic the cargo into the cell, and may also comprise a cleavable linker. This includes the intracellular delivery of cargo using nanoparticle and/or dendrimer-based carriers targeted to the cell surface receptor by decorating the carrier surface with one or more copies of the endocytosis domain, with or without the use of linkers.

Without intending to be limited to any particular theory or mechanism of action, the endocytosis domain is believed to permit the trafficking of the delivery construct into a cell after the construct binds to a receptor present on the surface of the cell. Such trafficking into a cell is referred to herein as "endocytosis". This trafficking permits the release of the delivery construct into the relevant intracellular compartment, including (but not limited to) the nucleus and nuclear envelope, ribosomal vesicles, endoplasmic reticulum, mitochondria, golgi apparatus, and cytosol.

In certain embodiments of the present invention, identification of proteases and peptidases that function biological processes that occur at the basolateral surface of these cells will be evaluated. These proteases and peptidases would fall into several categories that can be defined by their substrates: 1) pre-pro-hormones and enzymes that are secreted from epithelial basolateral surfaces and required trimming for their activation, 2) active hormones or enzymes whose activity is neutralized by a cleavage event in order to regulate their activity, and 3) systemic enzymes or growth factors whose actions at the basolateral surface are altered by enzymatic modification. Examples of several potential activities that fall into these various categories and which might be of useful for the basolateral cleavage of carrier-linker-cargo constructs include members of the S9B prolyl oligopeptidase subfamily, e.g., FAP and DDP IV, which have been described in the art.

The nucleic acid sequences and polynucleotides of the present invention can be prepared by any suitable method including, for example, cloning of appropriate sequences or by direct chemical synthesis by methods such as the phosphotriester method of Narang, et al., *Meth. Enzymol.,* 68:90-99 (1979); the phosphodiester method of Brown, et al., *Meth. Enzymol.,* 68:109-151 (1979); the diethylphosphoramidite method of Beaucage, et al., *Tetra. Lett.,* 22:1859-1862 (1981); the solid phase phosphoramidite triester method described by Beaucage & Caruthers, *Tetra. Letts.,* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL, Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Cells suitable for replicating and for supporting recombinant expression of protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as *E. coli*; various eukaryotic cells, such as Chinese hamster ovary cells (CHO), NSO, 292; Yeast; insect cells; and transgenic animals and transgenic plants, and the like. Standard technologies are known in the art to express foreign genes in these systems.

The pharmaceutical compositions of the present invention comprise a genetic fusion or chemical construct of the invention and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Except insofar as any conventional excipient, carrier or vehicle is incompatible with the delivery constructs of the present invention; its use in the pharmaceutical preparations of the invention is contemplated.

In certain embodiments, the pharmaceutical compositions of active compounds may be prepared with a carrier that will protect the composition against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems (J. R. Robinson, ed., Marcel Dekker, Inc., New York, 1978).

In certain embodiments, the delivery constructs of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the delivery constructs can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Generally, a pharmaceutically effective amount of the delivery construct of the invention is administered to a subject. The skilled artisan can readily determine if the dosage of the delivery construct is sufficient to deliver an effective amount of the macromolecule, as described below. In certain embodiments, between about 1.mu.g and about 1 g of delivery construct is administered. In other embodiments, between about 10.mu.g and about 500 mg of delivery construct is administered. In still other embodiments, between about 10.mu.g and about 100 mg of delivery construct is administered. In yet other embodiments, between about 10.mu.g and about 1000.mu.g of delivery construct is administered. In still other embodiments, between about 10.mu.g and about 250.mu.g of delivery construct is administered. In yet other embodiments, between about 10.mu.g and about 100.mu.g of delivery construct is administered. Preferably, between about 10.mu.g and about 50.mu.g of delivery construct is administered.

The delivery constructs of the invention offer several advantages over conventional techniques for local or systemic delivery of macromolecules to a subject. Foremost among such advantages is the ability to deliver the macromolecule without using a needle to puncture the skin of the subject. Many subjects require repeated, regular doses of macromolecules. For example, diabetics must inject insulin several times per day to control blood sugar concentrations. Such subjects' quality of life would be greatly improved if the delivery of a macromolecule could be accomplished without injection, by avoiding pain or potential complications associated therewith.

Furthermore, many embodiments of the delivery constructs can be constructed and expressed in recombinant systems. Recombinant technology allows one to make a delivery construct having an insertion site designed for introduction of any suitable macromolecule. Such insertion sites allow the skilled artisan to quickly and easily produce delivery constructs for delivery of new macromolecules, should the need to do so arise.

In addition, connection of the macromolecule to the remainder of the delivery construct with a linker that is cleaved by an enzyme present at a basal-lateral membrane of an epithelial cell allows the macromolecule to be liberated from the delivery construct and released from the remainder of the delivery construct soon after transcytosis across the epithelial membrane. Such liberation reduces the probability of induction of an immune response against the macromolecule. It also allows the macromolecule to interact with its target free from the remainder of the delivery construct.

Other advantages of the delivery constructs of the invention will be apparent to those of skill in the art.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present disclosure are generally performed according to conventional methods well known in the art and as described in various general and more specific references that are cited and discussed throughout the present specification unless otherwise indicated. See, e.g., Sambrook et al. Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of patients.

Definitions

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

| | |
|---|---|
| 1) | Alanine (A), Serine (S), and Threonine (T) |
| 2) | Aspartic acid (D) and Glutamic acid (E) |
| 3) | Asparagine (N) and Glutamine (Q) |
| 4) | Arginine (R) and Lysine (K) |
| 5) | Isoleucine (I), Leucine (L), Methionine (M), and Valine (V) |
| 6) | Phenylalanine (F), Tyrosine (Y), and Tryptophan (W) |

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (~0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included.

Exemplary amino acid substitutions are set forth in Table 1.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In various embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In various embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., at most 0.1, at most 0.01, or at most 0.001.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent, and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and e.g., will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, specific enzymatic activities, changes in temperature, pH, salt concentration, etc. when there is such a change in environment following transcytosis of the fusion molecules across a polarized epithelial membrane.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

Modified Cholix Toxin Polypeptides

Mature Cholix toxin (Jorgensen, R. et al., J Biol Chem 283(16):10671-10678 (2008)) as used herein is a 70.7 kD, 634 residue protein, whose sequence is set forth in SEQ ID NO: 1:

```
                                          (SEQ ID NO: 1)
VEDELNIFDECRSPCSLTPEPGKPIQSKLSIPSDVVLDEGVLYYSMTIND

EQNDIKDEDKGESIITIGEFATVRATRHYVNQDAPFGVIHLDITTENGTK

TYSYNRKEGEFAINWLVPIGEDSPASIKISVDELDQQRNIIEVPKLYSID

LDNQTLEQWKTQGNVSFSVTRPEHNIAISWPSVSYKAAQKEGSRHKRWAH

WHTGLALCWLVPMDAIYNYITQQNCTLGDNWFGGSYETVAGTPKVITVKQ

GIEQKPVEQRIHFSKGNAMSALAAHRVCGVPLETLARSRKPRDLTDDLSC

AYQAQNIVSLFVATRILFSHLDSVFTLNLDEQEPEVAERLSDLRRINENN

PGMVTQVLTVARQIYNDYVTHHPGLTPEQTSAGAQAADILSLFCPDADKS

CVASNNDQANINIESRSGRSYLPENRAVITPQGVINWTYQELEATHQALT

REGYVFVGYHGTNHVAAQTIVNRIAPVPRGNNTENEEKWGGLYVATHAEV

AHGYARIKEGTGEYGLPTRAERDARGVMLRVYIPRASLERFYRTNTPLEN

AEEHITQVIGHSLPLRNEAFTGPESAGGEDETVIGWDMAIHAVAIPSTIP

GNAYEELAIDEEAVAKEQSISTKPPYKERKDELK
```

In various embodiments, the Cholix toxin has an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 1.

An exemplary nucleic acid encoding the mature Cholix toxin is set forth in SEQ ID NO: 2:

```
                                                    (SEQ ID NO: 2)
ATGGTCGAAGAAGCTTTAAACATCTTTGATGAATGCCGTTCGCCATGTTCGTTGACCCCGGA

ACCGGGTAAGCCGATTCAATCAAAACTGTCTATCCCTAGTGATGTTGTTCTGGATGAAGGTG

TTCTGTATTACTCGATGACGATTAATGATGAGCAGAATGATATTAAGGATGAGGACAAAGGC

GAGTCCATTATCACTATTGGTGAATTTGCCACAGTACGCGCGACTAGACATTATGTTAATCAA

GATGCGCCTTTTGGTGTCATCCATTTAGATATTACGACAGAAAATGGTACAAAAACGTACTCT

TATAACCGCAAAGAGGGTGAATTTGCAATCAATTGGTTAGTGCCTATTGGTGAAGATTCTCCT
```

```
-continued
GCAAGCATCAAAATCTCCGTTGATGAGCTCGATCAGCAACGCAATATCATCGAGGTGCCTAA

ACTGTATAGTATTGATCTCGATAACCAAACGTTAGAGCAGTGGAAAACCCAAGGTAATGTTTC

TTTTTCGGTAACGCGTCCTGAACATAATATCGCTATCTCTTGGCCAAGCGTGAGTTACAAAG

CAGCGCAGAAAGAGGGTTCACGCCATAAGCGTTGGGCTCATTGGCATACAGGCTTAGCACT

GTGTTGGCTTGTGCCAATGGATGCTATCTATAACTATATCACCCAGCAAAATTGTACTTTAGG

GGATAATTGGTTTGGTGGCTCTTATGAGACTGTTGCAGGCACTCCGAAGGTGATTACGGTTA

AGCAAGGGATTGAACAAAAGCCAGTTGAGCAGCGCATCCATTTCTCCAAGGGGAATGCGAT

GAGCGCACTTGCTGCTCATCGCGTCTGTGGTGTGCCATTAGAAACTTTGGCGCGCAGTCGC

AAACCTCGTGATCTGACGGATGATTTATCATGTGCCTATCAAGCGCAGAATATCGTGAGTTTA

TTTGTCGCGACGCGTATCCTGTTCTCTCATCTGGATAGCGTATTTACTCTGAATCTTGACGAA

CAAGAACCAGAGGTGGCTGAACGTCTAAGTGATCTTCGCCGTATCAATGAAAATAACCCGG

GCATGGTTACACAGGTTTTAACCGTTGCTCGTCAGATCTATAACGATTATGTCACTCACCATC

CGGGCTTAACTCCTGAGCAAACCAGTGCGGGTGCACAAGCTGCCGATATCCTCTCTTTATTT

TGCCCAGATGCTGATAAGTCTTGTGTGGCTTCAAACAACGATCAAGCCAATATCAACATCGA

GTCTCGTTCTGGCCGTTCATATTTGCCTGAAAACCGTGCGGTAATCACCCCTCAAGGCGTCA

CAAATTGGACTTACCAGGAACTCGAAGCAACACATCAAGCTCTGACTCGTGAGGGTTATGTG

TTCGTGGGTTACCATGGTACGAATCATGTCGCTGCGCAAACCATCGTGAATCGCATTGCCCC

TGTTCCGCGCGGCAACAACACTGAAAACGAGGAAAAGTGGGGCGGGTTATATGTTGCAACT

CACGCTGAAGTTGCCCATGGTTATGCTCGCATCAAAGAAGGGACAGGGGAGTATGGCCTTC

CGACCCGTGCTGAGCGCGACGCTCGTGGGGTAATGCTGCGCGTGTATATCCCTCGTGCTTC

ATTAGAACGTTTTTATCGCACGAATACACCTTTGGAAAATGCTGAGGAGCATATCACGCAAGT

GATTGGTCATTCTTTGCCATTACGCAATGAAGCATTTACTGGTCCAGAAAGTGCGGGCGGGG

AAGACGAAACTGTCATTGGCTGGGATATGGCGATTCATGCAGTTGCGATCCCTTCGACTATC

CCAGGGAACGCTTACGAAGAATTGGCGATTGATGAGGAGGCTGTTGCAAAAGAGCAATCGA

TTAGCACAAAACCACCTTATAAAGAGCGCAAAGATGAACTTAAG
```

In various embodiments, the Cholix toxin contains an nucleic acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 2.

In various embodiments, the modified Cholix toxin used in the preparation of the fusion molecules is a truncated Cholix toxin, wherein the fusion molecule has the ability to activate the receptor for the biologically active cargo. A truncated Cholix toxin as described herein will be identified by reference to the amino acid residues comprising the truncated Cholix toxin, e.g., a truncated Cholix toxin consisting of amino acid residues 1-386 of SEQ ID NO: 1 will be identified as Cholix$^{386}$.

In various embodiments, the modified Cholix toxin used in the preparation of the fusion molecule is mutated Cholix toxin. As described herein, a mutated Cholix toxin wherein the mutation involves an amino acid residue deletion will be identified by reference to the amino acid residue being deleted, e.g., a mutated Cholix toxin wherein amino acid E581 of SEQ ID NO: 1 has been deleted, the will be identified as "Cholix ΔE581". A mutated Cholix toxin wherein the mutation involves an amino acid residue substitution will be identified by reference to the particular amino acid substitution at a specific amino acid residue. Thus, e.g., the term "S30A" indicates that the "S" (serine, in standard single letter code) residue at position 30 in SEQ ID NO: 1 has been substituted with an "A" (alanine, in standard single letter code) even if the residue appears in a truncated Cholix toxin, and the modified toxin will be identified as "Cholix$^{830.4}$".

Cholix toxin Domain Ia (amino acids 1-265 of SEQ ID NO: 1) is a "receptor binding domain" that functions as a ligand for a cell surface receptor and mediates binding of the fusion molecule to a cell, e.g., Domain Ia will bind to a cell surface receptor that is present on the apical membrane of an epithelial cell, with sufficient affinity to allow endocytosis of the fusion molecule. Domain Ia can bind to any receptor known to be present on the apical membrane of an epithelial cell by one of skill in the art without limitation. For example, the receptor binding domain can bind to α2-MR. Conservative or nonconservative substitutions can be made to the amino acid sequence of domain Ia, as long as the ability to mediate binding of the fusion molecule to a cell is not substantially eliminated. In various embodiments, the fusion molecules comprise a Cholix toxin comprising a mutated domain Ia.

In various embodiments, domain Ia comprises an antigen presenting cell (APC) receptor binding domain. In various embodiments, the APC receptor binding domain is the cell recognition domain of Cholix domain Ia or a portion of Cholix domain Ia sufficient to engage with a cell surface receptor on APCs.

In various embodiments, the APC receptor binding domain binds to a receptor identified as present on a dendritic cell or other APC. Examples of cell surface receptors on APCs can include, but are not limited to, DEC-205 (CD205), CD207, CD209, CD11a, CD11b, CD11c, CD36, CD14, CD50, CD54, CD58, CD68, CD80, CD83, CD86, CD102, CD3, CD14, CD19, Clec9a, CMFR-44, dectin-1, dectin-2, FLT3, HLA-DR, LOX-1, MHC II, BDCA-1, DC-SIGN, Toll-like receptors (TLR)-2, -3, -4, and -7, and α2-macroglobulin receptor ("α2-MR"). In various embodiments, the APC receptor binding domain is α2-MR.

Cholix toxin Domain II (amino acids 266-386 of SEQ ID NO: 1) is a "transcytosis domain" that mediates transcytosis from a lumen bordering the apical surface of a mucous membrane to the basolateral side of a mucous membrane. As referred to herein, "transcytosis" refers to the trafficking of the fusion molecule through a polarized epithelial cell. Such trafficking permits the release of the biologically active cargo from the basolateral membrane of the polarized epithelial cell. The fusion molecules of the present disclosure may comprise a modified Cholix toxin comprising the entire amino acid sequence of Domain II, or may comprise portions of Domain II, so long as transcytosis activity is not substantially eliminated. Further, conservative or nonconservative substitutions can be made to the amino acid sequence of the transcytosis domain, as long as transcytosis activity is not substantially eliminated. A representative assay that can routinely be used by one of skill in the art to determine whether a transcytosis domain has transcytosis activity is described herein. As used herein, the transcytosis activity is not substantially eliminated so long as the activity is, e.g., at least 40%, at least 50%, at least 60%, at least 70%, at least 75%, at least 80%, at least 85%, at least 90%, at least 95%, or at least 99% as compared to a modified Cholix toxin comprising the entire amino acid sequence of Domain II.

In various embodiments, the non-naturally occurring fusion molecules comprise a modified Cholix toxin truncated at an amino acid residue within Cholix toxin domain II, wherein the fusion molecule has the ability to activate the receptor for the biologically active cargo. In one embodiment, the truncated Cholix toxin is Cholix$^{386}$ (SEQ ID NO: 3). In one embodiment, the truncated Cholix toxin is Cholix$^{385}$ (SEQ ID NO: 4). In one embodiment, the truncated Cholix toxin is Cholix$^{384}$ (SEQ ID NO: 5). In one embodiment, the truncated Cholix toxin is Cholix$^{383}$ (SEQ ID NO: 6). In one embodiment, the truncated Cholix toxin is Cholix$^{382}$ (SEQ ID NO: 7). In one embodiment, the truncated Cholix toxin is Cholix$^{381}$ (SEQ ID NO: 8). In one embodiment, the truncated Cholix toxin is Cholix$^{380}$ (SEQ ID NO: 9). In one embodiment, the truncated Cholix toxin is Cholix$^{379}$ (SEQ ID NO: 10). In one embodiment, the truncated Cholix toxin is Cholix$^{378}$ (SEQ ID NO: 11). In one embodiment, the truncated Cholix toxin is Cholix$^{377}$ (SEQ ID NO: 12). In one embodiment, the truncated Cholix toxin is Cholix$^{376}$ (SEQ ID NO: 13). In one embodiment, the truncated Cholix toxin is Cholix$^{375}$ (SEQ ID NO: 14). In one embodiment, the truncated Cholix toxin is Cholix$^{374}$ (SEQ ID NO: 15). In one embodiment, the truncated Cholix toxin is Cholix$^{373}$ (SEQ ID NO: 16). In one embodiment, the truncated Cholix toxin is Cholix$^{372}$ (SEQ ID NO: 17). In one embodiment, the truncated Cholix toxin is Cholix$^{371}$ (SEQ ID NO: 18). In one embodiment, the truncated Cholix toxin is Cholix$^{370}$ (SEQ ID NO: 19). In one embodiment, the truncated Cholix toxin is Cholix$^{369}$ (SEQ ID NO: 20). In one embodiment, the truncated Cholix toxin is Cholix$^{368}$ (SEQ ID NO: 21). In one embodiment, the truncated Cholix toxin is Cholix$^{367}$ (SEQ ID NO: 22). In one embodiment, the truncated Cholix toxin is Cholix$^{366}$ (SEQ ID NO: 23). In one embodiment, the truncated Cholix toxin is Cholix$^{365}$ (SEQ ID NO: 24). In one embodiment, the truncated Cholix toxin is Cholix$^{364}$ (SEQ ID NO: 25). In one embodiment, the truncated Cholix toxin is Cholix$^{363}$ (SEQ ID NO: 26). In one embodiment, the truncated Cholix toxin is Cholix$^{362}$ (SEQ ID NO: 27). In one embodiment, the truncated Cholix toxin is Cholix$^{361}$ (SEQ ID NO: 28). In one embodiment, the truncated Cholix toxin is Cholix$^{360}$ (SEQ ID NO: 29). In one embodiment, the truncated Cholix toxin is Cholix$^{359}$ (SEQ ID NO: 30). In one embodiment, the truncated Cholix toxin is Cholix$^{358}$ (SEQ ID NO: 31). In one embodiment, the truncated Cholix toxin is Cholix$^{357}$ (SEQ ID NO: 32). In one embodiment, the truncated Cholix toxin is Cholix$^{356}$ (SEQ ID NO: 33). In one embodiment, the truncated Cholix toxin is Cholix$^{355}$ (SEQ ID NO: 34). In one embodiment, the truncated Cholix toxin is Cholix$^{354}$ (SEQ ID NO: 35). In one embodiment, the truncated Cholix toxin is Cholix$^{353}$ (SEQ ID NO: 36). In one embodiment, the truncated Cholix toxin is Cholix$^{352}$ (SEQ ID NO: 37). In one embodiment, the truncated Cholix toxin is Cholix$^{351}$ (SEQ ID NO: 38). In one embodiment, the truncated Cholix toxin is Cholix$^{350}$ (SEQ ID NO: 39). In one embodiment, the truncated Cholix toxin is Cholix$^{349}$ (SEQ ID NO: 40). In one embodiment, the truncated Cholix toxin is Cholix$^{348}$ (SEQ ID NO: 41).

Cholix toxin Domain Ib (amino acids 387-425 of SEQ ID NO: 1) is not essential for any known activity of Cholix, including cell binding, translocation, ER retention or ADP ribosylation activity. In various embodiments, the non-naturally occurring fusion molecules comprise a modified Cholix toxin truncated at an amino acid residue within Cholix toxin domain Ib, wherein the fusion molecule has the ability to activate the receptor for the biologically active cargo. In one embodiment, the truncated Cholix toxin is Cholix$^{425}$ (SEQ ID NO: 42). In one embodiment, the truncated Cholix toxin is Cholix$^{424}$ (SEQ ID NO: 43). In one embodiment, the truncated Cholix toxin is Cholix$^{423}$ (SEQ ID NO: 44). In one embodiment, the truncated Cholix toxin is Cholix$^{422}$ (SEQ ID NO: 45). In one embodiment, the truncated Cholix toxin is Cholix$_{421}$ (SEQ ID NO: 46). In one embodiment, the truncated Cholix toxin is Cholix$^{420}$ (SEQ ID NO: 47). In one embodiment, the truncated Cholix toxin is Cholix$^{419}$ (SEQ ID NO: 48). In one embodiment, the truncated Cholix toxin is Cholix$^{418}$ (SEQ ID NO: 49). In one embodiment, the truncated Cholix toxin is Cholix$^{417}$ (SEQ ID NO: 50). In one embodiment, the truncated Cholix toxin is Cholix$^{416}$ (SEQ ID NO: 51). In one embodiment, the truncated Cholix toxin is Cholix$^{415}$ (SEQ ID NO: 52). In one embodiment, the truncated Cholix toxin is Cholix$^{414}$ (SEQ ID NO: 53). In one embodiment, the truncated Cholix toxin is Cholix$^{413}$ (SEQ ID NO: 54). In one embodiment, the truncated Cholix toxin is Cholix$^{412}$ (SEQ ID NO: 55). In one embodiment, the truncated Cholix toxin is Cholix$^{411}$ (SEQ ID NO: 56). In one embodiment, the truncated Cholix toxin is Cholix$^{410}$ (SEQ ID NO: 57). In one embodiment, the truncated Cholix toxin is Cholix$^{409}$ (SEQ ID NO: 58). In one embodiment, the truncated Cholix toxin is Cholix$^{408}$ (SEQ ID NO: 59). In one embodiment, the truncated Cholix toxin is Cholix$^{407}$ (SEQ ID NO: 60). In one embodiment, the truncated Cholix toxin is Cholix$^{406}$ (SEQ ID NO: 61). In one embodiment, the truncated Cholix toxin is Cholix$^{405}$ (SEQ ID NO: 62). In one embodiment, the truncated Cholix toxin is Cholix$^{404}$ (SEQ ID NO: 63). In one embodiment, the truncated Cholix toxin is Cholix$^{403}$ (SEQ ID NO: 64). In one embodiment, the truncated Cholix toxin is Cholix$^{402}$ (SEQ ID NO: 65). In one embodiment, the truncated Cholix toxin is Cholix$^{401}$ (SEQ ID NO: 66). In one embodiment, the truncated Cholix toxin is Cholix$^{400}$ (SEQ ID NO: 67). In one embodiment, the truncated Cholix toxin is Cholix$^{399}$ (SEQ ID NO: 68). In one embodiment, the truncated Cholix toxin is Cholix$^{398}$ (SEQ ID NO: 69). In one embodiment, the truncated Cholix toxin is Cholix$^{397}$ (SEQ ID NO: 70). In one embodiment, the truncated Cholix toxin is Cholix$^{396}$ (SEQ ID NO: 71). In one embodiment, the truncated Cholix toxin is Cholix$^{395}$ (SEQ ID NO: 72). In one embodiment, the truncated Cholix toxin is Cholix$^{394}$ (SEQ ID NO: 73). In one embodiment, the truncated Cholix toxin is Cholix$^{393}$ (SEQ ID NO: 74). In one embodiment, the truncated Cholix toxin is Cholix$^{392}$ (SEQ ID NO: 75). In one embodiment, the truncated Cholix toxin is Cholix$^{391}$ (SEQ ID NO: 76). In one embodiment, the truncated Cholix toxin is Cholix$^{390}$ (SEQ ID NO: 77). In one embodiment, the truncated Cholix toxin is Cholix$^{389}$ (SEQ ID NO: 78). In one embodiment, the truncated Cholix toxin is Cholix$^{388}$ (SEQ ID NO: 79). In one embodiment, the truncated Cholix toxin is Cholix$^{387}$ (SEQ ID NO: 80).

Cholix toxin Domain III (amino acids 426-634 of SEQ ID NO: 1) is responsible for cytotoxicity and includes an endoplasmic reticulum retention sequence. Domain III mediates ADP ribosylation of elongation factor 2 ("EF2"), which inactivates protein synthesis. A Cholix that "lacks endogenous ADP ribosylation activity" or a "detoxified Cholix" refers to any Cholix described herein (including modified variants) that does not comprise Cholix domain III or which has been modified within domain III in a manner which detoxifies the molecule. For example, deletion of the glutamic acid (Glu) residue at amino acid position 581 of SEQ ID NO: 1 detoxifies the molecule. This detoxified Cholix is referred to as "Cholix ΔE581". In various embodiments, the portion of Cholix domain III other than the ER retention signal can be replaced by another amino acid sequence. This amino acid sequence can itself be non-immunogenic, slightly immunogenic, or highly immunogenic. A highly immunogenic ER retention domain is preferable for use in eliciting a humoral immune response. For example, Cholix domain III is itself highly immunogenic and can be used in fusion molecules where a robust humoral immune response is desired.

As used herein, "a detoxified Cholix sequence" may be a full length sequence or portion(s) of the full length sequence. Generally, a detoxified Cholix sequence has one or more domains or portions of domains with certain biological activities of a detoxified Cholix, such as a cell recognition domain, a translocation domain, or an endoplasmic reticulum retention domain. For example, a detoxified Cholix sequence may include only domain II and detoxified domain III. In another example, a detoxified Cholix sequence may include only domain Ia, domain II, and detoxified domain III. In another example, a detoxified Cholix sequence may include all of domains Ia, Ib, II, and detoxified III. Therefore, a detoxified Cholix sequence may be a contiguous sequence of the native Cholix, or it can be a sequence comprised of non-contiguous subsequences of the native Cholix that lacks ADP ribosylation activity. In one embodiment of the present disclosure, the non-naturally occurring fusion molecule comprises a mutated modified Cholix toxin, designated herein as Cholix toxin 4E581, having the amino acid sequence set forth in SEQ ID NO: 81.

Biologically Active Cargo

In addition to the modified Cholix toxin polypeptide, the fusion molecules of the present disclosure further comprise a biologically active cargo for delivery to a subject. A "biologically active cargo" as used herein includes, but is not limited to: a macromolecule, small molecule, peptide, polypeptide, nucleic acid, mRNA, miRNA, shRNA, siRNA, antisense molecule, antibody, DNA, plasmid, vaccine, polymer nanoparticle, or catalytically-active material.

In various embodiments, the biologically active cargo is a macromolecule that can perform a desirable biological activity when introduced to the bloodstream of the subject. For example, the biologically active cargo can have receptor binding activity, enzymatic activity, messenger activity (i.e., act as a hormone, cytokine, neurotransmitter, or other signaling molecule), luminescent or other detectable activity, or regulatory activity, or any combination thereof. In certain diagnostic embodiments, the biologically active cargo can be conjugated to or can itself be a pharmaceutically acceptable gamma-emitting moiety, including but not limited to, indium and technetium, magnetic particles, radiopaque materials such as air or barium and fluorescent compounds.

In various embodiments, the biologically active cargo of the fusion molecule can exert its effects in biological compartments of the subject other than the subject's blood. For example, in various embodiments, the biologically active cargo can exert its effects in the lymphatic system. In other embodiments, the biologically active cargo can exert its effects in an organ or tissue, such as, for example, the subject's liver, heart, lungs, pancreas, kidney, brain, bone marrow, etc. In such embodiments, the biologically active cargo may or may not be present in the blood, lymph, or other biological fluid at detectable concentrations, yet may still accumulate at sufficient concentrations at its site of action to exert a biological effect.

In various embodiments, the biologically active cargo is a protein that comprises more than one polypeptide subunit. For example, the protein can be a dimer, trimer, or higher order multimer. In various embodiments, two or more subunits of the protein can be connected with a covalent bond, such as, for example, a disulfide bond. In other embodiments, the subunits of the protein can be held together with non-covalent interactions. One of skill in the art can routinely identify such proteins and determine whether the subunits are properly associated using, for example, an immunoassay.

In various embodiments, the biologically active cargo to be delivered is selected from, e.g., cytokines and cytokine receptors such as Interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, lymphokine inhibitory factor, macrophage colony stimulating factor, platelet derived growth factor, stem cell factor, tumor growth factor-0, tumor necrosis factor, lymphotoxin, Fas, granulocyte colony stimulating factor, granulocyte macrophage colony stimulating factor, interferon-α, interferon-β, interferon-γ, growth factors and protein hormones such as erythropoietin, angiogenin, hepatocyte growth factor, fibroblast growth factor, keratinocyte growth factor, nerve growth factor, tumor growth factor-α, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II, chemokines such as ENA-78, ELC, GRO-α, GRO-β, GRO-γ, HRG, LEF, IP-10, MCP-1, MCP-2, MCP-3, MCP-4, MIP-1-α, MIP-1-β, MG, MDC, NT-3, NT-4, SCF, LIF, leptin, RANTES, lymphotactin, eotaxin-1, eotaxin-2, TARC, TECK, WAP-1, WAP-2, GCP-1, GCP-2; α-chemokine receptors, e.g., CXCR1, CXCR2, CXCR3, CXCR4, CXCR5, CXCR6, CXCR7; and β-chemokine receptors, e.g., CCR1, CCR2, CCR3, CCR4, CCR5, CCR6, CCR7.

Other examples of biologically active cargo that can be delivered according to the present disclosure include, but are not limited to, antineoplastic compounds, such as nitrosoureas, e.g., carmustine, lomustine, semustine, strepzotocin; methylhydrazines, e.g., procarbazine, dacarbazine; steroid hormones, e.g., glucocorticoids, estrogens, progestins, androgens, tetrahydrodesoxycaricosterone; immunoactive compounds such as immunosuppressives, e.g., pyrimethamine, trimethopterin, penicillamine, cyclosporine, azathioprine; and immunostimulants, e.g., levamisole, diethyl dithiocarbamate, enkephalins, endorphins; antimicrobial compounds such as antibiotics, e.g., 0-lactam, penicillin, cephalosporins, carbapenims and monobactams, 0-lactamase inhibitors, aminoglycosides, macrolides, tetracyclins, spectinomycin; antimalarials, amebicides; antiprotazoals; antifungals, e.g., amphotericin β, antivirals, e.g., acyclovir, idoxuridine, ribavirin, trifluridine, vidarbine, gancyclovir; parasiticides; anthelmintic; radiopharmaceutics; gastrointestinal drugs; hematologic compounds; immunoglobulins; blood clotting proteins, e.g., antihemophilic factor, factor IX complex; anticoagulants, e.g., dicumarol, heparin Na; fibrinosylin inhibitors, e.g., tranexamic acid; cardiovascular drugs; peripheral anti-adrenergic drugs; centrally acting antihypertensive drugs, e.g., methyldopa, methyldopa HCl; antihypertensive direct vasodilators, e.g., diazoxide, hydralazine HCI; drugs affecting renin-angiotensin system; peripheral vasodilators, e.g., phentolamine; antianginal drugs; cardiac glycosides; inodilators, e.g., amrinone, milrinone, enoximone, fenoximone, imazodan, sulmazole; antidysrhythmics; calcium entry blockers; drugs affecting blood lipids, e.g., ranitidine, bosentan, rezulin; respiratory drugs; sypathomimetic drugs, e.g., albuterol, bitolterol mesylate, dobutamine HCl, dopamine HCl, ephedrine So, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propranolol HCl; antimuscarinic drugs, e.g., anisotropine methylbromide, atropine SO4, clinidium Br, glycopyrrolate, ipratropium Br, scopolamine HBr; neuromuscular blocking drugs; depolarizing drugs, e.g., atracurium besylate, hexafluorenium Br, metocurine iodide, succinylcholine Cl, tubocurarine Cl, vecuronium Br; centrally acting muscle relaxants, e.g., baclofen; neurotransmitters and neurotransmitter agents, e.g., acetylcholine, adenosine, adenosine triphosphate; amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K+ channel toxins; antiparkinson drugs, e.g., amaltidine HCl, benztropine mesylate, carbidopa; diuretic drugs, e.g., dichlorphenamide, methazolamide, bendroflumethiazide, polythiazide; antimigraine drugs, e.g., carboprost tromethamine mesylate, methysergide maleate.

Still other examples of biologically active cargo that can be delivered according to the present disclosure include, but are not limited to, hormones such as pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists; hormonal contraceptives; testicular hormones; gastrointestinal hormones, e.g., cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, or sincalide.

Still other examples of biologically active cargo that can be delivered according to the present disclosure include, but are not limited to, enzymes such as hyaluronidase, streptokinase, tissue plasminogen activator, urokinase, PGE-adenosine deaminase; intravenous anesthetics such as droperidol, etomidate, fetanyl citrate/droperidol, hexobarbital, ketamine HCl, methohexital Na, thiamylal Na, thiopental Na; antiepileptics, e.g., carbamazepine, clonazepam, divalproex Na, ethosuximide, mephenyloin, paramethadione, phenyloin, primidone. In various embodiments, the biologically active cargo is an enzyme selected from hyaluronidase, streptokinase, tissue plasminogen activator, urokinase, PGE-adenosine deaminase.

Yet other examples of biologically active cargo that can be delivered according to the present disclosure include, but are not limited to, chemotherapeutics, such as chemotherapy or anti-tumor agents which are effective against various types of human cancers, including leukemia, lymphomas, carcinomas, sarcomas, myelomas etc., such as, for example, doxorubicin, mitomycin, cisplatin, daunorubicin, bleomycin, actinomycin D, and neocarzinostatin.

Modulators of Inflammation (Interleukin-10 and Related Cytokines)

Interleukin-10 (IL-10) is an important immunoregulatory cytokine produced by many cell populations and whose main biological function seems to be the limitation and termination of inflammatory responses and the regulation of differentiation and proliferation of several immune cells such as T cells, B cells, natural killer cells, antigen-presenting cells, mast cells, and granulocytes. More recent data suggests that IL-10 also mediates immunostimulatory properties that help to eliminate infectious and noninfectious particles with limited inflammation; Asadullah et al., *Pharmacol Rev,* 55:241-269, 2003. Moreover, numerous investigations suggest a major impact of IL-10 in inflammatory, malignant, and autoimmune diseases, and IL-10 overexpression was found in certain tumors such as melanoma, basal cell and squamous cell carcinoma and several lymphomas; Id. Five new human molecules structurally related to IL-10 have been discovered, IL-19 (Gallagher et al., *Genes Immun.,* 1:442-450, 2000); IL-20 (Blumberg et al., *Cell,* 104:9-19, 2001), IL-22 (Dumoutier et al., *Genes Immun.,* 1:488-494, 2000), IL-24 (Jiang et al., *Oncogene,* 11:2477-2486, 1995) and IL-26 (Knappe et al., *J. Virol.,* 74:3881-3887, 2000) and data suggests that immune cells are a major source of the new IL-10 family members; Wolk et al., *J. Immunol.,* 168:5397-5402, 2002.

While there were some promising results from IL-10 delivery on the course of several inflammatory diseases in experimental models, several clinical studies evaluating IL-10 as a therapeutic agent for the treatment of inflammatory and/or immune disorders remain somewhat disappointing, with much of the data conflicting; Asadullah et al.,

*Pharmacol Rev,* 55:241-269, 2003. Overall, the data suggests that IL-10 is safe and generally well tolerated, however, the ultimate local IL-10 concentration in the intestine after systemic administration with standard doses is too low, resulting in only marginal efficacy. Id. Unfortunately, the ability to sufficiently increase the doses is limited due to side effects (e.g., anemia, headache), and there are concerns higher doses of systemically administered IL-10 may be detrimental rather than helpful in certain indications, e.g., Crohn's; Herfarth et al, *Gut,* 50(2): 146-147, 2002.

In various embodiments, the biologically active cargo is a polypeptide that has been determined to be a modulator of inflammation in the GI tract selected from, e.g., interleukin-10, interleukin-19, interleukin-20, interleukin-22, interleukin-24, or interleukin-26. Interleukin-10 (IL-10) was first identified as a product of the type 2 helper T cell and later shown to be produced by other cell types including B cells and macrophages (Moore et al., Annu Rev Immunol, 19:683-765, 2001). It also inhibits the synthesis of several cytokines produced from type 1 helper T cells, such as γ-interferon, IL-2, and tumor necrosis factor-α (TNF-α) (Fiorentino et al., *J Immunol,* 146:3444-3451, 1991). The ability of IL-10 to inhibit cell-mediated immune response modulators and suppress antigen-presenting cell-dependent T cell responses demonstrates IL-10 has immunosuppressive properties. This cytokine also inhibits monocyte/macrophage production of other cytokines such as IL-1, IL-6, IL-8, granulocyte-macrophage colony-stimulating factor (GM-CSF), granulocyte colony-stimulating factor (G-CSF), and TNF-α.

The IL-10 protein forms a functional dimer that becomes biologically inactive upon disruption of the non-covalent interactions connecting its two monomer subunits. The N-terminus does not appear to be directly involved with IL-10 receptor activation. Thus, in one aspect of the disclosure, a fusion molecule is constructed via conjugation through the N-terminus of the IL-10 protein to the C-terminus of a modified Cholix toxin using a cleavable linker. Such a construction may result in a solution dimer as a result of IL-10 interactions.

In various embodiments, the biologically active cargo is human interleukin-10 having the amino acid sequence set forth in SEQ ID NO: 82:

```
                                     (SEQ ID NO: 82)
MHSSALLCCLVLLTGVRASPGQGTQSENSCTHFPGNLPNMLRDLRDAFSR

VKTFFQMKDQLDNLLLKESLLEDFKGYLGCQALSEMIQFYLEEVMPQAEN

QDPDIKAHVNSLGENLKTLRLRLRRCHRFLPCENKSKAVEQVKNAFNKLQ

EKGIYKAMSEFDIFINYIEAYMTMKIRN
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 82.

IL-19 a cytokine that belongs to the IL-10 cytokine subfamily. This cytokine is found to be preferentially expressed in monocytes. It can bind the IL-20 receptor complex and lead to the activation of the signal transducer and activator of transcription 3 (STAT3) (Yamamoto-Furusho J K, et al. Hum Immunol, 72(11):1029-32, 2011). In various embodiments, the biologically active cargo is human interleukin-19 having the amino acid sequence set forth in SEQ ID NO: 83:

```
                                     (SEQ ID NO: 83)
MKLQCVSLWLLGTILILCSVDNHGLRRCLISTDMHHIEESFQEIKRAIQA

KDTFPNVTILSTLETLQIIKPLDVCCVTKNLLAFYVDRVFKDHQEPNPKI

LRKISSIANSFLYMQKTLRQCQEQRQCHCRQEATNATRVIHDNYDQLEVH

AAAIKSLGELDVFLAWINKNHEVMSSA
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 83.

IL-20 is a cytokine structurally related to interleukin 10 (IL-10). This cytokine has been shown to transduce its signal through signal transducer and activator of transcription 3 (STAT3) in keratinocytes. A specific receptor for this cytokine is found to be expressed in skin and upregulated dramatically in psoriatic skin, suggesting a role for this protein in epidermal function and psoriasis (Yamamoto-Furusho J K, et al. Immunol Lett, 149(1-2):50-3 2013). In various embodiments, the biologically active cargo is human interleukin-20 having the amino acid sequence set forth in SEQ ID NO: 84:

```
                                  (SEQ ID NO: 84)
MKASSLAFSLLSAAFYLLWTPSTGLKTLNLGSCVIATNLQEIRN

GFSEIRGSVQAKDGNIDIRILRRTESLQDTKPANRCCLLRHLLR

LYLDRVFKNYQTPDHYTLRKISSLANSFLTIKKDLRLCHAHMTC

HCGEEAMKKYSQILSHFEKLEPQAAVVKALGELDILLQWMEETE
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 84.

IL-22 is a cytokine structurally related to interleukin 10 (IL-10). IL-22 secreting CD4(+) T (Th22) cells and IL-22 are involved in the pathogenesis of autoimmune disease, and may play an important role in the pathogenesis of NMO and MS (Xu et al., J Neuroimmunol., August 15; 261(1-2):87-91, 2013). In various embodiments, the biologically active cargo is human interleukin-22 having the amino acid sequence set forth in SEQ ID NO: 85:

```
                                  (SEQ ID NO: 85)
MAALQKSVSSFLMGTLATSCLLLLALLVQGGAAAPISSHCRLDK

SNFQQPYITNRTFMLAKEASLADNNTDVRLIGEKLFHGVSMSER

CYLMKQVLNFTLEEVLFPQSDRFQPYMQEVVPFLARLSNRLSTC

HIEGDDLHIQRNVQKLKDTVKKLGESGEIKAIGELDLLFMSLRN

ACI
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 85.

IL-24 is a cytokine structurally related to interleukin 10 (IL-10) which can induce apoptosis selectively in various cancer cells. Overexpression of this gene leads to elevated expression of several GADD family genes, which correlates with the induction of apoptosis. The phosphorylation of mitogen-activated protein kinase 14 (MAPK7/P38), and heat shock 27 kDa protein 1 (HSPB2/HSP27) are found to be induced by this gene in melanoma cells, but not in normal immortal melanocytes (Lin B W, et al., J Korean Med Sci, 28(6):833-9, 2013). In various embodiments, the biologically active cargo is human interleukin-24 having the amino acid sequence set forth in SEQ ID NO: 86:

```
                                        (SEQ ID NO: 86)
MNFQQRLQSLWTLASRPFCPPLLATASQMQMVVLPCLGFTLLLW

SQVSGAQGQEFHFGPCQVKGVVPQKLWEAFWAVKDTMQAQDNIT

SARLLQQEVLQNVSDAESCYLVHTLLEFYLKTVFKNYHNRTVEV

RTLKSFSTLANNFVLIVSQLQPSQENEMFSIRDSAHRRFLLFRR

AFKQLDVEAALTKALGEVDILLTWMQKFYKL
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 86.

IL-26 was identified by its overexpression specifically in herpesvirus saimiri-transformed T cells. The encoded protein is a member of the IL-10 family of cytokines. It is a secreted protein and may function as a homodimer. This protein is thought to contribute to the transformed phenotype of T cells after infection by herpesvirus saimiri (Corvaisier M, et al. PLoS Biol, 10(9):e1001395, 2012). In various embodiments, the biologically active cargo is human interleukin-26 having the amino acid sequence set forth in SEQ ID NO: 87:

```
                                        (SEQ ID NO: 87)
MLVNFILRCGLLLVTLSLAIAKHKQSSFTKSCYPRGTLSQAVDA

LYIKAAWLKATIPEDRIKNIRLLKKKTKKQFMKNCQFQEQLLSF

FMEDVFGQLQLQGCKKIRFVEDFHSLRQKLSHCISCASSAREMK

SITRMKRIFYRIGNKGIYKAISELDILLSWIKKLLESSQ
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 87.

Importantly, the non-naturally occurring fusion molecules which lack a cleavable linker can be advantageous in that the anchoring effect of the modified Cholix toxin by its receptor(s) at the surface of, e.g., immune cells that also express the receptor for the IL-10 (but in considerably lower quantity) can allow for greater exposure of the IL-10 at the surface of the targeted cells, and provide a synergistic effect via the binding of the Cholix to its receptor and the binding of IL-10 to the IL-10R.

Tumor Necrosis Factor Super Family

Tumor necrosis factor is a rapidly growing superfamily of cytokines (hereinafter "TNFSF") that interact with a corresponding superfamily of receptors (hereinafter "TNFSFR"). Since the discovery of tumor necrosis factor-alpha ("TNF-α") about 25 years ago, the TNFSF has grown to a large family of related proteins consisting of over 20 members that signal through over 30 receptors (see, e.g., "Therapeutic Targets of the TNF Superfamily", edited by Iqbal S. Grewal, Landes Bioscience/Springer Science+Business Media, LLC dual imprint/Springer series: Advances in Experimental Medicine and Biology, 2009). Members of TNFSF have wide tissue distribution and TNFSF ligand-receptor interactions are involved in numerous biological processes, ranging from hematopoiesis to pleiotropic cellular responses, including activation, proliferation, differentiation, and apoptosis. TNFSF ligand-receptor interactions have also been implicated in tumorigenesis, transplant rejection, septic shock, viral replication, bone resorption and autoimmunity. The particular response depends upon the receptor that is signaling, the cell type, and the concurrent signals received by the cell.

Because a number of TNFSF members are expressed on tumor cells, antibody based therapies are being developed to target these molecules and some are currently undergoing clinical trials (e.g., TNF-α for human use in the treatment of sarcomas and melanomas (Eggermont et al., Lancet Oncol, 4:429-437, 2003; Lans et al., Clin Cancer Res, 7:784-790, 2001). In addition, many of these molecules are also being exploited as targets for antibody-drug conjugates (e.g., CD30 and CD70), or exploited for radioimmunotherapy (e.g., the BLyS receptors TACI and BR3) (Buchsbaum et al., J Nucl Med, 44:434-436, 2003).

Similarly, because a number of TNFSF members have been implicated in both innate and adaptive immune responses such as defense against pathogens, inflammatory response and autoimmunity, approaches to target many of TNFSF receptors and ligands for treatment of autoimmunity and other inflammatory diseases are being exploited. Indeed, a number of biologic TNF blocking therapies (hereinafter "TNF inhibitors") including humanized/human monoclonal antibodies (e.g., infliximab (REMICADE®) or adalimumab (HUMIRA®)) or recombinant fusion proteins of IgG and soluble TNFSF receptors (e.g., etanercept (ENBREL®)) have been developed and are now being used in humans to inhibit the inflammation associated with Crohn's disease and rheumatoid arthritis (Mitoma et al., Arthritis Rheum, 58:1248-1257, 2008; Shealy et al., Handb Exp Pharmacol, 181:101-129, 2008). Thus, the potential to deliver such agents locally including, but not limited to, intestinal and pulmonary mucosa, would provide added benefits for efficacy and safety.

Although these various TNF inhibitors have been approved for human therapies and are being successfully used in human patients, there remains a number of toxicities associated with these TNF inhibitors, e.g., hepatotoxicity, thromboembolic complications, and increased risk of development of tuberculosis and lymphoma (Gardam et al., Lancet Infect Dis, 3:148-155, 2003). Moreover, while effective in halting progression of disease, these agents are very expensive, generally administered intravenously or subcutaneously, and do not cure the diseases. The continued examination of signal transduction of TNFSF members is needed to develop approaches for tissue specific interventions, which could allow targeted therapies to have fewer side effects.

In various embodiments, the biologically active cargo is a TNF inhibitor that is an isolated antibody or an antibody fragment. Isolated antibodies and antibody fragments useful in the constructs and methods of the present invention include, without limitation, monoclonal Abs (mAbs), polyclonal Abs, Ab fragments (e.g., Fab, Fab', F(ab')2, Fv, Fc, etc.), chimeric Abs, mini-Abs or domain Abs (dAbs), dual specific Abs, bispecific Abs, heteroconjugate Abs, single chain Abs (SCA), single chain variable region fragments (ScFv), fusion proteins comprising an Ab portion or multiple Ab portions, humanized Abs, fully human Abs, and any other modified configuration of the immunoglobulin (Ig) molecule that comprises an antigen recognition site of the required specificity.

Anti-TNF-α Antibodies. The FDA approved anti-TNF-α antibody, Adalimumab (Abbvie HUMIRA®; DrugBank DB 00051) has been used to treat humans. In various embodiments of the present invention, the biologically active cargo is a human antibody or antigen-binding fragment comprising the heavy chain variable region sequence set forth in SEQ ID NO: 88:

```
                                        (SEQ ID NO: 88)
EVQLVESGGGLVQPGRSLRLSCAASGFTFDDYAMHWVRQAPGKG

LEWVSAITWNSGHIDYADSVERGFTISRDNAKNSLYLQMNSLRA

EDTAVYYCAKVSYLSTASSLDYWGQGTLVTVSSASTKGPSVFPL

APSSKSTSGGTAALGCLVKDYFPEPVTVSWNSGALTSGVHTFPA

VLQSSGLYSLSSVVTVPSSSLGTQTYICNVNHKPSNTKVDKKVE

PKSC
``` and the light chain variable region sequence set forth in SEQ ID NO:89:

```
                                        (SEQ ID NO: 89)
DIQMTQSPSSLSASVGDRVTITCRASQGIRNYLAWYQQKPGKAP

KLLIYAASTLQSGVPSRFSGSGSGTDFTLTISSLQPEDVATYYC

QRYNRAPYTFGQGTKVEIKRTVAAPSVFIFPPSDEQLKSGTASV

VCLLNNFYPREAKVQWKVDNALQSGNSQESVTEQDSKDSTYSLS

STLTLSKADYEKHKVYACEVTHQGLSSPVTKSFNRGEC
``` or an antigen-binding or an immunologically functional immunoglobulin fragment thereof.

In various embodiments, the invention provides antibodies, comprising a heavy chain and a light chain, wherein the heavy chain comprises a heavy chain variable region, and wherein the heavy chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO:88; and wherein the light chain comprises a light chain variable region, and wherein the light chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in any of SEQ ID NO:89; wherein the antibody binds specifically to human TNF-α.

The FDA approved anti-TNF-α antibody, Infliximab (Centocor REMICADE®; DrugBank DB 00065) has been used to treat humans. In various embodiments of the present invention, the biologically active cargo is a human antibody or antigen-binding fragment comprising the heavy chain variable region sequence set forth in SEQ ID NO: 90:

```
                                        (SEQ ID NO: 90)
QVQLVESGGGVVQPGRSLRLSCAASGFTFSSYAMHWVRQAPGKGL

EWVAIISFDGSNKSSADSVKGRFTUSRRNSKNALFLQMNSLRAED

TAVFYCARDRGVSAGGNYYYYGMDVWGQGTTVTVSS
``` and the light chain variable region sequence set forth in SEQ ID NO:91:

```
                                        (SEQ ID NO: 91)
EIVLTQSPATLSLSPGERATLSCRASQSVSSYLAWYQQKPGQAPR

LLIYDASNRATGIPARFSGSGSGTRFTLTISSLEPEDFAVYYCQQ

RSNWPPFTFGPGTKVDIL
``` or an antigen-binding or an immunologically functional immunoglobulin fragment thereof.

In various embodiments, the invention provides antibodies, comprising a heavy chain and a light chain, wherein the heavy chain comprises a heavy chain variable region, and wherein the heavy chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO:90; and wherein the light chain comprises a light chain variable region, and wherein the light chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in any of SEQ ID NO:91; wherein the antibody binds specifically to human TNF-α.

Antibodies to several other TNFSF ligands or TNFSFRs have been described in the literature, and evaluated as therapeutic candidates in the treatment or prevention of a variety of inflammatory diseases, autoimmune diseases and cancer. Nucleotide and amino acid sequences of antibodies to the designated TNFSF polypeptides or TNFSFRs are readily available from publicly available databases. A comprehensive review of such antibodies as well as additional TNF inhibitors is provided in "Therapeutic Targets of the TNF Superfamily", edited by Iqbal S. Grewal, Landes Bioscience/Springer Science+Business Media, LLC dual imprint/Springer series: Advances in Experimental Medicine and Biology, 2009, which is hereby incorporated by reference in its entirety for the purpose of teaching such TNF inhibitors.

In various embodiments, the biologically active cargo is a TNFSF inhibitor that comprises a soluble receptor or soluble co-ligand. The terms "soluble receptor", "soluble cytokine receptor" (SCR) and "immunoadhesin" are used interchangeably to refer to soluble chimeric molecules comprising the extracellular domain of a receptor, e.g., a receptor of a TNFSF member and an Ig sequence, which retains the binding specificity of the receptor and is capable of binding to the TNFSF member. In various embodiments, a TNFSFSCR comprises a fusion of a TNFSFR amino acid sequence (or a portion thereof) from a TNFSF member extracellular domain capable of binding the TNFSF member (in some embodiments, an amino acid sequence that substantially retains the binding specificity of the TNFSFR) and an Ig sequence. Two distinct types of TNFSFR are known to exist: Type I TNFSFR (TNFSFRI) and Type II TNFSFR (TNFSFRII). In various embodiments, the TNFSF receptor is a human TNFSF receptor sequence, and the fusion is with an Ig constant domain sequence. In other embodiments, the Ig constant domain sequence is an Ig heavy chain constant domain sequence. In other embodiments, the association of two TNF receptor-Ig heavy chain fusions (e.g., via covalent linkage by disulfide bond(s)) results in a homodimeric Ig-like structure.

An example of a commercially available soluble receptor useful in the present invention is ENBREL® (etanercept). ENBREL® consists of recombinant human TNFR-p75-Fc dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept is produced by recombinant DNA technology in a Chinese hamster ovary (CHO) mammalian cell expression system. It consists of 934 amino acids. The product is made by encoding the DNA of the soluble portion of human TNFR-p75 with the Fc portion of IgG. In various embodiments of the present invention, the biologically active cargo is a TNF inhibitor that is dimeric fusion protein comprising the sequence set forth in SEQ ID NO: 92:

```
                                          (SEQ ID NO: 92)
LPAQVAFTPYAPEPGSTCRLREYYDQTAQMCCSKCSPGQHAKVFC

TKTSDTVCDSCEDSTYTQLWNWVPECLSCGSRCSSDQVETQACTR

EQNRICTCRPGWYCALSKQEGCRLCAPLRKCRPGFGVARPGTETS

DVVCKPCAPGTFSNTTSSTDICRPHQICNVVAIPGNASMDAVCTS

TSPTRSMAPGAVHLPQPVSTRSQHTQPTPEPSTAPSTSFLLPMGP

SPPAEGSTGDEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSREEMTKNQVSLTCLVKGFYPSDIAVEWESNG

QPENNYKTTPPVLDSDGSFFLYSKLTVDKSRWQQGNVFSCSVMHE

ALHNHYTQKSLSLSPGK
``` or a fragment or variant thereof.

In various embodiments, the biologically active cargo contains an amino acid sequence that shares an observed homology of at least about 75%, at least about 80%, at least about 85%, at least about 90%, 91%, 92%, 93%, 94%, 95%, 96%, 97%, 98%, or at least about 99% identity to the sequence of SEQ ID NO: 92.

An illustrative, but not limiting list of suitable TNFSF ligands and TNFSFRs from which a TNF inhibitor will be derived and used as a biologically active cargo in the constructs and methods of the present invention is provided in Table 2.

TABLE 2

|  | RefSeq (protein) |
|---|---|
| TNFSF Ligands | |
| Tumor necrosis factor-α ("TNF-α") | NP_000585.2 |
| lymphotoxin-α ("LT-α") | NP_000586.2 |
| lymphotoxin-β ("LT-β") | NP_002332.1 |
| CD30 ligand | NP_001235.1 |
| CD40 ligand | NP_000065.1 |
| CD70 ligand | NP_001243.1 |
| OX40 ligand | NP_001284491.1 |
| 41BB ligand | NP_001552.2 |
| Apo1 ligand (or FasL or CD95L) | NP_000630.1 |
| Apo2 ligand (or TRAIL, AIM-1 or AGP-1) | NP_001177871.1 |
| Apo3 ligand (or TWEAK) | NP_003800.1 |
| APRIL | NP_001185551.1 |
| LIGHT | NP_003798.2 |
| OPG ligand (or RANK ligand) | NP_003692.1 |
| BlyS (or THANK) | NP_001139117.1 |
| BCMA | NP_001183.2 |
| TACI | NP_036584.1 |
| TNFSFRs | |
| TNFR1 | NP_001056.1 |
| TNFR2 | NP_001057.1 |
| lymphotoxin-βR | NP_001257916.1 |
| CD40 | NP_001241.1 |
| CD95 (or FAS or APO-1) | NP_000034.1 |
| OPG | NP_002537.3 |
| RANK | NP_001257878.1 |
| CD30 | NP_001234.3 |
| CD27 | NP_001233.1 |
| OX40 (or CD134) | NP_003318.1 |
| 41BB | NP_001552.2 |
| NGFR | NP_002498.1 |
| BCMA | NP_001183.2 |
| TAC1 | NP_036584.1 |
| EDA2R | NP_001186616.1 |
| TROY | NP_001191387.1 |
| DR6 | NP_055267.1 |
| DR5 (or TRAILR2) | NP_003833.4 |
| DR4 | NP_003835.3 |
| DR3 | NP_001034753.1 |
| HVEM | NP_001284534.1 |
| LTβR | NP_001257916.1 |
| GITR | NP_004186.1 |
| DcR3 | NP_003814 |
| Fn14 (or TWEAKR) | NP_057723.1 |
| BAFF | NP_443177.1 |

Glucose-Lowering Agents

In various embodiments, the biologically active cargo is a glucose-lowering agent. In various embodiments, the glucose-lowering agent is a peptide that comprises about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 150, about 200, about 250, about 300, about 400, about 500, about 600, about 700, about 800, about 900 or about 1000 amino acids.

An illustrative, but not limiting, list of suitable glucose metabolism-related proteins to be used as the glucose-lowering agent in the fusion molecules of the present disclosure, or from which the glucose-lowering agents contemplated for use as a glucose-lowering agent could be derived, is provided in Table 3.

TABLE 3

| Glucose metabolism-related proteins | RefSeq (NCBI/Uniprot) |
|---|---|
| Glucagon proprotein | NP_002045.1 |
| Glucagon peptide | NP_002045.1 (aa 53-81) |

TABLE 3-continued

| Glucose metabolism-related proteins | RefSeq (NCBI/Uniprot) |
|---|---|
| Glucagon-like peptide 1 | NP_002045.1 (aa 98-128) |
| Glucagon-like peptide 2 | NP_002045.1 (aa 146-178) |
| Glicentin | P01275 (aa 21-89) |
| Glicentin-related polypeptide | P01275 (aa 21-50) |
| Gastric inhibitory polypeptide preprotein | NP_004114.1 |
| Gastric inhibitory polypeptide | NP_004114.1 (aa 52-93) |
| Dipeptidyl peptidase 4 | P27487 |
| Glucose transporter member 4 | NP_001033.1 |
| Preproglucagon | AAA52567.1 |
| Insulin receptor substrate 1 | NP_005535.1 |
| Insulin | P01308 |
| Apolipoprotein A-II | P02652 |
| Solute carrier family 2, faciliated glucose transporter member 1 | P11166 |
| Glycogen synthase 1 | P13807 |
| Glycogen synthase 2 | P54840 |
| Tyrosin-protein phosphatase non-receptor type 1 | P18031 |
| RAC-alpha serinel threonine-protein kinase | P31749 |
| Peroxisome proliferator-activated receptor gamma | P37231 |
| Hexokinase 3 | P52790 |
| Phosphatidylinositol-3,4,5-triphosphate 3-phosphatase and dual-specificty protein | P60484 |
| Pyruvate dehydrogenase kinase 1 | Q15118 |
| Calcium-binding and coiled-coil domain-containing protein 1 | Q9P1Z2 |
| Max-like protein X | Q9UH92 |
| Fructose-bisphosphate aldolase A | P04075 |
| Glucagon-like peptide 1 receptor | P43220 |
| Glucagon-like peptide 2 receptor | O95838 |
| Gastric inhibitory polypeptide receptor | P48546 |
| Insulin-like growth factor 1 receptor | P08069.1 |
| Insulin-like growth factor 2 receptor | P11717.3 |
| Insulin Receptor | P06213 |
| GLP-1 agonist-Exenatide | DB01276 |
| GLP-1 agonist-Liraglutide | DB06655 |

Glucagon-like peptide-1 (GLP-1), a member of the proglucagon incretin family synthesized in intestinal L-cells by tissue-specific post-translational processing of the glucagon precursor preproglucagon, is a potent glucose-lowering agent implicated in the control of appetite and satiety. GLP-1 acts through GLP-1 receptor (GLP-1R), which is widely distributed in tissues, including brain, pancreas, intestine, lung, stomach, and kidney. The effects of GLP-1 appear to be both insulinotropic and insulinomimetic, depending on the ambient glucose concentration. Due to their ability to increase insulin secretion from the pancreas, increase insulin-sensitivity in both alpha cells and beta cells, and decrease glucagon secretion from the pancreas, GLP-1 and its analogs have attracted considerable attention as a therapeutic strategy for diabetes.

Several clinical trials have studied the addition of GLP-1 agonists in conjunction with ongoing insulin therapy and several GLP-1 agonists have been approved for treatment of T2D, including, e.g., exenatide (tradename Byetta®, Amylin/Astrazeneca); liraglutide (tradename Victoza®, Novo Nordisk A/S); lixisenatide (tradename Lyxumia®, Sanofi); albiglutide (tradename Tanzeum®, Glaxo SmithKline); dulaglutide (tradename Trulicity®, Eli Lilly). While proven efficacious, the major drawback associated with the clinical use of GLP-1 agonists is the short biological half-life, necessitating continuous administration intravenously or by frequent subcutaneous injections, and all GLP-1 drugs approved to date are subcutaneous administered on a twice daily or once weekly basis. Moreover, there are safety concerns associated with the use of these GLP-1 agonists, namely, pancreatitis and pancreatic neoplasia, hypoglycemia, and renal impairment. Other reported side effects include gastrointestinal disorders, such as dyspepsia, decreased appetite, nausea, vomiting, abdominal pain, diarrhea, dizziness, headache, and feeling jittery. As such, there continues to be extensive research directed to preparing analogs of the natural GLP-1 that are longer lasting, as well as development of sustained release and other related technologies in order to lower the frequency of injections for the T2D patients.

In various embodiments, the biologically active cargo is GLP-1 agonist having the amino acid sequence set forth in SEQ ID NO: 93:

```
                                           (SEQ ID NO: 93)
HGEGTFTSDLSKQMEEEAVRLFIEWLKNGGPSSGAPPPS
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 93.

In various embodiments, the biologically active cargo is GLP-1 agonist having the amino acid sequence set forth in SEQ ID NO: 94:

```
                                           (SEQ ID NO: 94)
HAEGTFTSDVSSYLEGQAAKEEFIIAWLVKGRG
``` or a fragment or variant thereof.

In various embodiments, the biologically active cargo contains an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 94.

Human Growth Hormone

Growth Hormone (GH) (also known as somatropin or somatotropin) is the master hormone in the human body, and is synthesized and secreted by the endocrine system. This hormone controls essential functions like: growth and replication of cells in various organs of the body. Some of the essential functions of GH include: controlling muscle growth, improving bone mineralization and strength, reducing fat deposition, and sustaining good energy levels. The production and secretion of the growth hormone is controlled by Growth Hormone Releasing Hormone (GHRH), which is secreted by the hypothalamus. The GHRH stimulates the pituitary gland to produce GH, which is directly released into the blood stream. The GH in turn stimulates the liver to produce Insulin-like Growth Factor (IGF-1) which stimulates the proliferation of chondrocytes (cartilaginous cells), promotes differentiation of myoblasts and enhances protein synthesis, which in turn, helps in the growth of other muscles and tissue cells.

In the US, synthetically produced human growth hormone (HGH) has been used in the pediatric population to treat short stature due to growth hormone deficiency (GHD), Turner syndrome (TS), Noonan syndrome, Prader-Willi syndrome, short stature homeobox-containing gene (SHOX) deficiency, chronic renal insufficiency, idiopathic short stature and children small for gestational age. In adults, HGH has been used to treat short bowel syndrome, a condition in which nutrients are not properly absorbed due to sever intestinal disease or the surgical removal of a large portion of the small intestine, GH deficiency due to rare pituitary tumors or their treatment, and muscle-wasting disease associated with HIV/AIDS.

Growth hormone deficiency (GHD) is a rare disorder that includes a group of different pathologies characterized by the inadequate secretion of growth hormone (GH) from the anterior pituitary gland, a small gland located at the base of the brain that is responsible for the production of several hormones. GHD may occur by itself or in combination with other pituitary hormone deficiencies. GHD may be present from birth (congenital) or acquired as a result of trauma, infiltrations, tumor or radiation therapy. There is a third category that has no known cause (idiopathic). Childhood-onset GHD may be all three: congenital, acquired, or idiopathic. It results in growth retardation, short stature, and maturation delays reflected by the delay of lengthening of the bones of the extremities that is inappropriate to the chronological age of the child. Adult-onset GHD is most often acquired from a pituitary tumor or trauma to the brain but may also be idiopathic. It is characterized by a number of variable symptoms including reduced energy levels, altered body composition, osteoporosis (reduced bone mineral density), reduced muscle strength, lipid abnormalities such as increased LDL or cholesterol levels, insulin resistance, and impaired cardiac function. Adult GHD has been estimated to affect 1 in 100,000 people annually, while its incidence rate is approximately 2 cases per 100,000 population when childhood-onset GHD patients are considered. About 15-20% of the cases represent the transition of childhood GHD into adulthood (Stochholm K et al., *Eur J Endocrinol.*,155:61-71, 2006).

Turner (or Ullrich-Turner) syndrome (TS) is a chromosomal abnormality characterized by the absence of the entire chromosome X or a deletion within that chromosome and that affects development in females. The most common feature of Turner syndrome is short stature, which becomes evident by about age 5. This condition occurs in about 1 in 2,500 newborn girls worldwide, but it is much more common among pregnancies that do not survive to term (miscarriages and stillbirths). As a chromosomal condition, there is no cure for Turner syndrome.

Recombinant DNA-derived human growth hormone is the only drug approved specifically for treatment of GHD and TS. As of 2005, various recombinant human growth hormones (also referred to as somatropin [rDNA origin] for injection) available in the United States (and their manufacturers) included NUTROPIN® (Genentech), HUMATROPE® (Lilly), GENOTROPIN® (Pfizer), NORDITROPIN® (Novo), and SAIZEN® (Merck Serono). In 2006, the U.S. Food and Drug Administration (FDA) approved a version of rHGH called OMNITROPE® (Sandoz). A sustained-release form of human growth hormone, NUTROPIN DEPOT® (Genentech/Alkermes) was approved by the FDA in 1999, allowing for fewer injections (every 2 or 4 weeks instead of daily); however, the product was discontinued by Genentech/Alkermes in 2004 for financial reasons. Additional approved recombinant HGH products include SEROSTIM® (EMD Serono), TEV-TROPIN® (Teva) and ZORBITIVE® (Merck Serono) for short bowel syndrome.

While proven to be the most effective, spontaneous and trusted treatment option for the management of growth disorders such as GHD, these injectable rHGH's have some significant limitations including, e.g., 1) complications associated with prolonged use and high dosages which are severe and irreversible, and include, e.g., the probability of developing diabetes, cardiovascular disorders and colon cancer. Other common side effects include: joint pain, generalized edema, severe headache, hypoglycemia, wrist pain (carpel tunnel syndrome), increased level of LDL in the blood increasing the possibility of developing atherosclerosis, etc.; 2) HGH injections are not available over the counter, nevertheless, due to rigid FDA norms, black-marketing is rampant. The procurement of the HGH injections without medical prescription is considered illegal and is punishable by law, with imprisonment and fine; and 3) the cost of the treatment is exorbitant. Depending upon the pharmaceutical company the cost of HGH injections for a month of treatment, typically range from between $800 to $3000. Finally, conventional methods using rHGH typically involve multi-dose regimens in which the HGH is administered via subcutaneous injection. The inconvenience, pain and social stigma associated with such methods can be considerable. Management of the pediatric population to treat short stature due to growth hormone deficiency (GHD), Turner syndrome (TS) and related disorders, with these highly invasive and repetitive therapies can be especially difficult.

Full length human HGH consists of 191 amino acids. HGH produced using molecular biological techniques may have an amino acid sequence identical to naturally occurring HGH. Alternatively, the HGH used may be an HGH analog comprising one or more variations in amino acid sequence with respect to the native hormone. These amino acid variations may provide enhanced biological activity or some other biological or logistical advantages. In various embodiments, the recombinant HGH comprises the amino acid sequence set forth in Genbank Accession No. P01241. The HGH amino acid sequence (without the 26 aa signal sequence of P01241) is set forth in SEQ ID NO: 95:

```
                                           (SEQ ID NO: 95)
FPTIPLSRLFDNAMLRAHRLHQLAFDTYQEFEEAYIPKEQKYSFL

QNPQTSLCFSESIPTPSNREETQQKSNLELLRISLLLIQSWLEPV

QFLRSVFANSLVYGASDSNVYDLLKDLEEGIQTLMGRLEDGSPRT

GQIFKQTYSKFDTNSHNDDALLKNYGLLYCFRKDMDKVETFLRIV

QCRSVEGSCGF
```

HGH of the present disclosure refers to HGH from any source which has the sequence of SEQ ID NO: 95, including isolated, purified and/or recombinant HGH produced from any source or chemically synthesizes, for example using solid phase synthesis. Also included herein are conserved amino acid substitutions of native HGH. For example, conservative amino acid changes may be made, which although they alter the primary sequence of the protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. In various embodiments, the HGH has an amino acid sequence that shares an observed homology of, e.g., at least about 75%, at least about 80%, at least about 85%, at least about 90%, 91%, 92%, 93%, 94%, 95%, 96%, 97%, 98%, or at least about 99% with the sequence of SEQ ID NO: 95.

In various embodiments, the HGH contemplated for use in the fusion molecules of the present disclosure include human growth hormone variants and mutants which have been extensively described in the art (see, e.g. U.S. Pat. No.

8,637,646 (Wells et al) and references cited therein, and US 20110130331 (Guyon et al), each incorporated by reference in its entirety herein for the specific purpose of providing such growth hormone variants and mutants).

In various embodiments, the HGH contemplated for use in the fusion molecules of the present disclosure include, e.g., NUTROPIN® (Genentech), HUMATROPE® (Lilly), GENOTROPIN® (Pfizer), NORDITROPIN® (Novo), SAIZEN® (Merck Serono), OMNITROPE® (Sandoz), SEROSTIM® (EMD Serono), TEV-TROPIN® (Teva) and ZORBITIVE® (Merck Serono).

An illustrative, but not limiting, list of suitable growth hormone proteins to be used as the growth hormone in the fusion molecules of the present disclosure, or from which the growth hormones contemplated for use as a growth hormone could be derived, is provided in Table 4.

TABLE 4

|  | RefSeq (NCBI/Uniprot) |
|---|---|
| Growth Hormone Related Proteins | |
| Somatotropin | P01241 |
| Synthetic Human Growth Hormone | AAA72260.1 |
| Synthetic Human Growth Hormone Partial | CAA01435 |
| Synthetic Human Growth Hormone Partial | CAA00380 |
| Human Growth Hormone 2 | P01242 |
| Somatoliberin | P01286.1 |
| Appetite-regulating Hormone | Q9UBU3 |
| Leptin | P41159 |
| Growth Hormone Receptor Proteins | |
| Growth Hormone Receptor | P10912 |
| Growth Hormone-Releasing Hormone Receptor | Q02643 |
| Growth Hormone Secretagogue Receptor | Q92847 |
| Growth Hormone-Releasing Hormone Receptor form a | P78470 |
| Growth Hormone Receptor | E9PCN7 |

Insertion Site for Attachment of the Biologically Active Cargo

The biologically active cargo of the fusion molecule can be attached to the remainder of the fusion molecule by any method known by one of skill in the art without limitation. The biologically active cargo can be introduced into any portion of the fusion molecule that does not disrupt the cell-binding or transcytosis activity of the modified Cholix toxin. In various embodiments, the biologically active cargo is directly coupled to the N-terminus or C-terminus of the modified Cholix toxin. In various embodiments, the biologically active cargo can be connected with a side chain of an amino acid of the modified Cholix toxin. In various embodiments, the biologically active cargo is coupled to the modified Cholix with a non-cleavable peptide linker. In various embodiments, the biologically active cargo is coupled to the modified Cholix toxin with a cleavable linker such that cleavage at the cleavable linker(s) separates the biologically active cargo from the remainder of the fusion molecule. In various embodiments, the biologically active cargo is a polypeptide that may also comprise a short leader peptide that remains attached to the polypeptide following cleavage of the cleavable linker. For example, the biological active cargo can comprise a short leader peptide of greater than 1 amino acid, greater than 5 amino acids, greater than 10 amino acids, greater than 15 amino acids, greater than 20 amino acids, greater than 25 amino acids, greater than 30 amino acids, greater than 50 amino acids, or greater than 100 amino acids. In some cases, biological active cargo can comprise a short leader peptide of less than 100 amino acids, less than 50 amino acids, less than 30 amino acids, less than 25 amino acids, less than 20 amino acids, less than 15 amino acids, less than 10 amino acids, or less than 5 amino acids. In some cases, biological active cargo can comprise a short leader peptide of between 1-100 amino acids, between 5-10 amino acids, between 10 to 50 amino acids, or between 20 to 80 amino acids. In native Cholix toxin, the domain Ib loop spans amino acids 387 to 425, and is structurally characterized by a disulfide bond between two cysteines at positions 395 and 402. This domain Ib portion of Cholix toxin is not essential for any known activity of Cholix toxin, including cell binding, translocation, ER retention or ADP ribosylation activity. Accordingly, domain Ib can be deleted entirely, or modified to contain a biologically active cargo. Thus, in various embodiments, the biologically active cargo can be inserted into Cholix toxin domain Ib. If desirable, the biologically active cargo can be inserted into Cholix toxin domain Ib between the cysteines at positions 395 and 402 that are not crosslinked. This can be accomplished by reducing the disulfide linkage between the cysteines, by deleting one or both of the cysteines entirely from the Ib domain, by mutating one or both of the cysteines to other residues, for example, serine, or by other similar techniques. Alternatively, the biologically active cargo can be inserted into the domain Ib loop between the cysteines at positions 395 and 402. In such embodiments, the disulfide linkage between the cysteines can be used to constrain the biologically active cargo domain.

In embodiments where the biologically active cargo is expressed together with another portion of the fusion molecule as a fusion protein, the biologically active cargo can be can be inserted into the fusion molecule by any method known to one of skill in the art without limitation. For example, amino acids corresponding to the biologically active cargo can be directly inserted into the fusion molecule, with or without deletion of native amino acid sequences. In various embodiments, all or part of the Ib domain of Cholix toxin can be deleted and replaced with the biologically active cargo. In various embodiments, the cysteine residues of the Ib loop are deleted so that the biologically active cargo remains unconstrained. In other embodiments, the cysteine residues of the Ib loop are linked with a disulfide bond and constrain the biologically active cargo.

In embodiments where the biologically active cargo is not expressed together with the remainder of the fusion molecule as a fusion protein, the biologically active cargo can be connected with the remainder of the fusion molecule by any suitable method known by one of skill in the art, without limitation. More specifically, the exemplary methods described above for connecting a receptor binding domain to the remainder of the molecule are equally applicable for connecting the biologically active cargo to the remainder of the molecule.

Production of Fusion Proteins

In various embodiments, the non-naturally occurring fusion molecule is synthesized using recombinant DNA methodology. Generally this involves creating a DNA sequence that encodes the fusion molecule, placing the DNA in an expression cassette under the control of a particular promoter, expressing the molecule in a host, isolating the expressed molecule and, if required, renaturing the molecule.

DNA encoding the fusion molecules (e.g. Cholix$^{415}$-IL-10) described herein can be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862); the solid support method of U.S. Pat. No. 4,458,066, and the like.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences may be obtained by the ligation of shorter sequences.

Alternatively subsequences can be cloned and the appropriate subsequences cleaved using appropriate restriction enzymes. The fragments can then be ligated to produce the desired DNA sequence.

In various embodiments, DNA encoding fusion molecules of the present disclosure can be cloned using DNA amplification methods such as polymerase chain reaction (PCR). Thus, for example, the gene for the IL-10 is PCR amplified, using a sense primer containing the restriction site for, e.g., NdeI and an antisense primer containing the restriction site for HindIII. This can produce a nucleic acid encoding the mature IL-10 sequence and having terminal restriction sites. A modified Cholix toxin having "complementary" restriction sites can similarly be cloned and then ligated to the IL-10 and/or to a linker attached to the IL-10. Ligation of the nucleic acid sequences and insertion into a vector produces a vector encoding the IL-10 joined to the modified Cholix toxin.

Non-Cleavable Linkers

In various embodiments, the modified Cholix toxin and biologically active cargo can be separated by a peptide spacer consisting of one or more amino acids (e.g., up to 25 amino acids). Generally the spacer will have no specific biological activity other than to join the proteins or to preserve some minimum distance or other spatial relationship between them. In various embodiments, however, the constituent amino acids of the spacer can be selected to influence some property of the molecule such as the folding, net charge, or hydrophobicity.

In various embodiments, the linker is capable of forming covalent bonds to both the Cholix toxin and to the biologically active cargo. Suitable linkers are well known to those of skill in the art and include, but are not limited to, straight or branched-chain carbon linkers, heterocyclic carbon linkers, or peptide linkers. In various embodiments, the linker(s) can be joined to the constituent amino acids of the Cholix toxin and/or the biologically active cargo through their side groups (e.g., through a disulfide linkage to cysteine). In various embodiments, the linkers are joined to the alpha carbon amino and/or carboxyl groups of the terminal amino acids of the Cholix toxin and/or the biologically active cargo.

A bifunctional linker having one functional group reactive with a group on the Cholix toxin and another group reactive on the biologically active cargo, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) Cancer Res. 47: 4071-4075.

In various embodiments, the biologically active cargo to be delivered to the subject is coupled to the modified Cholix toxin using one or more non-cleavable peptide linkers comprising, e.g., the amino acid sequence GGGGS (SEQ ID NO: 96), GGGGSGGGGS (SEQ ID NO: 97), GGGGSGGGGSGGGGS (SEQ ID NO: 98), or GGGGSGGG (SEQ ID NO: 99), wherein the modified Cholix toxin targets said biologically active cargo to specific cells, including but not limited to, cells of the immune system such as macrophages, antigen-presenting cells and dendritic cells.

Cleavable Linkers

In various embodiments, the biologically active cargo to be delivered to the subject is coupled to the modified Cholix toxin using one or more cleavable linkers. The number of cleavable linkers present in the fusion molecule depends, at least in part, on the location of the biologically active cargo in relation to the modified Cholix toxin and the nature of the biologically active cargo. When the biologically active cargo can be separated from the remainder of the fusion molecule with cleavage at a single linker, the fusion molecules can comprise a single cleavable linker. Further, where the biologically active cargo is, e.g., a dimer or other multimer, each subunit of the biologically active cargo can be separated from the remainder of the fusion molecule and/or the other subunits of the biologically active cargo by cleavage at the cleavable linker.

In various embodiments, the cleavable linkers are cleavable by a cleaving enzyme that is present at or near the basolateral membrane of an epithelial cell. By selecting the cleavable linker to be cleaved by such enzymes, the biologically active cargo can be liberated from the remainder of the fusion molecule following transcytosis across the mucous membrane and release from the epithelial cell into the cellular matrix on the basolateral side of the membrane. Further, cleaving enzymes could be used that are present inside the epithelial cell, such that the cleavable linker is cleaved prior to release of the fusion molecule from the basolateral membrane, so long as the cleaving enzyme does not cleave the fusion molecule before the fusion molecule enters the trafficking pathway in the polarized epithelial cell that results in release of the fusion molecule and biologically active cargo from the basolateral membrane of the cell.

In various embodiments, the enzyme that is present at a basolateral membrane of a polarized epithelial cell is selected from, e.g., Cathepsin GI, Chymotrypsin I, Elastase I, Subtilisin AI, Subtilisin AII, Thrombin I, or Urokinase I. Table 5 presents these enzymes together with an amino acid sequence that is recognized and cleaved by the particular peptidase.

TABLE 5

Peptidases Present Near Basolateral Mucous Membranes or in Latter Aspects of the Transcytosis Pathway

| Peptidase | Amino Acid Sequence Cleaved |
|---|---|
| Cathepsin GI | AAPF (SEQ ID NO: 100) |
| Chymotrypsin I | GGF (SEQ ID NO: 101) |

TABLE 5-continued

Peptidases Present Near Basolateral Mucous Membranes or in Latter Aspects of the Transcytosis Pathway

| Peptidase | Amino Acid Sequence Cleaved |
|---|---|
| Elastase I | AAPV (SEQ ID NO: 102) |
| Subtilisin AI | GGL (SEQ ID NO: 103) |
| Subtilisin AII | AAL (SEQ ID NO: 104) |
| Thrombin I | FVR (SEQ ID NO: 105) |
| Urokinase I | VGR (SEQ ID NO: 106) |
| Furin | RKPR (SEQ ID NO: 107) |

In various embodiments, the cleavable linker exhibits a greater propensity for cleavage than the remainder of the delivery construct. As one skilled in the art is aware, many peptide and polypeptide sequences can be cleaved by peptidases and proteases. In various embodiments, the cleavable linker is selected to be preferentially cleaved relative to other amino acid sequences present in the delivery construct during administration of the delivery construct. In various embodiments, the receptor binding domain is substantially (e.g., about 99%, about 95%, about 90%, about 85%, about 80, or about 75%) intact following delivery of the delivery construct to the bloodstream of the subject. In various embodiments, the translocation domain is substantially (e.g., about 99%, about 95%, about 90%, about 85%, about 80, or about 75%) intact following delivery of the delivery construct to the bloodstream of the subject. In various embodiments, the macromolecule is substantially (e.g., about 99%, about 95%, about 90%, about 85%, about 80, or about 75%) intact following delivery of the delivery construct to the bloodstream of the subject. In various embodiments, the cleavable linker is substantially (e.g., about 99%, about 95%, about 90%, about 85%, about 80, or about 75%) cleaved following delivery of the delivery construct to the bloodstream of the subject.

In other embodiments, the cleavable linker is cleaved by a cleaving enzyme found in the plasma of the subject. Any cleaving enzyme known by one of skill in the art to be present in the plasma of the subject can be used to cleave the cleavable linker. Uses of such enzymes to cleave the cleavable linkers is less preferred than use of cleaving enzymes found near the basolateral membrane of a polarized epithelial cell because it is believed that more efficient cleavage will occur in near the basolateral membrane. However, if the skilled artisan determines that cleavage mediated by a plasma enzyme is sufficiently efficient to allow cleavage of a sufficient fraction of the delivery constructs to avoid adverse effects, such plasma cleaving enzymes can be used to cleave the delivery constructs. Accordingly, in various embodiments, the cleavable linker can be cleaved with an enzyme that is selected from the group consisting of caspase-1, caspase-3, proprotein convertase 1, proprotein convertase 2, proprotein convertase 4, proprotein convertase 4 PACE 4, prolyl oligopeptidase, endothelin cleaving enzyme, dipeptidyl-peptidase IV, signal peptidase, neprilysin, renin, and esterase (see, e.g., U.S. Pat. No. 6,673,574, incorporated by reference in its entirety herein). Table 6 presents these enzymes together with an amino acid sequence(s) recognized by the particular peptidase. The peptidase cleaves a peptide comprising these sequences at the N-terminal side of the amino acid identified with an asterisk.

TABLE 6

| Peptidase | Amino Acid Sequence Cleaved |
|---|---|
| Caspase-1 | Tyr-Val-Ala-Asp-Xaa* (SEQ ID NO: 108) |
| Caspase-3 | Asp-Xaa-Xaa-Asp-Xaa* (SEQ ID NO: 109) |
| Proprotein convertase 1 | Arg-(Xaa)$_n$-Arg-Xaa*; n = 0, 2, 4 or 6 (SEQ ID NO: 110) |
| Proprotein convertase 2 | Lys-(Xaa)$_n$-Arg-Xaa*; n = 0, 2, 4, or 6 (SEQ ID NO: 111) |
| Proprotein convertase 4 | Glu-Arg-Thr-Lys-Arg-Xaa* (SEQ ID NO: 112) |
| Proprotein convertase 4 PACE 4 | Arg-Val-Arg-Arg-Xaa* (SEQ ID NO: 113) Decanoyl-Arg-Val-Arg-Arg-Xaa* (SEQ ID NO: 114) |
| Prolyloligopeptidase Endothelin cleaving enzyme in combination with dipeptidyl-peptidase IV | Pro-Xaa*-Trp-Val-Pro-Xaa (SEQ ID NO: 115) |
| Signal peptidase | Trp-Val*-Ala-Xaa (SEQ ID NO: 116) |
| Neprilysin in combination with dipeptidyl-peptidase IV | Xaa-Phe*-Xaa-Xaa (SEQ ID NO: 117) Xaa-Tyr*-Xaa-Xaa (SEQ ID NO: 118) Xaa-Trp*-Xaa-Xaa (SEQ ID NO: 119) |
| Renin in combination with dipeptidyl-peptidase IV | Asp-Arg-Tyr-Ile-Pro-Phe-His-Leu*-Leu, (Val Ala or Pro)-Tyr-(Ser, Pro, or Ala) (SEQ ID NO: 120) |

Thus, in various embodiments, the cleavable linker can be any cleavable linker known by one of skill in the art to be cleavable by an enzyme that is present at the basolateral membrane of an epithelial cell. In various embodiments, the cleavable linker comprises a peptide. In other embodiments, the cleavable linker comprises a nucleic acid, such as RNA or DNA. In still other embodiments, the cleavable linker comprises a carbohydrate, such as a disaccharide or a trisaccharide.

Alternatively, in various embodiments, the cleavable linker can be any cleavable linker known by one of skill in the art to be cleavable by an enzyme that is present in the plasma of the subject to whom the delivery construct is administered. In various embodiments, the cleavable linker comprises a peptide. In other embodiments, the cleavable linker comprises a nucleic acid, such as RNA or DNA. In still other embodiments, the cleavable linker comprises a carbohydrate, such as a disaccharide or a trisaccharide.

In various embodiments, the peptidases exhibit much higher (e.g., 100%, 200%, or more increase in activity relative to the apical side) on the baso-lateral side (also referred to as basolateral). Thus, in various embodiments, the cleavable linker is cleavable by an enzyme that exhibits 50% higher activity on the basolateral side of the membrane than on the apical side of the membrane. In various embodiments, the cleavable linker is cleavable by an enzyme that exhibits 100% higher activity on the basolateral side of the membrane than on the apical side of the membrane. In various embodiments, the cleavable linker is cleavable by an enzyme that exhibits 200% higher activity on the basolateral side of the membrane than on the apical side of the membrane. In various embodiments, the cleavable linker is cleavable by an enzyme that exhibits 500% higher activity on the basolateral side of the membrane than on the apical side of the membrane. In various embodiments, the cleavable linker is cleavable by an enzyme that exhibits 1,000% higher activity on the basolateral side of the membrane than on the apical side of the membrane.

In various embodiments, the fusion molecule comprises a cleavable linker having an amino acid sequence selected from, e.g., SEQ ID NO: 100, SEQ ID NO: 101, SEQ ID NO: 102, SEQ ID NO: 103, SEQ ID NO: 104, SEQ ID NO: 105, SEQ ID NO: 106 or SEQ ID NO: 107 and is cleavable by an enzyme that exhibits higher activity on the basolateral side of a polarized epithelial cell than it does on the apical side of the polarized epithelial cell, and/or is cleavable by an enzyme that exhibits higher activity in the plasma than it does on the apical side of a polarized epithelial cell.

In various embodiments, the cleavable linker can be a cleavable linker that is cleaved following a change in the environment of the fusion molecule. For example, the cleavable linker can be a cleavable linker that is pH sensitive and is cleaved by a change in pH that is experienced when the fusion molecule is released from the basolateral membrane of a polarized epithelial cell. For instance, the intestinal lumen is strongly alkaline, while plasma is essentially neutral. Thus, a cleavable linker can be a moiety that is cleaved upon a shift from alkaline to neutral pH. The change in the environment of the fusion molecule that cleaves the cleavable linker can be any environmental change that that is experienced when the fusion molecule is released from the basolateral membrane of a polarized epithelial cell known by one of skill in the art, without limitation.

In various embodiments, the cleavable linker is cleaved by a cleaving enzyme found in the plasma of the subject. Any cleaving enzyme known by one of skill in the art to be present in the plasma of the subject can be used to cleave the cleavable linker. Accordingly, in various embodiments, the cleavable linker can be cleaved with an enzyme that is selected from e.g., SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119 or SEQ ID NO: 120.

In various embodiment, the cleavable linker is a linker that contains an amino acid sequence that is a known substrate for the tobacco etch virus (TEV) protease. Accordingly, in various embodiments, the cleavable linker comprises the amino acid sequence set forth in, e.g., (SEQ ID NO: 121)
GGGGSGGGENLYFQS.

Chemical Conjugation of the Cargo to the Modified Cholix Toxin

In various embodiments, the biologically active cargo to be delivered to the subject is chemically conjugated to the modified Cholix toxin. Means of chemically conjugating molecules are well known to those of skill.

The procedure for conjugating two molecules varies according to the chemical structure of the agent. Polypeptides typically contain variety of functional groups; e.g., carboxylic acid (COOH) or free amine (—$NH_2$) groups, that are available for reaction with a suitable functional group on the other peptide, or on a linker to join the molecules thereto.

Alternatively, the antibody and/or the biologically active cargo can be derivatized to expose or attach additional reactive functional groups. The derivatization can involve attachment of any of a number of linker molecules such as those available from Pierce Chemical Company, Rockford Ill.

In various embodiments, isolated modified Cholix toxins are prepared by bacterial fermentation and purified by established methods. The purified modified Cholix toxin is then modified at its C-terminus to allow direct chemical coupling through a free sulfhydryl residue located near the C-terminus of the protein. The C-terminal modification includes a cysteine-constrained loop harboring the consensus cleavage sequence for the highly selective protease from the tobacco etch virus (TEV), a second cysteine, and a hexa-histidine ($His_6$) tag. The second Cys is included to form a disulphide bridge with the Cys ultimately used for coupling. Adding the $His_6$ sequence to the protein simplifies the purification and the TEV cleavage sequence provides a mechanism to selectively remove the terminal Cys residue following mild reduction. TEV cleavage and mild reduction with 0.1 mM dithiotheitol following expression and isolation of the ntCholix constructs allows for the direct chemical coupling of a biologically active cargo via a maleimide-based reaction as a generic mechanism of cargo attachment. Following TEV protease cleavage, reduction, and cargo coupling through a maleimide reaction with the free sulfhydryl, removal of the freed C-terminal sequence was achieved by a second Ni' column chromatography step.

In various embodiments, the fusion molecule comprises particles which are decorated covalently with the modified Cholix toxin, and wherein the biologically active cargo is integrated into the particles. In various embodiments, the particles can be smaller than ~150 nm in diameter, smaller than ~100 nm, or smaller than ~50 nm.

In various embodiments, the fusion molecule comprises a biologically active cargo coupled non-covalently to the modified Cholix toxin. This fusion molecule could ferry, e.g., a non-covalently associated IL-10 across the epithelium such as a surface element of the IL-10 receptor (Josephson, K., Logsdon, N. J., Walter, M. R., Immunity 15: 35-46, 2001, incorporated by reference in its entirety herein).

Pharmaceutical Compositions and Delivery Methods

The pharmaceutical compositions of the present disclosure relate to compositions for administration to a human subject. The pharmaceutical compositions comprise the non-naturally occurring fusion molecules recited herein, alone or in combination. The pharmaceutical compositions may comprise additional molecules capable of altering the characteristics of the non-naturally occurring fusion molecules, for example, stabilizing, modulating and/or activating their function. The composition may, e.g., be in solid or liquid form and may be, inter alia, in the form of (a) powder(s), (a) tablet(s), (a) solution(s) or (an) aerosol(s). The pharmaceutical composition of the present disclosure may, optionally and additionally, comprise a pharmaceutically acceptable carrier. "Pharmaceutically acceptable carrier" refers to a non-toxic solid, semisolid or liquid filler, diluent, encapsulating material and any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants.

The pharmaceutical compositions are generally formulated appropriately for the immediate use intended for the fusion molecule. For example, if the fusion molecule is not to be administered immediately, the fusion molecule can be formulated in a composition suitable for storage. One such composition is a lyophilized preparation of the fusion molecule together with a suitable stabilizer. Alternatively, the fusion molecule composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the compositions include, but are not limited to, trehalose, serum albumin, phosphatidylcholine, lecithin, and arginine. Other compounds, compositions, and methods for stabilizing a lyophilized or liquid preparation of the fusion molecules may be found, for example, in U.S. Pat. Nos. 6,573,237, 6,525,102, 6,391,296, 6,255,284, 6,133,229, 6,007,791, 5,997,856, and 5,917,021.

In various embodiments, the pharmaceutical compositions of the present disclosure are formulated for oral delivery. The pharmaceutical compositions formulated for oral administration take advantage of the modified Cholix toxin's ability to mediate transcytosis across the gastrointestinal (GI) epithelium. It is anticipated that oral administration of these pharmaceutical compositions will result in absorption of the fusion molecule through polarized epithelial cells of the digestive mucosa, e.g., the intestinal mucosa, followed by release of the biologically active cargo at the basolateral side of the mucous membrane. In various embodiments, the epithelial cell is selected from the group consisting of nasal epithelial cells, oral epithelial cells, intestinal epithelial cells, rectal epithelial cells, vaginal epithelial cells, and pulmonary epithelial cells. Pharmaceutical compositions of the disclosure may include the addition of a transcytosis enhancer to facilitate transfer of the fusion protein across the GI epithelium. Such enhancers are known in the art. See Xia et al., (2000) J. Pharmacol. Experiment. Therap., 295:594-600; and Xia et al. (2001) Pharmaceutical Res., 18(2):191-195, each incorporated by reference in its entirety herein.

It is anticipated that once transported across the GI epithelium, the fusion molecules of the disclosure will exhibit extended half-life in serum, that is, the biologically active cargo of the fusion molecules will exhibit an extended serum half-life compared to the biologically active cargo in its non-fused state. As such, the oral formulations of the pharmaceutical compositions of the present disclosure are prepared so that they are suitable for transport to the GI epithelium and protection of the fusion molecule in the stomach. Such formulations may include carrier and dispersant components and may be in any suitable form, including aerosols (for oral or pulmonary delivery), syrups, elixirs, tablets, including chewable tablets, hard or soft capsules, troches, lozenges, aqueous or oily suspensions, emulsions, cachets or pellets granulates, and dispersible powders. In various embodiments, the pharmaceutical compositions are employed in solid dosage forms, e.g., tablets, capsules, or the like, suitable for simple oral administration of precise dosages.

In various embodiments, the oral formulation comprises a fusion molecule and one or more compounds that can protect the fusion molecule while it is in the stomach. For example, the protective compound should be able to prevent acid and/or enzymatic hydrolysis of the fusion molecule. In various embodiments, the oral formulation comprises a fusion molecule and one or more compounds that can facilitate transit of the construct from the stomach to the small intestine. In various embodiments, the one or more compounds that can protect the fusion molecule from degradation in the stomach can also facilitate transit of the construct from the stomach to the small intestine. For example, inclusion of sodium bicarbonate can be useful for facilitating the rapid movement of intra-gastric delivered materials from the stomach to the duodenum as described in Mrsny et al., Vaccine 17:1425-1433, 1999. Other methods for formulating compositions so that the fusion molecules can pass through the stomach and contact polarized epithelial membranes in the small intestine include, but are not limited to, enteric-coating technologies as described in DeYoung, Int J Pancreatol, 5 Suppl:31-6, 1989 and the methods provided in U.S. Pat. Nos. 6,613,332, 6,174,529, 6,086,918, 5,922,680, and 5,807,832, each incorporated by reference in its entirety herein.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the fusion molecule is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract. Compositions comprising fusion molecules may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing fusion molecules in admixture with non-toxic pharmaceutically acceptable excipients which are suitable for manufacture of tablets. These excipients may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the fusion molecule is mixed with an inert solid diluent, for example, calcium carbonate, calcium phosphate, or kaolin or as soft gelatin capsules wherein the fusion molecule is mixed with an aqueous or an oil medium, for example, arachis oil, peanut oil, liquid paraffin or olive oil.

In various embodiments, aqueous suspensions may contain a fusion molecule in the admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecylethyloxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives for example, ethyl or n-propyl p-hydroxybenzoate, one or more coloring agents, one or more flavoring agents and one or more sweetening agents such as sucrose or saccharin.

In various embodiments, oily suspensions may be formulated by suspending the fusion molecule in a vegetable oil, for example, *arachis* oil, olive oil, sesame oil or coconut oil, or in a mineral oil such as liquid paraffin. The oil suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

In various embodiments, the pharmaceutical compositions may be in the form of oil-in-water emulsions. The oil phase may be a vegetable oil, for example, olive oil or arachis oil, or a mineral oil for example, gum acacia or gum tragacanth, naturally-occurring phosphotides, for example soybean lecithin, and esters or partial esters derived from fatty acids and hexitol anhydrides, for example, sorbitan monooleate, and condensation products of the same partial esters with ethylene oxide, for example, polyoxyethylene sorbitan monooleate. The emulsions may also contain sweetening and flavoring agents.

In various embodiments wherein the pharmaceutical composition is in the form of a tablet or capsule, the tablet or capsule is coated or encapsulated to protect the biologically active cargo from enzymatic action in the stomach and to ensure that there is sufficient biologically active cargo to be absorbed by the subject to produce an effective response. Such coating or encapsulation methods include, e.g., encapsulation in nanoparticles composed of polymers with a hydrophobic backbone and hydrophilic branches as drug carriers, encapsulation in microparticles, insertion into liposomes in emulsions, and conjugation to other molecules. Examples of nanoparticles include mucoadhesive nanoparticles coated with chitosan and Carbopol (Takeuchi et al., Adv. Drug Deliv. Rev. 47(1):39-54, 2001) and nanoparticles containing charged combination polyesters, poly(2-sulfobutyl-vinyl alcohol) and poly(D,L-lactic-co-glycolic acid) (Jung et al., Eur. J. Pharm. Biopharm. 50(1):147-160, 2000).

Encapsulated or coated tablets can be used that release the biologically active cargo in a layer-by-layer manner, thereby releasing biologically active cargo over a pre-determined time frame while moving along the gastrointestinal tract. In addition, tablets comprising the biologically active cargo can be placed within a larger tablet, thereby protecting the inner tablet from environmental and processing conditions, such as temperature, chemical agents (e.g., solvents), pH, and moisture. The outer tablet and coatings further serve to protect the biologically active cargo in the gastric environment.

In various embodiments, pharmaceutical compositions may be formulated for oral delivery using polyester microspheres, zein microspheres, proteinoid microspheres, polycyanoacrylate microspheres, and lipid-based systems (see, for example, DiBase and Morrel, Oral Delivery of Microencapsulated Proteins, in Protein Delivery: Physical Systems, Sanders and Hendren (eds.), pages 255-288 (Plenum Press 1997)).

Surface active agents or surfactants promote absorption of polypeptides through mucosal membrane or lining Useful surface active agents or surfactants include fatty acids and salts thereof, bile salts, phospholipid, or an alkyl saccharide. Examples of fatty acids and salts thereof include sodium, potassium and lysine salts of caprylate ($C_8$), caprate ($C_{10}$), laurate ($C_{12}$) and myristate ($C_{14}$). Examples of bile salts include cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid. Examples of phospholipids include single-chain phospholipids, such as lysophosphatidylcholine, lysophosphatidylglycerol, lysophosphatidylethanolamine, lysophosphatidylinositol and lysophosphatidylserine; or double-chain phospholipids, such as diacylphosphatidylcholines, diacylphosphatidylglycerols, diacylphosphatidylethanolamines, diacylphosphatidylinositols and diacylphosphatidylserines. Examples of alkyl saccharides include alkyl glucosides or alkyl maltosides, such as decyl glucoside and dodecyl maltoside.

In another aspect, the present disclosure relates to methods of orally administering the pharmaceutical compositions of the disclosure. Without intending to be bound to any particular theory or mechanism of action, it is believed that oral administration of the fusion molecules results in absorption of the fusion molecule through polarized epithelial cells of the digestive mucosa, e.g., the intestinal mucosa, followed by cleavage of the fusion molecule and release of the biologically active cargo at the basolateral side of the mucous membrane. Thus, when the biologically active cargo exerts a biological activity in the liver, such as, for example, activities mediated by IL-10 binding to its cognate receptor, the biologically active cargo is believed to exert an effect in excess of what would be expected based on the plasma concentrations observed in the subject, i.e., oral administration of the fusion molecule can deliver a higher effective concentration of the delivered biologically active cargo to the liver of the subject than is observed in the subject's plasma.

In another aspect, the present disclosure relates to methods of orally administering the pharmaceutical compositions of the disclosure. Such methods may include, but are not limited to, steps of orally administering the compositions by the patient or a caregiver. Such administration steps may include administration on intervals such as once or twice per day depending on the fusion molecule, disease or patient condition or individual patient. Such methods also include the administration of various dosages of the individual fusion molecule. For instance, the initial dosage of a pharmaceutical composition may be at a higher level to induce a desired effect, such as reduction in blood glucose levels. Subsequent dosages may then be decreased once a desired effect is achieved. These changes or modifications to administration protocols may be done by the attending physician or health care worker.

These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The skilled person knows that the effective amount of a pharmaceutical composition administered to an individual will, inter alia, depend on the nature of the biologically active cargo. The length of treatment needed to observe changes and the interval following treatment for responses to occur vary depending on the desired effect. The particular amounts may be determined by conventional tests which are well known to the person skilled in the art.

The amount of biologically active cargo is an amount effective to accomplish the purpose of the particular active agent. The amount in the composition typically is a pharmacologically, biologically, therapeutically, or chemically effective amount. However, the amount can be less than a pharmacologically, biologically, therapeutically, or chemically effective amount when the composition is used in a dosage unit form, such as a capsule, a tablet or a liquid, because the dosage unit form may contain a multiplicity of carrier/biologically or chemically active agent compositions or may contain a divided pharmacologically, biologically, therapeutically, or chemically effective amount. The total effective amounts can then be administered in cumulative units containing, in total, pharmacologically, biologically, therapeutically or chemically active amounts of biologically active cargo.

In various embodiments, an amount of fusion molecule administered to the subject is at most 0.001 pg, at most 1 pg, at most 2 pg, at most 3 pg, at most 4 pg, at most 5 pg, at most 10 pg, at most 50 pg, at most 100 pg, at most 1 µg, at most 2 µg, at most 3 µg, at most 4 µg, at most 5 µg, at most 10 µg, at most 50 µg, at most 100 µg, at most 1 mg, at most 2 mg, at most 3 mg, at most 4 mg, at most 5 mg, at most 10 mg, at most 50 mg, at most 100 mg, or at most 1 g.

In various embodiments, an amount of fusion molecule administered to the subject is at least 0.001 pg, at least 1 pg, at least 2 pg, at least 3 pg, at least 4 pg, at least 5 pg, at least 10 pg, at least 50 pg, at least 100 pg, at least 1 µg, at least 2 µg, at least 3 µg, at least 4 µg, at least 5 µg, at least 10 µg, at least 50 µg, at least 100 µg, at least 1 mg, at least 2 mg, at least 3 mg, at least 4 mg, at least 5 mg, at least 10 mg, at least 50 mg, at least 100 mg, or at least 1 g.

In various embodiments, an amount of fusion molecule administered to the subject is from 0.001 pg and about 1 g, from 1 pg to 10 pg, from 50 pg to 100 pg, from 1 µg to 5 µg, from 10 µg to 20 µg, from 10 µg to 500 mg, from 10 µg to 100 mg, from 10 µg to 1000 µg, from 10 µg to 250 µg, from 10 µg to 100 µg, from 10 µg to 50 µg, from 1 mg to 5 mg, or from 10 mg to 100 mg.

The volume of a composition comprising the fusion molecule that is administered will generally depend on the concentration of fusion molecule and the formulation of the composition. In various embodiments, a unit dose of the fusion molecule composition is from 0.001 µl to 1 ml, from 1 µl to 100 µl, from 50 µl to 500 µl, from 0.01 ml to 1 ml, from 1 ml to 100 ml, from 0.05 ml to 1 ml. For example, the unit dose of the fusion molecule composition can be about 0.5 ml.

In some embodiments, a unit dose of the fusion molecule composition is at most about 0.001 µl, at most 1 µl, at most 10 µl, at most 50 µl, at most 200 µl, at most 0.01 ml, at most 0.05 ml, at most 0.1 ml, at most 0.2 ml, at most 0.5 ml, or at most 1 ml.

In some a unit dose of the fusion molecule composition is at least 0.001 µl, at least 1 µl, at least 10 µl, at least 50 µl, at least 200 µl, at least 0.01 ml, at least 0.05 ml, at least 0.1 ml, at least 0.2 ml, at least 0.5 ml, or at least 1 ml.

The fusion molecule compositions can be prepared in dosage forms containing between 1 and 50 doses (e.g., 0.5 ml to 25 ml), more usually between 1 and 10 doses (e.g., 0.5 ml to 5 ml).

The fusion molecule compositions of the disclosure can be administered in one dose or in multiple doses. A dose can be followed by one or more doses spaced by about 1 to about 6 hours, by about 6 to about 12 hours, by about 12 to about 24 hours, by about 1 day to about 3 days, by about 1 day to about 1 week, by about 1 week to about 2 weeks, by about 2 weeks to about 1 month, by about 4 to about 8 weeks, by about 1 to about 3 months, or by about 1 to about 6 months.

In various embodiments, the pharmaceutical compositions comprising the fusion molecules may be, though not necessarily, administered daily, in an effective amount to ameliorate a symptom. Generally, the total daily dosage can be administered at an amount of at least about 0.001 pg, at least about 0.1 mg, at least about 1 mg, at least about 10 mg, at least about 50 mg, at least about 100 mg, at least about 150 mg, at least about 200 mg, at least about 250 mg, at least about 300 mg, at least about 350 mg, at least about 400 mg, at least about 450 mg, at least about 500 mg per day, or at least about 1000 mg per day. For example, the dosage can be formulated for oral administration in capsules or tablets, such that 4 capsules or tablets, each containing 50 mg fusion molecule. Capsules or tablets for oral delivery can conveniently contain up to a full daily oral dose, e.g., 200 mg or more per day.

In various embodiments, the pharmaceutical compositions comprising the fusion molecules may be, though not necessarily, administered daily, in an effective amount to ameliorate a symptom. Generally, the total daily dosage can be administered at an amount of at most 50 mg per day, at most 100 mg per day, at most 150 mg per day, at most 200 mg per day, at most 250 mg per day, at most 300 mg per day, at most 350 mg per day, at most 400 mg per day, at most 450 mg per day, at most 500 mg per day, or at most 1000 mg per day.

As used herein, the terms "co-administration", "co-administered" and "in combination with", referring to the fusion molecules of the disclosure and one or more other therapeutic agents, is intended to mean, and does refer to and include the following: simultaneous administration of such combination of fusion molecules of the disclosure and therapeutic agent(s) to a patient in need of treatment, when such components are formulated together into a single dosage form which releases said components at substantially the same time to said patient; substantially simultaneous administration of such combination of fusion molecules of the disclosure and therapeutic agent(s) to a patient in need of treatment, when such components are formulated apart from each other into separate dosage forms which are taken at substantially the same time by said patient, whereupon said components are released at substantially the same time to said patient; sequential administration of such combination of fusion molecules of the disclosure and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of fusion molecules of the disclosure and therapeutic agent(s) to a patient in need of treatment, when such components are formulated together into a single dosage form which releases said components in a controlled manner whereupon they are released in a concurrent, consecutive, and/or overlapping manner at the same and/or different times to said patient, where each part may be administered by either the same or a different route.

In various embodiments, the pharmaceutical compositions comprising the fusion molecules may be co-administered with a second component, wherein the second component is a hormone, toxin, or bioactive agent which is capable of binding to the GM-1 (monosialotetrahexosylganglioside) receptor (Hakomori, Advances in Exp. Medicine and Biology, 174:333-339, 1984). In various embodiments, the second component is SV40 virus, polyoma virus, or a toxin such as cholera toxin, or exotoxin A from *Pseudomonas aeruginosa* (PE).

As used herein, the terms "cholera toxin" or "CT" refer to the eponymous virulence agent of *Vibrio cholerae* bacterium, which can cause acute, life-threatening massive watery diarrhea. CT is a protein complex composed of a single A subunit organized with a pentamer of B subunits that binds to cell surface $G_{M1}$ ganglioside structures at the apical surface of epithelia. CT is secreted by *V. cholera* following horizontal gene transfer with virulent strains of *V. cholerae* carrying a variant of lysogenic bacteriophage called CTXf or CTXφ. Recent cholera outbreaks, however, have suggested that strains of some serogroups (non-O1, non-O139) do not express CT but rather use other virulence factors. Detailed analyses of non-O1, non-O139 environmental and clinical data suggested the presence of a novel putative secreted exotoxin with some similarity to PE. The sequence of CT is known and has been described (Mekalanos J. J. et al Nature 306, page 551 (1983)).

As used herein the terms "exotoxin A from *Pseudomonas aeruginosa*", "*Pseudomonas* exotoxin A" or "PE" refer to an extremely active monomeric protein (molecular weight 66 kD), secreted by *Pseudomonas aeruginosa*, which inhibits protein synthesis in eukaryotic cells. The 613-residue sequence of PE is well known in the art and is set forth, for example, in U.S. Pat. No. 5,602,095. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although it has been known a large part of it, amino acids 365-380, can be deleted without loss of cytotoxicity. See Siegall et al., J Biol Chem, 264:14256-61 (1989).

Certain cytotoxic fragments of PE are known in the art and are often referenced by the molecular weight of the fragment, which designates for the person of skill in the art the particular composition of the PE fragment. For example, PE40 was one of the first fragments that was studied and used as the toxic portion of immunotoxins. The term designates a truncated form of PE in which domain Ia, the domain responsible for non-specific binding. See, e.g., Pai et al., Proc. Nat'l Acad. Sci. USA, 88:3358-3362 (1991); and Kondo et al., J. Biol. Chem., 263:9470-9475 (1988). Elimination of non-specific binding, however, can also be achieved by mutating certain residues of domain Ia. U.S. Pat. No. 5,512,658, for instance, discloses that a mutated PE in which domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as "PE4E."

In various embodiments, the combination therapy comprises administering the isolated fusion molecule composition and the second agent composition simultaneously, either in the same pharmaceutical composition or in separate pharmaceutical compositions. In various embodiments, isolated fusion molecule composition and the second agent composition are administered sequentially, i.e., the isolated fusion molecule composition is administered either prior to or after the administration of the second agent composition.

In various embodiments, the administrations of the isolated fusion molecule composition and the second agent composition are concurrent, i.e., the administration period of the isolated fusion molecule composition and the second agent composition overlap with each other.

In various embodiments, the administrations of the isolated fusion molecule composition and the second agent composition are non-concurrent. For example, in various embodiments, the administration of the isolated fusion molecule composition is terminated before the second agent composition is administered. In various embodiments, the administration second agent composition is terminated before the isolated fusion molecule composition is administered. In various embodiments, the administrations of the fusion molecule of the invention, whether alone or in combination with a therapeutic agent, can be archived with a meal, e.g. prior to the meal, during the meal or after the meal.

In some embodiments, the administration of the fusion molecule of the invention, whether alone or in combination with a therapeutic agent, can be archived prior to a meal. In various embodiments, the fusion molecule of the invention, whether alone or in combination with a therapeutic agent, can be administered more than 12 hours, more than 11 hours, more than 10 hours, more than 9 hours, more than 8 hours, more than 7 hours, more than 6 hours, more than 5 hours, more than 4 hours, more than 3 hours, more than 2 hours, more than 1 hour, more than 50 minutes, more than 40 minutes, more than 30 minutes, more than 20 minutes, more than 10 minutes, more than 5 minutes, or more than 1 minute prior to the meal. In various embodiments, the fusion molecule of the invention, whether alone or in combination with a therapeutic agent, can be administered less than 12 hours, less than 11 hours, less than 10 hours, less than 9 hours, less than 8 hours, less than 7 hours, less than 6 hours, less than 5 hours, less than 4 hours, less than 3 hours, less than 2 hours, less than 1 hour, less than 50 minutes, less than 40 minutes, less than 30 minutes, less than 20 minutes, less than 10 minutes, less than 5 minutes, or less than 1 minute prior to the meal. In various embodiments, the fusion molecule of the invention, whether alone or in combination with a therapeutic agent, can be administered between about 1 minute to about 10 minutes, between about 5 minutes to about 30 minutes, between about 20 minutes to about 60 minutes, between about 1 hour to about 3 hours, between about 2 hours to about 10 hours, or between about 5 hours to about 12 hour prior to the meal.

In some embodiments, the administration of the fusion molecule of the invention, whether alone or in combination with a therapeutic agent, can be archived after a meal. In various embodiments, the fusion molecule of the invention, whether alone or in combination with a therapeutic agent, can be administered more than 12 hours, more than 11 hours, more than 10 hours, more than 9 hours, more than 8 hours, more than 7 hours, more than 6 hours, more than 5 hours, more than 4 hours, more than 3 hours, more than 2 hours, more than 1 hour, more than 50 minutes, more than 40 minutes, more than 30 minutes, more than 20 minutes, more than 10 minutes, more than 5 minutes, or more than 1 minute after the meal. In some embodiments, the fusion molecule of the invention, whether alone or in combination with a therapeutic agent, can be administered less than 12 hours, less than 11 hours, less than 10 hours, less than 9 hours, less than 8 hours, less than 7 hours, less than 6 hours, less than 5 hours, less than 4 hours, less than 3 hours, less than 2 hours, less than 1 hour, less than 50 minutes, less than 40 minutes, less than 30 minutes, less than 20 minutes, less than 10 minutes, less than 5 minutes, or less than 1 minute after the meal. In various embodiments, the fusion molecule of the invention, whether alone or in combination with a therapeutic agent, can be administered less than 12 hours, less than 11 hours, less than 10 hours, less than 9 hours, less than 8 hours, less than 7 hours, less than 6 hours, less than 5 hours, less than 4 hours, less than 3 hours, less than 2 hours, less than 1 hour, less than 50 minutes, less than 40 minutes, less than 30 minutes, less than 20 minutes, less than 10 minutes, less than 5 minutes, or less than 1 minute prior to the meal. In various embodiments, the fusion molecule of the invention, whether alone or in combination with a therapeutic agent, can be administered between about 1 minute to about 10 minutes, between about 5 minutes to about 30 minutes, between about 20 minutes to about 60 minutes, between about 1 hour to about 3 hours, between about 2 hours to about 10 hours, or between about 5 hours to about 12 hour after the meal.

Methods of Use

In another aspect, the pharmaceutical compositions formulated for oral delivery are used to treat certain classes of diseases or medical conditions that are particularly amenable for oral formulation and delivery. Such classes of diseases or conditions include, e.g., viral disease or infections, cancer, a metabolic diseases, obesity, autoimmune diseases, inflammatory diseases, allergy, graft-vs-host disease, systemic microbial infection, anemia, cardiovascular disease, psychosis, genetic diseases, neurodegenerative diseases, disorders of hematopoietic cells, diseases of the endocrine system or reproductive systems, gastrointestinal diseases. In many chronic diseases, oral formulations of the fusion molecules of the disclosure are particularly useful because they allow long-term patient care and therapy via home oral administration without reliance on injectable treatment or drug protocols.

In various embodiments of the present disclosure, pharmaceutical compositions comprising the fusion molecules of the disclosure are provided for use in treating and/or preventing inflammatory diseases. "Inflammatory diseases" include all diseases associated with acute or chronic inflammation. Acute inflammation is the initial response of the body to harmful stimuli and results from an increased movement of plasma and leukocytes (such as e.g. granulocytes) from the blood into the injured tissues. A number of biochemical events propagates and matures the inflammatory response, involving the local vascular system, the immune system, and various cells within the injured tissue. Prolonged inflammation is referred to as chronic inflammation, which leads to a progressive shift in the type of cells present at the site of inflammation and is characterized by simultaneous destruction and healing of the tissue from the inflammatory process. Inflammatory diseases can be caused by e.g. burns, chemical irritants, frostbite, toxins, infection by pathogens, physical injury, immune reactions due to hypersensitivity, ionizing radiation, or foreign bodies, such as e.g. splinters, dirt and debris. Examples of inflammatory diseases are well known in the art.

In various embodiments, the inflammatory disease is selected from the group consisting of inflammatory bowel disease, psoriasis and bacterial sepsis. The term "inflammatory bowel disease", as used herein, refers to a group of inflammatory conditions of the colon and small intestine including, for example, Crohn's disease, ulcerative colitis, collagenous colitis, lymphocytic colitis, ischaemic colitis, diversion colitis, Behcet's syndrome and indeterminate colitis.

"Crohn's disease", in accordance with the present disclosure, is a T-helper Type 1 (Th 1) inflammatory bowel disease, which has an immune response pattern that includes an increased production of interleukin-12, tumour necrosis factor (TNF), and interferon-y (Romagnani. Inflamm Bowel Dis 1999; 5:285-94), and which can have a devastating impact on the lifestyle of a patient afflicted therewith. Common symptoms of Crohn's disease include diarrhea, cramping, abdominal pain, fever, and even rectal bleeding. Crohn's disease and complications associated with it often results in the patient requiring surgery, often more than once. There is no known cure for Crohn's disease, and long-term, effective treatment options are limited. The goals of treatment are to control inflammation, correct nutritional deficiencies, and relieve symptoms like abdominal pain, diarrhea, and rectal to bleeding. While treatment can help control the disease by lowering the number of times a person experiences a recurrence, there is no cure. Treatment may include drugs, nutrition supplements, surgery, or a combination of these options. Common treatments which may be administered for treatment include anti-inflammation drugs, including sulfasalazine, cortisone or steroids, including prednisone, immune system suppressors, such as 6-mercaptopurine or azathioprine, and antibiotics.

"Psoriasis", in accordance with the present disclosure, is a disease which affects the skin and joints. It commonly causes red scaly patches to appear on the skin. The scaly patches caused by psoriasis, called psoriatic plaques, are areas of inflammation and excessive skin production. Skin rapidly accumulates at these sites and takes a silvery-white appearance. Plaques frequently occur on the skin of the elbows and knees, but can affect any area including the scalp and genitals. Psoriasis is hypothesized to be immune-mediated and is not contagious. The disorder is a chronic recurring condition which varies in severity from minor localised patches to complete body coverage. Fingernails and toenails are frequently affected (psoriatic nail dystrophy)—and can be seen as an isolated finding. Psoriasis can also cause inflammation of the joints, which is known as psoriatic arthritis. Ten to fifteen percent of people with psoriasis have psoriatic arthritis.

The term “bacterial sepsis”, as used herein, refers to life-threatening conditions resulting from the circulation of bacteria in the blood stream. Sepsis results in generalized systemic production of proinflammatory cytokines that results in tissue damage and ultimately septic shock due to failure of the microcirculation.

Another aspect of the present disclosure relates to methods for treatment, prophylaxis and/or prevention of an autoimmune disease, comprising administering to said patient a therapeutically effective amount (either as monotherapy or in a combination therapy regimen) of a fusion molecule described herein, in pharmaceutically acceptable carrier.

An autoimmune disease, as pertains to the present disclosure, is a disease or disorder arising from and directed against an individual’s own tissues or a co-segregate or manifestation thereof or resulting condition therefrom. In various embodiments the autoimmune disease is selected from the group consisting of systemic lupus erythematosus (SLE), pemphigus vulgaris, myasthenia gravis, hemolytic anemia, thrombocytopenia purpura, Grave’s disease, Sjogren’s disease, dermatomyositis, Hashimoto’s disease, polymyositis, inflammatory bowel disease, multiple sclerosis (MS), diabetes mellitus, rheumatoid arthritis, and scleroderma.

“Rheumatoid arthritis”, in accordance with the present disclosure, is an autoimmune disorder that causes the body’s immune system to attack the bone joints (Muller B et al., Springer Semin Immunopathol., 20:181-96, 1998). Rheumatoid arthritis is a chronic, systemic inflammatory disorder that may affect many tissues and organs, but principally attacks synovial joints. The process produces an inflammatory response of the synovium (synovitis) secondary to hyperplasia of synovial cells, excess synovial fluid, and the development of pannus in the synovium. The pathology of the disease process often leads to the destruction of articular cartilage and ankylosis of the joints. Rheumatoid arthritis can also produce diffuse inflammation in the lungs, pericardium, pleura, and sclera, and also nodular lesions, most common in subcutaneous tissue under the skin.

In various embodiments of the present disclosure, pharmaceutical compositions comprising the fusion molecules of the disclosure are provided for use in the treatment, prophylaxis and/or prevention of a cancer, comprising administering to said patient a therapeutically effective amount (either as monotherapy or in a combination therapy regimen) of a fusion molecule described herein, in pharmaceutically acceptable carrier. Cancers to be treated include, but are not limited to, non-Hodgkin’s lymphomas, Hodgkin’s lymphoma, chronic lymphocytic leukemia, hairy cell leukemia, acute lymphoblastic leukemia, multiple myeloma, carcinomas of the pancreas, colon, gastric intestine, prostate, bladder, kidney ovary, cervix, breast, lung, nasopharynx, malignant melanoma and rituximab resistant NHL and leukemia.

In various embodiments, the therapeutically effective amount of a fusion molecule described herein will be administered in combination with one or more other therapeutic agents. Such therapeutic agents may be accepted in the art as a standard treatment for a particular disease state as described herein, such as inflammatory disease, autoimmune disease, or cancer. Exemplary therapeutic agents contemplated include, but are not limited to, cytokines, growth factors, steroids, NSAIDs, DMARDs, anti-inflammatories, chemotherapeutics, radiotherapeutics, or other active and ancillary agents.

In various embodiments, the present disclosure provides a method of treating a subject having a metabolic disorder, said method comprising orally administering a fusion molecule of the present disclosure in an amount sufficient to treat said disorder, wherein said metabolic disorder is diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, or hyperlipidemia.

In another aspect, the present disclosure provides a method of treating a subject having a fatty liver disease (e.g., nonalcoholic fatty liver disease (NAFLD); nonalcoholic steatohepatitis (NASH)), a gastrointestinal disease, or a neurodegenerative disease, said method comprising orally administering a fusion molecule of the present disclosure in an amount sufficient to treat said disease.

In another aspect, the present disclosure relates to the use of a non-naturally occurring fusion molecule of the present disclosure for the preparation of a medicament for treatment, prophylaxis and/or prevention of GH deficient growth disorders in a subject in need thereof.

In another aspect, the present disclosure provides a method of treating a subject having a GH deficient growth disorder, said method comprising orally administering a fusion molecule of the present disclosure in an amount sufficient to treat said disorder, wherein said disorder is growth hormone deficiency (GHD), Turner syndrome (TS), Noonan syndrome, Prader-Willi syndrome, short stature homeobox-containing gene (SHOX) deficiency, chronic renal insufficiency, and idiopathic short stature short bowel syndrome, GH deficiency due to rare pituitary tumors or their treatment, and muscle-wasting disease associated with HIV/AIDS.

Polynucleotides Encoding Fusion molecules

In another aspect, the disclosure provides polynucleotides comprising a nucleotide sequence encoding the non-naturally occurring fusion molecules. These polynucleotides are useful, for example, for making the fusion molecules. In yet another aspect, the disclosure provides an expression system that comprises a recombinant polynucleotide sequence encoding a modified Cholix toxin, and a polylinker insertion site for a polynucleotide sequence encoding a biologically active cargo. The polylinker insertion site can be anywhere in the polynucleotide sequence so long as the polylinker insertion does not disrupt the receptor binding domain or the transcytosis domain of the modified Cholix toxin. In various embodiments, the expression system may comprise a polynucleotide sequence that encodes a cleavable linker so that cleavage at the cleavable linker separates a biologically active cargo encoded by a nucleic acid inserted into the polylinker insertion site from the remainder of the encoded fusion molecule. Thus, in embodiments where the polylinker insertion site is at an end of the encoded construct, the polynucleotide comprises one nucleotide sequence encoding a cleavable linker between the polylinker insertion site and the remainder of the polynucleotide. In embodiments where the polylinker insertion site is not at the end of the encoded construct, the polylinker insertion site can be flanked by nucleotide sequences that each encode a cleavable linker.

Various in vitro methods that can be used to prepare a polynucleotide encoding a modified Cholix toxin useful in the fusion molecules of the disclosure include, but are not limited to, reverse transcription, the polymerase chain reaction (PCR), the ligase chain reaction (LCR), the transcription-based amplification system (TAS), the self-sustained sequence replication system (3SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of a modified Cholix toxin or a nucleotide encoding, e.g., a receptor binding domain.

Guidance for using these cloning and in vitro amplification methodologies are described in, for example, U.S. Pat. No. 4,683,195; Mullis et al., 1987, Cold Spring Harbor Symp. Quant. Biol. 51:263; and Erlich, ed., 1989, PCR Technology, Stockton Press, NY. Polynucleotides encoding a fusion molecule or a portion thereof also can be isolated by screening genomic or cDNA libraries with probes selected from the sequences of the desired polynucleotide under stringent, moderately stringent, or highly stringent hybridization conditions.

Construction of nucleic acids encoding the fusion molecules of the disclosure can be facilitated by introducing an insertion site for a nucleic acid encoding the biologically active cargo into the construct. In various embodiments, an insertion site for the biologically active cargo can be introduced between the nucleotides encoding the cysteine residues of domain Ib of the modified Cholix toxin. In other embodiments, the insertion site can be introduced anywhere in the nucleic acid encoding the construct so long as the insertion does not disrupt the functional domains encoded thereby. In various embodiments, the insertion site can be in the ER retention domain.

Further, the polynucleotides can also encode a secretory sequence at the amino terminus of the encoded fusion molecule. Such constructs are useful for producing the fusion molecules in mammalian cells as they simplify isolation of the immunogen.

Furthermore, the polynucleotides of the disclosure also encompass derivative versions of polynucleotides encoding a fusion molecule. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the fusion molecule. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the inaccuracy incorporation rate of the polymerase used in the PCR reaction and result in random mutagenesis of the amplified nucleic acid.

Accordingly, in various embodiments, the disclosure provides a polynucleotide that encodes a fusion molecule. The fusion molecule comprises a modified Cholix toxin and a biologically active cargo to be delivered to a subject; and, optionally, a non-cleavable or cleavable linker. Cleavage at the cleavable linker can separate the biologically active cargo from the remainder of the fusion molecule. The cleavable linker can be cleaved by an enzyme that is present at a basolateral membrane of a polarized epithelial cell of the subject or in the plasma of the subject.

In various embodiments, the polynucleotide hybridizes under stringent hybridization conditions to any polynucleotide of this disclosure. In further embodiments, the polynucleotide hybridizes under stringent conditions to a nucleic acid that encodes any fusion molecule of the disclosure.

In still another aspect, the disclosure provides expression vectors for expressing the fusion molecules. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation or mRNA. Techniques for construction of expression vectors and expression of genes in cells comprising the expression vectors are well known in the art. See, e.g., Sambrook et al., 2001, Molecular Cloning—A Laboratory Manual, 3rd edition, Cold Spring Harbor Laboratory, Cold Spring Harbor, N.Y., and Ausubel et al., eds., Current Edition, Current Protocols in Molecular Biology, Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter.

The expression vectors should contain expression and replication signals compatible with the cell in which the fusion molecules are expressed. Expression vectors useful for expressing fusion molecules include viral vectors such as retroviruses, adenoviruses and adeno-associated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells.

The expression vectors can be introduced into the cell for expression of the fusion molecules by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY.

The expression vectors can also contain a purification moiety that simplifies isolation of the fusion molecule. For example, a polyhistidine moiety of, e.g., six histidine residues, can be incorporated at the amino terminal end of the protein. The polyhistidine moiety allows convenient isolation of the protein in a single step by nickel-chelate chromatography. In various embodiments, the purification moiety can be cleaved from the remainder of the fusion molecule following purification. In other embodiments, the moiety does not interfere with the function of the functional domains of the fusion molecule and thus need not be cleaved.

In yet another aspect, the disclosure provides a cell comprising an expression vector for expression of the fusion molecules, or portions thereof. The cell is selected for its ability to express high concentrations of the fusion molecule to facilitate purification of the protein. In various embodiments, the cell is a prokaryotic cell, for example, E. coli. As described in the examples, the fusion molecules are properly folded and comprise the appropriate disulfide linkages when expressed in E. coli.

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the fusion molecules. For example, Chinese hamster ovary (CHO) cells can be used to express the fusion molecules.

The fusion molecules of the disclosure can be produced by recombination, as described below. However, the fusion molecules may also be produced by chemical synthesis using methods known to those of skill in the art.

Methods for expressing and purifying the fusion molecules of the disclosure are described extensively in the examples below. Generally, the methods rely on introduction of an expression vector encoding the fusion molecule to a cell that can express the fusion molecule from the vector. The fusion molecule can then be purified for administration to a subject.

Transcytosis Testing

The function of the transcytosis domain can be tested as a function of the fusion molecule's ability to pass through an epithelial membrane. Because transcytosis first requires binding to the cell, these assays can also be used to assess the function of the cell recognition domain.

The fusion molecule's transcytosis activity can be tested by any method known by one of skill in the art, without limitation. In various embodiments, transcytosis activity can be tested by assessing the ability of a fusion molecule to enter a non-polarized cell to which it binds. Without intending to be bound to any particular theory or mechanism of action, it is believed that the same property that allows a transcytosis domain to pass through a polarized epithelial cell also allows molecules bearing the transcytosis domain to enter non-polarized cells. Thus, the fusion molecule's ability to enter the cell can be assessed, for example, by detecting the physical presence of the construct in the interior of the cell. For example, the fusion molecule can be labeled with, for example, a fluorescent marker, and the fusion molecule exposed to the cell. Then, the cells can be washed, removing any fusion molecule that has not entered the cell, and the amount of label remaining determined. Detecting the label in this traction indicates that the fusion molecule has entered the cell.

In other embodiments, the fusion molecule's transcytosis ability can be tested by assessing the fusion molecule's ability to pass through a polarized epithelial cell. For example, the fusion molecule can be labeled with, for example, a fluorescent marker and contacted to the apical membranes of a layer of epithelial cells. Fluorescence detected on the basolateral side of the membrane formed by the epithelial cells indicates that the transcytosis domain is functioning properly.

Cleavable Linker Cleavage Testing

The function of the cleavable linker can generally be tested in a cleavage assay. Any suitable cleavage assay known by one of skill in the art, without limitation, can be used to test the cleavable linkers. Both cell-based and cell-free assays can be used to test the ability of an enzyme to cleave the cleavable linkers.

An exemplary cell-free assay for testing cleavage of cleavable linkers comprises preparing extracts of polarized epithelial cells and exposing a labeled fusion molecule bearing a cleavable linker to the fraction of the extract that corresponds to membrane-associated enzymes. In such assays, the label can be attached to either the biologically active cargo to be delivered or to the remainder of the fusion molecule. Among these enzymes are cleavage enzymes found near the basolateral membrane of a polarized epithelial cell, as described above. Cleavage can be detected, for example, by binding the fusion molecule with, for example, an antibody and washing off unbound molecules. If label is attached to the biologically active cargo to be delivered, then little or no label should be observed on the molecule bound to the antibodies. Alternatively, the binding agent used in the assay can be specific for the biologically active cargo, and the remainder of the construct can be labeled. In either case, cleavage can be assessed.

Cleavage can also be tested using cell-based assays that test cleavage by polarized epithelial cells assembled into membranes. For example, a labeled fusion molecule, or portion of a fusion molecule comprising the cleavable linker, can be contacted to either the apical or basolateral side of a monolayer of suitable epithelial cells, such as, for example, Coco-2 cells, under conditions that permit cleavage of the linker. Cleavage can be detected by detecting the presence or absence of the label using a reagent that specifically binds the fusion molecule, or portion thereof. For example, an antibody specific for the fusion molecule can be used to bind a fusion molecule comprising a label distal to the cleavable linker in relation to the portion of the fusion molecule bound by the antibody. Cleavage can then be assessed by detecting the presence of the label on molecules bound to the antibody. If cleavage has occurred, little or no label should be observed on the molecules bound to the antibody. By performing such experiments, enzymes that preferentially cleave at the basolateral membrane rather than the apical membrane can be identified, and, further, the ability of such enzymes to cleave the cleavable linker in a fusion molecule can be confirmed.

Further, cleavage can also be tested using a fluorescence reporter assay as described in U.S. Pat. No. 6,759,207. Briefly, in such assays, the fluorescence reporter is contacted to the basolateral side of a monolayer of suitable epithelial cells under conditions that allow the cleaving enzyme to cleave the reporter. Cleavage of the reporter changes the structure of the fluorescence reporter, changing it from a non-fluorescent configuration to a fluorescent configuration. The amount of fluorescence observed indicates the activity of the cleaving enzyme present at the basolateral membrane.

Further, cleavage can also be tested using an intra-molecularly quenched molecular probe, such as those described in U.S. Pat. No. 6,592,847. Such probes generally comprise a fluorescent moiety that emits photons when excited with light of appropriate wavelength and a quencher moiety that absorbs such photons when in close proximity to the fluorescent moiety. Cleavage of the probe separates the quenching moiety from the fluorescent moiety, such that fluorescence can be detected, thereby indicating that cleavage has occurred. Thus, such probes can be used to identify and assess cleavage by particular cleaving enzymes by contacting the basolateral side of a monolayer of suitable epithelial cells with the probe under conditions that allow the cleaving enzyme to cleave the probe. The amount of fluorescence observed indicates the activity of the cleaving enzyme being tested.

Exemplary Cholix Toxin-Biologically Active Cargo Fusion Molecules

Embodiments of the present disclosure include, but are not limited to, the fusion molecules described in Table 7.

TABLE 7

| Modified Cholix Toxin (SEQ ID NO) | Cleavable Linker (SEQ ID NO) | Biologically Active Cargo (SEQ ID NO) |
|---|---|---|
| SEQ ID NO: 3 | SEQ ID NOs: 96-121 No Linker | SEQ ID NOs: 82-95 |
| SEQ ID NO: 4 | SEQ ID NOs: 96-121 No Linker | SEQ ID NOs: 82-95 |
| SEQ ID NO: 5 | SEQ ID NOs: 96-121 No Linker | SEQ ID NOs: 82-95 |
| SEQ ID NO: 6 | SEQ ID NOs: 96-121 No Linker | SEQ ID NOs: 82-95 |
| SEQ ID NO: 7 | SEQ ID NOs: 96-121 No Linker | SEQ ID NOs: 82-95 |
| SEQ ID NO: 8 | SEQ ID NOs: 96-121 No Linker | SEQ ID NOs: 82-95 |
| SEQ ID NO: 9 | SEQ ID NOs: 96-121 No Linker | SEQ ID NOs: 82-95 |
| SEQ ID NO: 10 | SEQ ID NOs: 96-121 No Linker | SEQ ID NOs: 82-95 |
| SEQ ID NO: 11 | SEQ ID NOs: 96-121 No Linker | SEQ ID NOs: 82-95 |
| SEQ ID NO: 12 | SEQ ID NOs: 96-121 No Linker | SEQ ID NOs: 82-95 |
| SEQ ID NO: 13 | SEQ ID NOs: 96-121 No Linker | SEQ ID NOs: 82-95 |
| SEQ ID NO: 14 | SEQ ID NOs: 96-121 No Linker | SEQ ID NOs: 82-95 |
| SEQ ID NO: 15 | SEQ ID NOs: 96-121 No Linker | SEQ ID NOs: 82-95 |
| SEQ ID NO: 16 | SEQ ID NOs: 96-121 No Linker | SEQ ID NOs: 82-95 |
| SEQ ID NO: 17 | SEQ ID NOs: 96-121 No Linker | SEQ ID NOs: 82-95 |
| SEQ ID NO: 18 | SEQ ID NOs: 96-121 No Linker | SEQ ID NOs: 82-95 |
| SEQ ID NO: 19 | SEQ ID NOs: 96-121 No Linker | SEQ ID NOs: 82-95 |
| SEQ ID NO: 20 | SEQ ID NOs: 96-121 No Linker | SEQ ID NOs: 82-95 |
| SEQ ID NO: 21 | SEQ ID NOs: 96-121 No Linker | SEQ ID NOs: 82-95 |
| SEQ ID NO: 22 | SEQ ID NOs: 96-121 No Linker | SEQ ID NOs: 82-95 |
| SEQ ID NO: 23 | SEQ ID NOs: 96-121 No Linker | SEQ ID NOs: 82-95 |
| SEQ ID NO: 24 | SEQ ID NOs: 96-121 No Linker | SEQ ID NOs: 82-95 |
| SEQ ID NO: 25 | SEQ ID NOs: 96-121 No Linker | SEQ ID NOs: 82-95 |
| SEQ ID NO: 26 | SEQ ID NOs: 96-121 No Linker | SEQ ID NOs: 82-95 |
| SEQ ID NO: 27 | SEQ ID NOs: 96-121 No Linker | SEQ ID NOs: 82-95 |
| SEQ ID NO: 28 | SEQ ID NOs: 96-121 No Linker | SEQ ID NOs: 82-95 |
| SEQ ID NO: 29 | SEQ ID NOs: 96-121 No Linker | SEQ ID NOs: 82-95 |
| SEQ ID NO: 30 | SEQ ID NOs: 96-121 No Linker | SEQ ID NOs: 82-95 |
| SEQ ID NO: 31 | SEQ ID NOs: 96-121 No Linker | SEQ ID NOs: 82-95 |
| SEQ ID NO: 32 | SEQ ID NOs: 96-121 No Linker | SEQ ID NOs: 82-95 |
| SEQ ID NO: 33 | SEQ ID NOs: 96-121 No Linker | SEQ ID NOs: 82-95 |
| SEQ ID NO: 34 | SEQ ID NOs: 96-121 No Linker | SEQ ID NOs: 82-95 |
| SEQ ID NO: 35 | SEQ ID NOs: 96-121 No Linker | SEQ ID NOs: 82-95 |
| SEQ ID NO: 36 | SEQ ID NOs: 96-121 No Linker | SEQ ID NOs: 82-95 |
| SEQ ID NO: 37 | SEQ ID NOs: 96-121 No Linker | SEQ ID NOs: 82-95 |
| SEQ ID NO: 38 | SEQ ID NOs: 96-121 No Linker | SEQ ID NOs: 82-95 |
| SEQ ID NO: 39 | SEQ ID NOs: 96-121 No Linker | SEQ ID NOs: 82-95 |
| SEQ ID NO: 40 | SEQ ID NOs: 96-121 No Linker | SEQ ID NOs: 82-95 |
| SEQ ID NO: 41 | SEQ ID NOs: 96-121 No Linker | SEQ ID NOs: 82-95 |
| SEQ ID NO: 42 | SEQ ID NOs: 96-121 No Linker | SEQ ID NOs: 82-95 |
| SEQ ID NO: 43 | SEQ ID NOs: 96-121 No Linker | SEQ ID NOs: 82-95 |
| SEQ ID NO: 44 | SEQ ID NOs: 96-121 No Linker | SEQ ID NOs: 82-95 |
| SEQ ID NO: 45 | SEQ ID NOs: 96-121 No Linker | SEQ ID NOs: 82-95 |
| SEQ ID NO: 46 | SEQ ID NOs: 96-121 No Linker | SEQ ID NOs: 82-95 |
| SEQ ID NO: 47 | SEQ ID NOs: 96-121 No Linker | SEQ ID NOs: 82-95 |
| SEQ ID NO: 48 | SEQ ID NOs: 96-121 No Linker | SEQ ID NOs: 82-95 |
| SEQ ID NO: 49 | SEQ ID NOs: 96-121 No Linker | SEQ ID NOs: 82-95 |
| SEQ ID NO: 50 | SEQ ID NOs: 96-121 No Linker | SEQ ID NOs: 82-95 |
| SEQ ID NO: 51 | SEQ ID NOs: 96-121 No Linker | SEQ ID NOs: 82-95 |
| SEQ ID NO: 52 | SEQ ID NOs: 96-121 No Linker | SEQ ID NOs: 82-95 |
| SEQ ID NO: 53 | SEQ ID NOs: 96-121 No Linker | SEQ ID NOs: 82-95 |
| SEQ ID NO: 54 | SEQ ID NOs: 96-121 No Linker | SEQ ID NOs: 82-95 |
| SEQ ID NO: 55 | SEQ ID NOs: 96-121 No Linker | SEQ ID NOs: 82-95 |
| SEQ ID NO: 56 | SEQ ID NOs: 96-121 No Linker | SEQ ID NOs: 82-95 |
| SEQ ID NO: 57 | SEQ ID NOs: 96-121 No Linker | SEQ ID NOs: 82-95 |
| SEQ ID NO: 58 | SEQ ID NOs: 96-121 No Linker | SEQ ID NOs: 82-95 |
| SEQ ID NO: 59 | SEQ ID NOs: 96-121 No Linker | SEQ ID NOs: 82-95 |
| SEQ ID NO: 60 | SEQ ID NOs: 96-121 No Linker | SEQ ID NOs: 82-95 |
| SEQ ID NO: 61 | SEQ ID NOs: 96-121 No Linker | SEQ ID NOs: 82-95 |
| SEQ ID NO: 62 | SEQ ID NOs: 96-121 No Linker | SEQ ID NOs: 82-95 |
| SEQ ID NO: 63 | SEQ ID NOs: 96-121 No Linker | SEQ ID NOs: 82-95 |
| SEQ ID NO: 64 | SEQ ID NOs: 96-121 No Linker | SEQ ID NOs: 82-95 |
| SEQ ID NO: 65 | SEQ ID NOs: 96-121 No Linker | SEQ ID NOs: 82-95 |
| SEQ ID NO: 66 | SEQ ID NOs: 96-121 No Linker | SEQ ID NOs: 82-95 |
| SEQ ID NO: 67 | SEQ ID NOs: 96-121 No Linker | SEQ ID NOs: 82-95 |
| SEQ ID NO: 68 | SEQ ID NOs: 96-121 No Linker | SEQ ID NOs: 82-95 |
| SEQ ID NO: 69 | SEQ ID NOs: 96-121 No Linker | SEQ ID NOs: 82-95 |
| SEQ ID NO: 70 | SEQ ID NOs: 96-121 No Linker | SEQ ID NOs: 82-95 |
| SEQ ID NO: 71 | SEQ ID NOs: 96-121 No Linker | SEQ ID NOs: 82-95 |
| SEQ ID NO: 72 | SEQ ID NOs: 96-121 No Linker | SEQ ID NOs: 82-95 |
| SEQ ID NO: 73 | SEQ ID NOs: 96-121 No Linker | SEQ ID NOs: 82-95 |
| SEQ ID NO: 74 | SEQ ID NOs: 96-121 No Linker | SEQ ID NOs: 82-95 |
| SEQ ID NO: 75 | SEQ ID NOs: 96-121 No Linker | SEQ ID NOs: 82-95 |
| SEQ ID NO: 76 | SEQ ID NOs: 96-121 No Linker | SEQ ID NOs: 82-95 |
| SEQ ID NO: 77 | SEQ ID NOs: 96-121 No Linker | SEQ ID NOs: 82-95 |
| SEQ ID NO: 78 | SEQ ID NOs: 96-121 No Linker | SEQ ID NOs: 82-95 |

TABLE 7-continued

| Modified Cholix Toxin (SEQ ID NO) | Cleavable Linker (SEQ ID NO) | Biologically Active Cargo (SEQ ID NO) |
|---|---|---|
| SEQ ID NO: 79 | SEQ ID NOs: 96-121 No Linker | SEQ ID NOs: 82-95 |
| SEQ ID NO: 80 | SEQ ID NOs: 96-121 No Linker | SEQ ID NOs: 82-95 |
| SEQ ID NO: 81 | SEQ ID NOs: 96-121 No Linker | SEQ ID NOs: 82-95 |

In various embodiments, the fusion molecule comprises a modified Cholix toxin having the amino acid sequence of SEQ ID NO: 80 and a biologically active cargo having the amino acid sequence of SEQ ID NO: 82

In various embodiments, the fusion molecule comprises a modified Cholix toxin having the amino acid sequence of SEQ ID NO: 70 and a biologically active cargo having the amino acid sequence of SEQ ID NO: 82.

In various embodiments, the fusion molecule comprises a modified Cholix toxin having the amino acid sequence of SEQ ID NO: 42 and a biologically active cargo having the amino acid sequence of SEQ ID NO: 82.

In various embodiments, the fusion molecule comprises the amino acid sequence set forth in SEQ ID NO: 114.

In various embodiments, the fusion molecule comprises the amino acid sequence set forth in SEQ ID NO: 115.

In various embodiments, the fusion molecule comprises a modified Cholix toxin having the amino acid sequence of SEQ ID NO: 52 and a biologically active cargo that is an antibody comprising a heavy chain variable having the amino acid sequence of SEQ ID NO: 88 and a light chain variable having the amino acid sequence of SEQ ID NO: 89.

In various embodiments, the fusion molecule comprises a modified Cholix toxin having the amino acid sequence of SEQ ID NO: 52 and a biologically active cargo that is an antibody comprising a heavy chain variable having the amino acid sequence of SEQ ID NO: 90 and a light chain variable having the amino acid sequence of SEQ ID NO: 91

In various embodiments, the fusion molecule comprises a modified Cholix toxin having the amino acid sequence of SEQ ID NO: 52 and a biologically active cargo having the amino acid sequence of SEQ ID NO: 92.

In various embodiments, the fusion molecule comprises a modified Cholix toxin having the amino acid sequence of SEQ ID NO: 52 and a biologically active cargo having the amino acid sequence of SEQ ID NO: 93.

In various embodiments, the fusion molecule comprises a modified Cholix toxin having the amino acid sequence of SEQ ID NO: 52 and a biologically active cargo having the amino acid sequence of SEQ ID NO: 94.

In various embodiments, the fusion molecule comprises a modified Cholix toxin having the amino acid sequence of SEQ ID NO: 52 and a biologically active cargo having the amino acid sequence of SEQ ID NO: 95.

In various embodiments, the fusion molecule comprises a modified Cholix toxin having the amino acid sequence of SEQ ID NO: 80 and a biologically active cargo that is an antibody comprising a heavy chain variable having the amino acid sequence of SEQ ID NO: 88 and a light chain variable having the amino acid sequence of SEQ ID NO: 89.

In various embodiments, the fusion molecule comprises a modified Cholix toxin having the amino acid sequence of SEQ ID NO: 80 and a biologically active cargo that is an antibody comprising a heavy chain variable having the amino acid sequence of SEQ ID NO: 90 and a light chain variable having the amino acid sequence of SEQ ID NO: 91

In various embodiments, the fusion molecule comprises a modified Cholix toxin having the amino acid sequence of SEQ ID NO: 80 and a biologically active cargo having the amino acid sequence of SEQ ID NO: 92.

In various embodiments, the fusion molecule comprises a modified Cholix toxin having the amino acid sequence of SEQ ID NO: 80 and a biologically active cargo having the amino acid sequence of SEQ ID NO: 93.

In various embodiments, the fusion molecule comprises a modified Cholix toxin having the amino acid sequence of SEQ ID NO: 80 and a biologically active cargo having the amino acid sequence of SEQ ID NO: 94. In various embodiments, the fusion molecule comprises a modified Cholix toxin having the amino acid sequence of SEQ ID NO: 80 and a biologically active cargo having the amino acid sequence of SEQ ID NO: 95.

In various embodiments, the fusion molecule comprises a modified Cholix toxin having the amino acid sequence of SEQ ID NO: 70 and a biologically active cargo that is an antibody comprising a heavy chain variable having the amino acid sequence of SEQ ID NO: 88 and a light chain variable having the amino acid sequence of SEQ ID NO: 89.

In various embodiments, the fusion molecule comprises a modified Cholix toxin having the amino acid sequence of SEQ ID NO: 70 and a biologically active cargo that is an antibody comprising a heavy chain variable having the amino acid sequence of SEQ ID NO: 90 and a light chain variable having the amino acid sequence of SEQ ID NO: 91

In various embodiments, the fusion molecule comprises a modified Cholix toxin having the amino acid sequence of SEQ ID NO: 70 and a biologically active cargo having the amino acid sequence of SEQ ID NO: 92.

In various embodiments, the fusion molecule comprises a modified Cholix toxin having the amino acid sequence of SEQ ID NO: 70 and a biologically active cargo having the amino acid sequence of SEQ ID NO: 93.

In various embodiments, the fusion molecule comprises a modified Cholix toxin having the amino acid sequence of SEQ ID NO: 70 and a biologically active cargo having the amino acid sequence of SEQ ID NO: 94.

In various embodiments, the fusion molecule comprises a modified Cholix toxin having the amino acid sequence of SEQ ID NO: 70 and a biologically active cargo having the amino acid sequence of SEQ ID NO: 95.

In various embodiments, the fusion molecule comprises a modified Cholix toxin having the amino acid sequence of SEQ ID NO: 42 and a biologically active cargo that is an antibody comprising a heavy chain variable having the amino acid sequence of SEQ ID NO: 88 and a light chain variable having the amino acid sequence of SEQ ID NO: 89.

In various embodiments, the fusion molecule comprises a modified Cholix toxin having the amino acid sequence of SEQ ID NO: 42 and a biologically active cargo that is an antibody comprising a heavy chain variable having the amino acid sequence of SEQ ID NO: 90 and a light chain variable having the amino acid sequence of SEQ ID NO: 91.

In various embodiments, the fusion molecule comprises a modified Cholix toxin having the amino acid sequence of SEQ ID NO: 42 and a biologically active cargo having the amino acid sequence of SEQ ID NO: 92.

In various embodiments, the fusion molecule comprises a modified Cholix toxin having the amino acid sequence of SEQ ID NO: 42 and a biologically active cargo having the amino acid sequence of SEQ ID NO: 93.

In various embodiments, the fusion molecule comprises a modified Cholix toxin having the amino acid sequence of SEQ ID NO: 42 and a biologically active cargo having the amino acid sequence of SEQ ID NO: 94.

In various embodiments, the fusion molecule comprises a modified Cholix toxin having the amino acid sequence of SEQ ID NO: 42 and a biologically active cargo having the amino acid sequence of SEQ ID NO: 95.

The following examples merely illustrate the disclosure, and are not intended to limit the disclosure in any way.

Example 1

A plasmid construct was prepared encoding mature *Vibrio cholera* Cholix and used to express the mature Cholix protein in an *E. coli* expression system as previously described; see, e.g., Jorgensen, R. et al., *J Biol Chem*, 283(16):10671-10678 (2008). A non-toxic mutant form of the Cholix gene (hereinafter referred to as "ntCholix") was also prepared by genetic deletion of a glutamic acid at amino acid position 581 (ΔE581) which is analogous to a deletion (ΔE553) in the PE protein that renders it non-toxic without significantly altering its conformation; Killeen, K. P. and Collier, R. J., *Biochim Biophys Acta*, 1138:162-166 (1992). Protein expression was achieved using *E. coli* DH5a cells (Invitrogen, Carlsbad, Calif.) following transformation by heat-shock (1 min at 42° C.) with the appropriate plasmid. Transformed cells, selected on antibiotic-containing media, were isolated and grown in Luria-Bertani broth (Difco). Protein expression was induced by addition of 1 mM isopropyl-D-thiogalactopyranoside (IPTG). Two hours following IPTG induction, cells were harvested by centrifugation at 5,000×g for 10 min at 4° C. Inclusion bodies were isolated following cell lysis and proteins were solubilized in 6 M guanidine HCl and 2 mM EDTA (pH 8.0) plus 65 mM dithiothreitol. Following refolding and purification, proteins were stored at ~5 ml/ml in PBS (pH 7.4) lacking $Ca^{2+}$ and $Mg^{2+}$ at −80° C. All proteins used in these studies were confirmed to be at >90% purity based upon size exclusion chromatography.

The ntCholix form was then modified at its C-terminus to allow direct chemical coupling through a free sulfhydryl residue located near the C-terminus of the protein. The strategy for the C-terminal modification is depicted in FIG. 1. The C-terminal modification included a cysteine-constrained loop harboring the consensus cleavage sequence (ENLFQS) for the highly selective protease from the tobacco etch virus (TEV), a second cysteine, and a hexa-histadine ($His_6$) tag. The second Cys was included to form a disulphide bridge with the Cys ultimately used for coupling. Adding the $His_6$ sequence to the protein simplified the purification and the TEV cleavage sequence provided a mechanism to selectively remove the terminal Cys residue following mild reduction. TEV cleavage and mild reduction with 0.1 mM dithiotheitol following expression and isolation of the ntCholix constructs allowed for the direct chemical coupling of a cargo, Alexa Fluor® 488 fluorescent dye, via a maleimide-based reaction as a generic mechanism of cargo attachment. The resultant construct is referred to herein as ntCholix-Alexa488. Following TEV protease cleavage, reduction, and cargo coupling through a maleimide reaction with the free sulfhydryl, removal of the freed C-terminal sequence was achieved by a second Ni' column chromatography step.

Example 2

Trans-epithelial transport of ntCholix-Alexa488 was assessed using Caco-2 monolayers in vitro. First, Caco-2 cells (passage number 25-35) were grown to confluent monolayers as previously described; Rubas, W. et al., *Pharm Res*, 10:113-118 (1993). Briefly, cells were maintained at 37° C. in DMEM/high growth media enriched with 2 mM L-glutamine, 10% fetal bovine serum, and 100 Units of penicillin/streptomycin in an atmosphere of 5% $CO_2$ and 90% humidity. Cells were passaged every week at a split ratio of 1:3 in 75 $cm^2$ flasks and seeded onto prewetted and collagen-coated permeable (0.4 μm pore size) polycarbonate (Transwell™) filter supports from Corning Costar (Cambridge, Mass.) at a density of 63,000 cells/$cm^2$. Growth media was replaced every other day. Confluent monolayers, determined by the acquisition of significant trans-epithelial resistance (TEER) determine using an volt-ohm-meter (World Precision Instruments, Sarasota, Fla.), were used 20-26 days post seeding.

Two additional materials were also prepared to be used as controls to assess the in vitro transport of Cholix. As an internal control for filter damage, tetramethylrhodamine isothiocyanate (TRITC)-labeled 70 kDa dextan was obtained from commercial source (Sigma). As a control for non-specific dye-mediated transport we reacted some of the free amines on the surface of bovine serum albumin (BSA; Sigma) with Alexa488 carboxylic acid succinimidyl ester (A488-CASE; Invitrogen). The coupling reaction was carried out for 4 hr at room temperature at neutral pH at a molar ratio of 10:1 A488-CASE:BSA at which point excess glycine was added to quench the reaction. The resulting purified product contained ~3 Alexa488 molecules per BSA molecule. Tetramethylrhodamine isothiocyanate (TRITC)-labeled 70 kDa dextan (Sigma) was used as an internal control for filter damage. Fluorescence measurements were made using a BMG labtech FLUOstar Omega instrument set at 540 nm excitation and 610 nm emission for TRITC-Dextran (optimal Ex=547 and Em=572) and 480 nm excitation and 520 nm emission for Alexa488 proteins (optimal Ex=496 and Em=519).

Trans-epithelial transport flux rates were measured in vitro in the apical (Ap) to basolateral (Bl) and the Bl to Ap directions using polarized monolayers of Caco-2 cells to describe mucosal to serosal and serosal to mucosal flux events, respectively. Just prior to initiation of a transport study, the transepithelial resistance (TEER) of each filter was measured; monolayers TEER reading of <200 Ω·cm2 were excluded from the study. Ap and Bl media was removed from included monolayers and these surfaces were washed with once with phosphate buffered saline (PBS). One set of monolayers then received an Ap (donor) application of 100 μL PBS containing 10 μg ntCholix-A488 and 10 TRITC-Dextran or 10 μg BSA-A488 and 10 μg TRITC-Dextran. Receiver (Bl) compartments then received 500 μL PBS to set the $T_0$ for the transport study. Both donor and receiver compartments were sampled after 4 hr of incubation at 37° C. to determine the amount of material transported across the monolayer and the amount retained at the apical surface, respectively.

Figure 2:
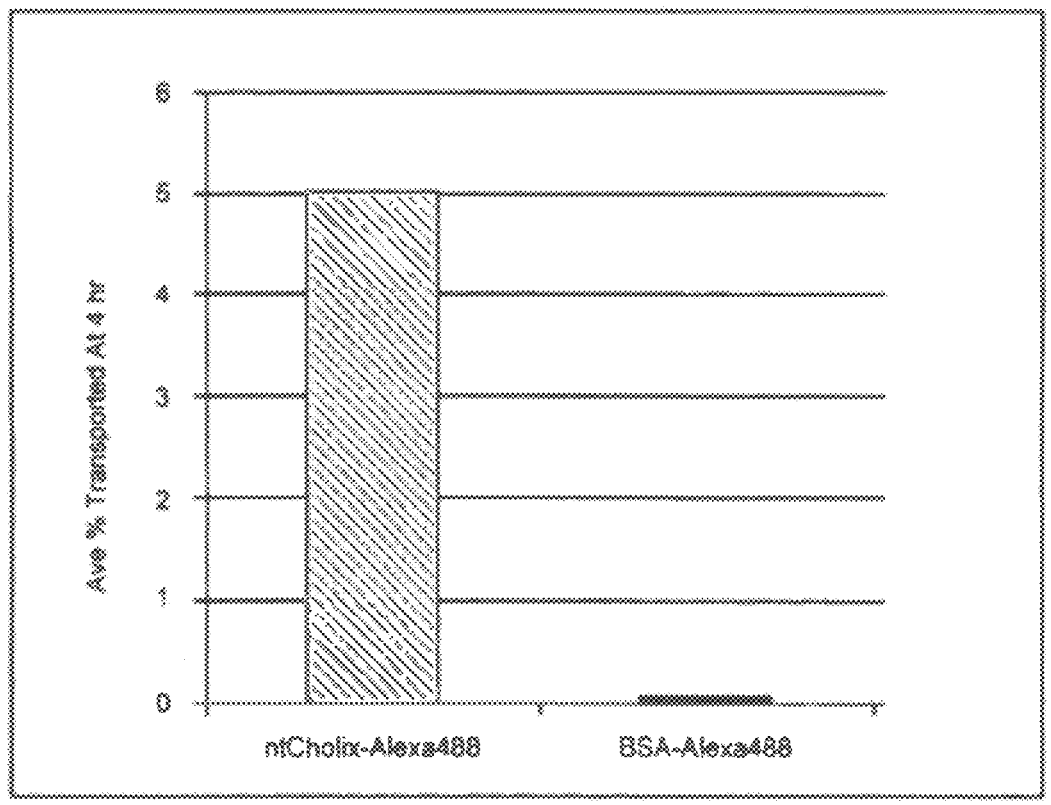

After 4 hour of exposure we observed ~5% of the material added to the apical surface of these monolayers to be transported (see FIG. 2). Any filters showing levels of 75 kDa TRITC-Dextran in the basal compartment were excluded from the analysis. A control protein of BSA-Alexa488 failed to show any significant levels in the basal compartment over this same 4 hr period (see FIG. 2). The averages of transport were 5.025±1.13% for Cholix and 0.56±0.33 for BSA (N=4). This data establishes that a genetically detoxified form of Cholix can efficiently transport in vitro across polarized monolayers of a human intestinal cancer cell line, Caco-2.

Example 3

Also prepared and expressed in *E. coli.* was a variant of Cholix truncated at amino acid $A^{386}$ (Cholix$^{386}$) as well as a genetic ligation of green fluorescent protein (GFP) at the C-terminus of Cholix$^{386}$ (Cholix$^{386}$GFP). Protein expression was achieved using *E. coli* DH5a cells (Invitrogen, Carlsbad, Calif.) following transformation by heat-shock (1 min at 42° C.) with the appropriate plasmid. Transformed cells, selected on antibiotic-containing media, were isolated and grown in Luria-Bertani broth (Difco). Protein expression was induced by addition of 1 mM isopropyl-D-thiogalactopyranoside (IPTG). Two hours following IPTG induction, cells were harvested by centrifugation at 5,000×g for 10 min at 4° C. Inclusion bodies were isolated following cell lysis and proteins were solubilized in 6 M guanidine HCl and 2 mM EDTA (pH 8.0) plus 65 mM dithiothreitol. Following refolding and purification, proteins were stored at ~5 ml/ml in PBS (pH 7.4) lacking Ca' and Mg' at −80° C. Cholix$^{386}$GFP refolding was monitored by acquisition and retention of the fluorescence signature associated with this fluorescent protein; Sample et al., *Chem Soc Rev*, 38(10): p. 2852-64 (2009). Green fluorescent protein (GFP) was purchased from Upstate (Charlottesville, Va.). All proteins used in these studies were confirmed to be at >90% purity based upon size exclusion chromatography.

Polystyrene beads (10 nm diameter) containing a covalently integrated red fluorescent dye with excitation/emission properties of 468/508 nm and having aldehyde surface functional groups (XPR-582) were obtained from Duke Scientific (Palo Alto, Calif.). One hundred μl of XPR-582 beads (at 2% solids) was mixed with approximately 2.5 nmoles GFP or Cholix$^{386}$GFP in a final volume of 200 μl neutral (pH 7.0) phosphate buffered saline (PBS). After 2 hr of gentle rocking at room temperature, 20 μl of a 2 mg/ml solution of bovine serum albumin (BSA; Sigma, St. Louis, Mo.) in PBS was added. Preparations were then dialyzed by three cycles of dilution with PBS and concentration using a 100,000 molecular weight cutoff Microcon filter device from Millipore (Bedford, Mass.). Final preparations of coated beads were at 1% solids.

Example 4

A549 (ATCC CCL-185™), L929 (ATCC CRL-2148™), and Caco-2 (ATCC HTB-37™) cells were maintained in 5% $CO_2$ at 37° C. in complete media: Dulbecco's modified Eagle's medium F12 (DMEM F12) supplemented with 10% fetal bovine serum, 2.5 mM glutamine, 100 U of penicillin/ml, and 100 μg of streptomycin/ml (Gibco BRL, Grand Island, N.Y.). Cells were fed every 2 to 3 days with this media (designated complete medium) and passaged every 5 to 7 days. For assays, cells were seeded into 24- or 96-well plates and grown to confluence.

Caco-2 cells were grown as confluent monolayers on collagen-coated 0.4-μm pore size polycarbonate membrane transwell supports (Corning-Costar, Cambridge, Mass.) and used 18-25 days after attaining a trans-epithelial electrical resistance (TEER) of >250 Ω·cm2 as measured using a chopstick Millicell-ERS® voltmeter (Millipore). Apical to basolateral (A→B) and basolateral to apical (B→A) transport of Cholix or Cholix$^{386}$GFP across these monolayer was determined by measuring the amount of transported protein 4 hr after a 20 μg application at 37° C. TEER measurements and the extent of 10 kDa fluorescent dextran (measured using an HPLC size exclusion protocol) were used to verify monolayer barrier properties during the course of the study. The extent of Cholix transport was determined by titration of collected media in the cell-based cytotoxicity assay. Transported Cholix$^{386}$GFP was measured by enzyme linked immunosorbant assay (ELISA) using anti-GFP antibody for capture and the polyclonal sera to Cholix for detection.

Transport rates across polarized Caco-2 cells monolayers in vitro were comparable for Cholix, ntCholix and Cholix$^{386}$GFP as assess by ELISA format analysis. In the case of Cholix, polarized Caco-2 cells were not intoxicated by the protein when examined for TUNEL detection of apoptosis or lactate dehydrogenase (LDH) release. Importantly, Cholix and Cholix-based protein chimeras were found to transport efficiently from the apical to basolateral surface of Caco-2 monolayers but not in the basolateral to apical direction. These transport rates and directionality were comparable to that previously observed for PE tested in this same format. Additionally, we observed that addition rabbit anti-Cholix antisera failed to block the effective transport of Cholix or Cholix-related proteins across Caco-2 monolayers in vitro.

Confocal fluorescence microscopy was used to examine the nature of Cholix$^{386}$GFP transcytosis across Caco-2 monolayers in vitro. A time course study showed Cholix$^{386}$GFP entering into epithelial cells within 5 minutes of its apical application and transporting through cells to the basolateral region of the cell within 15 minutes. In samples exposed to apical Cholix$^{386}$GFP for 15 minutes with subsequent removal of excess Cholix$^{386}$GFP from the apical chamber, GFP fluorescence was observed to continue in the direction of the basolateral surface of the cell and not back toward the apical surface. This unidirectional movement of Cholix$^{386}$GFP was confirmed by measuring Cholix$^{386}$GFP content in the apical and basolateral compartments over this time course. Application of Cholix$^{386}$GFP at the basolateral surface of Caco-2 monolayers did not show any significant fluorescence entering into the cells, consistent with transport studies. Western blot analysis of transported Cholix, ntCholix and Cholix$^{386}$GFP suggested that these proteins transported without major alterations.

In vitro studies also showed that 100 nm diameter fluorescent latex beads chemically coupled to Cholix$^{386}$GFP efficiently transported across Caco-2 monolayers following an apical application. Latex bead selection with a 100 nm diameter provided a material that could readily fit within the lumen of a 125 nm diameter endosome derived from a clatherin-coated pit. Thus, these studies suggest Cholix$^{386}$GFP-latex beads to move through polarized Caco-2 cells by a mechanism consistent with endosome uptake at the apical cell surface followed by endosome-based intracellular trafficking. Pre-incubation of Cholix$^{386}$GFP-coupled 100 nm diameter fluorescent latex beads with anti-Cholix antisera failed to alter the transport of these beads. A similar amount of GFP chemically coupled to 100 nm diameter fluorescent latex beads did not facilitate the in vitro transport of these particles across Caco-2 monolayers. Confocal fluorescence microscopy studies were consistent with differences observed for in transcytosis latex bead coated with Cholix$^{386}$GFP versus GFP.

The result that Cholix is capable of transporting across polarized epithelial barriers similar to PE is unanticipated. While their structures are similar as suggested by crystallographic analysis, their surfaces amino acid composition is strikingly different; indeed, alignment methods based upon amino acid similarity would not readily match these two proteins. This is important in that the ability of a pathogen-derived protein, such as these two virulence factors, to interact with host cell receptors is presumed to involve surface-expressed amino acid components. As both of these proteins (with their substantially different amino acid sequences) transport efficiently across polarized epithelia, it is highly likely that some other mechanism forms that basis for this transport capacity. It is our contention that the structural relationships shared by PE and Cholix forms the basis of the inherent capacity for their efficient transcytosis. While both PE and Cholix proteins would have the capacity to bind to an apical surface receptor to gain access to endosomal compartments it is more likely that this interaction and the potential for other receptors involved in the intracellular trafficking of these proteins would be based upon conformational structures rather than specific amino acids on the protein surface.

Example 5

In this Example, the preparation of a non-naturally occurring fusion molecule as a single amino acid sequence and comprising a modified Cholix toxin sequence, a cleavable linker sequence, and a biologically active cargo, is generally described.

Seven exemplary fusion molecule expression vectors for delivering the polypeptides interleukin-10 (SEQ ID NO: 82), interleukin-19 (SEQ ID NO: 83), interleukin-20 (SEQ ID NO: 84), interleukin-22 (SEQ ID NO: 85), interleukin-24 (SEQ ID NO: 86), or interleukin-26 (SEQ ID NO: 87) are constructed as generally described below. First, the polypeptide genes are amplified by PCR, incorporating restriction enzymes pairs of NdeI and EcoRI, PstI and PstI, AgeI and EcoRI, or PstI and EcoRI sites at two ends of the PCR products. After restriction enzyme digestion, the PCR products are cloned into an appropriate plasmid for cellular expression, which is digested with the corresponding restriction enzyme pairs. The resulting constructs comprise a modified Cholix toxin comprising an amino acid sequence encoding amino acids 1-386 of SEQ ID NO: 1 (Cholix$^{386}$) and the respective polypeptides, and are also tagged with a 6-His motif at the N-terminus of the polypeptide to facilitate purification. The final plasmids are verified by restriction enzyme digestions and DNA sequencing.

Also prepared was a non-naturally occurring fusion molecule comprising a Cholix$^{415}$ (SEQ ID NO: 52), a cleavable linker sequence having the amino acid sequence set forth in SEQ ID NO: 121, and a biologically active cargo that is a IL-10 polypeptide consisting of amino acid residues 20-178 of SEQ ID NO: 82 (this fusion molecule is designated "Cholix$^{415}$-TEV-IL-10", see FIG. 3 (SEQ ID NO: 122)), and a non-naturally occurring fusion molecule comprising a Cholix$^{415}$ (SEQ ID NO: 52), a non-cleavable linker sequence having the amino acid sequence set forth in SEQ ID NO: 98, and a biologically active cargo that is a IL-10 polypeptide consisting of amino acid residues 20-178 of SEQ ID NO: 82 (this fusion molecule is designated "Cholix$^{415}$-(G$_4$S)$_3$-IL-10", see FIG. 3 (SEQ ID NO: 123)).

Expression vectors comprising non-cleavable or cleavable linkers are constructed by introducing sequences encoding the appropriate amino acid sequence. To do so, oligonucleotides that encode sequences complementary to appropriate restriction sites and the amino acid sequence of the desired linker are synthesized, then ligated into an expression vector prepared as described above between the modified Cholix sequence and the polypeptide sequence.

In various embodiments, the fusion molecules are expressed as follows: E. coli BL21(DE3) pLysS competent cells (Novagen, Madison, Wis.) are transformed using a standard heat-shock method in the presence of the appropriate plasmid to generate fusion molecule expression cells, selected on ampicillin-containing media, and isolated and grown in Luria-Bertani broth (Difco; Becton Dickinson, Franklin Lakes, N.J.) with antibiotic, then induced for protein expression by the addition of 1 mM isopropyl-D-thiogalactopyranoside (IPTG) at OD 0.6. Two hours following IPTG induction, cells are harvested by centrifugation at 5,000 rpm for 10 min. Inclusion bodies are isolated following cell lysis and proteins are solubilized in the buffer containing 100 mM Tris-HCl (pH 8.0), 2 mM EDTA, 6 M guanidine HCl, and 65 mM dithiothreitol. Solubilized fusion molecule is refolded in the presence of 0.1 M Tris, pH=7.4, 500 mM L-arginine, 0.9 mM GSSG, 2 mM EDTA. The refolded proteins are purified by Q sepharose Ion Exchange and Superdex 200 Gel Filtration chromatography (Amersham Biosciences, Inc., Sweden). The purity of proteins is assessed by SDS-PAGE and analytic HPLC (Agilent, Inc. Palo Alto, Calif.).

Figure 4:
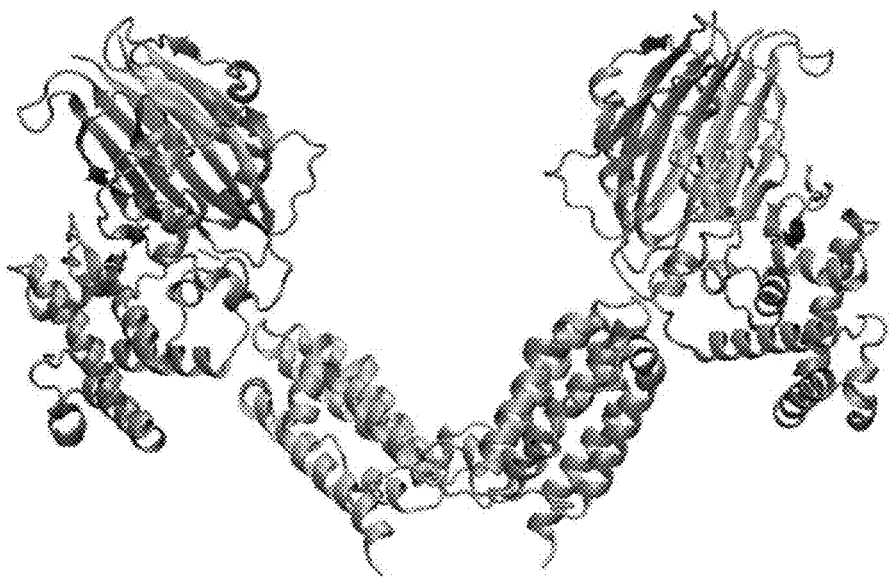

FIG. 4 is a ribbon diagram representation of an exemplary fusion molecule, e.g., Cholix$^{415}$-TEV-IL-10 after refolding that would be driven by IL-10 dimerization. IL-10 dimerization is envisaged to result in purple Cholix$^{415}$/blue hIL-10 and orange Cholix$^{415}$/green organization shown.

Figure 5:
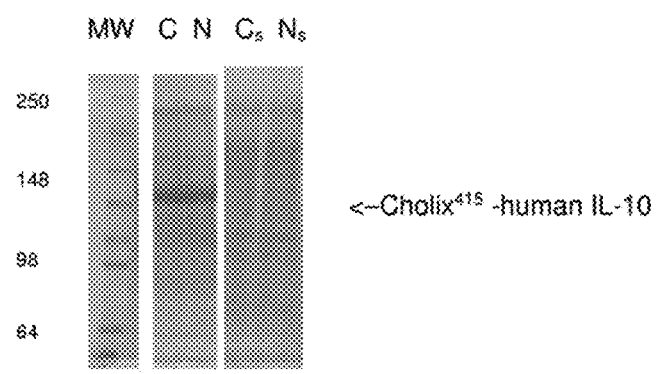

Cholix$^{415}$-TEV-IL-10 and Cholix$^{415}$-(G$_4$S)$_3$-IL-10 were evaluated to verify the proper folding with regard to their anticipated molecular size. Following induction, expressed protein was collected from inclusion bodies. The extent of Cholix$^{415}$-TEV-IL-10 (depicted as "C" on the gel) expression and Cholix$^{415}$-(G$_4$S)$_3$-IL-10 (depicted as "N" on the gel) expression in inclusion bodies showed an apparent molecular weight of ~66 kDa that was comparable to the calculated mass of 66380.78 and 65958.25 Daltons, respectively. See FIG. 5. The lack of these proteins in supernatant media following inclusion body removal for the TEV linker (Cs) and non-TEV linker (Ns) are shown to demonstrate the extent and specificity of chimera induction. SeeBlue® Plus2 Prestained MW standards are shown.

Example 6

This example describes in vitro methods to verify the proper folding of the fusion molecules with regard to their ability to carry a biologically active cargo across an intact epithelium.

Figure 6:
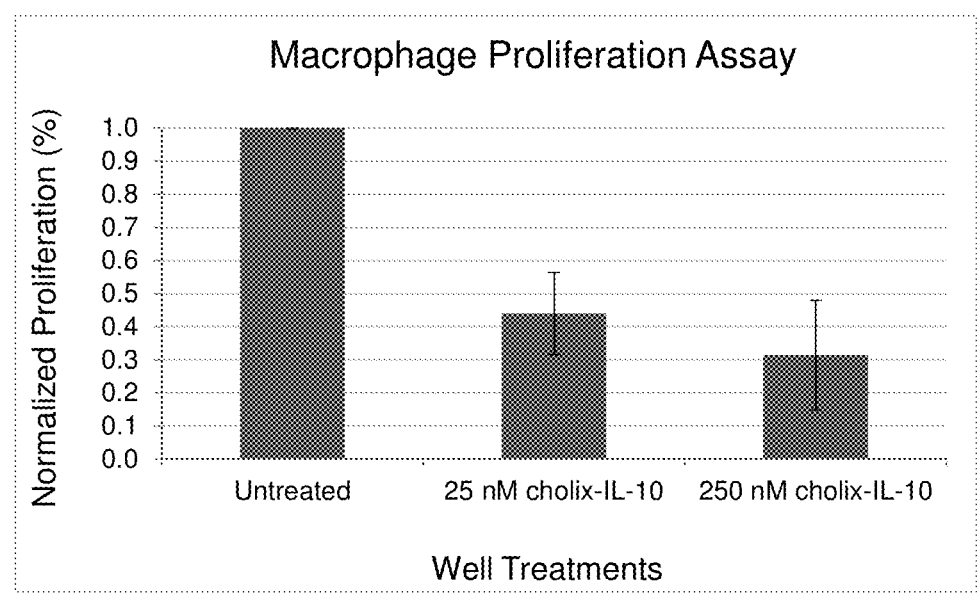

The J774 mouse macrophage cell line can be used as an IL-10 responsive cell line (O'Farrell A M, et al., EMBO J, 17(4):1006-18, 1998). IL-10 naturally forms a dimer that is required for its optimal activity. Cholix$^{415}$-(G$_4$S)$_3$-IL-10 expressed by E coli was collected from inclusion bodies and folded using a disulphide shuffle exchange buffer system. The resulting material was purified by ion exchange and size exclusion chromatography that resulted in the isolation of a protein of ~130 kDa, the anticipated size of an IL-10 dimer conjoined to two Cholix$^{415}$ molecules (hereinafter "dimer Cholix$^{415}$-IL-10" fusion molecule). The preparation had a protein purity of ~85-90% based upon SDS PAGE. Cultures of the J774.2 cell line were treated for 48 h with dimer Cholix$^{415}$-IL-10 fusion molecule at concentrations of 25 nM and 250 nM. Compared to untreated matched cells, dimer Cholix$^{415}$-IL-10 fusion molecule produced a dose-dependent decrease in cell number as assessed by flow cytometry of live/dead cells (see FIG. 6). Values represent n=4±standard deviation.

Alternatively, one could co-culture the IL-10 responsive cells in the basal compartment of the cell monolayers used for apical to basolateral transcytosis (Rubas W, et al., Pharm Res. 13(1):23-6, 1996).

Example 7

In this example, dimer Cholix$^{415}$-(G$_4$S)$_3$-IL-10 fusion molecule was evaluated for its effect on the barrier properties of Caco-2 cell monolayers in vitro. Caco-2 cells (a human colon cancer derived cell line) with media from the basolateral compartment being sampled periodically for several hours (Rubas W, et al., J Pharm Sci., 85(2):165-9, 1996). Caco-2 (ATCC HTB-37™) cells are maintained in 5% CO$_2$ at 37° C. in complete media: Dulbecco's modified Eagle's medium F12 (DMEM F12) supplemented with 10% fetal bovine serum, 2.5 mM glutamine, 100 U of penicillin/ml, and 100 µg of streptomycin/ml (Gibco BRL, Grand Island, N.Y.). Cells are fed every 2 to 3 days with this media (designated complete medium) and passaged every 5 to 7 days. For assays, cells are seeded into 24- or 96-well plates and grown to confluence.

Figure 7:
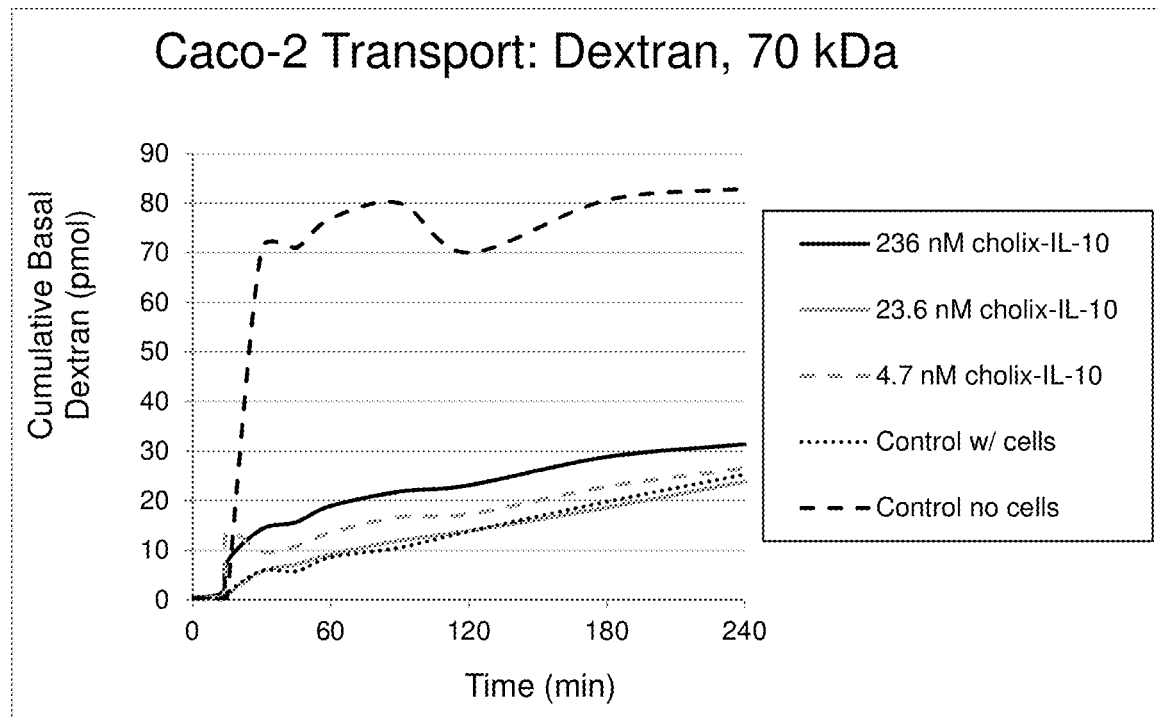
Figure 8:
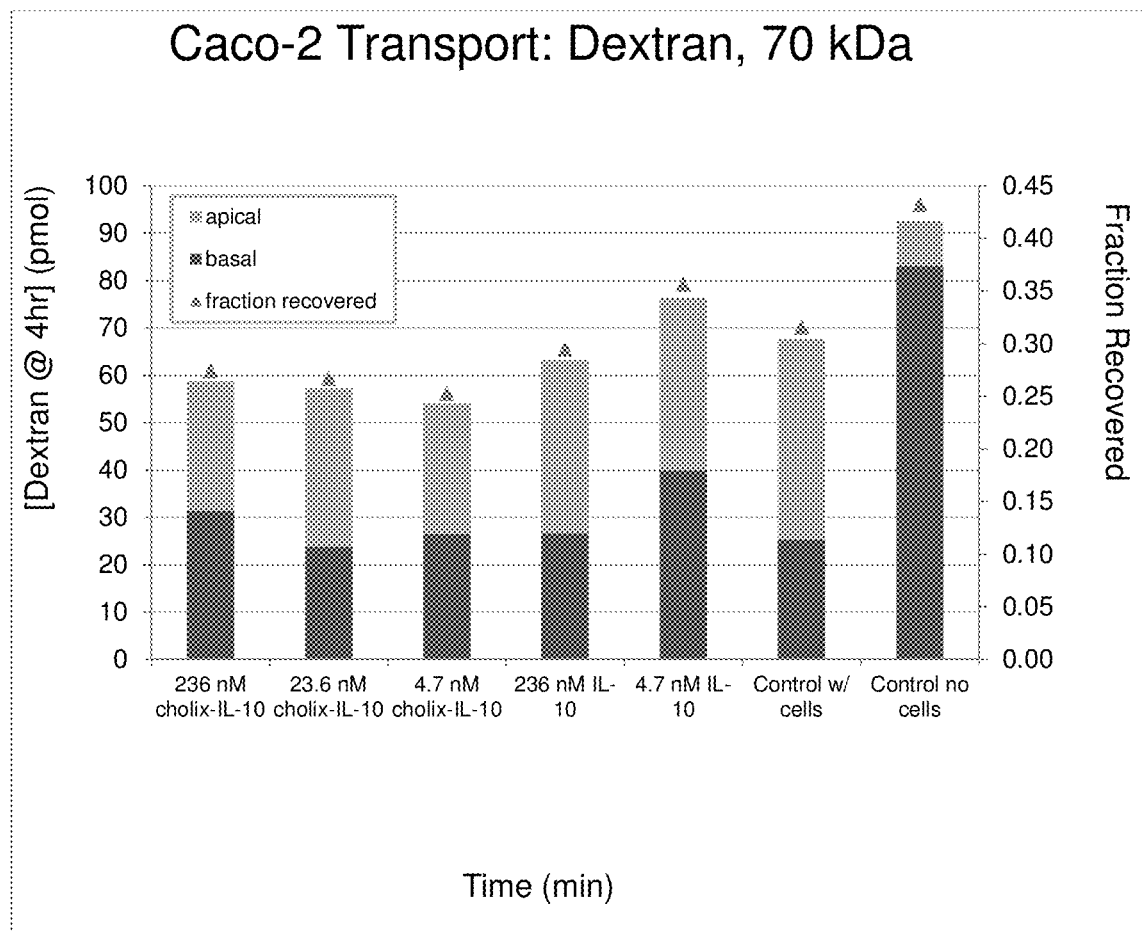

Established Caco-2 monolayers used for these studies had transepithelial electrical resistance (TER) values of between ~450-600 Ω·cm$^2$ (579 Ω·cm$^2$ average) as measured using a chopstick Millicell-ERS® voltmeter (Millipore). Fluorescein-labeled 70 kDa dextran and varying concentrations (4.7 nM, 23.6 nM and 236 nM) of dimer Cholix$^{415}$-(G$_4$S)$_3$-IL-10 fusion molecule were added to the apical surface of these monolayers and the cumulative amount of florescence detected in the basal compartment monitored over time by collecting 150 µL volumes with replacement. As depicted in FIG. 7 and FIG. 8, in the absence of Caco-2 cells on the filter support, the dextran rapidly moved from the apical to basal compartment. By comparison, the extent of 70 kDa dextran transport was much less across Caco-2 monolayers and the various dimer Cholix$^{415}$-IL-10 fusion molecules failed to have any dose-dependent effect on the extent of 70 kDa dextran transport across these Caco-2 monolayers and were not strikingly different from results obtained with Caco-2 monolayers not exposed to dimer Cholix$^{415}$-IL-10 fusion molecules. The dimer Cholix$^{415}$-(G$_4$S)$_3$-IL-10 fusion molecule does not overtly affect the barrier properties of Caco-2 cell monolayers in vitro.

Example 8

In this example, an ELISA assay is performed to evaluate the ability of the dimer Cholix$^{415}$-(G$_4$S)$_3$-IL-10 fusion molecule to move across Caco-2 cell monolayers. A549 (ATCC CCL-185™), L929 (ATCC CRL-2148™), and Caco-2 (ATCC HTB-37™) cells are maintained in 5% CO$_2$ at 37° C. in complete media: Dulbecco's modified Eagle's medium F12 (DMEM F12) supplemented with 10% fetal bovine serum, 2.5 mM glutamine, 100 U of penicillin/ml, and 100 µg of streptomycin/ml (Gibco BRL, Grand Island, N.Y.). Cells are fed every 2 to 3 days with this media (designated complete medium) and passaged every 5 to 7 days. For assays, cells are seeded into 24- or 96-well plates and grown to confluence.

Figure 9A:
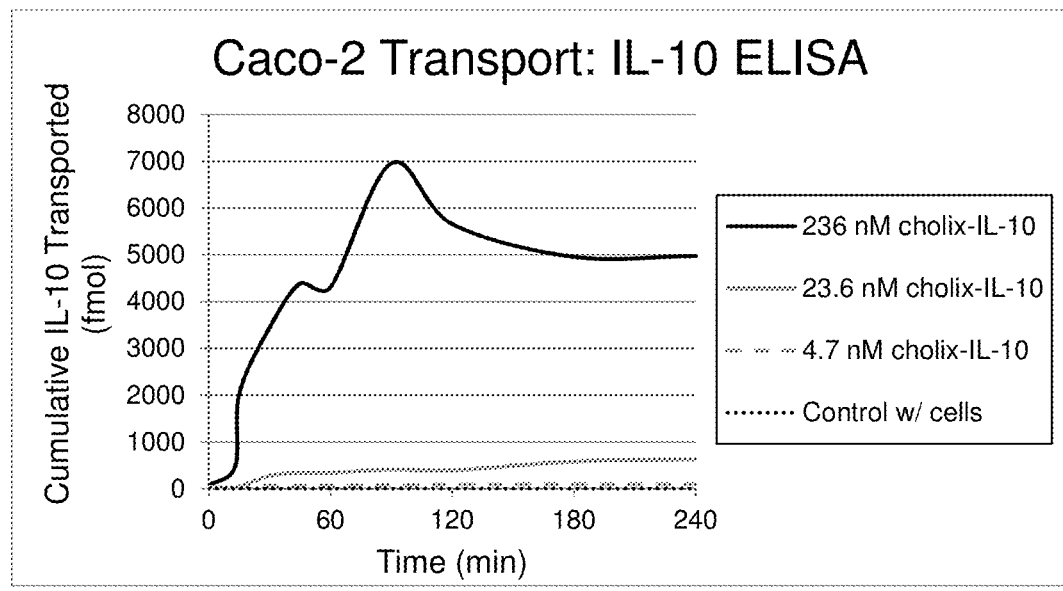
Figure 9B:
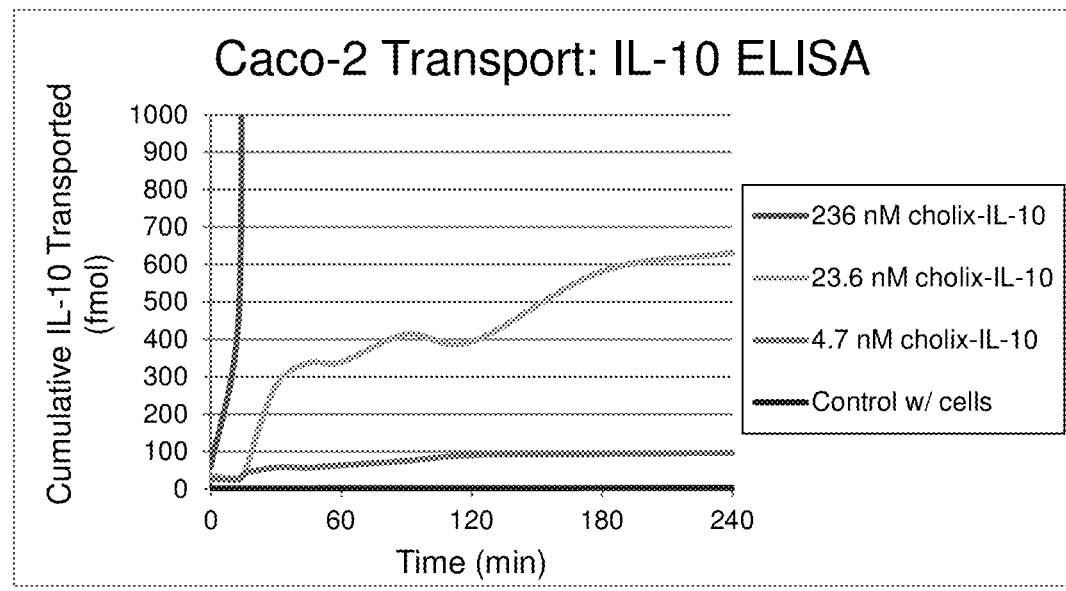

Caco-2 cells are grown as confluent monolayers on collagen-coated 0.4-µm pore size polycarbonate membrane transwell supports (Corning-Costar, Cambridge, Mass.) and used 18-25 days after attaining a trans-epithelial electrical resistance (TER) of >250 Ω·cm2 as measured using a chopstick Millicell-ERS® voltmeter (Millipore). Apical to basolateral (A→B) transport of dimer Cholix$^{415}$-(G$_4$S)$_3$-IL-10 fusion molecule across these monolayer is determined by measuring the amount of transported protein 4 hr after a 4.7 nM, 23.6 nM and 236 nM application at 37° C. TER measurements and the extent of 10 kDa fluorescent dextran (measured using an HPLC size exclusion protocol) are used to verify monolayer barrier properties during the course of the study. The extent of Cholix transport is determined by titration of collected media in the cell-based cytotoxicity assay. Transported dimer Cholix$^{415}$-(G$_4$S)$_3$-IL-10 fusion molecule is measured by enzyme linked immunosorbant assay (ELISA) using anti-IL-10 antibody for capture and the polyclonal sera to Cholix for detection. As depicted in FIGS. 9 (A and B), dimer Cholix$^{415}$-(G$_4$S)$_3$-IL-10 fusion molecule moves across Caco-2 cell monolayers.

Example 9

In this Example, the preparation of a non-naturally occurring fusion molecule that lacks a cleavable sequence is described. These fusions molecules are designed to specifically target the submucosal/GI space and limit the actions of the biologically active cargo to that space.

A plasmid construct is prepared encoding the non-toxic mutant form of the Cholix toxin, Cholix toxin ΔE581 (SEQ ID NO: 81). Protein expression is achieved using *E. coli* DH5a cells (Invitrogen, Carlsbad, Calif.) following transformation by heat-shock (1 min at 42° C.) with the appropriate plasmid. Transformed cells, selected on antibiotic-containing media, are isolated and grown in Luria-Bertani broth (Difco). Protein expression is induced by addition of 1 mM isopropyl-D-thiogalactopyranoside (IPTG). Two hours following IPTG induction, cells are harvested by centrifugation at 5,000×g for 10 min at 4° C. Inclusion bodies are isolated following cell lysis and proteins are solubilized in 6 M guanidine HCl and 2 mM EDTA (pH 8.0) plus 65 mM dithiothreitol. Following refolding and purification, proteins are stored at ~5 ml/ml in PBS (pH 7.4) lacking Ca$_{2+}$ and Mg$^{2+}$ at –80° C. All proteins used in these studies are confirmed to be at >90% purity based upon size exclusion chromatography.

The Cholix toxin 4E581 protein is then modified at its C-terminus to allow direct chemical coupling through a free sulfhydryl residue located near the C-terminus of the protein. The C-terminal modification includes a cysteine-constrained loop harboring the consensus cleavage sequence for the highly selective protease from the tobacco etch virus (TEV), a second cysteine, and a hexa-histadine (His$_6$) tag. The second Cys is included to form a disulphide bridge with the Cys ultimately used for coupling. Adding the His$_6$ sequence to the protein simplifies the purification and the TEV cleavage sequence provides a mechanism to selectively remove the terminal Cys residue following mild reduction. TEV cleavage and mild reduction with 0.1 mM dithiotheitol following expression and isolation of the ntCholix constructs allows for the direct chemical coupling of a biologically active cargo via a maleimide-based reaction as a generic mechanism of cargo attachment. Following TEV protease cleavage, reduction, and cargo coupling through a maleimide reaction with the free sulfhydryl, removal of the freed C-terminal sequence was achieved by a second Ni' column chromatography step.

Example 10

Trans-epithelial transport of Cholix toxin 4E581-cargo is assessed using Caco-2 monolayers in vitro. Caco-2 cells (passage number 25-35) are grown to confluent monolayers as previously described; Rubas, W. et al., *Pharm Res,* 10:113-118 (1993). Briefly, cells are maintained at 37° C. in DMEM/high growth media enriched with 2 mM L-glutamine, 10% fetal bovine serum, and 100 Units of penicillin/streptomycin in an atmosphere of 5% $CO_2$ and 90% humidity. Cells are passaged every week at a split ratio of 1:3 in 75 $cm^2$ flasks and seeded onto prewetted and collagen-coated permeable (0.4 µm pore size) polycarbonate (Transwell™) filter supports from Corning Costar (Cambridge, Mass.) at a density of 63,000 cells/$cm^2$. Growth media is replaced every other day. Confluent monolayers, determined by the acquisition of significant trans-epithelial resistance (TEER) determine using an volt-ohm-meter (World Precision Instruments, Sarasota, Fla.), are used 20-26 days post seeding.

Trans-epithelial transport flux rates are measured in vitro in the apical (Ap) to basolateral (Bl) and the Bl to Ap directions using polarized monolayers of Caco-2 cells to describe mucosal to serosal and serosal to mucosal flux events, respectively. Just prior to initiation of a transport study, the transepithelial resistance (TEER) of each filter is measured; monolayers TEER reading of <200 Ω·cm2 are excluded from the study. Ap and Bl media is removed from included monolayers and these surfaces are washed once with phosphate buffered saline (PBS). One set of monolayers then receives an Ap (donor) application of 100 µL PBS containing 10 µg Cholix toxin 4E581-cargo and 10 µg TRITC-Dextran or 10 µg BSA-cargo and 10 µg TRITC-Dextran. Receiver (Bl) compartments then receive 500 µL PBS to set the $T_0$ for the transport study. Both donor and receiver compartments are sampled after 4 hr of incubation at 37° C. to determine the amount of material transported across the monolayer and the amount retained at the apical surface, respectively.

Example 11

This example describes the preparation and expression in *E. coli.* of a fusion molecule comprising a modified Cholix toxin comprising a sequence encoding amino acids 1-415 of SEQ ID NO: 1 directly fused at its C-terminus to an IL-10 polypeptide (referred to as a "$Cholix^{415}$-IL-10 fusion molecule"). Protein expression is achieved using *E. coli* DH5α cells (Invitrogen, Carlsbad, Calif.) following transformation by heat-shock (1 min at 42° C.) with the appropriate plasmid. Transformed cells, selected on antibiotic-containing media, are isolated and grown in Luria-Bertani broth (Difco). Protein expression is induced by addition of 1 mM isopropyl-D-thiogalactopyranoside (IPTG). Two hours following IPTG induction, cells are harvested by centrifugation at 5,000×g for 10 min at 4° C. Inclusion bodies are isolated following cell lysis and proteins are solubilized in 6 M guanidine HCl and 2 mM EDTA (pH 8.0) plus 65 mM dithiothreitol. Following refolding and purification, proteins are stored at ~5 ml/ml in PBS (pH 7.4) lacking $Ca^{2+}$ and $Mg^{2+}$ at −80° C. All proteins used in these studies were confirmed to be at >90% purity based upon size exclusion chromatography.

Polystyrene beads (10 nm diameter) containing a covalently integrated red fluorescent dye with excitation/emission properties of 468/508 nm and having aldehyde surface functional groups (XPR-582) are obtained from Duke Scientific (Palo Alto, Calif.). One hundred µl of XPR-582 beads (at 2% solids) are mixed with approximately 2.5 nmoles IL-10 or $Cholix^{415}$-IL-10 fusion molecule in a final volume of 200 µl neutral (pH 7.0) phosphate buffered saline (PBS). After 2 hr of gentle rocking at room temperature, 20 µl of a 2 mg/ml solution of bovine serum albumin (BSA; Sigma, St. Louis, Mo.) in PBS is added. Preparations are then dialyzed by three cycles of dilution with PBS and concentration using a 100,000 molecular weight cutoff Microcon filter device from Millipore (Bedford, Mass.). Final preparations of coated beads were at 1% solids.

Example 12

In this Example, non-naturally occurring isolated fusion molecules comprising the modified Cholix toxin sequence of SEQ ID NO: 52 ($Cholix^{415}$), a cleavable linker sequence (SEQ ID NO: 121) or a non-cleavable linker (SEQ ID NO: 98), and a biologically active cargo that is a TNFSF inhibitor, are prepared as described in Example 5, and evaluated as described in the Examples above to confirm proper folding, proper size, Six exemplary fusion molecule expression vectors (3 for each linker) were prepared to test for the ability of the fusion molecules to transport apical to basal across epithelial cells a TNFSF inhibitor selected from: 1) a TNF inhibitor that is an antibody comprising the heavy chain variable region and light chain variable region sequences of SEQ ID NO: 88 and 89; 2) a TNF inhibitor that is an antibody comprising the heavy chain variable region and light chain variable region sequences of SEQ ID NO: 90 and 91; and 3) a TNFSF inhibitor that is a dimer of a soluble human TNFR-p75 with the Fc portion of IgG comprising the sequence of SEQ ID NO: 92.

Example 13

In this Example, non-naturally occurring isolated fusion molecules comprising the modified Cholix toxin sequence of SEQ ID NO: 52 ($Cholix^{415}$), a cleavable linker sequence (SEQ ID NO: 121) or a non-cleavable linker (SEQ ID NO: 98), and a biologically active cargo that is a glucose-lowering agent, are prepared as described in Example 5, and evaluated as described in the Examples above to confirm proper folding, proper size, Four exemplary fusion molecule expression vectors (2 for each linker) were prepared to test for the ability of the fusion molecules to transport apical to basal across epithelial cells a glucose-lowering agent selected from: 1) a GLP-1 agonist comprising the sequence of SEQ ID NO: 93; and 2) a GLP-1 agonist comprising the sequence of SEQ ID NO: 94.

Example 14

In this Example, non-naturally occurring isolated fusion molecules comprising the modified Cholix toxin sequence of SEQ ID NO: 52 ($Cholix^{415}$), a cleavable linker sequence (SEQ ID NO: 121) or a non-cleavable linker (SEQ ID NO: 98), and a biologically active cargo that is a human growth hormone, are prepared as described in Example 5, and evaluated as described in the Examples above to confirm proper folding, proper size, Two exemplary fusion molecule expression vectors (one for each linker) were prepared to test for the ability of the fusion molecules to transport apical to basal across epithelial cells a human growth hormone comprising the sequence of SEQ ID NO: 95.

Example 15

This example describes histological detection in tissues of a representative biologically active cargo of the fusion molecules prepared in Example 5. Following administration of a fusion molecule, animals are euthanized by $CO_2$ asphyxiation and exsanguinated by cardiac puncture. Specific tissues (lymph nodes, trachea, brain, spleen liver, GI tract) are removed, briefly rinsed in PBS to remove any residual blood and frozen in OCT. Sections (5 microns thick) are placed onto slides. Slides are fixed in acetone for 10 min and rinsed with PBS. Slides are incubated with 3% peroxidase for 5 min. Slides are then blocked with protein for an additional 5 min. Primary antibody to the respective biologically active cargo is incubated onto slides for 30 min at a 1:100 dilution followed by PBS washes. Biotin-labeled secondary antibody is then incubated for approximately 15 minutes followed by PBS washes. Streptavidin HRP label is incubated onto slides for 15 min followed by PBS washes. HRP Chromagen is applied for 5 min followed by several rinses in distilled $H_2O$. Finally, the slides are counterstained with hematoxylin for 1 min, coverslipped, and examined for the presence of the biologically active cargo.

The fusion molecules of the disclosure offer several advantages over conventional techniques for local or systemic delivery of macromolecules to a subject. Foremost among such advantages is the ability to deliver the biologically active cargo to a subject without using a needle to puncture the skin of the subject. Many subjects require repeated, regular doses of macromolecules. For example, diabetics must inject insulin several times per day to control blood sugar concentrations. Such subjects' quality of life would be greatly improved if the delivery of a macromolecule could be accomplished without injection, by avoiding pain or potential complications associated therewith.

In addition, coupling of the biologically active cargo to the remainder of the fusion molecule with a linker that is cleaved by an enzyme present at a basolateral membrane of an epithelial cell allows the biologically active cargo to be liberated from the fusion molecule and released from the remainder of the fusion molecule soon after transcytosis across the epithelial membrane. Such liberation reduces the probability of induction of an immune response against the biologically active cargo. It also allows the biologically active cargo to interact with its target free from the remainder of the fusion molecule.

In addition, the non-naturally occurring fusion molecules which lack a cleavable linker can be advantageous in that the anchoring effect of the modified Cholix toxin by its receptor(s) at the surface of, e.g., immune cells that also express the receptor for the biologically active cargo (but in considerably lower quantity) can allow for greater exposure of the biologically active cargo at the surface of the targeted cells, and provide a synergistic effect via the binding of the Cholix to its receptor and, e.g., binding of IL-10 to the IL-10R.

Moreover, once transported across the GI epithelium, the fusion molecules of the disclosure will exhibit extended half-life in serum, that is, the biologically active cargo of the fusion molecules will exhibit an extended serum half-life compared to the biologically active cargo in its non-fused state, and oral administration of the fusion molecule can deliver a higher effective concentration of the delivered biologically active cargo to the liver of the subject than is observed in the subject's plasma.

Furthermore, the embodiments of the fusion molecules can be constructed and expressed in recombinant systems. Recombinant technology allows one to make a fusion molecule having an insertion site designed for introduction of any suitable biologically active cargo. Such insertion sites allow the skilled artisan to quickly and easily produce fusion molecules for delivery of new biologically active cargo, should the need to do so arise.

All of the articles and methods disclosed and claimed herein can be made and executed without undue experimentation in light of the present disclosure. While the articles and methods of this disclosure have been described in terms of embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by embodiments and optional features, modification and variation of the concepts herein disclosed may be resorted to by those skilled in the art, and that such modifications and variations are considered to be within the scope of this disclosure as defined by the appended claims.

Sequence Listings

The amino acid sequences listed in the accompanying sequence listing are shown using standard three letter code for amino acids, as defined in 37 C.F.R. 1.822.

SEQ ID NO: 1 is the 634 amino acid sequence of mature *Vibrio cholera* Cholix toxin.

SEQ ID NO: 2 is a nucleic acid sequence encoding the 634 amino acid sequence mature *V. cholera* Cholix toxin.

SEQ ID NOs: 3-80 are the amino acid sequences of various truncated Cholix toxins derived from the mature Cholix toxin sequence set forth in SEQ ID NO: 1.

SEQ ID NO: 81 is the amino acid sequence of a mutated Cholix toxin wherein the amino acid residue E581 of SEQ ID NO: 1 has been deleted.

SEQ ID NO: 82 is the amino acid sequence of human interleukin-10 (IL-10).

SEQ ID NO: 83 is the amino acid sequence of human interleukin-19 (IL-19).

SEQ ID NO: 84 is the amino acid sequence of human interleukin-20 (IL-20).

SEQ ID NO: 85 is the amino acid sequence of human interleukin-22 (IL-22).

SEQ ID NO: 86 is the amino acid sequence of human interleukin-24 (IL-24).

SEQ ID NO: 87 is the amino acid sequence of human interleukin-26 (IL-26).

SEQ ID NO: 88—heavy chain variable region sequence for an anti-TNF-alpha antibody.
SEQ ID NO: 89—light chain variable region sequence for an anti-TNF-alpha antibody.
SEQ ID NO: 90—heavy chain variable region sequence for an anti-TNF-alpha antibody.
SEQ ID NO: 91—light chain variable region sequence for an anti-TNF-alpha antibody.
SEQ ID NO: 92—amino acid sequence of human TNFR-p75-Fc dimeric fusion protein.
SEQ ID NO: 93—GLP-1 agonist peptide amino acid sequence (exenatide)
SEQ ID NO: 94—GLP-1 agonist peptide amino acid sequence (Liraglutide)
SEQ ID NO: 95—amino acid sequence of human growth hormone (somatotropin)
SEQ ID NOs: 96-121 are the amino acid sequences of various peptide linkers
SEQ ID NO: 122 is the amino acid sequence of a Cholix$^{415}$-TEV-IL-10 fusion molecule.
SEQ ID NO: 123 is the amino acid sequence of a Cholix$^{415}$-(G$_4$S)$_3$-IL-10 fusion molecule.

```
SEQUENCE LISTINGS
mature Vibrio cholera Cholix
toxin amino acid sequence
                                    SEQ ID NO: 1
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQR1HFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRSYLPENRAVITPQGVTNWTYQELEATHQALT

REGYVFVGYHGTNHVAAQTIVNRIAPVPRGNNTENEEKWGGLYVA

THAEVAHGYARIKEGTGEYGLPTRAERDARGVMLRVYIPRASLER

FYRTNTPLENAEEHITQVIGHSLPLRNEAFTGPESAGGEDETVIG

WDMAIHAVAIPSTIPGNAYEELAIDEEAVAKEQSISTKPPYKERK

DELK nucleic acid sequence encoding
the mature V. cholera Cholix toxin
                                    SEQ ID NO: 2
ATGGTCGAAGAAGCTTTAAACATCTTTGATGAATGCCGTTCGCCA

TGTTCGTTGACCCCGGAACCGGGTAAGCCGATTCAATCAAAACTG

TCTATCCCTAGTGATGTTGTTCTGGATGAAGGTGTTCTGTATTAC

TCGATGACGATTAATGATGAGCAGAATGATATTAAGGATGAGGAC

AAAGGCGAGTCCATTACTACTATTGGTGAATTTGCCACAGTACGC

GCGACTAGACATTATGTTAATCAAGATGCGCCTTTTGGTGTCATC

CATTTAGATATTACGACAGAAAATGGTACAAAAACGTACTCTTAT

AACCGCAAAGAGGGTGAATTTGCAATCAATTGGTTAGTGCCTATT

-continued

GGTGAAGATTCTCCTGCAAGCATCAAAATCTCCGTTGATGAGCTC

GATCAGCAACGCAATATCATCGAGGTGCCTAAACTGTATAGTATT

GATCTCGATAACCAAACGTTAGAGCAGTGGAAAACCCAAGGTAAT

GTTTCTTTTTCGGTAACGCGTCCTGAACATAATATCGCTATCTCT

TGGCCAAGCGTGAGTTACAAAGCAGCGCAGAAAGAGGGTTCACGC

CATAAGCGTTGGGCTCATTGGCATACAGGCTTAGCACTGTGTTGG

CTTGTGCCAATGGATGCTATCTATAACTATATCACCCAGCAAAAT

TGTACTTTAGGGGATAATTGGTTTGGTGGCTCTTATGAGACTGTT

GCAGGCACTCCGAAGGTGATTACGGTTAAGCAAGGGATTGAACAA

AAGCCAGTTGAGCAGCGCATCCATTTCTCCAAGGGGAATGCGATG

AGCGCACTTGCTGCTCATCGCGTCTGTGGTGTGCCATTAGAAACT

TTGGCGCGCAGTCGCAAACCTCGTGATCTGACGGATGATTTATCA

TGTGCCTATCAAGCGCAGAATATCGTGAGTTTATTTGTCGCGACG

CGTATCCTGTTCTCTCATCTGGATAGCGTATTTACTCTGAATCTT

GACGAACAAGAACCAGAGGTGGCTGAACGTCTAAGTGATCTTCGC

CGTATCAATGAAAATAACCCGGGCATGGTTACACAGGTTTTAACC

GTTGCTCGTCAGATCTATAACGATTATGTCACTCACCATCCGGGC

TTAACTCCTGAGCAAACCAGTGCGGGTGCACAAGCTGCCGATATC

CTCTCTTTATTTTGCCCAGATGCTGATAAGTCTTGTGTGGCTTCA

AACAACGATCAAGCCAATATCAACATCGAGTCTCGTTCTGGCCGT

TCATATTTGCCTGAAAACCGTGCGGTAATCACCCCTCAAGGCGTC

ACAAATTGGACTTACCAGGAACTCGAAGCAACACATCAAGCTCTG

ACTCGTGAGGGTTATGTGTTCGTGGGTTACCATGGTACGAATCAT

GTCGCTGCGCAAACCATCGTGAATCGCATTGCCCCTGTTCCGCGC

GGCAACAACACTGAAAACGAGGAAAAGTGGGGCGGGTTATATGTT

GCAACTCACGCTGAAGTTGCCCATGGTTATGCTCGCATCAAAGAA

GGGACAGGGGAGTATGGCCTTCCGACCCGTGCTGAGCGCGACGCT

CGTGGGGTAATGCTGCGCGTGTATATCCCTCGTGCTTCATTAGAA

CGTTTTTATCGCACGAATACACCTTTGGAAAATGCTGAGGAGCAT

ATCACGCAAGTGATTGGTCATTCTTTGCCATTACGCAATGAAGCA

TTTACTGGTCCAGAAAGTGCGGGCGGGGAAGACGAAACTGTCATT

GGCTGGGATATGGCGATTCATGCAGTTGCGATCCCTTCGACTATC

CCAGGGAACGCTTACGAAGAATTGGCGATTGATGAGGAGGCTGTT

GCAAAAGAGCAATCGATTAGCACAAAACCACCTTATAAAGAGCGC

AAAGATGAACTTAAG modified Vibrio cholera Cholix toxin
amino acid sequence Cholix$^{386}$
                                    SEQ ID NO: 3
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW
```

-continued

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQA modified Vibrio cholera Cholix toxin amino
acid sequence Cholix[385]

SEQ ID NO: 4

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQ modified Vibrio cholera Cholix toxin amino
acid sequence Cholix[384]

SEQ ID NO: 5

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGA modified Vibrio cholera Cholix toxin amino
acid sequence Cholix[383]

SEQ ID NO: 6

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAG modified Vibrio cholera Cholix
toxin amino acid sequence Cholix[382]

SEQ ID NO: 7

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSA modified Vibrio cholera Cholix toxin amino
acid sequence Cholix[381]

SEQ ID NO: 8

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTS modified Vibrio cholera Cholix
toxin amino acid sequence Cholix[380]

SEQ ID NO: 9

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQT modified Vibrio cholera Cholix
toxin amino acid sequence Cholix[379]

SEQ ID NO: 10

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQ modified Vibrio cholera Cholix toxin
amino acid sequence Cholix378
SEQ ID NO: 11

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPE modified Vibrio cholera Cholix toxin
amino acid sequence Cholix377
SEQ ID NO: 12

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTP modified Vibrio cholera Cholix toxin
amino acid sequence Cholix376
SEQ ID NO: 13

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLT modified Vibrio cholera Cholix toxin
amino acid sequence Cholix375
SEQ ID NO: 14

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGL modified Vibrio cholera Cholix toxin
amino acid sequence Cholix374
SEQ ID NO: 15

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPG modified Vibrio cholera Cholix toxin amino
acid sequence Cholix373
SEQ ID NO: 16

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHP modified Vibrio cholera Cholix toxin amino
acid sequence Cholix372
SEQ ID NO: 17

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHH modified Vibrio cholera Cholix toxin amino
acid sequence Cholix371
SEQ ID NO: 18

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTH modified Vibrio cholera Cholix toxin amino
acid sequence Cholix370
SEQ ID NO: 19
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVT modified Vibrio cholera Cholix toxin amino
acid sequence Cholix369
SEQ ID NO: 20
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYV modified Vibrio cholera Cholix toxin amino
acid sequence Cholix368
SEQ ID NO: 21
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDY modified Vibrio cholera Cholix toxin amino
acid sequence Cholix367
SEQ ID NO: 22
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYND modified Vibrio cholera Cholix toxin amino
acid sequence Cholix366
SEQ ID NO: 23
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYN modified Vibrio cholera Cholix toxin amino
acid sequence Cholix365
SEQ ID NO: 24
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIY modified Vibrio cholera Cholix toxin amino
acid sequence Cholix364
SEQ ID NO: 25
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQI modified Vibrio cholera Cholix toxin amino
acid sequence Cholix363
SEQ ID NO: 26
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQ modified *Vibrio cholera* Cholix toxin amino
acid sequence Cholix[362]
SEQ ID NO: 27

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

AR modified *Vibrio cholera* Cholix toxin amino
acid sequence Cholix[361]
SEQ ID NO: 28

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

A modified *Vibrio cholera* Cholix toxin amino
acid sequence Cholix[360]
SEQ ID NO: 29

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV modified *Vibrio cholera* Cholix toxin amino
acid sequence Cholix[359]
SEQ ID NO: 30

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLT modified *Vibrio cholera* Cholix toxin amino
acid sequence Cholix[358]
SEQ ID NO: 31

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVL modified *Vibrio cholera* Cholix toxin amino
acid sequence Cholix[357]
SEQ ID NO: 32

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQV modified *Vibrio cholera* Cholix toxin amino
acid sequence Cholix[356]
SEQ ID NO: 33

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQ modified *Vibrio cholera* Cholix toxin amino
acid sequence Cholix[355]
SEQ ID NO: 34

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVT modified *Vibrio cholera* Cholix toxin amino
acid sequence Cholix[354]
SEQ ID NO: 35

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMV modified *Vibrio cholera* Cholix toxin amino
acid sequence Cholix[353]
SEQ ID NO: 36

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGM modified *Vibrio cholera* Cholix toxin amino
acid sequence Cholix[352]
SEQ ID NO: 37

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPG modified *Vibrio cholera* Cholix toxin amino
acid sequence Cholix[351]
SEQ ID NO: 38

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNP modified *Vibrio cholera* Cholix toxin amino
acid sequence Cholix[350]
SEQ ID NO: 39

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENN modified *Vibrio cholera* Cholix toxin amino
acid sequence Cholix[349]
SEQ ID NO: 40

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINEN modified *Vibrio cholera* Cholix toxin amino
acid sequence Cholix[348]
SEQ ID NO: 41

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINE modified *Vibrio cholera* Cholix toxin amino
acid sequence Cholix[425]
SEQ ID NO: 42

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIESRSGRSYLPEN modified *Vibrio cholera* Cholix toxin amino
acid sequence Cholix[424]

SEQ ID NO: 43

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRSYLPE modified *Vibrio cholera* Cholix toxin amino
acid sequence Cholix[423]

SEQ ID NO: 44

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRSYLP modified *Vibrio cholera* Cholix toxin amino
acid sequence Cholix[422]

SEQ ID NO: 45

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRSYL modified *Vibrio cholera* Cholix toxin amino
acid sequence Cholix[421]

SEQ ID NO: 46

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRSY modified *Vibrio cholera* Cholix toxin amino
acid sequence Cholix[420]

SEQ ID NO: 47

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRS modified *Vibrio cholera* Cholix toxin amino
acid sequence Cholix[419]

SEQ ID NO: 48

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIESRSGR modified *Vibrio cholera* Cholix toxin amino
acid sequence Cholix[418]

SEQ ID NO: 49

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIESRSG modified *Vibrio cholera* Cholix toxin amino
acid sequence Cholix⁴¹⁷
SEQ ID NO: 50
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIESRS modified *Vibrio cholera* Cholix toxin amino
acid sequence Cholix⁴¹⁶
SEQ ID NO: 51
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIESR modified *Vibrio cholera* Cholix toxin amino
acid sequence Cholix⁴¹⁵
SEQ ID NO: 52
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIES modified *Vibrio cholera* Cholix toxin amino
acid sequence Cholix⁴¹⁴
SEQ ID NO: 53
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSLFCPDADKSCVAS

NNDQANINIE modified *Vibrio cholera* Cholix toxin amino
acid sequence Cholix⁴¹³
SEQ ID NO: 54
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINI modified *Vibrio cholera* Cholix toxin amino
acid sequence Cholix⁴¹²
SEQ ID NO: 55
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANIN modified *Vibrio cholera* Cholix toxin amino
acid sequence Cholix⁴¹¹
SEQ ID NO: 56
VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANI modified *Vibrio cholera* Cholix toxin amino
acid sequence Cholix[410]

SEQ ID NO: 57

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQAN modified *Vibrio cholera* Cholix toxin amino
acid sequence Cholix[409]

SEQ ID NO: 58

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQA modified *Vibrio cholera* Cholix toxin amino
acid sequence Cholix[408]

SEQ ID NO: 59

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQ modified *Vibrio cholera* Cholix toxin amino
acid sequence Cholix[407]

SEQ ID NO: 60

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

ND modified *Vibrio cholera* Cholix toxin amino
acid sequence Cholix[406]

SEQ ID NO: 61

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

N modified *Vibrio cholera* Cholix toxin amino
acid sequence Cholix[405]

SEQ ID NO: 62

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN modified *Vibrio cholera* Cholix toxin amino
acid sequence Cholix[404]

SEQ ID NO: 63

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVAS modified *Vibrio cholera* Cholix toxin amino
acid sequence Cholix^403
SEQ ID NO: 64
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVA modified *Vibrio cholera* Cholix toxin amino
acid sequence Cholix^402
SEQ ID NO: 65
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCV modified *Vibrio cholera* Cholix toxin amino
acid sequence Cholix^401
SEQ ID NO: 66
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSC modified *Vibrio cholera* Cholix toxin amino
acid sequence Cholix^400
SEQ ID NO: 67
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKS modified *Vibrio cholera* Cholix toxin amino
acid sequence Cholix^399
SEQ ID NO: 68
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADK modified *Vibrio cholera* Cholix toxin amino
acid sequence Cholix^398
SEQ ID NO: 69
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDAD modified *Vibrio cholera* Cholix toxin amino
acid sequence Cholix^397
SEQ ID NO: 70
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDA modified *Vibrio cholera* Cholix toxin amino
acid sequence Cholix^396
SEQ ID NO: 71
VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPD modified *Vibrio cholera* Cholix toxin amino
acid sequence Cholix[395]
SEQ ID NO: 72

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCP modified *Vibrio cholera* Cholix toxin amino
acid sequence Cholix[394]
SEQ ID NO: 73

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFC modified *Vibrio cholera* Cholix toxin amino
acid sequence Cholix[393]
SEQ ID NO: 74

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLF modified *Vibrio cholera* Cholix toxin amino
acid sequence Cholix[392]
SEQ ID NO: 75

VEDELNIFDECRSPCSLTPEPGKPIQSKLSIPSDVVLDEGVLYYS

MTINDEQNDIKDEDKGESITTIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILSL modified *Vibrio cholera* Cholix toxin amino
acid sequence Cholix[391]
SEQ ID NO: 76

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADILS modified *Vibrio cholera* Cholix toxin amino
acid sequence Cholix[390]
SEQ ID NO: 77

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADIL modified *Vibrio cholera* Cholix toxin amino
acid sequence Cholix[389]
SEQ ID NO: 78

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAADI modified *Vibrio cholera* Cholix toxin amino
acid sequence Cholix[388]
SEQ ID NO: 79

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHEIPGLTPEQTSAGAQAAD modified *Vibrio cholera* Cholix toxin amino acid sequence Cholix[387]

SEQ ID NO: 80

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAA modified *Vibrio cholera* Cholix toxin amino acid sequence Cholix Δ581

SEQ ID NO: 81

VEDELNIFDECRSPCSLTPEPGKPIQSKLSIPSDVVLDEGVLYYS

MTINDEQNDIKDEDKGESIITIGEFATVRATRHYVNQDAPFGVIH

LDITTENGTKTYSYNRKEGEFAINWLVPIGEDSPASIKISVDELD

QQRNIIEVPKLYSIDLDNQTLEQWKTQGNVSFSVTRPEHNIAISW

PSVSYKAAQKEGSRHKRWAHWHTGLALCWLVPMDAIYNYITQQNC

TLGDNWFGGSYETVAGTPKVITVKQGIEQKPVEQRIHFSKGNAMS

ALAAHRVCGVPLETLARSRKPRDLTDDLSCAYQAQNIVSLFVATR

ILFSHLDSVFTLNLDEQEPEVAERLSDLRRINENNPGMVTQVLTV

ARQIYNDYVTHHPGLTPEQTSAGAQAADILSLFCPDADKSCVASN

NDQANINIESRSGRSYLPENRAVITPQGVTNWTYQELEATHQALT

REGYVFVGYHGTNHVAAQTIVNRIAPVPRGNNTENEEKWGGLYVA

THAEVAHGYARIKEGTGEYGLPTRAERDARGVMLRVYIPRASLER

FYRTNTPLENAEEHITQVIGHSLPLRNEAFTGPESAGGEDTVIGW

DMAIHAVAIPSTIPGNAYEELAIDEEAVAKEQSISTKPPYKERKD

ELK human interleukin-10 amino acid sequence

SEQ ID NO: 82

MHSSALLCCLVLLTGVRASPGQGTQSENSCTHFPGNLPNMLRDLR

DAFSRVKTFFQMKDQLDNLLLKESLLEDFKGYLGCQALSEMIQFY

LEEVMPQAENQDPDIKAHVNSLGENLKTLRLRLRRCHRFLPCENK

SKAVEQVKNAFNKLQEKGIYKAMSEFDIFINYIEAYMTMKIRN human interleukin-19 amino acid sequence

SEQ ID NO: 83

MKLQCVSLWLLGTILILCSVDNHGLRRCLISTDMHHIEESFQEIK

RAIQAKDTFPNVTILSTLETLQIIKPLDVCCVTKNLLAFYVDRVF

KDHQEPNPKILRKISSIANSFLYMQKTLRQCQEQRQCHCRQEATN

ATRVIHDNYDQLEVHAAAIKSLGELDVFLAWINKNHEVMSSA human interleukin-20 amino acid sequence

SEQ ID NO: 84

MKASSLAFSLLSAAFYLLWTPSTGLKTLNLGSCVIATNLQEIRNG

FSEIRGSVQAKDGNIDIRILRRTESLQDTKPANRCCLLRHLLRLY

LDRVFKNYQTPDHYTLRKISSLANSFLTIKKDLRLCHAHMTCHCG

EEAMKKYSQILSHFEKLEPQAAVVKALGELDILLQWMEETE human interleukin-22 amino acid sequence

SEQ ID NO: 85

MAALQKSVSSFLMGTLATSCLLLLALLVQGGAAAPISSHCRLDKS

NFQQPYITNRTFMLAKEASLADNNTDVRLIGEKLFHGVSMSERCY

LMKQVLNFTLEEVLFPQSDRFQPYMQEVVPFLARLSNRLSTCHIE

GDDLHIQRNVQKLKDTVKKLGESGEIKAIGELDLLFMSLRNACI human interleukin-24 amino acid sequence

SEQ ID NO: 86

MNFQQRLQSLWTLASRPFCPPLLATASQMQMVVLPCLGFTLLLW

SQVSGAQGQEFHFGPCQVKGVVPQKLWEAFWAVKDTMQAQDNIT

SARLLQQEVLQNVSDAESCYLVHTLLEFYLKTVFKNYHNRTVEV

RTLKSFSTLANNFVLIVSQLQPSQENEMFSIRDSAHRRFLLFRR

AFKQLDVEAALTKALGEVDILLTWMQKFYKL human interleukin-26 amino acid sequence

SEQ ID NO: 87

MLVNFILRCGLLLVTLSLAIAKHKQSSFTKSCYPRGTLSQAVDA

LYIKAAWLKATIPEDRIKNIRLLKKKTKKQFMKNCQFQEQLLSF

FMEDVFGQLQLQGCKKIRFVEDFHSLRQKLSHCISCASSAREMK

SITRMKRIFYRIGNKGIYKAISELDILLSWIKKLLESSQ heavy chain variable region sequence for an anti-TNF-alpha antibody

SEQ ID NO: 88

EVQLVESGGGLVQPGRSLRLSCAASGFTFDDYAMHWVRQAPGKG

LEWVSAITWNSGHIDYADSVERGFTISRDNAKNSLYLQMNSLRA

EDTAVYYCAKVSYLSTASSLDYWGQGTLVTVSSASTKGPSVFPL

APSSKSTSGGTAALGCLVKDYFPEPVTVSWNSGALTSGVHTFPA

VLQSSGLYSLSSVVTVPSSSLGTQTYICNVNHKPSNTKVDKKVE

PKSC light chain variable region sequence for an anti-TNF-alpha antibody

SEQ ID NO: 89

DIQMTQSPSSLSASVGDRVTITCRASQGIRNYLAWYQQKPGKA

PKLLIYAASTLQSGVPSRFSGSGSGTDFTLTISSLQPEDVATY

YCQRYNRAPYTFGQGTKVEIKRTVAAPSVFIFPPSDEQLKSGT

ASVVCLLNNFYPREAKVQWKVDNALQSGNSQESVTEQDSKDST

YSLSSTLTLSKADYEKHKVYACEVTHQGLSSPVTKSFNRGEC

-continued heavy chain variable region sequence for
an anti-TNF-alpha antibody
SEQ ID NO: 90
QVQLVESGGGVVQPGRSLRLSCAASGFTFSSYAMHWVRQAPGK

GLEWVAIISFDGSNKSSADSVKGRFTYSRRNSKNALFLQMNSL

RAEDTAVFYCARDRGVSAGGNYYYYGMDVWGQGTTVTVSS light chain variable region
sequence for an anti-TNF-alpha antibody
SEQ ID NO: 91
EIVLTQSPATLSLSPGERATLSCRASQSVSSYLAWYQQKPGQA

PRLLIYDASNRATGIPARFSGSGSGTRFTLTISSLEPEDFAVY

YCQQRSNWPPFTFGPGTKVDIL amino acid sequence of human TNFR-p75-Fc
dimeric fusion protein
SEQ ID NO: 92
LPAQVAFTPYAPEPGSTCRLREYYDQTAQMCCSKCSPGQHAKV

FCTKTSDTVCDSCEDSTYTQLWNWVPECLSCGSRCSSDQVETQ

ACTREQNRICTCRPGWYCALSKQEGCRLCAPLRKCRPGFGVAR

PGTETSDVVCKPCAPGTFSNTTSSTDICRPHQICNVVAIPGNA

SMDAVCTSTSPTRSMAPGAVHLPQPVSTRSQHTQPTPEPSTAP

STSFLLPMGPSPPAEGSTGDEPKSCDKTHTCPPCPAPELLGGP

SVFLFPPKPKDTLMISRTPEVTCVVVDVSHEDPEVKFNWYVDG

VEVHNAKTKPREEQYNSTYRVVSVLTVLHQDWLNGKEYKCKVS

NKALPAPIEKTISKAKGQPREPQVYTLPPSREEMTKNQVSLTC

LVKGFYPSDIAVEWESNGQPENNYKTTPPVLDSDGSFFLYSKL

TVDKSRWQQGNVFSCSVMHEALHNHYTQKSLSLSPGK

GLP-1 agonist peptide amino acid
sequence (exenatide)
SEQ ID NO: 93
HGEGTFTSDLSKQMEEEAVRLFIEWLKNGGPSSGAPPPS GLP-1 agonist peptide amino
acid sequence (Liraglutide)
SEQ ID NO: 94
HAEGTFTSDVSSYLEGQAAKEEFIIAWLVKGRG amino acid sequence of human growth hormone
(somatotropin)
SEQ ID NO: 95
FPTIPLSRLFDNAMLRAHRLHQLAFDTYQEFEEAYIPKEQKYSFL

QNPQTSLCFSESIPTPSNREETQQKSNLELLRISLLLIQSWLEPV

QFLRSVFANSLVYGASDSNVYDLLKDLEEGIQTLMGRLEDGSPRT

GQIFKQTYSKFDTNSHNDDALLKNYGLLYCFRKDMDKVETFLRIV

QCRSVEGSCGF amino acid sequence of a peptide linker
SEQ ID NO: 96
GGGGS amino acid sequence of a peptide linker
SEQ ID NO: 97
GGGGSGGGGS amino acid sequence of a peptide linker
SEQ ID NO: 98
GGGGSGGGGSGGGGS amino acid sequence of a peptide linker
SEQ ID NO: 99
GGGGSGGG amino acid sequence of a peptide linker
SEQ ID NO: 100
AAPF amino acid sequence of a peptide linker
SEQ ID NO: 101
GGF amino acid sequence of a peptide linker
SEQ ID NO: 102
AAPV amino acid sequence of a peptide linker
SEQ ID NO: 103
GGL amino acid sequence of a peptide linker
SEQ ID NO: 104
AAL amino acid sequence of a peptide linker
SEQ ID NO: 105
FVR amino acid sequence of a peptide linker
SEQ ID NO: 106
VGR amino acid sequence of a peptide linker
SEQ ID NO: 107
RKPR amino acid sequence of a peptide linker
SEQ ID NO: 108
Y V A D Xaa
Xaa = any amino acid amino acid sequence of a peptide linker
SEQ ID NO: 109
D Xaa Xaa D Xaa
Xaa = any amino acid amino acid sequence of a peptide linker
SEQ ID NO: 110
R (Xaa)$_n$ R Xaa
Xaa = any amino acid n = 0, 2, 4 or 6 amino acid sequence of a peptide linker
SEQ ID NO: 111
K (Xaa)$_n$ R Xaa
Xaa = any amino acid n = 0, 2, 4 or 6 amino acid sequence of a peptide linker
SEQ ID NO: 112
E R T K R Xaa
Xaa = any amino acid amino acid sequence of a peptide linker
SEQ ID NO: 113
R V R R Xaa
Xaa = any amino acid amino acid sequence of a peptide linker
SEQ ID NO: 114
Decanoyl-R V R R Xaa
Xaa = any amino acid amino acid sequence of a peptide linker
SEQ ID NO: 115
P Xaa W V P Xaa
Xaa = any amino acid amino acid sequence of a peptide linker
SEQ ID NO: 116
W V A Xaa
Xaa = any amino acid

```
amino acid sequence of a peptide linker
                                    SEQ ID NO: 117
Xaa F Xaa Xaa
Xaa = any amino acid amino acid sequence of a peptide linker
                                    SEQ ID NO: 118
Xaa Y Xaa Xaa
Xaa = any amino acid n= 0, 2, 4 or 6 amino acid sequence of a peptide linker
                                    SEQ ID NO: 119
Xaa W Xaa Xaa
Xaa = any amino acid n= 0, 2, 4 or 6 amino acid sequence of a peptide linker
                                    SEQ ID NO: 120
D R W I P F H L L
in combination with (V, A or P)-Y-(S, P or A)

amino acid sequence of a peptide linker
                                    SEQ ID NO: 121
GGGGSGGGENLYFQS amino acid sequence of a Cholix$^{415}$-TEV-IL-10
fusion molecule
                                    SEQ ID NO: 122
MVEEALNIFD

```
Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                    165                 170                 175

Ala Ile Ser Trp Pro Ser Val Ser Tyr Lys Ala Ala Gln Lys Glu Gly
                180                 185                 190

Ser Arg His Lys Arg Trp Ala His Trp His Thr Gly Leu Ala Leu Cys
            195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
            290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn Arg Ala Val Ile Thr Pro Gln
            420                 425                 430

Gly Val Thr Asn Trp Thr Tyr Gln Glu Leu Glu Ala Thr His Gln Ala
            435                 440                 445

Leu Thr Arg Glu Gly Tyr Val Phe Val Gly Tyr His Gly Thr Asn His
450                 455                 460

Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
                485                 490                 495

His Ala Glu Val Ala His Gly Tyr Ala Arg Ile Lys Glu Gly Thr Gly
                500                 505                 510

Glu Tyr Gly Leu Pro Thr Arg Ala Glu Arg Asp Ala Arg Gly Val Met
            515                 520                 525

Leu Arg Val Tyr Ile Pro Arg Ala Ser Leu Glu Arg Phe Tyr Arg Thr
530                 535                 540

Asn Thr Pro Leu Glu Asn Ala Glu Glu His Ile Thr Gln Val Ile Gly
```

```
                   545                 550                 555                 560
His Ser Leu Pro Leu Arg Asn Glu Ala Phe Thr Gly Pro Glu Ser Ala
                       565                 570                 575

Gly Gly Glu Asp Glu Thr Val Ile Gly Trp Asp Met Ala Ile His Ala
                580                 585                 590

Val Ala Ile Pro Ser Thr Ile Pro Gly Asn Ala Tyr Glu Glu Leu Ala
            595                 600                 605

Ile Asp Glu Glu Ala Val Ala Lys Glu Gln Ser Ile Ser Thr Lys Pro
    610                 615                 620

Pro Tyr Lys Glu Arg Lys Asp Glu Leu Lys
625                 630

<210> SEQ ID NO 2
<211> LENGTH: 1905
<212> TYPE: DNA
<213> ORGANISM: vibrio cholerae

<400> SEQUENCE: 2
atggtcgaag aagctttaaa catctttgat gaatgccgtt cgccatgttc gttgaccccg      60
gaaccgggta agccgattca atcaaaactg tctatcccta gtgatgttgt tctggatgaa     120
ggtgttctgt attactcgat gacgattaat gatgagcaga atgatattaa ggatgaggac     180
aaaggcgagt ccattatcac tattggtgaa tttgccacag tacgcgcgac tagacattat     240
gttaatcaag atgcgccttt tggtgtcatc catttagata ttacgacaga aatggtaca      300 aaaacgtact cttataaccg caaagagggt gaatttgcaa tcaattggtt agtgcctatt     360
ggtgaagatt ctcctgcaag catcaaaatc tccgttgatg agctcgatca gcaacgcaat     420
atcatcgagg tgcctaaact gtatagtatt gatctcgata ccaaacgtt agagcagtgg      480 aaaacccaag gtaatgtttc tttttcggta acgcgtcctg aacataatat cgctatctct     540
tggccaagcg tgagttacaa agcagcgcag aaagagggtt cacgccataa gcgttgggct     600
cattggcata caggcttagc actgtgttgg cttgtgccaa tggatgctat ctataactat     660
atcacccagc aaaattgtac tttagggat aattggtttg gtggctctta tgagactgtt      720
gcaggcactc cgaaggtgat tacggttaag caagggattg aacaaaagcc agttgagcag     780
cgcatccatt tctccaaggg gaatgcgatg agcgcacttg ctgctcatcg cgtctgtggt     840
gtgccattag aaactttggc gcgcagtcgc aaacctcgtg atctgacgga tgattatca      900 tgtgcctatc aagcgcagaa tatcgtgagt ttatttgtcg cgacgcgtat cctgttctct     960
catctggata gcgtatttac tctgaatctt gacgaacaag aaccagaggt ggctgaacgt    1020
ctaagtgatc ttcgccgtat caatgaaaat aacccgggca tggttacaca ggtttttaacc   1080 gttgctcgtc agatctataa cgattatgtc actcaccatc cgggcttaac tcctgagcaa    1140
accagtgcgg gtgcacaagc tgccgatatc ctctctttat tttgcccaga tgctgataag    1200
tcttgtgtgg cttcaaacaa cgatcaagcc aatatcaaca tcgagtctcg ttctggccgt    1260
tcatatttgc ctgaaaaccg tgcggtaatc accctcaag gcgtcacaaa ttggacttac     1320
caggaactcg aagcaacaca tcaagctctg actcgtgagg ttatgtgtt cgtgggttac     1380 catggtacga atcatgtcgc tgcgcaaacc atcgtgaatc gcattgcccc tgttccgcgc    1440
ggcaacaaca ctgaaaacga ggaaaagtgg ggcgggttat atgttgcaac tcacgctgaa    1500
gttgcccatg ttatgctcg catcaaagaa gggacagggg agtatggcct tccgacccgt     1560
gctgagcgcg acgtcgtgg ggtaatgctg cgcgtgtata tccctcgtgc ttcattagaa      1620
```

-continued

```
cgtttttatc gcacgaatac acctttggaa aatgctgagg agcatatcac gcaagtgatt    1680
ggtcattctt tgccattacg caatgaagca tttactggtc cagaaagtgc gggcggggaa    1740
gacgaaactg tcattggctg ggatatggcg attcatgcag ttgcgatccc ttcgactatc    1800
ccagggaacg cttacgaaga attggcgatt gatgaggagg ctgttgcaaa agagcaatcg    1860
attagcacaa aaccaccttaa taaagagcgc aaagatgaac ttaag                   1905
```

<210> SEQ ID NO 3
<211> LENGTH: 386
<212> TYPE: PRT
<213> ORGANISM: vibrio cholerae

<400> SEQUENCE: 3

```
Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
```

```
                    325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
                355                 360                 365

Val Thr His His Pro Gly Leu Thr Pro Glu Gln Thr Ser Ala Gly Ala
            370                 375                 380

Gln Ala
385

<210> SEQ ID NO 4
<211> LENGTH: 385
<212> TYPE: PRT
<213> ORGANISM: vibrio cholerae

<400> SEQUENCE: 4

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300
```

```
Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
            325                 330                 335

Ala Glu Arg Leu Ser Asp Leu Arg Arg Ile Asn Glu Asn Asn Pro Gly
        340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
370                 375                 380

Gln
385

<210> SEQ ID NO 5
<211> LENGTH: 384
<212> TYPE: PRT
<213> ORGANISM: vibrio cholerae

<400> SEQUENCE: 5

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Gly Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285
```

```
Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

<210> SEQ ID NO 6
<211> LENGTH: 383
<212> TYPE: PRT
<213> ORGANISM: vibrio cholerae

<400> SEQUENCE: 6

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
```

```
                275                 280                 285
Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly
    370                 375                 380

<210> SEQ ID NO 7
<211> LENGTH: 382
<212> TYPE: PRT
<213> ORGANISM: vibrio cholerae

<400> SEQUENCE: 7

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270
```

```
Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala
    370                 375                 380

<210> SEQ ID NO 8
<211> LENGTH: 381
<212> TYPE: PRT
<213> ORGANISM: vibrio cholerae

<400> SEQUENCE: 8

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270
```

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser
    370                 375                 380

<210> SEQ ID NO 9
<211> LENGTH: 380
<212> TYPE: PRT
<213> ORGANISM: vibrio cholerae

<400> SEQUENCE: 9

Val Glu Asp Glu Leu Asn Ile Phe Asp Glu Cys Arg Ser Pro Cys Ser
1               5                   10                  15

Leu Thr Pro Glu Pro Gly Lys P

```
                    260                 265                 270
Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
            290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr
            370                 375                 380

<210> SEQ ID NO 10
<211> LENGTH: 379
<212> TYPE: PRT
<213> ORGANISM: vibrio cholerae

<400> SEQUENCE: 10

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255
```

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln
    370                 375

<210> SEQ ID NO 11
<211> LENGTH: 378
<212> TYPE: PRT
<213> ORGANISM: vibrio cholerae

<400> SEQUENCE: 11

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
            85                  90                  95

Asn Gly Thr Lys Thr Tyr Ser Tyr Asn Arg Lys Glu Gly Glu Phe Ala
        100                 105                 110

Ile Asn Trp Leu Val Pro Ile Gly Glu Asp Ser Pro Ala Ser Ile Lys
    115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
              260                 265                 270

Ala Ala His Arg Val Cys Gly Val Pro Leu Glu Thr Leu Ala Arg Ser
          275                 280                 285

Arg Lys Pro Arg Asp Leu Thr Asp Asp Leu Ser Cys Ala Tyr Gln Ala
      290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                  325                 330                 335

Ala Glu Arg Leu Ser Asp Leu Arg Arg Ile Asn Glu Asn Asn Pro Gly
              340                 345                 350

Met Val Thr Gln Val Leu Thr Val Ala Arg Gln Ile Tyr Asn Asp Tyr
          355                 360                 365

Val Thr His His Pro Gly Leu Thr Pro Glu
      370                 375

<210> SEQ ID NO 12
<211> LENGTH: 377
<212> TYPE: PRT
<213> ORGANISM: vibrio cholerae

<400> SEQUENCE: 12

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
              20                  25                  30

Ser Asp Val Val Leu Asp Glu Gly Val Leu Tyr Tyr Ser Met Thr Ile
          35                  40                  45

Asn Asp Glu Gln Asn Asp Ile Lys Asp Glu Asp Lys Gly Glu Ser Ile
      50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                  85                  90                  95

Asn Gly Thr Lys Thr Tyr Ser Tyr Asn Arg Lys Glu Gly Glu Phe Ala
              100                 105                 110

Ile Asn Trp Leu Val Pro Ile Gly Glu Asp Ser Pro Ala Ser Ile Lys
          115                 120                 125

Ile Ser Val Asp Glu Leu Asp Gln Gln Arg Asn Ile Ile Glu Val Pro
      130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                  165                 170                 175

Ala Ile Ser Trp Pro Ser Val Ser Tyr Lys Ala Ala Gln Lys Glu Gly
              180                 185                 190

Ser Arg His Lys Arg Trp Ala His Trp His Thr Gly Leu Ala Leu Cys
          195                 200                 205

Trp Leu Val Pro Met Asp Ala Ile Tyr Asn Tyr Ile Thr Gln Gln Asn
      210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro

```
                    245                 250                 255
Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro
    370                 375

<210> SEQ ID NO 13
<211> LENGTH: 376
<212> TYPE: PRT
<213> ORGANISM: vibrio cholerae

<400> SEQUENCE: 13

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240
```

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr
    370                 375

<210> SEQ ID NO 14
<211> LENGTH: 375
<212> TYPE: PRT
<213> ORGANISM: vibrio cholerae

<400> SEQUENCE: 14

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

-continued

```
Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
        260                 265                 270

Ala Ala His Arg Val Cys Gly Val Pro Leu Glu Thr Leu Ala Arg Ser
    275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu
    370                 375

<210> SEQ ID NO 15
<211> LENGTH: 374
<212> TYPE: PRT
<213> ORGANISM: vibrio cholerae

<400> SEQUENCE: 15

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
```

```
                225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
                260                 265                 270
Ala Ala His Arg Val Cys Gly Val Pro Leu Glu Thr Leu Ala Arg Ser
                275                 280                 285
Arg Lys Pro Arg Asp Leu Thr Asp Asp Leu Ser Cys Ala Tyr Gln Ala
                290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro Gly
                340                 345                 350
Met Val Thr Gln Val Leu Thr Val Ala Arg Gln Ile Tyr Asn Asp Tyr
                355                 360                 365
Val Thr His His Pro Gly
                370

<210> SEQ ID NO 16
<211> LENGTH: 373
<212> TYPE: PRT
<213> ORGANISM: vibrio cholerae

<400> SEQUENCE: 16

Val Glu Asp Glu Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
                20                  25                  30
Ser Asp Val Val Leu Asp Glu Gly Val Leu Tyr Tyr Ser Met Thr Ile
                35                  40                  45
Asn Asp Glu Gln Asn Asp Ile Lys Asp Glu Asp Lys Gly Glu Ser Ile
                50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
                100                 105                 110
Ile Asn Trp Leu Val Pro Ile Gly Glu Asp Ser Pro Ala Ser Ile Lys
                115                 120                 125
Ile Ser Val Asp Glu Leu Asp Gln Gln Arg Asn Ile Ile Glu Val Pro
                130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
                180                 185                 190
Ser Arg His Lys Arg Trp Ala His Trp His Thr Gly Leu Ala Leu Cys
                195                 200                 205
Trp Leu Val Pro Met Asp Ala Ile Tyr Asn Tyr Ile Thr Gln Gln Asn
                210                 215                 220
```

-continued

```
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro
    370

<210> SEQ ID NO 17
<211> LENGTH: 372
<212> TYPE: PRT
<213> ORGANISM: vibrio cholerae

<400> SEQUENCE: 17

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220
```

```
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
        260                 265                 270

Ala Ala His Arg Val Cys Gly Val Pro Leu Glu Thr Leu Ala Arg Ser
    275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His
    370

<210> SEQ ID NO 18
<211> LENGTH: 371
<212> TYPE: PRT
<213> ORGANISM: vibrio cholerae

<400> SEQUENCE: 18

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
```

```
            210                 215                 220
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
                275                 280                 285

Arg Lys Pro Arg Asp Leu Thr Asp Asp Leu Ser Cys Ala Tyr Gln Ala
                290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
                355                 360                 365

Val Thr His
    370

<210> SEQ ID NO 19
<211> LENGTH: 370
<212> TYPE: PRT
<213> ORGANISM: vibrio cholerae

<400> SEQUENCE: 19

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205
```

```
Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
            355                 360                 365

Val Thr
370

<210> SEQ ID NO 20
<211> LENGTH: 369
<212> TYPE: PRT
<213> ORGANISM: vibrio cholerae

<400> SEQUENCE: 20

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
            130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
            195                 200                 205
```

```
Trp Leu Val Pro Met Asp Ala Ile Tyr Asn Tyr Ile Thr Gln Gln Asn
            210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val

<210> SEQ ID NO 21
<211> LENGTH: 368
<212> TYPE: PRT
<213> ORGANISM: vibrio cholerae

<400> SEQUENCE: 21

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205
```

Trp Leu Val Pro Met Asp Ala Ile Tyr Asn Tyr Ile Thr Gln Gln Asn
            210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

<210> SEQ ID NO 22
<211> LENGTH: 367
<212> TYPE: PRT
<213> ORGANISM: vibrio cholerae

<400> SEQUENCE: 22

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn

```
            210                 215                 220
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
                275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp
                355                 360                 365

<210> SEQ ID NO 23
<211> LENGTH: 366
<212> TYPE: PRT
<213> ORGANISM: vibrio cholerae

<400> SEQUENCE: 23

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220
```

```
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn
            355                 360                 365

<210> SEQ ID NO 24
<211> LENGTH: 365
<212> TYPE: PRT
<213> ORGANISM: vibrio cholerae

<400> SEQUENCE: 24

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
            85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
            195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240
```

Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
        260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
        340                 345                 350

Met Val Thr Gln Val Leu Thr Val Ala Arg Gln Ile Tyr
        355                 360                 365

<210> SEQ ID NO 25
<211> LENGTH: 364
<212> TYPE: PRT
<213> ORGANISM: vibrio cholerae

<400> SEQUENCE: 25

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro

```
            245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
            290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                    325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile
                355                 360
```

<210> SEQ ID NO 26
<211> LENGTH: 363
<212> TYPE: PRT
<213> ORGANISM: vibrio cholerae

<400> SEQUENCE: 26

```
Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255
```

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln
        355                 360

<210> SEQ ID NO 27
<211> LENGTH: 362
<212> TYPE: PRT
<213> ORGANISM: vibrio cholerae

<400> SEQUENCE: 27

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg
        355                 360

<210> SEQ ID NO 28
<211> LENGTH: 361
<212> TYPE: PRT
<213> ORGANISM: vibrio cholerae

<400> SEQUENCE: 28

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser

```
              275                 280                 285
Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Ile Asn Glu Asn Asn Pro Gly
            340                 345                 350

Met Val Thr Gln Val Leu Thr Val Ala
        355                 360

<210> SEQ ID NO 29
<211> LENGTH: 360
<212> TYPE: PRT
<213> ORGANISM: vibrio cholerae

<400> SEQUENCE: 29

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285
```

```
Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val
            355                 360

<210> SEQ ID NO 30
<211> LENGTH: 359
<212> TYPE: PRT
<213> ORGANISM: vibrio cholerae

<400> SEQUENCE: 30

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300
```

```
Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
            325                 330                 335

Ala Glu Arg Leu Ser Asp Leu Arg Arg Ile Asn Glu Asn Asn Pro Gly
        340                 345                 350

Met Val Thr Gln Val Leu Thr
            355

<210> SEQ ID NO 31
<211> LENGTH: 358
<212> TYPE: PRT
<213> ORGANISM: vibrio cholerae

<400> SEQUENCE: 31

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
```

```
                305                 310                 315                 320
Leu Asp Ser Val Phe Thr Leu Asn Leu Asp Glu Gln Glu Pro Glu Val
                    325                 330                 335

Ala Glu Arg Leu Ser Asp Leu Arg Arg Ile Asn Glu Asn Asn Pro Gly
                340                 345                 350

Met Val Thr Gln Val Leu
                355

<210> SEQ ID NO 32
<211> LENGTH: 357
<212> TYPE: PRT
<213> ORGANISM: vibrio cholerae

<400> SEQUENCE: 32

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp Thr Gly Leu Ala Leu Cys
        195                 200                 205

Trp Leu Val Pro Met Asp Ala Ile Tyr Asn Tyr Ile Thr Gln Gln Asn
        210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320
```

```
Leu Asp Ser Val Phe Thr Leu Asn Leu Asp Glu Gln Glu Pro Glu Val
            325                 330                 335

Ala Glu Arg Leu Ser Asp Leu Arg Arg Ile Asn Glu Asn Asn Pro Gly
        340                 345                 350

Met Val Thr Gln Val
        355

<210> SEQ ID NO 33
<211> LENGTH: 356
<212> TYPE: PRT
<213> ORGANISM: vibrio cholerae

<400> SEQUENCE: 33

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
            325                 330                 335
```

Ala Glu Arg Leu Ser Asp Leu Arg Arg Ile Asn Glu Asn Asn Pro Gly
            340                 345                 350

Met Val Thr Gln
        355

<210> SEQ ID NO 34
<211> LENGTH: 355
<212> TYPE: PRT
<213> ORGANISM: vibrio cholerae

<400> SEQUENCE: 34

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly

Met Val Thr
        355

<210> SEQ ID NO 35
<211> LENGTH: 354
<212> TYPE: PRT
<213> ORGANISM: vibrio cholerae

<400> SEQUENCE: 35

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val

<210> SEQ ID NO 36
<211> LENGTH: 353
<212> TYPE: PRT
<213> ORGANISM: vibrio cholerae

<400> SEQUENCE: 36

```
Val Glu Asp Glu Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
                20                  25                  30
Ser Asp Val Val Leu Asp Glu Gly Val Leu Tyr Tyr Ser Met Thr Ile
            35                  40                  45
Asn Asp Glu Gln Asn Asp Ile Lys Asp Glu Asp Lys Gly Glu Ser Ile
        50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
        210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
        275                 280                 285
Arg Lys Pro Arg Asp Leu Thr Asp Asp Leu Ser Cys Ala Tyr Gln Ala
    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro Gly
            340                 345                 350

Met
```

```
<210> SEQ ID NO 37
<211> LENGTH: 352
<212> TYPE: PRT
<213> ORGANISM: vibrio cholerae

<400> SEQUENCE: 37
```

| | | | | | | | | | | | | | | |
|---|---|---|---|---|---|---|---|---|---|---|---|---|---|---|
| Val | Glu | Asp | Glu | Leu | Asn | Ile | Phe | Asp | Glu | Cys | Arg | Ser | Pro | Cys | Ser |
| 1 | | | | 5 | | | | | 10 | | | | | 15 | |
| Leu | Thr | Pro | Glu | Pro | Gly | Lys | Pro | Ile | Gln | Ser | Lys | Leu | Ser | Ile | Pro |
| | | | 20 | | | | | 25 | | | | | 30 | | |
| Ser | Asp | Val | Val | Leu | Asp | Glu | Gly | Val | Leu | Tyr | Tyr | Ser | Met | Thr | Ile |
| | | 35 | | | | | 40 | | | | | 45 | | | |
| Asn | Asp | Glu | Gln | Asn | Asp | Ile | Lys | Asp | Glu | Asp | Lys | Gly | Glu | Ser | Ile |
| | 50 | | | | | 55 | | | | | 60 | | | | |
| Ile | Thr | Ile | Gly | Glu | Phe | Ala | Thr | Val | Arg | Ala | Thr | Arg | His | Tyr | Val |
| 65 | | | | | 70 | | | | | 75 | | | | | 80 |
| Asn | Gln | Asp | Ala | Pro | Phe | Gly | Val | Ile | His | Leu | Asp | Ile | Thr | Thr | Glu |
| | | | | 85 | | | | | 90 | | | | | 95 | |
| Asn | Gly | Thr | Lys | Thr | Tyr | Ser | Tyr | Asn | Arg | Lys | Glu | Gly | Glu | Phe | Ala |
| | | | 100 | | | | | 105 | | | | | 110 | | |
| Ile | Asn | Trp | Leu | Val | Pro | Ile | Gly | Glu | Asp | Ser | Pro | Ala | Ser | Ile | Lys |
| | | | 115 | | | | | 120 | | | | | 125 | | |
| Ile | Ser | Val | Asp | Glu | Leu | Asp | Gln | Gln | Arg | Asn | Ile | Ile | Glu | Val | Pro |
| | 130 | | | | | 135 | | | | | 140 | | | | |
| Lys | Leu | Tyr | Ser | Ile | Asp | Leu | Asp | Asn | Gln | Thr | Leu | Glu | Gln | Trp | Lys |
| 145 | | | | | 150 | | | | | 155 | | | | | 160 |
| Thr | Gln | Gly | Asn | Val | Ser | Phe | Ser | Val | Thr | Arg | Pro | Glu | His | Asn | Ile |
| | | | | 165 | | | | | 170 | | | | | 175 | |
| Ala | Ile | Ser | Trp | Pro | Ser | Val | Ser | Tyr | Lys | Ala | Ala | Gln | Lys | Glu | Gly |
| | | | 180 | | | | | 185 | | | | | 190 | | |
| Ser | Arg | His | Lys | Arg | Trp | Ala | His | Trp | His | Thr | Gly | Leu | Ala | Leu | Cys |
| | | 195 | | | | | 200 | | | | | 205 | | | |
| Trp | Leu | Val | Pro | Met | Asp | Ala | Ile | Tyr | Asn | Tyr | Ile | Thr | Gln | Gln | Asn |
| | 210 | | | | | 215 | | | | | 220 | | | | |
| Cys | Thr | Leu | Gly | Asp | Asn | Trp | Phe | Gly | Gly | Ser | Tyr | Glu | Thr | Val | Ala |
| 225 | | | | | 230 | | | | | 235 | | | | | 240 |
| Gly | Thr | Pro | Lys | Val | Ile | Thr | Val | Lys | Gln | Gly | Ile | Glu | Gln | Lys | Pro |
| | | | | 245 | | | | | 250 | | | | | 255 | |
| Val | Glu | Gln | Arg | Ile | His | Phe | Ser | Lys | Gly | Asn | Ala | Met | Ser | Ala | Leu |
| | | | 260 | | | | | 265 | | | | | 270 | | |
| Ala | Ala | His | Arg | Val | Cys | Gly | Val | Pro | Leu | Glu | Thr | Leu | Ala | Arg | Ser |
| | | 275 | | | | | 280 | | | | | 285 | | | |
| Arg | Lys | Pro | Arg | Asp | Leu | Thr | Asp | Asp | Leu | Ser | Cys | Ala | Tyr | Gln | Ala |
| | 290 | | | | | 295 | | | | | 300 | | | | |
| Gln | Asn | Ile | Val | Ser | Leu | Phe | Val | Ala | Thr | Arg | Ile | Leu | Phe | Ser | His |
| 305 | | | | | 310 | | | | | 315 | | | | | 320 |
| Leu | Asp | Ser | Val | Phe | Thr | Leu | Asn | Leu | Asp | Glu | Gln | Glu | Pro | Glu | Val |
| | | | | 325 | | | | | 330 | | | | | 335 | |
| Ala | Glu | Arg | Leu | Ser | Asp | Leu | Arg | Arg | Ile | Asn | Glu | Asn | Asn | Pro | Gly |
| | | | 340 | | | | | 345 | | | | | 350 | | |

```
<210> SEQ ID NO 38
<211> LENGTH: 351
<212> TYPE: PRT
<213> ORGANISM: vibrio cholerae
```

<400> SEQUENCE: 38

```
Val Glu Asp Glu Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
            20                  25                  30
Ser Asp Val Val Leu Asp Gly Val Leu Tyr Tyr Ser Met Thr Ile
        35                  40                  45
Asn Asp Glu Gln Asn Asp Ile Lys Asp Glu Asp Lys Gly Glu Ser Ile
    50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
    210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
        275                 280                 285
Arg Lys Pro Arg Asp Leu Thr Asp Asp Leu Ser Cys Ala Tyr Gln Ala
    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro
            340                 345                 350
```

<210> SEQ ID NO 39
<211> LENGTH: 350
<212> TYPE: PRT
<213> ORGANISM: vibrio cholerae

<400> SEQUENCE: 39

```
Val Glu Asp Glu Leu Asn Ile Phe Asp Glu Cys Arg Ser Pro Cys Ser
1               5                   10                  15
```

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn
            340                 345                 350

<210> SEQ ID NO 40
<211> LENGTH: 349
<212> TYPE: PRT
<213> ORGANISM: vibrio cholerae

<400> SEQUENCE: 40

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

```
Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
    195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn
            340                 345

<210> SEQ ID NO 41
<211> LENGTH: 348
<212> TYPE: PRT
<213> ORGANISM: vibrio cholerae

<400> SEQUENCE: 41

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
```

```
                65                  70                  75                  80
Asn Gln Asp Ala Pro Phe Gly Val Ile His Leu Asp Ile Thr Thr Glu
                    85                  90                  95
Asn Gly Thr Lys Thr Tyr Ser Tyr Asn Arg Lys Glu Gly Glu Phe Ala
                100                 105                 110
Ile Asn Trp Leu Val Pro Ile Gly Glu Asp Ser Pro Ala Ser Ile Lys
            115                 120                 125
Ile Ser Val Asp Glu Leu Asp Gln Gln Arg Asn Ile Ile Glu Val Pro
        130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
                180                 185                 190
Ser Arg His Lys Arg Trp Ala His Trp His Thr Gly Leu Ala Leu Cys
                195                 200                 205
Trp Leu Val Pro Met Asp Ala Ile Tyr Asn Tyr Ile Thr Gln Gln Asn
        210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
                260                 265                 270
Ala Ala His Arg Val Cys Gly Val Pro Leu Glu Thr Leu Ala Arg Ser
            275                 280                 285
Arg Lys Pro Arg Asp Leu Thr Asp Leu Ser Cys Ala Tyr Gln Ala
        290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu
                340                 345

<210> SEQ ID NO 42
<211> LENGTH: 425
<212> TYPE: PRT
<213> ORGANISM: vibrio cholerae

<400> SEQUENCE: 42

Val Glu Asp Glu Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
                20                  25                  30
Ser Asp Val Val Leu Asp Glu Gly Val Leu Tyr Tyr Ser Met Thr Ile
            35                  40                  45
Asn Asp Glu Gln Asn Asp Ile Lys Asp Glu Asp Lys Gly Glu Ser Ile
        50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                85                  90                  95
```

-continued

```
Asn Gly Thr Lys Thr Tyr Ser Tyr Asn Arg Lys Glu Gly Glu Phe Ala
             100                 105                 110

Ile Asn Trp Leu Val Pro Ile Gly Glu Asp Ser Pro Ala Ser Ile Lys
         115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn
            420                 425

<210> SEQ ID NO 43
<211> LENGTH: 424
<212> TYPE: PRT
<213> ORGANISM: vibrio cholerae

<400> SEQUENCE: 43

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45
```

```
Asn Asp Glu Gln Asn Asp Ile Lys Asp Glu Asp Lys Gly Glu Ser Ile
     50                  55                  60
Ile Thr Ile Gly Glu Phe Ala Thr Val Arg Ala Thr Arg His Tyr Val
 65                  70                  75                  80
Asn Gln Asp Ala Pro Phe Gly Val Ile His Leu Asp Ile Thr Thr Glu
                 85                  90                  95
Asn Gly Thr Lys Thr Tyr Ser Tyr Asn Arg Lys Glu Gly Glu Phe Ala
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
    210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
        275                 280                 285
Arg Lys Pro Arg Asp Leu Thr Asp Asp Leu Ser Cys Ala Tyr Gln Ala
    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro Gly
            340                 345                 350
Met Val Thr Gln Val Leu Thr Val Ala Arg Gln Ile Tyr Asn Asp Tyr
        355                 360                 365
Val Thr His His Pro Gly Leu Thr Pro Glu Gln Thr Ser Ala Gly Ala
    370                 375                 380
Gln Ala Ala Asp Ile Leu Ser Leu Phe Cys Pro Asp Ala Asp Lys Ser
385                 390                 395                 400
Cys Val Ala Ser Asn Asn Asp Gln Ala Asn Ile Asn Ile Glu Ser Arg
                405                 410                 415
Ser Gly Arg Ser Tyr Leu Pro Glu
            420

<210> SEQ ID NO 44
<211> LENGTH: 423
<212> TYPE: PRT
<213> ORGANISM: vibrio cholerae
```

```
<400> SEQUENCE: 44

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415
```

```
Ser Gly Arg Ser Tyr Leu Pro
            420

<210> SEQ ID NO 45
<211> LENGTH: 422
<212> TYPE: PRT
<213> ORGANISM: vibrio cholerae

<400> SEQUENCE: 45

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
```

```
              355                 360                 365
Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu
            420

<210> SEQ ID NO 46
<211> LENGTH: 421
<212> TYPE: PRT
<213> ORGANISM: vibrio cholerae

<400> SEQUENCE: 46

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300
```

```
Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr
            420

<210> SEQ ID NO 47
<211> LENGTH: 420
<212> TYPE: PRT
<213> ORGANISM: vibrio cholerae

<400> SEQUENCE: 47

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255
```

```
Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
            290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser
            420

<210> SEQ ID NO 48
<211> LENGTH: 419
<212> TYPE: PRT
<213> ORGANISM: vibrio cholerae

<400> SEQUENCE: 48

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
            85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
            130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
```

```
                195                 200                 205
Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg

<210> SEQ ID NO 49
<211> LENGTH: 418
<212> TYPE: PRT
<213> ORGANISM: vibrio cholerae

<400> SEQUENCE: 49

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
```

```
                145                 150                 155                 160
Thr Gln Gly Asn Val Ser Phe Ser Val Thr Arg Pro Glu His Asn Ile
                    165                 170                 175
Ala Ile Ser Trp Pro Ser Val Ser Tyr Lys Ala Ala Gln Lys Glu Gly
                    180                 185                 190
Ser Arg His Lys Arg Trp Ala Trp His Thr Gly Leu Ala Leu Cys
                    195                 200                 205
Trp Leu Val Pro Met Asp Ala Ile Tyr Asn Tyr Ile Thr Gln Gln Asn
        210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                    245                 250                 255
Val Glu Gln Arg Ile His Phe Ser Lys Gly Asn Ala Met Ser Ala Leu
                    260                 265                 270
Ala Ala His Arg Val Cys Gly Val Pro Leu Glu Thr Leu Ala Arg Ser
                    275                 280                 285
Arg Lys Pro Arg Asp Leu Thr Asp Asp Leu Ser Cys Ala Tyr Gln Ala
                    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                    325                 330                 335
Ala Glu Arg Leu Ser Asp Leu Arg Arg Ile Asn Glu Asn Asn Pro Gly
                    340                 345                 350
Met Val Thr Gln Val Leu Thr Val Ala Arg Gln Ile Tyr Asn Asp Tyr
                    355                 360                 365
Val Thr His His Pro Gly Leu Thr Pro Glu Gln Thr Ser Ala Gly Ala
                    370                 375                 380
Gln Ala Ala Asp Ile Leu Ser Leu Phe Cys Pro Asp Ala Asp Lys Ser
385                 390                 395                 400
Cys Val Ala Ser Asn Asn Asp Gln Ala Asn Ile Asn Ile Glu Ser Arg
                    405                 410                 415
Ser Gly

<210> SEQ ID NO 50
<211> LENGTH: 417
<212> TYPE: PRT
<213> ORGANISM: vibrio cholerae

<400> SEQUENCE: 50

Val Glu Asp Glu Leu Asn Ile Phe Asp Glu Cys Arg Ser Pro Cys Ser
1                   5                   10                  15
Leu Thr Pro Glu Pro Gly Lys Pro Ile Gln Ser Lys Leu Ser Ile Pro
                    20                  25                  30
Ser Asp Val Val Leu Asp Glu Gly Val Leu Tyr Tyr Ser Met Thr Ile
                    35                  40                  45
Asn Asp Glu Gln Asn Asp Ile Lys Asp Glu Lys Gly Glu Ser Ile
        50                  55                  60
Ile Thr Ile Gly Glu Phe Ala Thr Val Arg Ala Thr Arg His Tyr Val
65                  70                  75                  80
Asn Gln Asp Ala Pro Phe Gly Val Ile His Leu Asp Ile Thr Thr Glu
                    85                  90                  95
Asn Gly Thr Lys Thr Tyr Ser Tyr Asn Arg Lys Glu Gly Glu Phe Ala
```

```
            100                 105                 110
Ile Asn Trp Leu Val Pro Ile Gly Glu Asp Ser Pro Ala Ser Ile Lys
        115                 120                 125
Ile Ser Val Asp Glu Leu Asp Gln Gln Arg Asn Ile Ile Glu Val Pro
    130                 135                 140
Lys Leu Tyr Ser Ile Asp Leu Asp Asn Gln Thr Leu Glu Gln Trp Lys
145                 150                 155                 160
Thr Gln Gly Asn Val Ser Phe Ser Val Thr Arg Pro Glu His Asn Ile
                165                 170                 175
Ala Ile Ser Trp Pro Ser Val Ser Tyr Lys Ala Ala Gln Lys Glu Gly
            180                 185                 190
Ser Arg His Lys Arg Trp Ala His Trp His Thr Gly Leu Ala Leu Cys
        195                 200                 205
Trp Leu Val Pro Met Asp Ala Ile Tyr Asn Tyr Ile Thr Gln Gln Asn
    210                 215                 220
Cys Thr Leu Gly Asp Asn Trp Phe Gly Gly Ser Tyr Glu Thr Val Ala
225                 230                 235                 240
Gly Thr Pro Lys Val Ile Thr Val Lys Gln Gly Ile Glu Gln Lys Pro
                245                 250                 255
Val Glu Gln Arg Ile His Phe Ser Lys Gly Asn Ala Met Ser Ala Leu
            260                 265                 270
Ala Ala His Arg Val Cys Gly Val Pro Leu Glu Thr Leu Ala Arg Ser
        275                 280                 285
Arg Lys Pro Arg Asp Leu Thr Asp Asp Leu Ser Cys Ala Tyr Gln Ala
    290                 295                 300
Gln Asn Ile Val Ser Leu Phe Val Ala Thr Arg Ile Leu Phe Ser His
305                 310                 315                 320
Leu Asp Ser Val Phe Thr Leu Asn Leu Asp Glu Gln Glu Pro Glu Val
                325                 330                 335
Ala Glu Arg Leu Ser Asp Leu Arg Arg Ile Asn Glu Asn Asn Pro Gly
            340                 345                 350
Met Val Thr Gln Val Leu Thr Val Ala Arg Gln Ile Tyr Asn Asp Tyr
        355                 360                 365
Val Thr His His Pro Gly Leu Thr Pro Glu Gln Thr Ser Ala Gly Ala
    370                 375                 380
Gln Ala Ala Asp Ile Leu Ser Leu Phe Cys Pro Asp Ala Asp Lys Ser
385                 390                 395                 400
Cys Val Ala Ser Asn Asn Asp Gln Ala Asn Ile Asn Ile Glu Ser Arg
                405                 410                 415
Ser
```

<210> SEQ ID NO 51
<211> LENGTH: 416
<212> TYPE: PRT
<213> ORGANISM: vibrio cholerae

<400> SEQUENCE: 51

```
Val Glu Asp Glu Leu Asn Ile Phe Asp Glu Cys Arg Ser Pro Cys Ser
1               5                   10                  15
Leu Thr Pro Glu Pro Gly Lys Pro Ile Gln Ser Lys Leu Ser Ile Pro
            20                  25                  30
Ser Asp Val Val Leu Asp Glu Gly Val Leu Tyr Tyr Ser Met Thr Ile
        35                  40                  45
Asn Asp Glu Gln Asn Asp Ile Lys Asp Glu Asp Lys Gly Glu Ser Ile
```

```
            50                  55                  60
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
                115                 120                 125

Ile Ser Val Asp Glu Leu Asp Gln Gln Arg Asn Ile Ile Glu Val Pro
                130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
                180                 185                 190

Ser Arg His Lys Arg Trp Ala His Trp His Thr Gly Leu Ala Leu Cys
                195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
                275                 280                 285

Arg Lys Pro Arg Asp Leu Thr Asp Asp Leu Ser Cys Ala Tyr Gln Ala
                290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
                355                 360                 365

Val Thr His His Pro Gly Leu Thr Pro Glu Gln Thr Ser Ala Gly Ala
                370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

<210> SEQ ID NO 52
<211> LENGTH: 415
<212> TYPE: PRT
<213> ORGANISM: vibrio cholerae

<400> SEQUENCE: 52

Val Glu Asp Glu Leu Asn Ile Phe Asp Glu Cys Arg Ser Pro Cys Ser
 1               5                  10                  15
```

-continued

Leu Thr Pro Glu Pro Gly Lys Pro Ile Gln Ser Lys Leu Ser Ile Pro
           20                  25                  30

Ser Asp Val Val Leu Asp Glu Gly Val Leu Tyr Tyr Ser Met Thr Ile
       35                  40                  45

Asn Asp Glu Gln Asn Asp Ile Lys Asp Glu Lys Gly Glu Ser Ile
   50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
               85                  90                  95

Asn Gly Thr Lys Thr Tyr Ser Tyr Asn Arg Lys Glu Gly Glu Phe Ala
               100                 105                 110

Ile Asn Trp Leu Val Pro Ile Gly Glu Asp Ser Pro Ala Ser Ile Lys
       115                 120                 125

Ile Ser Val Asp Glu Leu Asp Gln Gln Arg Asn Ile Ile Glu Val Pro
   130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
               165                 170                 175

Ala Ile Ser Trp Pro Ser Val Ser Tyr Lys Ala Ala Gln Lys Glu Gly
               180                 185                 190

Ser Arg His Lys Arg Trp Ala His Trp His Thr Gly Leu Ala Leu Cys
       195                 200                 205

Trp Leu Val Pro Met Asp Ala Ile Tyr Asn Tyr Ile Thr Gln Gln Asn
   210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
               245                 250                 255

Val Glu Gln Arg Ile His Phe Ser Lys Gly Asn Ala Met Ser Ala Leu
               260                 265                 270

Ala Ala His Arg Val Cys Gly Val Pro Leu Glu Thr Leu Ala Arg Ser
       275                 280                 285

Arg Lys Pro Arg Asp Leu Thr Asp Asp Leu Ser Cys Ala Tyr Gln Ala
   290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
               325                 330                 335

Ala Glu Arg Leu Ser Asp Leu Arg Arg Ile Asn Glu Asn Pro Gly
               340                 345                 350

Met Val Thr Gln Val Leu Thr Val Ala Arg Gln Ile Tyr Asn Asp Tyr
       355                 360                 365

Val Thr His His Pro Gly Leu Thr Pro Glu Gln Thr Ser Ala Gly Ala
   370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser
               405                 410                 415

<210> SEQ ID NO 53
<211> LENGTH: 414
<212> TYPE: PRT

<213> ORGANISM: vibrio cholerae

<400> SEQUENCE: 53

```
Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp Lys Ser
385                 390                 395                 400
```

Cys Val Ala Ser Asn Asn Asp Gln Ala Asn Ile Asn Ile Glu
                405                 410

<210> SEQ ID NO 54
<211> LENGTH: 413
<212> TYPE: PRT
<213> ORGANISM: vibrio cholerae

<400> SEQUENCE: 54

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile
                405                 410

<210> SEQ ID NO 55
<211> LENGTH: 412
<212> TYPE: PRT
<213> ORGANISM: vibrio cholerae

<400> SEQUENCE: 55

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val 325                 330                 335
Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
                355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn
                405                 410

<210> SEQ ID NO 56
<211> LENGTH: 411
<212> TYPE: PRT
<213> ORGANISM: vibrio cholerae

<400> SEQUENCE: 56

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

```
Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile
                405                 410

<210> SEQ ID NO 57
<211> LENGTH: 410
<212> TYPE: PRT
<213> ORGANISM: vibrio cholerae

<400> SEQUENCE: 57

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255
```

```
Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn
                405                 410

<210> SEQ ID NO 58
<211> LENGTH: 409
<212> TYPE: PRT
<213> ORGANISM: vibrio cholerae

<400> SEQUENCE: 58

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
```

```
                210                 215                 220
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
                275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
        370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala
                405

<210> SEQ ID NO 59
<211> LENGTH: 408
<212> TYPE: PRT
<213> ORGANISM: vibrio cholerae

<400> SEQUENCE: 59

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
                35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
                115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175
```

```
Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln
                405

<210> SEQ ID NO 60
<211> LENGTH: 407
<212> TYPE: PRT
<213> ORGANISM: vibrio cholerae

<400> SEQUENCE: 60

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140
```

```
Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
        180                 185                 190

Ser Arg His Lys Arg Trp Ala His Trp His Thr Gly Leu Ala Leu Cys
            195                 200                 205

Trp Leu Val Pro Met Asp Ala Ile Tyr Asn Tyr Ile Thr Gln Gln Asn
        210                 215                 220

Cys Thr Leu Gly Asp Asn Trp Phe Gly Ser Tyr Glu Thr Val Ala
225                 230                 235                 240

Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
        260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
            325                 330                 335

Ala Glu Arg Leu Ser Asp Leu Arg Arg Ile Asn Glu Asn Asn Pro Gly
        340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
        370                 375                 380

Gln Ala Ala Asp Ile Leu Ser Leu Phe Cys Pro Asp Ala Asp Lys Ser
385                 390                 395                 400

Cys Val Ala Ser Asn Asn Asp
                405

<210> SEQ ID NO 61
<211> LENGTH: 406
<212> TYPE: PRT
<213> ORGANISM: vibrio cholerae

<400> SEQUENCE: 61

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
            85                  90                  95

Asn Gly Thr Lys Thr Tyr Ser Tyr Asn Arg Lys Glu Gly Glu Phe Ala
```

```
                100              105              110
Ile Asn Trp Leu Val Pro Ile Gly Glu Asp Ser Pro Ala Ser Ile Lys
            115              120              125
Ile Ser Val Asp Glu Leu Asp Gln Gln Arg Asn Ile Ile Glu Val Pro
            130              135              140
Lys Leu Tyr Ser Ile Asp Leu Asp Asn Gln Thr Leu Glu Gln Trp Lys
145              150              155              160
Thr Gln Gly Asn Val Ser Phe Ser Val Thr Arg Pro Glu His Asn Ile
                165              170              175
Ala Ile Ser Trp Pro Ser Val Ser Tyr Lys Ala Ala Gln Lys Glu Gly
            180              185              190
Ser Arg His Lys Arg Trp Ala His Trp His Thr Gly Leu Ala Leu Cys
            195              200              205
Trp Leu Val Pro Met Asp Ala Ile Tyr Asn Tyr Ile Thr Gln Gln Asn
            210              215              220
Cys Thr Leu Gly Asp Asn Trp Phe Gly Gly Ser Tyr Glu Thr Val Ala
225              230              235              240
Gly Thr Pro Lys Val Ile Thr Val Lys Gln Gly Ile Glu Gln Lys Pro
                245              250              255
Val Glu Gln Arg Ile His Phe Ser Lys Gly Asn Ala Met Ser Ala Leu
            260              265              270
Ala Ala His Arg Val Cys Gly Val Pro Leu Glu Thr Leu Ala Arg Ser
            275              280              285
Arg Lys Pro Arg Asp Leu Thr Asp Asp Leu Ser Cys Ala Tyr Gln Ala
            290              295              300
Gln Asn Ile Val Ser Leu Phe Val Ala Thr Arg Ile Leu Phe Ser His
305              310              315              320
Leu Asp Ser Val Phe Thr Leu Asn Leu Asp Glu Gln Glu Pro Glu Val
                325              330              335
Ala Glu Arg Leu Ser Asp Leu Arg Arg Ile Asn Glu Asn Asn Pro Gly
            340              345              350
Met Val Thr Gln Val Leu Thr Val Ala Arg Gln Ile Tyr Asn Asp Tyr
            355              360              365
Val Thr His His Pro Gly Leu Thr Pro Glu Gln Thr Ser Ala Gly Ala
            370              375              380
Gln Ala Ala Asp Ile Leu Ser Leu Phe Cys Pro Asp Ala Asp Lys Ser
385              390              395              400
Cys Val Ala Ser Asn Asn
                405

<210> SEQ ID NO 62
<211> LENGTH: 405
<212> TYPE: PRT
<213> ORGANISM: vibrio cholerae

<400> SEQUENCE: 62

Val Glu Asp Glu Leu Asn Ile Phe Asp Glu Cys Arg Ser Pro Cys Ser
1               5               10              15
Leu Thr Pro Glu Pro Gly Lys Pro Ile Gln Ser Lys Leu Ser Ile Pro
                20              25              30
Ser Asp Val Val Leu Asp Glu Gly Val Leu Tyr Tyr Ser Met Thr Ile
            35              40              45
Asn Asp Glu Gln Asn Asp Ile Lys Asp Glu Asp Lys Gly Glu Ser Ile
        50              55              60
```

```
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp Lys Ser
385                 390                 395                 400

Cys Val Ala Ser Asn
                405

<210> SEQ ID NO 63
<211> LENGTH: 404
<212> TYPE: PRT
<213> ORGANISM: vibrio cholerae

<400> SEQUENCE: 63

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30
```

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
 50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
             100                 105                 110

Ile Asn Trp Leu Val Pro Ile Gly Glu Asp Ser Pro Ala Ser Ile Lys
         115                 120                 125

Ile Ser Val Asp Glu Leu Asp Gln Gln Arg Asn Ile Ile Glu Val Pro
     130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                 165                 170                 175

Ala Ile Ser Trp Pro Ser Val Ser Tyr Lys Ala Ala Gln Lys Glu Gly
             180                 185                 190

Ser Arg His Lys Arg Trp Ala His Trp His Thr Gly Leu Ala Leu Cys
         195                 200                 205

Trp Leu Val Pro Met Asp Ala Ile Tyr Asn Tyr Ile Thr Gln Gln Asn
     210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                 245                 250                 255

Val Glu Gln Arg Ile His Phe Ser Lys Gly Asn Ala Met Ser Ala Leu
             260                 265                 270

Ala Ala His Arg Val Cys Gly Val Pro Leu Glu Thr Leu Ala Arg Ser
         275                 280                 285

Arg Lys Pro Arg Asp Leu Thr Asp Asp Leu Ser Cys Ala Tyr Gln Ala
     290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                 325                 330                 335

Ala Glu Arg Leu Ser Asp Leu Arg Arg Ile Asn Glu Asn Asn Pro Gly
             340                 345                 350

Met Val Thr Gln Val Leu Thr Val Ala Arg Gln Ile Tyr Asn Asp Tyr
         355                 360                 365

Val Thr His His Pro Gly Leu Thr Pro Glu Gln Thr Ser Ala Gly Ala
     370                 375                 380

Gln Ala Ala Asp Ile Leu Ser Leu Phe Cys Pro Asp Ala Asp Lys Ser
385                 390                 395                 400

Cys Val Ala Ser

<210> SEQ ID NO 64
<211> LENGTH: 403
<212> TYPE: PRT
<213> ORGANISM: vibrio cholerae

<400> SEQUENCE: 64

```
Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                      70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala
```

```
<210> SEQ ID NO 65
<211> LENGTH: 402
<212> TYPE: PRT
<213> ORGANISM: vibrio cholerae

<400> SEQUENCE: 65
```

| | | | | | | | | | | | | | | |
|---|---|---|---|---|---|---|---|---|---|---|---|---|---|---|
| Val | Glu | Asp | Glu | Leu | Asn | Ile | Phe | Asp | Glu | Cys | Arg | Ser | Pro | Cys | Ser |
| 1 | | | | 5 | | | | | 10 | | | | | 15 | |
| Leu | Thr | Pro | Glu | Pro | Gly | Lys | Pro | Ile | Gln | Ser | Lys | Leu | Ser | Ile | Pro |
| | | 20 | | | | | 25 | | | | | 30 | | | |
| Ser | Asp | Val | Val | Leu | Asp | Glu | Gly | Val | Leu | Tyr | Tyr | Ser | Met | Thr | Ile |
| | | 35 | | | | 40 | | | | | 45 | | | | |
| Asn | Asp | Glu | Gln | Asn | Asp | Ile | Lys | Asp | Glu | Asp | Lys | Gly | Glu | Ser | Ile |
| 50 | | | | | 55 | | | | | 60 | | | | | |
| Ile | Thr | Ile | Gly | Glu | Phe | Ala | Thr | Val | Arg | Ala | Thr | Arg | His | Tyr | Val |
| 65 | | | | | 70 | | | | | 75 | | | | | 80 |
| Asn | Gln | Asp | Ala | Pro | Phe | Gly | Val | Ile | His | Leu | Asp | Ile | Thr | Thr | Glu |
| | | | | 85 | | | | | 90 | | | | | 95 | |
| Asn | Gly | Thr | Lys | Thr | Tyr | Ser | Tyr | Asn | Arg | Lys | Glu | Gly | Glu | Phe | Ala |
| | | | 100 | | | | | 105 | | | | | 110 | | |
| Ile | Asn | Trp | Leu | Val | Pro | Ile | Gly | Glu | Asp | Ser | Pro | Ala | Ser | Ile | Lys |
| | | | 115 | | | | | 120 | | | | | 125 | | |
| Ile | Ser | Val | Asp | Glu | Leu | Asp | Gln | Gln | Arg | Asn | Ile | Ile | Glu | Val | Pro |
| | 130 | | | | | 135 | | | | | 140 | | | | |
| Lys | Leu | Tyr | Ser | Ile | Asp | Leu | Asp | Asn | Gln | Thr | Leu | Glu | Gln | Trp | Lys |
| 145 | | | | | 150 | | | | | 155 | | | | | 160 |
| Thr | Gln | Gly | Asn | Val | Ser | Phe | Ser | Val | Thr | Arg | Pro | Glu | His | Asn | Ile |
| | | | | 165 | | | | | 170 | | | | | 175 | |
| Ala | Ile | Ser | Trp | Pro | Ser | Val | Ser | Tyr | Lys | Ala | Ala | Gln | Lys | Glu | Gly |
| | | | 180 | | | | | 185 | | | | | 190 | | |
| Ser | Arg | His | Lys | Arg | Trp | Ala | His | Trp | His | Thr | Gly | Leu | Ala | Leu | Cys |
| | | 195 | | | | | 200 | | | | | 205 | | | |
| Trp | Leu | Val | Pro | Met | Asp | Ala | Ile | Tyr | Asn | Tyr | Ile | Thr | Gln | Gln | Asn |
| 210 | | | | | 215 | | | | | 220 | | | | | |
| Cys | Thr | Leu | Gly | Asp | Asn | Trp | Phe | Gly | Gly | Ser | Tyr | Glu | Thr | Val | Ala |
| 225 | | | | | 230 | | | | | 235 | | | | | 240 |
| Gly | Thr | Pro | Lys | Val | Ile | Thr | Val | Lys | Gln | Gly | Ile | Glu | Gln | Lys | Pro |
| | | | 245 | | | | | 250 | | | | | 255 | | |
| Val | Glu | Gln | Arg | Ile | His | Phe | Ser | Lys | Gly | Asn | Ala | Met | Ser | Ala | Leu |
| | | | 260 | | | | | 265 | | | | | 270 | | |
| Ala | Ala | His | Arg | Val | Cys | Gly | Val | Pro | Leu | Glu | Thr | Leu | Ala | Arg | Ser |
| | | 275 | | | | | 280 | | | | | 285 | | | |
| Arg | Lys | Pro | Arg | Asp | Leu | Thr | Asp | Asp | Leu | Ser | Cys | Ala | Tyr | Gln | Ala |
| | 290 | | | | | 295 | | | | | 300 | | | | |
| Gln | Asn | Ile | Val | Ser | Leu | Phe | Val | Ala | Thr | Arg | Ile | Leu | Phe | Ser | His |
| 305 | | | | | 310 | | | | | 315 | | | | | 320 |
| Leu | Asp | Ser | Val | Phe | Thr | Leu | Asn | Leu | Asp | Glu | Gln | Glu | Pro | Glu | Val |
| | | | | 325 | | | | | 330 | | | | | 335 | |
| Ala | Glu | Arg | Leu | Ser | Asp | Leu | Arg | Arg | Ile | Asn | Glu | Asn | Asn | Pro | Gly |
| | | | 340 | | | | | 345 | | | | | 350 | | |
| Met | Val | Thr | Gln | Val | Leu | Thr | Val | Ala | Arg | Gln | Ile | Tyr | Asn | Asp | Tyr |
| | | 355 | | | | | 360 | | | | | 365 | | | |
| Val | Thr | His | His | Pro | Gly | Leu | Thr | Pro | Glu | Gln | Thr | Ser | Ala | Gly | Ala |
| | 370 | | | | | 375 | | | | | 380 | | | | |

```
Gln Ala Ala Asp Ile Leu Ser Leu Phe Cys Pro Asp Ala Asp Lys Ser
385                 390                 395                 400

Cys Val

<210> SEQ ID NO 66
<211> LENGTH: 401
<212> TYPE: PRT
<213> ORGANISM: vibrio cholerae

<400> SEQUENCE: 66

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350
```

```
Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp Lys Ser
385                 390                 395                 400

Cys

<210> SEQ ID NO 67
<211> LENGTH: 400
<212> TYPE: PRT
<213> ORGANISM: vibrio cholerae

<400> SEQUENCE: 67

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320
```

```
Leu Asp Ser Val Phe Thr Leu Asn Leu Asp Glu Gln Glu Pro Glu Val
            325                 330                 335

Ala Glu Arg Leu Ser Asp Leu Arg Arg Ile Asn Glu Asn Asn Pro Gly
        340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp Lys Ser
385                 390                 395                 400
```

<210> SEQ ID NO 68
<211> LENGTH: 399
<212> TYPE: PRT
<213> ORGANISM: vibrio cholerae

<400> SEQUENCE: 68

```
Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
            85                  90                  95

Asn Gly Thr Lys Thr Tyr Ser Tyr Asn Arg Lys Glu Gly Glu Phe Ala
        100                 105                 110

Ile Asn Trp Leu Val Pro Ile Gly Glu Asp Ser Pro Ala Ser Ile Lys
    115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
            165                 170                 175

Ala Ile Ser Trp Pro Ser Val Ser Tyr Lys Ala Ala Gln Lys Glu Gly
        180                 185                 190

Ser Arg His Lys Arg Trp Ala His Trp His Thr Gly Leu Ala Leu Cys
    195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
            245                 250                 255

Val Glu Gln Arg Ile His Phe Ser Lys Gly Asn Ala Met Ser Ala Leu
        260                 265                 270

Ala Ala His Arg Val Cys Gly Val Pro Leu Glu Thr Leu Ala Arg Ser
    275                 280                 285

Arg Lys Pro Arg Asp Leu Thr Asp Asp Leu Ser Cys Ala Tyr Gln Ala
290                 295                 300
```

```
Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
            325                 330                 335

Ala Glu Arg Leu Ser Asp Leu Arg Arg Ile Asn Glu Asn Asn Pro Gly
        340                 345                 350

Met Val Thr Gln Val Leu Thr Val Ala Arg Gln Ile Tyr Asn Asp Tyr
    355                 360                 365

Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp Lys
385                 390                 395

<210> SEQ ID NO 69
<211> LENGTH: 398
<212> TYPE: PRT
<213> ORGANISM: vibrio cholerae

<400> SEQUENCE: 69

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
```

```
            275                 280                 285
Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
                355                 360                 365

Val Thr His His Pro Gly Leu Thr Pro Glu Gln Thr Ser Ala Gly Ala
370                 375                 380

Gln Ala Ala Asp Ile Leu Ser Leu Phe Cys Pro Asp Ala Asp
385                 390                 395

<210> SEQ ID NO 70
<211> LENGTH: 397
<212> TYPE: PRT
<213> ORGANISM: vibrio cholerae

<400> SEQUENCE: 70

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255
```

```
Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala
385                 390                 395

<210> SEQ ID NO 71
<211> LENGTH: 396
<212> TYPE: PRT
<213> ORGANISM: vibrio cholerae

<400> SEQUENCE: 71

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
        35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240
```

```
Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp
385                 390                 395

<210> SEQ ID NO 72
<211> LENGTH: 395
<212> TYPE: PRT
<213> ORGANISM: vibrio cholerae

<400> SEQUENCE: 72

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
```

```
                    210                 215                 220
Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro
385                 390                 395

<210> SEQ ID NO 73
<211> LENGTH: 394
<212> TYPE: PRT
<213> ORGANISM: vibrio cholerae

<400> SEQUENCE: 73

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val

```
Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
            275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
            355                 360                 365

Val Thr His His Pro Gly Leu Thr Pro Glu Gln Thr Ser Ala Gly Ala
        370                 375                 380

Gln Ala Ala Asp Ile Leu Ser Leu Phe Cys
385                 390

<210> SEQ ID NO 74
<211> LENGTH: 393
<212> TYPE: PRT
<213> ORGANISM: vibrio cholerae

<400> SEQUENCE: 74

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175
```

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
370                 375                 380

Gln Ala Ala Asp Ile Leu Ser Leu Phe
385                 390

<210> SEQ ID NO 75
<211> LENGTH: 392
<212> TYPE: PRT
<213> ORGANISM: vibrio cholerae

<400> SEQUENCE: 75

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys

-continued

```
            145                 150                 155                 160
        Thr Gln Gly Asn Val Ser Phe Ser Val Thr Arg Pro Glu His Asn Ile
                        165                 170                 175
        Ala Ile Ser Trp Pro Ser Val Ser Tyr Lys Ala Ala Gln Lys Glu Gly
                        180                 185                 190
        Ser Arg His Lys Arg Trp Ala Trp His Thr Gly Leu Ala Leu Cys
                        195                 200                 205
        Trp Leu Val Pro Met Asp Ala Ile Tyr Asn Tyr Ile Thr Gln Gln Asn
                210                 215                 220
        Cys Thr Leu Gly Asp Asn Trp Phe Gly Gly Ser Tyr Glu Thr Val Ala
        225                 230                 235                 240
        Gly Thr Pro Lys Val Ile Thr Val Lys Gln Gly Ile Glu Gln Lys Pro
                        245                 250                 255
        Val Glu Gln Arg Ile His Phe Ser Lys Gly Asn Ala Met Ser Ala Leu
                        260                 265                 270
        Ala Ala His Arg Val Cys Gly Val Pro Leu Glu Thr Leu Ala Arg Ser
                        275                 280                 285
        Arg Lys Pro Arg Asp Leu Thr Asp Asp Leu Ser Cys Ala Tyr Gln Ala
                        290                 295                 300
        Gln Asn Ile Val Ser Leu Phe Val Ala Thr Arg Ile Leu Phe Ser His
        305                 310                 315                 320
        Leu Asp Ser Val Phe Thr Leu Asn Leu Asp Glu Gln Glu Pro Glu Val
                        325                 330                 335
        Ala Glu Arg Leu Ser Asp Leu Arg Arg Ile Asn Glu Asn Asn Pro Gly
                        340                 345                 350
        Met Val Thr Gln Val Leu Thr Val Ala Arg Gln Ile Tyr Asn Asp Tyr
                        355                 360                 365
        Val Thr His His Pro Gly Leu Thr Pro Glu Gln Thr Ser Ala Gly Ala
                        370                 375                 380
        Gln Ala Ala Asp Ile Leu Ser Leu
        385                 390

<210> SEQ ID NO 76
<211> LENGTH: 391
<212> TYPE: PRT
<213> ORGANISM: vibrio cholerae

<400> SEQUENCE: 76

Val Glu Asp Glu Leu Asn Ile Phe Asp Glu Cys Arg Ser Pro Cys Ser
        1               5                   10                  15
        Leu Thr Pro Glu Pro Gly Lys Pro Ile Gln Ser Lys Leu Ser Ile Pro
                        20                  25                  30
        Ser Asp Val Val Leu Asp Glu Gly Val Leu Tyr Tyr Ser Met Thr Ile
                        35                  40                  45
        Asn Asp Glu Gln Asn Asp Ile Lys Asp Glu Lys Gly Glu Ser Ile
        50                  55                  60
        Ile Thr Ile Gly Glu Phe Ala Thr Val Arg Ala Thr Arg His Tyr Val
        65                  70                  75                  80
        Asn Gln Asp Ala Pro Phe Gly Val Ile His Leu Asp Ile Thr Thr Glu
                        85                  90                  95
        Asn Gly Thr Lys Thr Tyr Ser Tyr Asn Arg Lys Glu Gly Glu Phe Ala
                        100                 105                 110
        Ile Asn Trp Leu Val Pro Ile Gly Glu Asp Ser Pro Ala Ser Ile Lys
                        115                 120                 125
```

```
Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
370                 375                 380

Gln Ala Ala Asp Ile Leu Ser
385                 390

<210> SEQ ID NO 77
<211> LENGTH: 390
<212> TYPE: PRT
<213> ORGANISM: vibrio cholerae

<400> SEQUENCE: 77

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Lys Gly Glu Ser Ile
        50                  55                  60

Ile Thr Ile Gly Glu Phe Ala Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110
```

```
Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
        290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
        370                 375                 380

Gln Ala Ala Asp Ile Leu
385                 390

<210> SEQ ID NO 78
<211> LENGTH: 389
<212> TYPE: PRT
<213> ORGANISM: vibrio cholerae

<400> SEQUENCE: 78

Val Glu Asp Glu Leu Asn Ile Phe Asp Glu Cys Arg Ser Pro Cys Ser
1               5

```
            85                   90                   95
Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
                180                 185                 190

Ser Arg His Lys Arg Trp Ala His Trp His Thr Gly Leu Ala Leu Cys
                195                 200                 205

Trp Leu Val Pro Met Asp Ala Ile Tyr Asn Tyr Ile Thr Gln Gln Asn
            210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
                260                 265                 270

Ala Ala His Arg Val Cys Gly Val Pro Leu Glu Thr Leu Ala Arg Ser
                275                 280                 285

Arg Lys Pro Arg Asp Leu Thr Asp Asp Leu Ser Cys Ala Tyr Gln Ala
                290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
                340                 345                 350

Met Val Thr Gln Val Leu Thr Val Ala Arg Gln Ile Tyr Asn Asp Tyr
                355                 360                 365

Val Thr His His Pro Gly Leu Thr Pro Glu Gln Thr Ser Ala Gly Ala
                370                 375                 380

Gln Ala Ala Asp Ile
385

<210> SEQ ID NO 79
<211> LENGTH: 388
<212> TYPE: PRT
<213> ORGANISM: vibrio cholerae

<400> SEQUENCE: 79

Val Glu Asp Glu Leu Asn Ile Phe Asp Glu Cys Arg Ser Pro Cys Ser
1               5                   10                  15

Leu Thr Pro Glu Pro Gly Lys Pro Ile Gln Ser Lys Leu Ser Ile Pro
            20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
50                  55                  60
```

```
Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp
385

<210> SEQ ID NO 80
<211> LENGTH: 387
<212> TYPE: PRT
<213> ORGANISM: vibrio cholerae

<400> SEQUENCE: 80

Val Glu Asp Glu Leu Asn Ile Phe Asp Glu Cys Arg Ser Pro Cys Ser
 1               5                  10                  15

Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45
```

Asn Asp Glu Gln Asn Asp Ile Lys Asp Glu Asp Lys Gly Glu Ser Ile
         50                  55                  60

Ile Thr Ile Gly Glu Phe Ala Thr Val Arg Ala Thr Arg His Tyr Val
 65                  70                  75                  80

Asn Gln Asp Ala Pro Phe Gly Val Ile His Leu Asp Ile Thr Thr Glu
                 85                  90                  95

Asn Gly Thr Lys Thr Tyr Ser Tyr Asn Arg Lys Glu Gly Glu Phe Ala
                100                 105                 110

Ile Asn Trp Leu Val Pro Ile Gly Glu Asp Ser Pro Ala Ser Ile Lys
            115                 120                 125

Ile Ser Val Asp Glu Leu Asp Gln Gln Arg Asn Ile Ile Glu Val Pro
        130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Leu Ser Cys Ala Tyr Gln Ala
290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala
385

<210> SEQ ID NO 81
<211> LENGTH: 633
<212> TYPE: PRT
<213> ORGANISM: vibrio cholerae
<220> FEATURE:
<223> OTHER INFORMATION: mature Cholix Toxin deleted at amio acid
      residue 581

<400> SEQUENCE: 81

Val Glu Asp Glu Leu Asn Ile Phe Asp Glu Cys Arg Ser Pro Cys Ser

-continued

```
1               5                   10                  15
Leu Thr Pro Glu Pro Gly Lys Pro Ile Gln Ser Lys Leu Ser Ile Pro
                20                  25                  30

Ser Asp Val Val Leu Asp Glu Gly Val Leu Tyr Tyr Ser Met Thr Ile
            35                  40                  45

Asn Asp Glu Gln Asn Asp Ile Lys Asp Glu Asp Lys Gly Glu Ser Ile
        50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
            130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
            290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
            370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn Arg Ala Val Ile Thr Pro Gln
            420                 425                 430
```

Gly Val Thr Asn Trp Thr Tyr Gln Glu Leu Glu Ala Thr His Gln Ala
            435                 440                 445

Leu Thr Arg Glu Gly Tyr Val Phe Val Gly Tyr His Gly Thr Asn His
450                 455                 460

Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
                485                 490                 495

His Ala Glu Val Ala His Gly Tyr Ala Arg Ile Lys Glu Gly Thr Gly
            500                 505                 510

Glu Tyr Gly Leu Pro Thr Arg Ala Glu Arg Asp Ala Arg Gly Val Met
            515                 520                 525

Leu Arg Val Tyr Ile Pro Arg Ala Ser Leu Glu Arg Phe Tyr Arg Thr
530                 535                 540

Asn Thr Pro Leu Glu Asn Ala Glu Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Thr Val Ile Gly Trp Asp Met Ala Ile His Ala Val
            580                 585                 590

Ala Ile Pro Ser Thr Ile Pro Gly Asn Ala Tyr Glu Glu Leu Ala Ile
            595                 600                 605

Asp Glu Glu Ala Val Ala Lys Glu Gln Ser Ile Ser Thr Lys Pro Pro
610                 615                 620

Tyr Lys Glu Arg Lys Asp Glu Leu Lys
625                 630

<210> SEQ ID NO 82
<211> LENGTH: 178
<212> TYPE: PRT
<213> ORGANISM: Homo sapiens

<400> SEQUENCE: 82

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile 165                 170                 175

Arg Asn

<210> SEQ ID NO 83
<211> LENGTH: 177
<212> TYPE: PRT
<213> ORGANISM: Homo sapiens

<400> SEQUENCE: 83

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
                20                  25                  30

Asp Met His His Ile Glu Glu Ser Phe Gln Glu Ile Lys Arg Ala Ile
            35                  40                  45

Gln Ala Lys Asp Thr Phe Pro Asn Val Thr Ile Leu Ser Thr Leu Glu
    50                  55                  60

Thr Leu Gln Ile Ile Lys Pro Leu Asp Val Cys Cys Val Thr Lys Asn
65                  70                  75                  80

Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
                100                 105                 110

Tyr Met Gln Lys Thr Leu Arg Gln Cys Gln Glu Gln Arg Gln Cys His
                115                 120                 125

Cys Arg Gln Glu Ala Thr Asn Ala Thr Arg Val Ile His Asp Asn Tyr
    130                 135                 140

Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Ser Ser
                165                 170                 175

Ala

<210> SEQ ID NO 84
<211> LENGTH: 176
<212> TYPE: PRT
<213> ORGANISM: Homo sapiens

<400> SEQUENCE: 84

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
                20                  25                  30

Cys Val Ile Ala Thr Asn Leu Gln Glu Ile Arg Asn Gly Phe Ser Glu
                35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
                115                 120                 125

```
His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

<210> SEQ ID NO 85
<211> LENGTH: 179
<212> TYPE: PRT
<213> ORGANISM: Homo sapiens

<400> SEQUENCE: 85

```
Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
                20                  25                  30

Ala Ala Pro Ile Ser Ser His Cys Arg Leu Asp Lys Ser Asn Phe Gln
                35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
                100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
                130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 86
<211> LENGTH: 207
<212> TYPE: PRT
<213> ORGANISM: Homo sapiens

<400> SEQUENCE: 86

```
Met Asn Phe Gln Gln Arg Leu Gln Ser Leu Trp Thr Leu Ala Ser Arg
1               5                   10                  15

Pro Phe Cys Pro Pro Leu Leu Ala Thr Ala Ser Gln Met Gln Met Val
                20                  25                  30

Val Leu Pro Cys Leu Gly Phe Thr Leu Leu Leu Trp Ser Gln Val Ser
                35                  40                  45

Gly Ala Gln Gly Gln Glu Phe His Phe Gly Pro Cys Gln Val Lys Gly
    50                  55                  60

Val Val Pro Gln Lys Leu Trp Glu Ala Phe Trp Ala Val Lys Asp Thr
65                  70                  75                  80

Met Gln Ala Gln Asp Asn Ile Thr Ser Ala Arg Leu Leu Gln Gln Glu
                85                  90                  95

Val Leu Gln Asn Val Ser Asp Ala Glu Ser Cys Tyr Leu Val His Thr
```

```
                    100                 105                 110
Leu Leu Glu Phe Tyr Leu Lys Thr Val Phe Lys Asn Tyr His Asn Arg
            115                 120                 125

Thr Val Glu Val Arg Thr Leu Lys Ser Phe Ser Thr Leu Ala Asn Asn
            130                 135                 140

Phe Val Leu Ile Val Ser Gln Leu Gln Pro Ser Gln Glu Asn Glu Met
145                 150                 155                 160

Phe Ser Ile Arg Asp Ser Ala His Arg Arg Phe Leu Leu Phe Arg Arg
                165                 170                 175

Ala Phe Lys Gln Leu Asp Val Glu Ala Ala Leu Thr Lys Ala Leu Gly
                180                 185                 190

Glu Val Asp Ile Leu Leu Thr Trp Met Gln Lys Phe Tyr Lys Leu
                195                 200                 205

<210> SEQ ID NO 87
<211> LENGTH: 171
<212> TYPE: PRT
<213> ORGANISM: Homo sapiens

<400> SEQUENCE: 87

Met Leu Val Asn Phe Ile Leu Arg Cys Gly Leu Leu Leu Val Thr Leu
1               5                   10                  15

Ser Leu Ala Ile Ala Lys His Lys Gln Ser Ser Phe Thr Lys Ser Cys
                20                  25                  30

Tyr Pro Arg Gly Thr Leu Ser Gln Ala Val Asp Ala Leu Tyr Ile Lys
            35                  40                  45

Ala Ala Trp Leu Lys Ala Thr Ile Pro Glu Asp Arg Ile Lys Asn Ile
        50                  55                  60

Arg Leu Leu Lys Lys Lys Thr Lys Lys Gln Phe Met Lys Asn Cys Gln
65                  70                  75                  80

Phe Gln Glu Gln Leu Leu Ser Phe Phe Met Glu Asp Val Phe Gly Gln
                85                  90                  95

Leu Gln Leu Gln Gly Cys Lys Lys Ile Arg Phe Val Glu Asp Phe His
            100                 105                 110

Ser Leu Arg Gln Lys Leu Ser His Cys Ile Ser Cys Ala Ser Ser Ala
        115                 120                 125

Arg Glu Met Lys Ser Ile Thr Arg Met Lys Arg Ile Phe Tyr Arg Ile
    130                 135                 140

Gly Asn Lys Gly Ile Tyr Lys Ala Ile Ser Glu Leu Asp Ile Leu Leu
145                 150                 155                 160

Ser Trp Ile Lys Lys Leu Leu Glu Ser Ser Gln
                165                 170

<210> SEQ ID NO 88
<211> LENGTH: 224
<212> TYPE: PRT
<213> ORGANISM: Artificial Sequence
<220> FEATURE:
<223> OTHER INFORMATION: heavy chain variable region sequence for an
      anti-TNF-alpha antibody

<400> SEQUENCE: 88

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
```

```
            35                  40                  45
Ser Ala Ile Thr Trp Asn Ser Gly His Ile Asp Tyr Ala Asp Ser Val
 50                  55                  60
Glu Arg Gly Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Lys Val Ser Tyr Leu Ser Thr Ala Ser Ser Leu Asp Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
210                 215                 220

<210> SEQ ID NO 89
<211> LENGTH: 214
<212> TYPE: PRT
<213> ORGANISM: Artificial Sequence
<220> FEATURE:
<223> OTHER INFORMATION: light chain variable region sequence for an
      anti-TNF-alpha antibody

<400> SEQUENCE: 89

Asp Ile Gln Met Thr Gln Ser Pro Ser Ser Leu Ser Ala Ser Val Gly
1                5                  10                  15
Asp Arg Val Thr Ile Thr Cys Arg Ala Ser Gln Gly Ile Arg Asn Tyr
                20                  25                  30
Leu Ala Trp Tyr Gln Gln Lys Pro Gly Lys Ala Pro Lys Leu Leu Ile
            35                  40                  45
Tyr Ala Ala Ser Thr Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Arg Tyr Asn Arg Ala Pro Tyr
                 85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 90
<211> LENGTH: 126
<212> TYPE: PRT
<213> ORGANISM: Artificial Sequence
<220> FEATURE:
<223> OTHER INFORMATION: heavy chain variable region sequence for an
      anti-TNF-alpha antibody

<400> SEQUENCE: 90

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Ile Ile Ser Phe Asp Gly Ser Asn Lys Ser Ser Ala Asp Ser Val
        50                  55                  60

Lys Gly Arg Phe Thr Tyr Ser Arg Arg Asn Ser Lys Asn Ala Leu Phe
65                  70                  75                  80

Leu Gln Met Asn Ser Leu Arg Ala Glu Asp Thr Ala Val Phe Tyr Cys
                85                  90                  95

Ala Arg Asp Arg Gly Val Ser Ala Gly Gly Asn Tyr Tyr Tyr Tyr Gly
                100                 105                 110

Met Asp Val Trp Gly Gln Gly Thr Thr Val Thr Val Ser Ser
            115                 120                 125

<210> SEQ ID NO 91
<211> LENGTH: 108
<212> TYPE: PRT
<213> ORGANISM: Artificial Sequence
<220> FEATURE:
<223> OTHER INFORMATION: light chain variable region sequence for an
      anti-TNF-alpha antibody

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Arg Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Leu
            100                 105

<210> SEQ ID NO 92
<211> LENGTH: 467

```
<212> TYPE: PRT
<213> ORGANISM: Artificial Sequence
<220> FEATURE:
<223> OTHER INFORMATION: amino acid sequence of human TNFR-p75-Fc
      dimeric fusion protein

<400> SEQUENCE: 92

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
        50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
        370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 93
<211> LENGTH: 39
<212> TYPE: PRT
<213> ORGANISM: Artificial Sequence
<220> FEATURE:
<223> OTHER INFORMATION: GLP-1 agonist peptide amino acid sequence
      (exenatide)

<400> SEQUENCE: 93

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 94
<211> LENGTH: 33
<212> TYPE: PRT
<213> ORGANISM: Artificial
<220> FEATURE:
<223> OTHER INFORMATION: GLP-1 agonist peptide amino acid sequence
      (Liraglutide)

<400> SEQUENCE: 94

His Ala Glu Gly Thr Phe Thr Ser Asp Val Ser Ser Tyr Leu Glu Gly
1               5                   10                  15

Gln Ala Ala Lys Glu Glu Phe Ile Ile Ala Trp Leu Val Lys Gly Arg
            20                  25                  30

Gly

<210> SEQ ID NO 95
<211> LENGTH: 191
<212> TYPE: PRT
<213> ORGANISM: Artificial Sequence
<220> FEATURE:
<223> OTHER INFORMATION: human growth hormone (somatotropin)

<400> SEQUENCE: 95

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60
```

Glu Glu Thr Gln Gln Lys Ser Asn Leu Glu Leu Arg Ile Ser Leu
65                  70                  75                  80

Leu Leu Ile Gln Ser Trp Leu Glu Pro Val Gln Phe Leu Arg Ser Val
            85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190

<210> SEQ ID NO 96
<211> LENGTH: 5
<212> TYPE: PRT
<213> ORGANISM: Artificial Sequence
<220> FEATURE:
<223> OTHER INFORMATION: peptide

<400> SEQUENCE: 96

Gly Gly Gly Gly Ser
1               5

<210> SEQ ID NO 97
<211> LENGTH: 10
<212> TYPE: PRT
<213> ORGANISM: Artificial Sequence
<220> FEATURE:
<223> OTHER INFORMATION: peptide

<400> SEQUENCE: 97

Gly Gly Gly Gly Ser Gly Gly Gly Gly Ser
1               5                   10

<210> SEQ ID NO 98
<211> LENGTH: 15
<212> TYPE: PRT
<213> ORGANISM: Artificial Sequence
<220> FEATURE:
<223> OTHER INFORMATION: peptide

<400> SEQUENCE: 98

Gly Gly Gly Gly Ser Gly Gly Gly Gly Ser Gly Gly Gly Gly Ser
1               5                   10                  15

<210> SEQ ID NO 99
<211> LENGTH: 8
<212> TYPE: PRT
<213> ORGANISM: Artificial Sequence
<220> FEATURE:
<223> OTHER INFORMATION: peptide

<400> SEQUENCE: 99

Gly Gly Gly Gly Ser Gly Gly Gly
1               5

<210> SEQ ID NO 100

```
<211> LENGTH: 4
<212> TYPE: PRT
<213> ORGANISM: Artificial Sequence
<220> FEATURE:
<223> OTHER INFORMATION: peptide

<400> SEQUENCE: 100

Ala Ala Pro Phe
1

<210> SEQ ID NO 101
<211> LENGTH: 3
<212> TYPE: PRT
<213> ORGANISM: Artificial Sequence
<220> FEATURE:
<223> OTHER INFORMATION: peptide

<400> SEQUENCE: 101

Gly Gly Phe
1

<210> SEQ ID NO 102
<211> LENGTH: 4
<212> TYPE: PRT
<213> ORGANISM: Artificial Sequence
<220> FEATURE:
<223> OTHER INFORMATION: peptide

<400> SEQUENCE: 102

Ala Ala Pro Val
1

<210> SEQ ID NO 103
<211> LENGTH: 3
<212> TYPE: PRT
<213> ORGANISM: Artificial Sequence
<220> FEATURE:
<223> OTHER INFORMATION: peptide

<400> SEQUENCE: 103

Gly Gly Leu
1

<210> SEQ ID NO 104
<211> LENGTH: 3
<212> TYPE: PRT
<213> ORGANISM: Artificial Sequence
<220> FEATURE:
<223> OTHER INFORMATION: peptide

<400> SEQUENCE: 104

Ala Ala Leu
1

<210> SEQ ID NO 105
<211> LENGTH: 3
<212> TYPE: PRT
<213> ORGANISM: Artificial Sequence
<220> FEATURE:
<223> OTHER INFORMATION: peptide

<400> SEQUENCE: 105

Phe Val Arg
1

<210> SEQ ID NO 106
<211> LENGTH: 3
```

```
<212> TYPE: PRT
<213> ORGANISM: Artificial Sequence
<220> FEATURE:
<223> OTHER INFORMATION: peptide

<400> SEQUENCE: 106

Val Gly Arg
1

<210> SEQ ID NO 107
<211> LENGTH: 4
<212> TYPE: PRT
<213> ORGANISM: Artificial Sequence
<220> FEATURE:
<223> OTHER INFORMATION: peptide

<400> SEQUENCE: 107

Arg Lys Pro Arg
1

<210> SEQ ID NO 108
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 5
<223> OTHER INFORMATION: Xaa = Any Amino Acid

<400> SEQUENCE: 108

Tyr Val Ala Asp Xaa
1               5

<210> SEQ ID NO 109
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 2, 3, 5
<223> OTHER INFORMATION: Xaa = Any Amino Acid

<400> SEQUENCE: 109

Asp Xaa Xaa Asp Xaa
1               5

<210> SEQ ID NO 110
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 2, 5
<223> OTHER INFORMATION: Xaa = Any Amino Acid

<400> SEQUENCE: 110

Arg Xaa Asn Arg Xaa
1               5

<210> SEQ ID NO 111
<211> LENGTH: 5
<212> TYPE: PRT
<213> ORGANISM: Artificial Sequence
```

```
<220> FEATURE:
<223> OTHER INFORMATION: Peptide
<220> FEATURE:
<221> NAME/KEY: Variant
<222> LOCATION: 2, 5
<223> OTHER INFORMATION: Xaa = Any Amino Acid

<400> SEQUENCE: 111

Lys Xaa Asn Arg Xaa
1               5

<210> SEQ ID NO 112
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 6
<223> OTHER INFORMATION: Xaa = Any Amino Acid

<400> SEQUENCE: 112

Glu Arg Thr Lys Arg Xaa
1               5

<210> SEQ ID NO 113
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 5
<223> OTHER INFORMATION: Xaa = Any Amino Acid

<400> SEQUENCE: 113

Arg Val Arg Arg Xaa
1               5

<210> SEQ ID NO 114
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 6
<223> OTHER INFORMATION: Xaa = Any Amino Acid

<400> SEQUENCE: 114

Asp Arg Val Arg Arg Xaa
1               5

<210> SEQ ID NO 115
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 2, 6
<223> OTHER INFORMATION: Xaa = Any Amino Acid

<400> SEQUENCE: 115

Pro Xaa Trp Val Pro Xaa
1               5
```

```
<210> SEQ ID NO 116
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 4
<223> OTHER INFORMATION: Xaa = Any Amino Acid

<400> SEQUENCE: 116

Trp Val Ala Xaa
1

<210> SEQ ID NO 117
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 1, 3, 4
<223> OTHER INFORMATION: Xaa = Any Amino Acid

<400> SEQUENCE: 117

Xaa Phe Xaa Xaa
1

<210> SEQ ID NO 118
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 1, 3, 4
<223> OTHER INFORMATION: Xaa = Any Amino Acid

<400> SEQUENCE: 118

Xaa Tyr Xaa Xaa
1

<210> SEQ ID NO 119
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: Variant
<222> LOCATION: 1, 3, 4
<223> OTHER INFORMATION: Xaa = Any Amino Acid

<400> SEQUENCE: 119

Xaa Trp Xaa Xaa
1

<210> SEQ ID NO 120
<211> LENGTH: 16
<212> TYPE: PRT
<213> ORGANISM: Artificial Sequence
<220> FEATURE:
<223> OTHER INFORMATION: Peptide

<400> SEQUENCE: 120
```

```
Asp Arg Tyr Ile Pro Phe His Leu Leu Val Ala Pro Tyr Ser Pro Ala
1               5                   10                  15
```

<210> SEQ ID NO 121
<211> LENGTH: 15
<212> TYPE: PRT
<213> ORGANISM: Artificial Sequence
<220> FEATURE:
<223> OTHER INFORMATION: Peptide

<400> SEQUENCE: 121

```
Gly Gly Gly Gly Ser Gly Gly Gly Glu Asn Leu Tyr Phe Gln Ser
1               5                   10                  15
```

<210> SEQ ID NO 122
<211> LENGTH: 590
<212> TYPE: PRT
<213> ORGANISM: Artificial Sequence
<220> FEATURE:
<223> OTHER INFORMATION: amino acid sequence of a Cholix415-TEV-IL-10
      fusion molecule

<400> SEQUENCE: 122

```
Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
                20                  25                  30

Pro Gly Asp Val Val Leu Asp Glu Gly Val Leu Tyr Tyr Ser Met Thr
            35                  40                  45

Ile Asn Asp Glu Gln Asn Asp Ile Lys Asp Glu Asp Lys Gly Glu Ser
50                  55                  60

Ile Ile Thr Ile Gly Glu Phe Ala Thr Val Arg Ala Thr Arg His Tyr
65                  70                  75                  80

Val Ser Gln Asp Ala Pro Phe Gly Val Ile Asn Leu Asp Ile Thr Thr
                85                  90                  95

Glu Asn Gly Thr Lys Thr Tyr Ser Phe Asn Arg Lys Glu Ser Glu Phe
            100                 105                 110

Ala Ile Asn Trp Leu Val Pro Ile Gly Glu Asp Ser Pro Ala Ser Ile
        115                 120                 125

Lys Ile Ser Ile Asp Glu Leu Asp Gln Gln Arg Asn Ile Ile Glu Val
    130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Ile Asp Ala Ile Tyr Asn Tyr Ile Thr Gln Gln
    210                 215                 220

Asn Cys Thr Leu Gly Asp Asn Trp Phe Gly Gly Ser Tyr Glu Thr Val
225                 230                 235                 240

Ala Gly Thr Pro Lys Ala Ile Thr Val Lys Gln Gly Ile Glu Gln Lys
                245                 250                 255

Pro Val Glu Gln Arg Ile His Phe Ser Lys Lys Asn Ala Met Glu Ala
            260                 265                 270

Leu Ala Ala His Arg Val Cys Gly Val Pro Leu Glu Thr Leu Ala Arg
```

```
                275                 280                 285
Ser Arg Lys Pro Arg Asp Leu Pro Asp Leu Ser Cys Ala Tyr Asn
290                 295                 300

Ala Gln Gln Ile Val Ser Leu Phe Leu Ala Thr Arg Ile Leu Phe Thr
305                 310                 315                 320

His Ile Asp Ser Ile Phe Thr Leu Asn Leu Asp Gly Gln Glu Pro Glu
            325                 330                 335

Val Ala Glu Arg Leu Asp Asp Leu Arg Arg Ile Asn Glu Asn Asn Pro
        340                 345                 350

Gly Met Val Ile Gln Val Leu Thr Val Ala Arg Gln Ile Tyr Asn Asp
    355                 360                 365

Tyr Val Thr His His Pro Gly Leu Thr Pro Glu Gln Thr Ser Ala Gly
370                 375                 380

Ala Gln Ala Ala Asp Ile Leu Ser Leu Phe Cys Pro Asp Ala Asp Lys
385                 390                 395                 400

Ser Cys Val Ala Ser Asn Ser Asp Gln Ala Asn Ile Asn Ile Glu Ser
            405                 410                 415

Gly Gly Gly Gly Ser Gly Gly Gly Glu Asn Leu Tyr Phe Gln Ser Pro
        420                 425                 430

Gly Gln Gly Thr Gln Ser Glu Asn Ser Cys Thr His Phe Pro Gly Asn
    435                 440                 445

Leu Pro Asn Met Leu Arg Asp Leu Arg Asp Ala Phe Ser Arg Val Lys
450                 455                 460

Thr Phe Phe Gln Met Lys Asp Gln Leu Asp Asn Leu Leu Leu Lys Glu
465                 470                 475                 480

Ser Leu Leu Glu Asp Phe Lys Gly Tyr Leu Gly Cys Gln Ala Leu Ser
            485                 490                 495

Glu Met Ile Gln Phe Tyr Leu Glu Glu Val Met Pro Gln Ala Glu Asn
        500                 505                 510

Gln Asp Pro Asp Ile Lys Ala His Val Asn Ser Leu Gly Glu Asn Leu
    515                 520                 525

Lys Thr Leu Arg Leu Arg Leu Arg Arg Cys His Arg Phe Leu Pro Cys
530                 535                 540

Glu Asn Lys Ser Lys Ala Val Glu Gln Val Lys Asn Ala Phe Asn Lys
545                 550                 555                 560

Leu Gln Glu Lys Gly Ile Tyr Lys Ala Met Ser Glu Phe Asp Ile Phe
            565                 570                 575

Ile Asn Tyr Ile Glu Ala Tyr Met Thr Met Lys Ile Arg Asn
        580                 585                 590

<210> SEQ ID NO 123
<211> LENGTH: 590
<212> TYPE: PRT
<213> ORGANISM: Artificial Sequence
<220> FEATURE:
<223> OTHER INFORMATION: amino acid sequence of a Cholix415-(G4S)3-IL-10
      fusion molecule

<400> SEQUENCE: 123

Met Val Glu Glu Ala Leu Asn Ile Phe Asp Glu Cys Arg Ser Pro Cys
1               5                   10                  15

Ser Leu Thr Pro Glu Pro Gly Lys Pro Ile Gln Ser Lys Leu Ser Ile
            20                  25                  30

Pro Gly Asp Val Val Leu Asp Glu Gly Val Leu Tyr Tyr Ser Met Thr
        35                  40                  45
```

-continued

```
Ile Asn Asp Glu Gln Asn Asp Ile Lys Asp Glu Asp Lys Gly Glu Ser
 50                  55                  60

Ile Ile Thr Ile Gly Glu Phe Ala Thr Val Arg Ala Thr Arg His Tyr
 65                  70                  75                  80

Val Ser Gln Asp Ala Pro Phe Gly Val Ile Asn Leu Asp Ile Thr Thr
                 85                  90                  95

Glu Asn Gly Thr Lys Thr Tyr Ser Phe Asn Arg Lys Glu Ser Glu Phe
                100                 105                 110

Ala Ile Asn Trp Leu Val Pro Ile Gly Glu Asp Ser Pro Ala Ser Ile
            115                 120                 125

Lys Ile Ser Ile Asp Glu Leu Asp Gln Gln Arg Asn Ile Ile Glu Val
130                 135                 140

Pro Lys Leu Tyr Ser Ile Asp Leu Asp Asn Gln Thr Leu Glu Gln Trp
145                 150                 155                 160

Lys Thr Gln Gly Asn Val Ser Phe Ser Val Thr Arg Pro Glu His Asn
                165                 170                 175

Ile Ala Ile Ser Trp Pro Ser Val Ser Tyr Lys Ala Ala Gln Lys Glu
            180                 185                 190

Gly Ser Arg His Lys Arg Trp Ala His Trp His Thr Gly Leu Ala Leu
        195                 200                 205

Cys Trp Leu Val Pro Ile Asp Ala Ile Tyr Asn Tyr Ile Thr Gln Gln
210                 215                 220

Asn Cys Thr Leu Gly Asp Asn Trp Phe Gly Ser Tyr Glu Thr Val
225                 230                 235                 240

Ala Gly Thr Pro Lys Ala Ile Thr Val Lys Gln Gly Ile Glu Gln Lys
                245                 250                 255

Pro Val Glu Gln Arg Ile His Phe Ser Lys Lys Asn Ala Met Glu Ala
            260                 265                 270

Leu Ala Ala His Arg Val Cys Gly Val Pro Leu Glu Thr Leu Ala Arg
        275                 280                 285

Ser Arg Lys Pro Arg Asp Leu Pro Asp Leu Ser Cys Ala Tyr Asn
        290                 295                 300

Ala Gln Gln Ile Val Ser Leu Phe Leu Ala Thr Arg Ile Leu Phe Thr
305                 310                 315                 320

His Ile Asp Ser Ile Phe Thr Leu Asn Leu Asp Gly Gln Glu Pro Glu
                325                 330                 335

Val Ala Glu Arg Leu Asp Asp Leu Arg Arg Ile Asn Glu Asn Asn Pro
            340                 345                 350

Gly Met Val Ile Gln Val Leu Thr Val Ala Arg Gln Ile Tyr Asn Asp
        355                 360                 365

Tyr Val Thr His His Pro Gly Leu Thr Pro Glu Gln Thr Ser Ala Gly
370                 375                 380

Ala Gln Ala Ala Asp Ile Leu Ser Leu Phe Cys Pro Asp Ala Asp Lys
385                 390                 395                 400

Ser Cys Val Ala Ser Asn Ser Asp Gln Ala Asn Ile Asn Ile Glu Ser
                405                 410                 415

Gly Gly Gly Gly Ser Gly Gly Gly Ser Gly Gly Gly Ser Pro
            420                 425                 430

Gly Gln Gly Thr Gln Ser Glu Asn Ser Cys Thr His Phe Pro Gly Asn
        435                 440                 445

Leu Pro Asn Met Leu Arg Asp Leu Arg Asp Ala Phe Ser Arg Val Lys
450                 455                 460

Thr Phe Phe Gln Met Lys Asp Gln Leu Asp Asn Leu Leu Leu Lys Glu
```

-continued

```
465                 470                 475                 480
Ser Leu Leu Glu Asp Phe Lys Gly Tyr Leu Gly Cys Gln Ala Leu Ser
                485                 490                 495

Glu Met Ile Gln Phe Tyr Leu Glu Glu Val Met Pro Gln Ala Glu Asn
                500                 505                 510

Gln Asp Pro Asp Ile Lys Ala His Val Asn Ser Leu Gly Glu Asn Leu
                515                 520                 525

Lys Thr Leu Arg Leu Arg Leu Arg Arg Cys His Arg Phe Leu Pro Cys
        530                 535                 540

Glu Asn Lys Ser Lys Ala Val Glu Gln Val Lys Asn Ala Phe Asn Lys
545                 550                 555                 560

Leu Gln Glu Lys Gly Ile Tyr Lys Ala Met Ser Glu Phe Asp Ile Phe
                565                 570                 575

Ile Asn Tyr Ile Glu Ala Tyr Met Thr Met Lys Ile Arg Asn
                580                 585                 590
```

What is claimed is:

1. An isolated delivery construct comprising (i) a variant form of a Cholix polypeptide set forth in SEQ ID NO: 1 that lacks domain III and Ib loop and (ii) a heterologous therapeutic cargo, wherein the variant form of the Cholix polypeptide set forth in SEQ ID NO: 1 that lacks domain III and Ib loop is capable of transcytosing across a polarized epithelial cell.

2. A pharmaceutical composition comprising the isolated delivery construct of claim 1 and a pharmaceutically acceptable carrier.

* * * * *